(12) United States Patent
Maertens et al.

(10) Patent No.: US 12,123,041 B2
(45) Date of Patent: Oct. 22, 2024

(54) METHOD FOR THE PRODUCTION OF AMINO SUGAR-CONTAINING PRODUCTS

(71) Applicant: Universiteit Gent, Ghent (BE)

(72) Inventors: Jo Maertens, Ghent (BE); David Bauwens, Ghent (BE); Wouter Van Bellegem, Ekeren (BE); Pieter Coussement, Gentbrugge (BE); Dries Duchi, Bavikhove (BE); Marjan De Mey, Ghent (BE)

(73) Assignee: Universiteit Gent, Ghent (BE)

( * ) Notice: Subject to any disclaimer, the term of this patent is extended or adjusted under 35 U.S.C. 154(b) by 206 days.

(21) Appl. No.: 17/276,793

(22) PCT Filed: Sep. 20, 2019

(86) PCT No.: PCT/EP2019/075371
§ 371 (c)(1),
(2) Date: Mar. 16, 2021

(87) PCT Pub. No.: WO2020/058493
PCT Pub. Date: Mar. 26, 2020

(65) Prior Publication Data
US 2021/0355520 A1    Nov. 18, 2021

(30) Foreign Application Priority Data

Sep. 21, 2018 (EP) .................... 18195892

(51) Int. Cl.
| | |
|---|---|
| *C12P 19/28* | (2006.01) |
| *C12N 9/10* | (2006.01) |
| *C12P 19/26* | (2006.01) |
| *C12P 19/30* | (2006.01) |
| *C12P 19/32* | (2006.01) |
| *C12P 19/44* | (2006.01) |

(52) U.S. Cl.
CPC ............... *C12P 19/44* (2013.01); *C12P 19/26* (2013.01); *C12Y 205/01007* (2013.01)

(58) Field of Classification Search
CPC ....................... C12N 9/1085; C12Y 205/01007
See application file for complete search history.

(56) References Cited

U.S. PATENT DOCUMENTS

| | | | | |
|---|---|---|---|---|
| 2011/0281817 | A1* | 11/2011 | Nielsen | .................... C08L 5/08 435/97 |
| 2020/0140908 | A1 | 5/2020 | Maertens et al. | |

FOREIGN PATENT DOCUMENTS

| | | |
|---|---|---|
| CA | 2796284 A1 | 10/2011 |
| EP | 2927316 A1 | 10/2015 |
| WO | 2011/130836 A1 | 10/2011 |
| WO | 2012/007481 A2 | 1/2012 |

OTHER PUBLICATIONS

Zhou et al., Cell Mol Life Sci 63:2260-2290, 2006 (Year: 2006).*
Ishiguro et al., J. Bacteriol. 127:1119-1126, 1976 (Year: 1976).*
Turnbough, C., J. Bacteriol. 153:998-1007, 1983 (Year: 1983).*
Ling et al., Emerging Topics in Life Sciences 2:377-388, Sep. 11, 2018 (Year: 2018).*
Liu et al., Metabolic Engineering 23:42-52; 2014 (Year: 2014).*
Barreteau et al., FEMS Microbiol. Rev. 32:168-207, 2008 (Year: 2008).*
Harris et al., Cell 165:1479-1492, 2016 (Year: 2016).*
Lobo et al., BMC Biotechnology 13:46, 2013, 15 pages (Year: 2013).*
Geremia et al., Proc. Natl. Acad. Sci. 91:2669-2673, 1994 (Year: 1994).*
Yu et al., "Metabolic engineering of *Escherichia coli* for biosynthesis of hyaluronic acid", Metabolic Engineering 10:24-32, 2008 (Year: 2008).*
El Zoeiby et al., "Structure and function of the Mur enzymes: development of novel inhibitors", Mol. Microbiol. 47:1-12, 2003 (Year: 2003).*
Brown et al., J. Bacteriol. 177:4194-4197, 1995 (Year: 1995).*
Ward et al., bioRxiv [Preprint] Aug. 2, 2023:doi: 10.1101/2023.08.02.551708, 31 pages (Year: 2023).*
Aguilar-Uscanga et al., "A Study of the Yeast Cell Wall Composition and Structure in Response to Growth Conditions and Mode of Cultivation," Letters in Applied Microbiology, vol. 37, (Jun. 2003), pp. 268-274.
Antoine et al., "Large Scale in Vivo Synthesis of Globotriose and Globotetraose by High Cell Density Culture of Metabolically Engineered *Escherichia coli*," Biochimie., vol. 87, No. 2, (Feb. 2005), pp. 197-203.
Bernardi et al., "Interfering with the Sugar Code: Design and Synthesis of Oligosaccharide Mimics, " Chemistry—A European J., vol. 14, No. 25, (Aug. 2008), pp. 7434-7441.
Bertozzi et al., "Cracking the Carbohydrate Code for Selectin Recognition," Chem. Biology, vol. 2, No. 11, (Nov. 1995), pp. 703-708.
Boddy et al., "Cell-Based Production of Nonulosonates," WO/2011/130836, PCT/CA2011/000449, Issued, (Apr. 2011).
Boltje et al., "Opportunities and Challenges in Synthetic Oligosaccharide and Glycoconjugate Research," Nat. Chemistry, vol. 1, No. 8, (Oct. 2009), pp. 611-622.
Bowles et al., "Glycosyltransferases of Lipophilic Small Molecules," Annu. Rev. Plant Biol., vol. 57, (Jun. 2006), pp. 567-597.
Bowles et al., "Glycosyltransferases: Managers of Small Molecules," Curr. Opinion in Plant Biology, vol. 8, (Jun. 2005), pp. 254-263.

(Continued)

*Primary Examiner* — David Steadman
(74) *Attorney, Agent, or Firm* — TraskBritt

(57) ABSTRACT

A method or producing amino sugar (containing) products using metabolically engineered microorganisms is disclosed, wherein the conversion of UDP-N-acetylglucosamine to cell envelope precursors and molecules is reduced by altering the activity of enzymes involved in the synthesis of cell envelope precursors and molecules.

2 Claims, 19 Drawing Sheets

Specification includes a Sequence Listing.

(56) References Cited

OTHER PUBLICATIONS

Byun et al., "Production of GDP-L-Fucose, L-Fucose Donor for Fucosyloligosaccharide Synthesis, in Recombinant *Escherichia coli*," Applied Microbiol. Biotechnology, vol. 74, No. 4, (Mar. 2007), pp. 768-775.

Chang et al., "Avenaciolides: Potential MurA-Targeted Inhibitors Against Peptidoglycan Biosynthesis in Methicillin-Resistant *Staphylococcus aureus* (MRSA)," J. Am. Chemica. Soc., vol. 137, (Mar. 2015), pp. 267-275.

Cocinero et al., "Carbohydrates," Topics in Current Chemistry, vol. 364, (Feb. 2015), pp. 299-334.

De Bruyn et al., "Biotechnological Advances in UDP-Sugar-Based Glycosylation of Small Molecules," Biotechnology Advances, vol. 33, No. 2, (Mar. 2015), pp. 288-302.

De Bruyn et al., "Development of an in Vivo Glucosylation Platform by Coupling Production to Growth: Production of Phenolic Glucosides by a Glycosyltransferase of Vitis Vinifera," Biotechnol. Bioengineering, vol. 112, No. 8, (Feb. 2015), pp. 1594-1603.

De Bruyn et al., "Metabolic Engineering of *Escherichia coli* into a Versatile Gycosylation Platform: Production of Bio-Active Quercetin Glycosides," Microbial. Cell Factories, vol. 14, No. 1, (Sep. 2015), pp. 138.

Demchick et al., "The Permeability of the Wall Fabric of *Escherichia coli* and Bacillus Subtilis," vol. 178, No. 3, (Feb. 1996), pp. 768-773.

Desmet et al., "Enzymatic Glycosylation of Small Molecules: Challenging Substrates Require Tailored Catalysts," CheEmistry—A European J., vol. 18, No. 35, (Aug. 2012), pp. 10786-801.

Gabius et al., "An Introduction to the Sugar Code," Histochemistry and Cell Biology, vol. 147, No. 2, (Feb. 2017), pp. 111-117.

Gabius et al., "Biological Information Transfer beyond the Genetic Code: The Sugar Code," Naturwissenshaften, vol. 87, No. 3, (Apr. 2000), pp. 108-121.

Gabius et al., "From Lectin Structure to Functional Glycomics: Principles of the Sugar Code," Trends in Biochemical Sciences, vol. 36, No. 6, (Jun. 2011), pp. 298-313.

Goedl et al., "Recombinant Sucrose Phosphorylase from Leuconostoc Mesenteroides: Characterization, Kinetic Studies of Transglucosylation, and Application of Immobilised Enzyme for Production of Alfa-D-Glucose 1-Phosphate," J. Biotechnology, vol. 129, No. 1, (Mar. 2007), pp. 77-86.

Goh et al. "Concurrent Growth Rate and Transcript Analyses Reveal Essential Gene Stringency in *Escherichia coli*," PLoS One, vol. 4, No. 6, (Jun. 2009), e6061.

Graslund et al., "Protein Production and Purification," Nat. Methods, vol. 5, No. 2, (Feb. 2008), pp. 135-146.

Hendlin et al., "Phosphonomycin, a New Antibiotic Produced by Strains of *Streptomyces*," Science, vol. 166, Issue 3901, (Oct. 1969), pp. 122-123.

Hrast et al., "Inhibitors of the Peptidoglycan Biosynthesis Enzymes MurA-F," Bioorganic Chemistry, vol. 55, (Aug. 2014), pp. 2-15.

International Search Report for International Application No. PCT/EP2019/075371, mailed Jan. 7, 2020, 5 pages.

International Written Opinion for International Application No. PCT/EP2019/075371, mailed Jan. 7, 2020, 5 pages.

Kahan et al., "The Mechanism of Action of Fosfomycin (Phosphonomycin)," Annals of the New York Academy of Sciences, vol. 235, (May 1974), pp. 364-386.

Kogure et al., "Efficient Production of 2-Deoxy-Scyllo-Inosose from d-Glucose by Metabolically Engineered Recombinant *Escherichia coli*," J. Biotechnology, vol. 129, No. 3, (Jan. 2007), pp. 502-509.

Lairson et al., "Glycosyltransferases: Structures, Functions, and Mechanisms," Annu. Rev. Biochem., vol. 77, (Jul. 2008), pp. 521-555.

Lipke et al., "Cell Wall Architecture in Yeast ?: New Structure and New Challenges," vol. 180, No. 15, (Aug. 1998), pp. 3735-3740.

Merzendorfer et al., "The Cellular Basis of Chitin Synthesis in Fungi and Insects ?: Common Principles and Differences," European J. of Cell Biology, vol. 90, No. 9, (Sep. 2011), pp. 759-769.

Molina-Lopez et al., "A Peptide Inhibitor of MurA UDP-N-Acetylglucosamine Enolpyruvyl Transferase ?: The First Committed Step in Peptidoglycan Biosynthesis," Peptides, vol. 27, No. 3000, (Aug. 2006), pp. 3115-3121.

Priem, et al., "A New Fermentation Process Allows Large-Scale Production of Human Milk Oligosaccharides by Metabolically Engineered Bacteria," Glycobiology, vol. 12, No. 4, pp. 235-240 (Aug. 2001).

Rodriguez-Diaz et al., "Metabolic Engineering of Lactobacillus Casei for Production of UDP-N-Acetylglucosamine," Biotechnol. Bioengineering, vol. 109, vol. 7, (Jul. 2012), pp. 1704-1712.

Ross et al., "Higher Plant Glycosyltransferases," Genome Biology, vol. 2, No. 2, (Feb. 2001).

Rozman et al., "Discovery of New MurA Inhibitors Using Induced-Fit Simulation and Docking," Bioorganic & Medicinal Chemistry Letters, vol. 27, (Feb. 2017), pp. 944-949.

Ruffing et al., "Metabolic Engineering of Microbes for Oligosaccharide and Polysaccharide Synthesis," Microbial. Cell Factories, vol. 5, (Jul. 2006), pp. 25.

Samain et al., "Gram-Scale Synthesis of Recombiant Chitooligosaccharides in *Escherichia coli*," Carbohydrate Research, vol. 302, (Apr. 1997), pp. 35-42.

Silhavy et al., "The Bacterial Cell Envelope," Cold Spring Harbor Perspectives in Biology, vol. 2, No. 5, (May 2010), pp. 1-16.

Tweeddale et al., "Effect of Slow Growth on Metabolism of *Escherichia coli*, as Revealed by Global Metabolite Pool ('Metabolome') Analysis," vol. 180, No. 19, (Jul. 1998), pp. 5109-5116.

Varki et al., "Biological Roles of Oligosaccharides ?: All of the Theories Are Correct," Glycobiology, vol. 3, No. 2, (Apr. 1993), pp. 97-130.

Westbrook et al., "Metabolic Engineering to Enhance Heterologous Production of Hyaluronic Acid in Bacillus Subtilis," Metabolic Engineering, vol. 47, (Nov. 2017), pp. 401-413.

Xie et al., "On the Evolution of Fungal and Yeast Cell Walls Xianfa," Yeast, vol. 27, No. 8, (Aug. 2010), pp. 479-488.

Yonekura-Sakakibara et al., "An Evolutionary View of Functional Diversity in Family 1 Glycosyltransferases," The Plant Journal, vol. 66, (Jan. 2011), pp. 182-193.

Zhang et al., "A Two-Step Fermentation Process for Efficient Production of Penta-N-Acetyl-Chitopentaose in Recombinant *Escherichia coli*," Biotechnology Letters, vol. 29, No. 11, (Jun. 2007), pp. 1729-1733.

Zhang et al., "Large-Scale Synthesis of Globotriose Derivatives through Recombinant *E. coli*," Organic & Biomolecular Chemistry, vol. 1, No. 17, (Jun. 2003), pp. 3048-3053.

Harris et al "Surface Area to Volume Ratio: A Natural Variable for Bacterial Morphogenesis" Trends Microbiol. 26(10) Oct. 2018; pp. 815-832.

Real et al. "Localization of the Bacillus subtilis murB gene within the dow cluster is important for growth and sporulation" J Bacteriol., vol. 88, No. 5, (Mar. 2006) pp. 1721-1732.

Willdigg et al. "A Decrease in Fatty Acid Synthesis Rescues Cells with Limited Peptidoglycan Synthesis Capacity" mBio. 14(2) Published Apr. 5, 2023; e00475-23.

Du et al. "Two active forms of UDP-N-acetylglucosamine enolpyruvyl transferase in gram-positive bacteria," J Bacteriol. Aug. 2000; 182(15):4146-52).

Aguiar et al. "Ashbya gossypii beyond industrial riboflavin production: A historical perspective and emerging biotechnological applications" Biotechnol Adv vol. 33, Issue 8, Dec. 2015, pp. 1774-1786.

Ceroni et al "Burden-driven feedback control of gene expression" Nat Methods 15, 387-393 (Mar. 26, 2018).

Czajka et al "Synthetic biology for manufacturing chemicals: constraints drive the use of non-conventional microbial platforms" Appl Microbiol Biotechnol (Oct. 2017) 101(20), 7427-7434.

Davey et al."Engineered signal-coupled inducible promoters: measuring the apparent RNA-polymerase resource budget," Nucleic Acids Research, vol. 48, Issue 17, 25, pp. 9995-10012 (Sep. 2020), https://doi.org/10.1093/nar/gkaa734.

Fang et al. "Microbial production of vitamin B12: a review and future perspectives" Microb Cell Fact, Jan. 30, 2017;16(1):15, doi: 10.1186/s12934-017-0631-y.

(56) References Cited

OTHER PUBLICATIONS

Liu et al "Enhanced hyaluronic acid production by a two-stage culture strategy based on the modeling of batch and fed-batch cultivation of *Streptococcus zooepidemicus*" Bioresour Technol (Nov. 2008), 99, 8532-8536.

Show Et "Overview of citric acid production from Aspergillus Niger" Frontiers in Life Science, (Accepted Mar. 21, 2015) vol. 8, No. 3, 271-283.

Zhang et al. "Genetic and biochemical characterization of genes involved in hyaluronic acid synthesis in *Streptococcus zooepidemicus*" Appl Microbiol Biotechnol (Apr. 2016) vol. 100(8), 3611-3620.

* cited by examiner

METHOD FOR THE PRODUCTION OF AMINO SUGAR-CONTAINING PRODUCTS

CROSS-REFERENCE TO RELATED APPLICATIONS

This application is a national phase entry under 35 U.S.C. § 371 of International Patent Application PCT/EP2019/075371, filed Sep. 20, 2019, designating the United States of America and published as International Patent Publication WO 2020/058493 A1 on Mar. 26, 2020, which claims the benefit under Article 8 of the Patent Cooperation Treaty to European Patent Application Serial No. 18195892.7, filed Sep. 21, 2018.

TECHNICAL FIELD

The disclosure relates to genetically engineered organisms, especially microorganisms such as bacteria and yeasts, for the production of amino sugar-containing products such as specialty saccharides, oligo- and polysaccharides, glycolipids, glycosides, glycoproteins, glycosylphosphates, nucleosides and glycosylsulphates. More specifically, the disclosure relates to microorganisms that are metabolically engineered so that these microorganisms can produce the amino sugar (containing) products in large quantities and at a high rate by bypassing classical technical problems that occur in bio-catalytic or fermentative production processes.

STATEMENT ACCORDING TO 37 C.F.R. § 1.821 (c) or (e)—SEQUENCE LISTING SUBMITTED AS A TXT AND PDF FILES

Pursuant to 37 C.F.R. § 1.821 (c) or (e), files containing a TXT version and a PDF version of the Sequence Listing have been submitted concomitant with this application, the contents of which are hereby incorporated by reference. The name of the TXT file is SEQLIST.TXT. the date of creation is Mar. 16, 2021 and the size of the file is 132,593 bytes.

BACKGROUND

For a long time, saccharides, the most abundant biomolecules in nature, have predominantly been viewed as energy-supplier, backbone of nucleic acids or as main cell wall substituent. However, it is becoming increasingly apparent that this emerging third class of information-bearing molecules, poly- and oligosaccharides, are involved in numerous key biological processes as carriers of molecular information (Gabius and Roth 2017; Cocinero and Carcabal 2013). These complex carbohydrates possess a high conformational flexibility, and thus encode for extremely dense information via their structure (Varki 1993; Gabius and Roth 2017; Cocinero and Carcabal 2013; Gabius 2000). Moreover, specific biological activities are increasingly attributed to defined structural groups of molecules, resulting in ground-breaking discoveries (Gabius et al., 2011; Bernardi and Cheshev 2008; Varki 1993; Bertozzi 1995; Boltje, Buskas, and Boone 2009). As such, numerous saccharides and derivatives, i.e., oligo- and polysaccharides, glycolipids, glycosides, glycoproteins, nucleosides, glycosylphosphates and glycosylsulphates have a vast potential in multiple sectors, e.g., the cosmetics, food, agriculture, pharma.

Nowadays, these saccharides and derivatives are typically obtained either via extraction processes from natural producers, via not very efficient or sustainable, low-yielding chemical synthesis or via bioconversion processes. For these bioconversion processes, isolated and purified enzymes (so called in vitro bioconversions) and whole cell biocatalysts are commonly used. In essence these bioconversion processes convert one or more precursors into a desired bioproduct making use of one or multiple carbohydrate-active enzymes, such as glycoside hydrolases (GHs), transglycosidases (TGs), glycoside phosphorylases (GPs) and (Leloir) glycosyltransferases (GTs) (Desmet et al., 2012). Each of them has its own characteristics and drawbacks concerning substrate usage, yields and scale-up.

The last type of carbohydrate-active enzymes are GT glycosyltransferases, which can transfer the sugar residue from an activated sugar donor, typically a nucleotide sugar, to various acceptors (Lairson et al., 2008), display superior conversion efficiencies (up to 100%) towards an enormous variety of small molecules. The uridine diphosphate (UDP) sugars form the largest group of nucleotide sugars (Yonekura-Sakakibara and Hanada, 2011) and consequently give rise to the large class of uridine glycosyltransferases (UGTs), which are characterized by a unique carboxyterminal consensus sequence (Ross et al., 2001).

These UDP-sugars and corresponding UGTs are thus capable of efficiently glycosylating various compounds from diverse chemical classes in a regio- and stereoselective way (Bowles et al., 2005, 2006). In this context, the nucleotide sugar UDP-N-acetylglucosamine (UDP-GlcNAc), and the derived nucleotide sugars UDP-N-acetylmannosamine (UDP-ManNAc), CMP-N-acetylneuramic acid (CMP-Neu5Ac) and UDP-N-acetylgalactosamine (UDP-GalNAc) (FIG. 1), are key building blocks for the synthesis of numerous amino sugar-containing products such as specialty saccharides, oligo- and polysaccharides, glycolipids, glycosides, glycoproteins, nucleosides, glycosylphosphates and glycosylsulphates.

With regard to in vitro bioconversions, their application is typically hampered because these require multiple enzymatic steps and/or because additional cofactors are required (NADH, NADPH, UTP, etc.), which are expensive. Other drawbacks of in vitro synthesis are the fact that the expression and purification of many enzymes is laborious and their purification process may result in a decreased enzymatic activity. Furthermore, each enzyme in such a multi-enzyme bioconversion process has its own optimal process parameters, resulting in very complicated optimization schemes. In such a process, the reaction equilibria may also play an important role. For instance, when using a phosphorylase, a set substrate/product ratio that limits product yield will be at hand. This may also lead to complicated downstream processing schemes to separate the product from the substrate (Goedl et al., 2007; Gräslund et al., 2008).

Alternatively, microbial hosts may be used to synthesize in vivo aforementioned amino sugar-containing products. Typically, whole cells have been metabolically engineered to produce saccharides and derivatives by expressing UGTs in a micro-organism; thus making use of their intracellular UDP-sugar pool. This methodology is the basis for in vivo UDP-sugar-based glycosylation and eliminates the need for extensive enzyme purification and the addition of expensive cofactors.

However, these UDP-sugars have also an essential role in the host's metabolism. More specific, UDP-GlcNAc is an essential cell envelope precursor in the cell. The bacterial cell envelope is a complex multi-layered structure that serves to protect these organisms from their unpredictable and often hostile environment. The cell envelopes of most bacteria fall into one of two major groups. Gram-negative bacteria are surrounded by a thin peptidoglycan cell wall, which itself is surrounded by an outer membrane containing lipopolysaccharide. Gram-positive bacteria lack an outer membrane but are surrounded by layers of peptidoglycan many times thicker than is found in the Gram-negatives. Threading through these layers of peptidoglycan are long anionic polymers, called teichoic acids (Silhavy, Kahne, and Walker 2010; Neidhardt and Curtiss 1996). Bacterial peptidoglycan is a major component of the bacterial cell wall, and it provides rigidity and enables bacteria to survive in hypotonic environments. Peptidoglycan forms around 90% of the dry weight of gram-positive bacteria but only 10% of gram-negative strains. For both gram-positive and Gram-negative bacteria, particles of approximately 2 nm can pass through the peptidoglycan (Demchick and Koch 1996).

Peptidoglycan, also known as murein, is a polymer consisting of alternating residues of β-(1,4) linked N-acetylglucosamine (GlcNAc) and N-acetylmuramic acid (MurNac). Attached to the N-acetylmuramic acid is a peptide chain of three to five amino acids. The peptide chain may be cross-linked to the peptide chain of another strand forming the 3D mesh-like layer. Peptidoglycan serves a structural role in the bacterial cell wall, giving structural strength, as well as counteracting the osmotic pressure of the cytoplasm. Peptidoglycan is also involved in binary fission during bacterial cell reproduction (Neidhardt and Curtiss 1996; Silhavy, Kahne, and Walker 2010).

The peptidoglycan biosynthesis pathway is one of the best-known processes in bacteria. The Mur enzymes, MurA-F, catalyse the last six steps in the formation of the final cytoplasmic peptidoglycan biosynthesis precursor uridine 5'-diphosphate (UDP)-N-acetylmuramyl-pentapeptide (FIG. 2). MurA and MurB catalyse the formation of UDP-N-acetyl muramic acid (UDP-MurNAc) from UDP-N-acetyl glucosamine (UDP-GlcNAc). First, MurA catalyses the transfer of enolpyruvate from phosphoenolpyruvate to UDP-GlcNAc. The resulting product, UDP-GlcNAc-enolpyruvate then undergoes a reduction that is catalysed by MurB. In the next steps, the Mur ligases (MurC-F) catalyse the sequential addition of 1-Ala, d-Glu, and meso-diaminopimelic acid (in Gram-negative bacteria) or 1-Lys (in Gram-positive bacteria), and the dipeptide d-Ala-d-Ala to UDP-MurNAc, to form the target UDP-MurNAc-pentapeptide (Neidhardt and Curtiss 1996). However, apart from some fundamental studies on gene stringency (Goh et al., 2009) or on antibacterial agents (Kahan et al., 1974; Hendlin et al., 1967; Chang et al., 2015; Molina-Lopez, Sanschagrin, and Levesque 2006; Hrast et al., 2014; Rozman et al., 2017), the synthesis of these cell envelope precursors and molecules has not yet been targeted for metabolic engineering purposes applications, i.e., due to its complex endogenous regulation system and its essential nature. This is also observed by Westbrook et al. (Westbrook et al., 2018). Attempts to reduce the expression of essential genes involved in the cell wall synthesis in order to obtain equal amounts of the hyaluronic acid (HA) precursors UDP-GlcNAc and UDP-α-D-glucuronic acid (UDP-GlcUA) resulted in poor growth and genetic instability, as certain derived B. subtilis strains lost the mucoid phenotype for HA production (Westbrook et al., 2018).

Pseudopeptidoglycan (also known as pseudomurein) is a major cell wall component of some Archaea that differs from bacterial peptidoglycan in chemical structure, but resembles bacterial peptidoglycan in function and physical structure. The basic components are N-acetylglucosamine and N-acetyltalosaminuronic acid (peptidoglycan has N-acetylmuramic acid instead), which are linked by β-1,3-glycosidic bonds.

The cell wall of yeast and other fungi consists of three main groups of polysaccharides: polymers of mannose (mannoproteins, ca 40% of the cell dry mass), polymers of glucose (β-glucan, ca 60% of the cell wall dry mass) and polymers of N-acetylglucosamine (chitin, ca 2% of the cell wall dry mass). β-Glucan may be divided into two subtypes following the mode of glucose linkages: long chains of ca 1500 β-1,3-glucose units, which represents ca 85% of total cell wall β-glucan, and short chain of ca 150 β-1,6-glucose units that accounts for ca 15% of the β-glucan (Aguilar-Uscanga and Francois 2003; Lipke and Ovalle 1998; Xie and Lipke 2011). In response to cell wall perturbations or cell wall mutations a cell wall compensatory mechanism is activated, which results in a strong increase of chitin that may reach up to 20% of the cell wall dry mass.

The chitin biosynthesis pathway utilizes UDP-GlcNAc in a polymerization reaction to form chitin, catalysed by a polymer chitin synthase (pCHS). The pCHS reaction occurs in specialized microdomains of the plasma membrane. The pCHS is an integral membrane protein complex that polymerizes and extrudes chitin. pCHS encoding genes of fungi may be found in multiple copies and are divided into two families based on amino acid sequence motifs. Each family contains several classes. The yeast *Saccharomyces cerevisiae* contains three pCHS genes, CHS1, CHS2 and CHS3, which have different roles in the life cycle, with CHS3 producing most of the chitin in this organism including the lateral cell wall. In insects, only two pCHS encoding genes have been identified to date and are divided into class A and class B (Merzendorfer 2011).

To improve these whole cell biocatalyst processes, metabolic engineering efforts have predominantly focused on augmenting the product yield, e.g., by applying two-phase production systems avoiding losses of precursors to sinks, by increasing the flux of the biosynthesis pathway and by supplying direct precursors of these special carbohydrates (De Bruyn, Van Brempt, et al., 2015; De Bruyn, De Paepe, et al., 2015; Fierfort and Samain 2008; Samain et al., 1997; Priem et al., 2002; Antoine et al., 2005; Ruffing and Chen 2006; Kogure et al., 2007; J. Zhang et al., 2003; D. Zhang, Wang, and Qi 2007; Rodríguez-Diaz, Rubio-del-Campo, and Yebra 2012; Byun et al., 2007; Jennewein 2014; Boddy, Christopher et al., 2011). In addition, only non-essential genes of minor precursor sink pathways, e.g., enterobacterial common antigen biosynthesis, are targeted for modification (Boddy, Christopher et al., 2011) as decreasing or deleting the expression of essential genes would yield lower growth or no growth, respectively (Tweeddale, Robb, and Ferenci 2006). For this reason, the major precursor sink of the nucleotide sugar UDP-GlcNAc pool, i.e., (pseudo) peptidoglycan or chitin, is not be targeted yet.

In this context, a first drawback of whole cell production systems for the production of amino sugar-containing products and derivatives is that metabolic engineering of the microbial cell to increase the nucleotide sugar UDP-GlcNAc pool and its conversion to amino sugar-containing products is not straightforward due to its role as cell wall precursor (i.e., (pseudo) peptidoglycan or chitin) and hence its essential function in the cell. Moreover, the concentration of UDP-GlcNAc (as well as that of (the) other nucleotide sugars), increases with decreasing growth rate (Tweeddale, Robb, and Ferenci 2006). Hence, a second drawback of whole cell production systems for the production of special carbohydrates is that there is typically a need for two phases, a growth phase, in which biomass is formed (or biomass synthesis), followed by a production phase of the envisaged product. This means that the growth phase and the production phase are separated in the time (consecutive phases). This results in very low overall production rates of the desired product(s). In addition, this type of process is hard to optimize. Indeed, fermentation processes have been developed making use of metabolically engineered cells that over-express production pathway genes. A large amount of the substrate is converted into biomass, resulting in only a minor flux of the substrate towards the product (D. Zhang, Wang, and Qi 2007; Byun et al., 2007).

Alternatively, the metabolism of the organism may be split in two parts: 1) a so-called "production part," and 2) a "biomass formation part" (Maertens, Beauprez, and De Mey 2010). This is achieved by splitting a saccharide into an activated saccharide and a (non-activated) sugar, which are the precursors of either the production part or biomass formation part and, additionally, by rendering genes less-functional or non-functional that encode for enzymes that convert the intermediates from the production part into intermediates of the biomass formation part of the metabolism. As such, both biomass and product formation are ensured, however, this inherently goes at the expense of yield as one part of the splitted sugar is used for biomass formation and not for production of the specialty sugar. In this context, UDP-GlcNAc, is used either as "production part" or "biomass formation part," but not both at the same time. Another drawback of this approach is that the fermentation process requires a disaccharide, oligosaccharide, polysaccharide or mixture thereof as carbon-source in combination with a suitable enzyme enabling the splitting of these carbon sources into the required activated sugar, in this context UDP-GlcNAc, and a (non-activated) sugar to fuel either the production of the special carbohydrates and biomass formation. Hence, cheap carbon sources such as the monosaccharides glucose or glycerol cannot be used, as they cannot be split in two parts, one to fuel the biomass formation and one to fuel production.

BRIEF SUMMARY

The disclosure overcomes the above-described disadvantages as it provides metabolically engineered organisms that are capable of producing desired products with a high productivity and a guaranteed high yield. This is accomplished by tuning the enzyme activity/activities converting the nucleotide sugar UDP-GlcNAc to essential cell envelope precursors and molecules.

DETAILED DESCRIPTION

Figure 1:
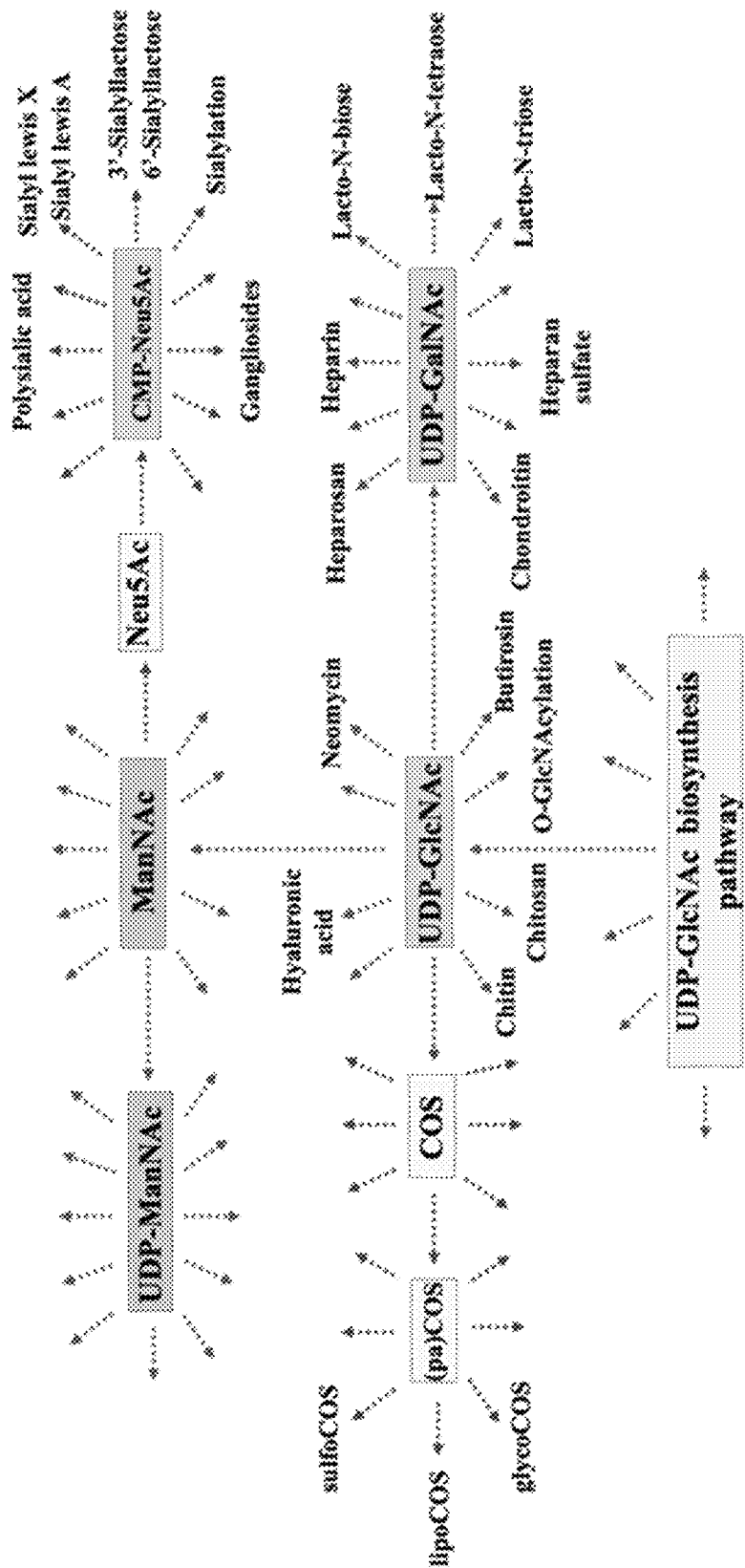
FIG. 1. Overview of the derivatives of UDP-GlcNAc. With GlcNAc=N-acetylglucosamine; paCOS=partially acetylated chito-oligosaccharides; GalNAc=N-acetylgalactosamine; ManNAc=N-acetylmannosamine; Neu5Ac=N-acetylneuraminic acid, lipo-COS=acylated chitooligosaccharides, sulfoCOS=sulfated chitooligosaccharides, glycoCOS=glycosylated chitooligosaccharides.
Figure 2:
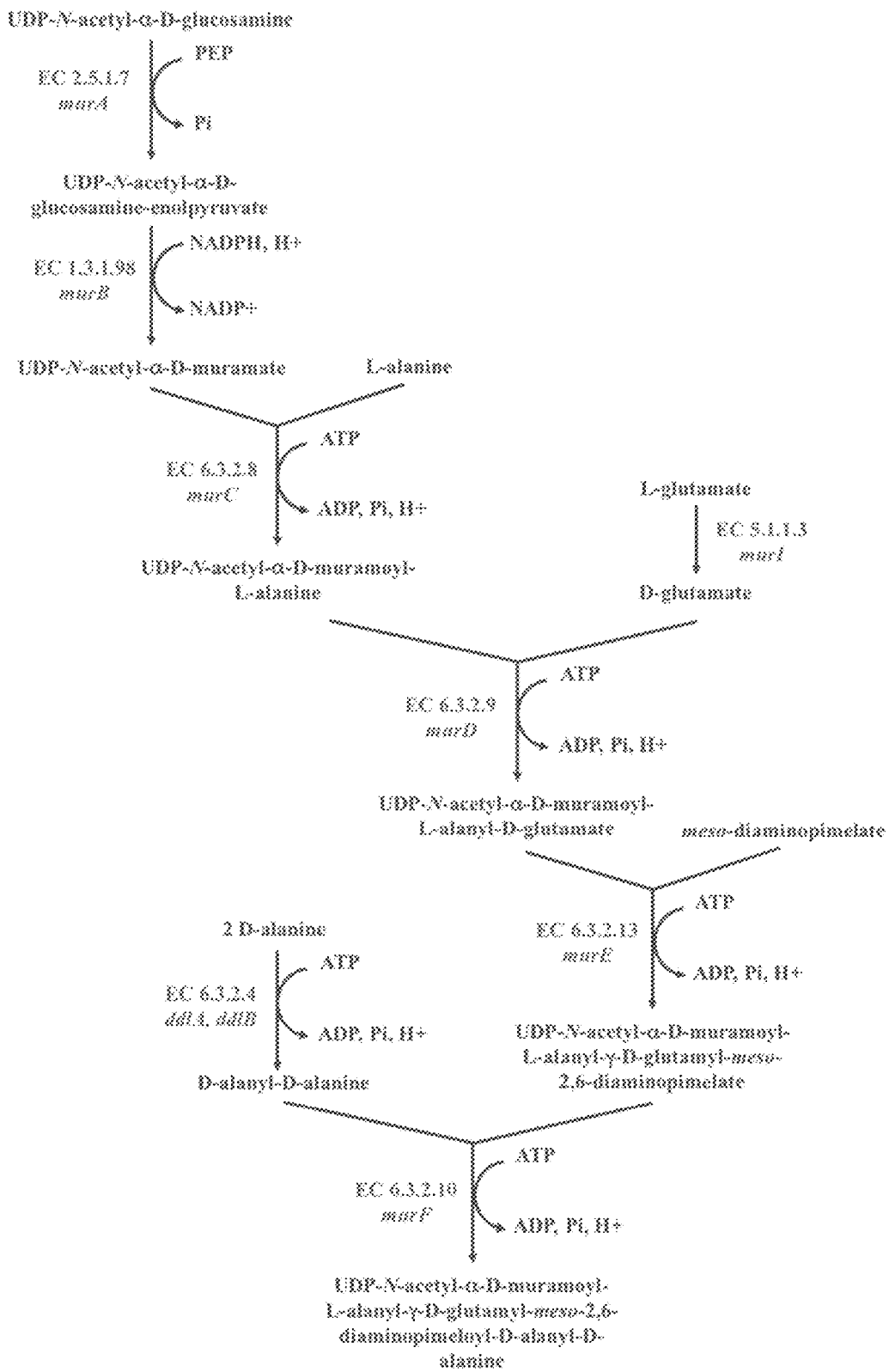
FIG. 2. Peptidoglycan biosynthesis pathway obtained from ECOCYC (Keseler et al., 2013). EC number for each reaction step and corresponding gene in Escherichia coli is given left from the arrow.
Figure 3A:
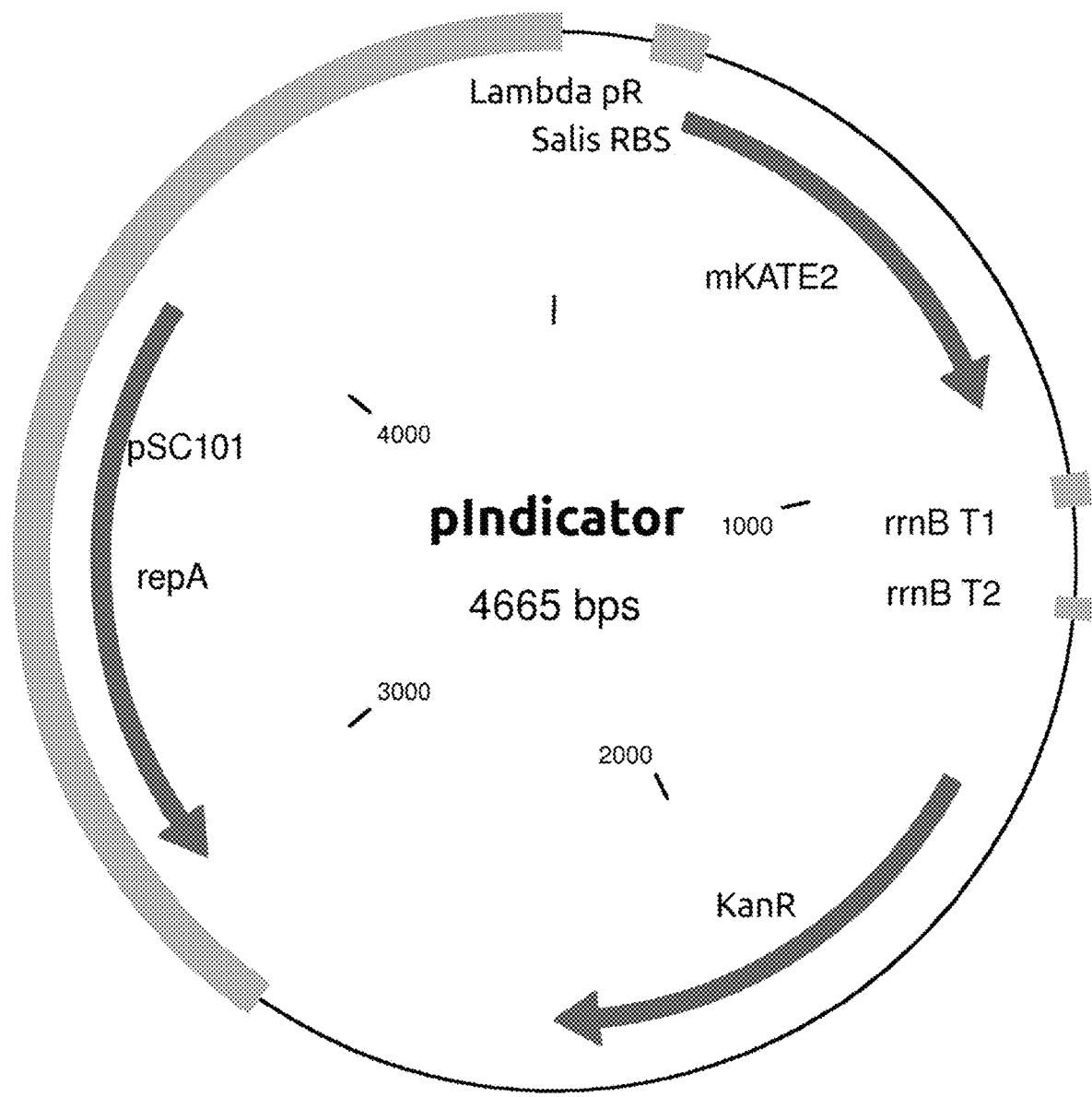
FIGS. 3A-3E. Detailed plasmid maps of constructed vectors. Bars indicate special regions (an origin of replication, a specific promoter (e.g., P14), terminator (e.g., rrnB T1), or something else (e.g., FRT site)). Arrows depict specific coding sequences. TCC stands for translational coupling cassette.
Figure 3B:
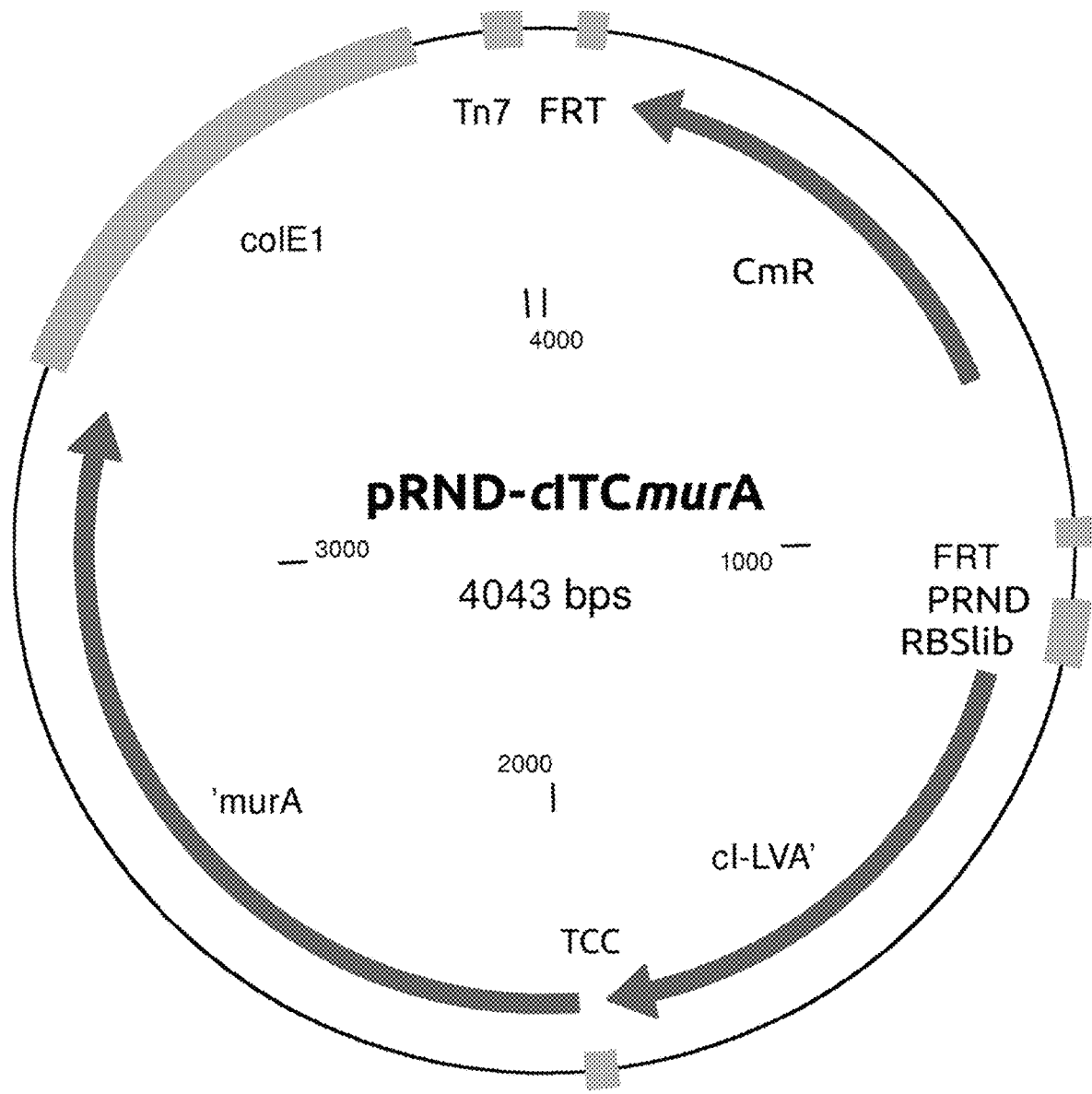
Figure 3C:
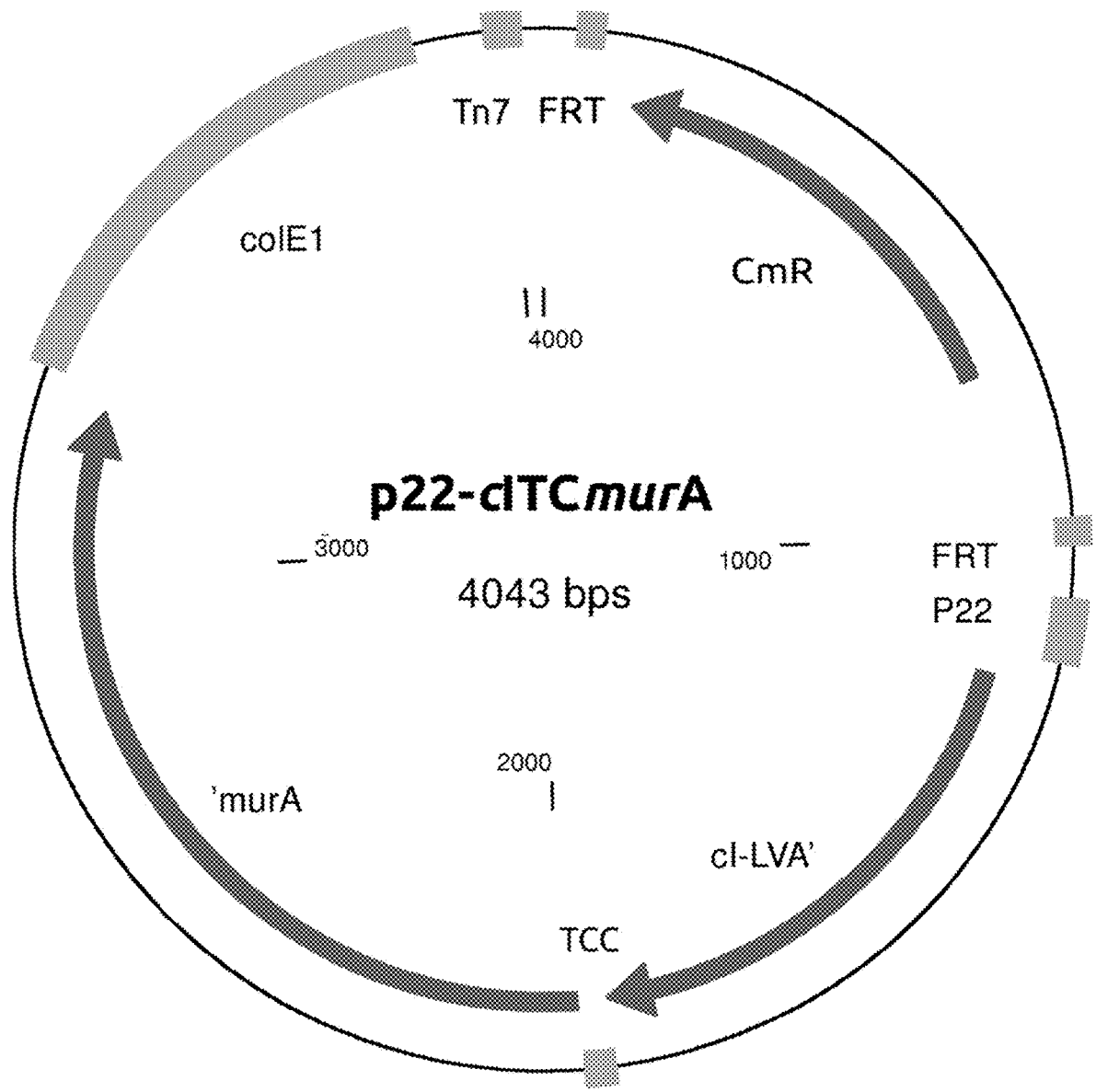
Figure 3D:
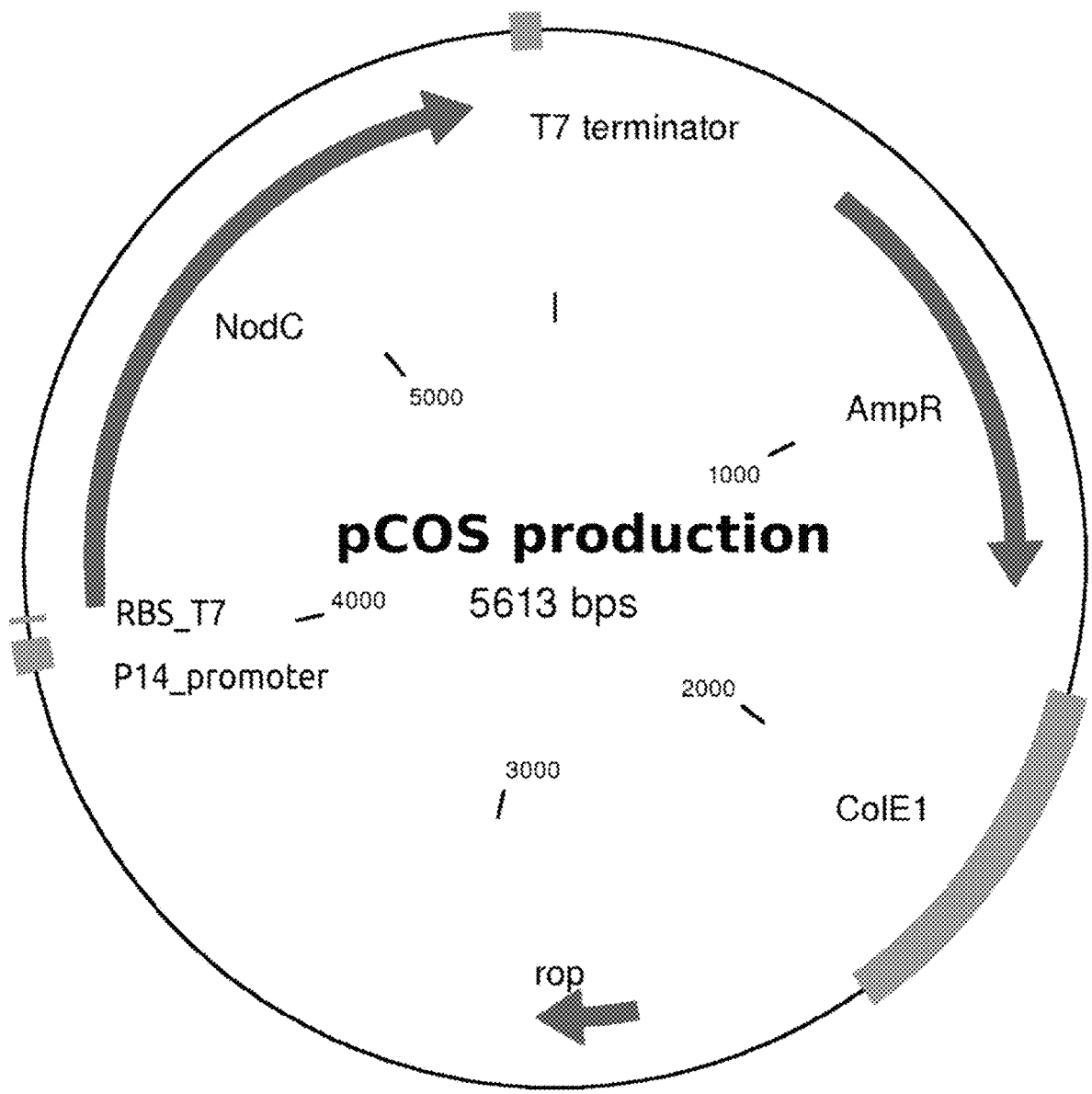
Figure 3E:
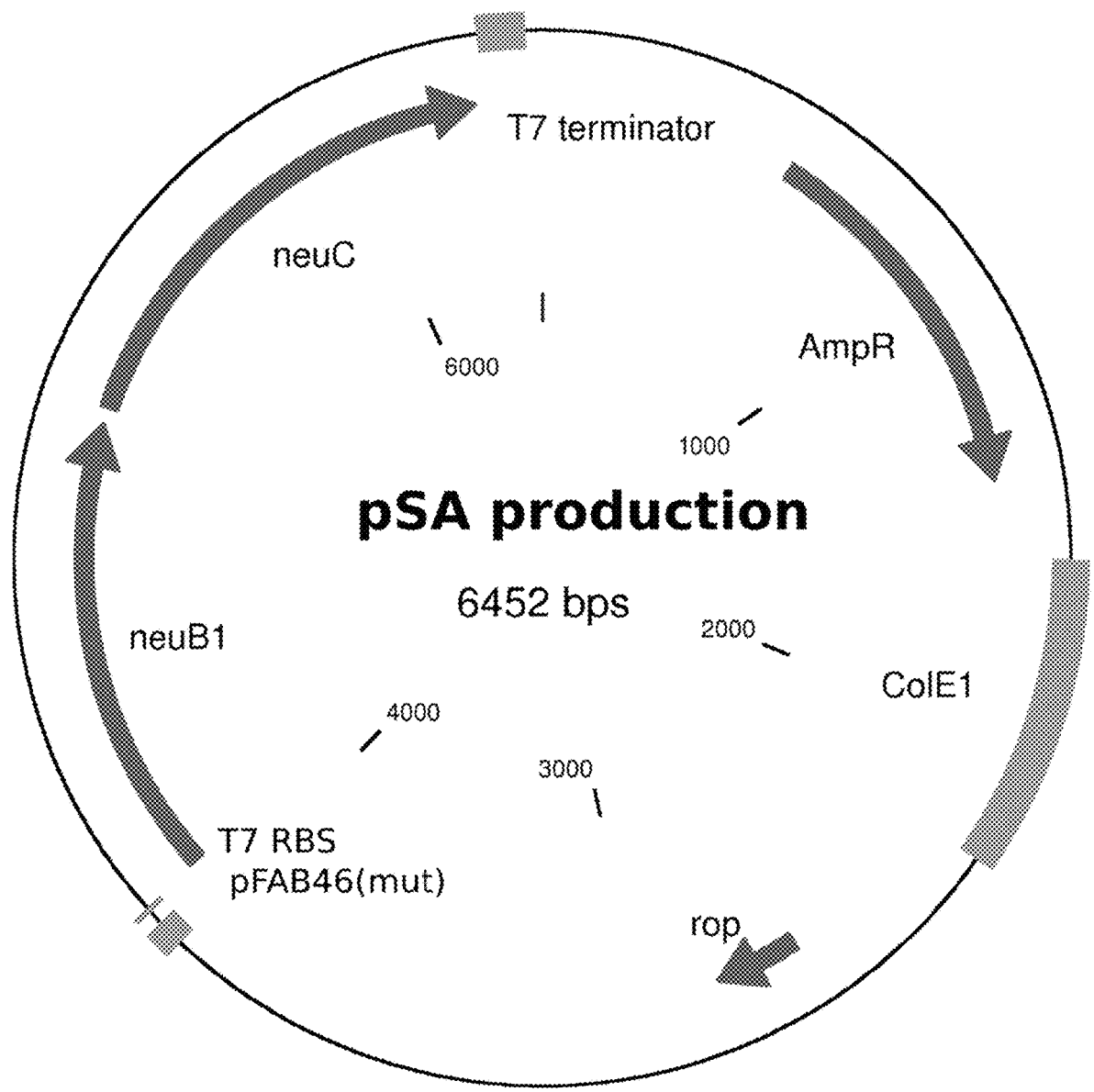

This disclosure describes metabolically engineered organisms, especially microorganisms, that are capable of producing amino sugar-containing products, especially UDP-N-acetylglucosamine (UDP-GlcNAc), UDP-GlcNAc-derived saccharides, UDP-GlcNAc-derived nucleosides, UDP-GlcNAc-derived glycolipids, UDP-GlcNAc-derived glycosides, UDP-GlcNAc-derived glycoproteins, UDP-GlcNAc-derived glycosylphosphates, UDP-GlcNAc-derived glycosylsulphates, saccharides derived from UDP-GlcNAc-derived nucleosides, glycolipids derived from UDP-GlcNAc-derived nucleosides, glycosides derived from UDP-GlcNac-derived nucleosides, glycoproteins derived from UDP-GlcNAc-derived nucleosides, glycosylphosphates derived from UDP-GlcNAc-derived nucleosides, glycosylsulphates derived from UDP-GlcNAc-derived nucleosides, with a guaranteed high yield and a high productivity.

The term "metabolically engineering" refers to the practice of optimizing genetic and regulatory processes within the organism to increase the organism's production of a certain desired amino sugar-containing product. To this end, any well-known technique that may be used to (genetically) modify an organism's metabolism and, hence, phenotype, may be used as is described in (Verpoorte et al., 1999; Yadav et al., 2013; De Mey et al., 2007; Tyo, Alper, and Stephanopoulos 2007; Gaj, Sirk, and Barbas 2014; De Bruyn, Van Brempt, et al., 2015; Farmer and Liao 2000; Biggs et al., 2014; Stephanopoulos 2012; Trantas et al., 2015; Pirie et al., 2013; Patil, Åkesson, and Nielsen 2004; Alper and Stephanopoulos 2007; Bhan, Xu, and Koffas 2013; Moon et al., 2012; Biggs et al., 2016; Ajikumar et al., 2010; Geert Peters et al., 2015; and Coussement et al., 2014).

The microorganisms of this disclosure are metabolically engineered so that the flux of UDP-GlcNAc to the biomass component "cell envelope precursors and molecules" is reduced while the microorganisms retain their capacities to grow. This is achieved by altering the enzyme activity and/or activities catalyzing essential reactions converting UDP-GlcNAc to cell envelope precursors and molecules.

Using the engineered organisms of this disclosure, product formation through the conversion of UDP-GlcNAc to an amino sugar-containing product is not impaired by excessive withdrawal of this precursor for the formation of cell envelope precursors and molecules, i.e., biomass production instead of product formation. More specific, the essential reactions converting UDP-GlcNAc to cell envelope precursors and molecules are reduced enabling increased UDP-GlcNAc availability for the formation of an amino sugar-containing product. This reduction of essential reactions involved in the formation of cell envelope precursors and molecules is not accompanied with decreased cell fitness, e.g., cell growth, which normally occurs when cognate essential genes are rendered less-functional or non-functional.

This means that the former drawback of having to produce biomass before the actual production of the product may start, is eliminated. This methodology results in high production rates, without the inherent problems that come with multi-enzymes systems and two phase fermentation systems.

The present disclosure relates to a method of producing at least one amino sugar-containing product chosen from the group consisting of especially UDP-N-acetylglucosamine (UDP-GlcNAc), UDP-GlcNAc-derived saccharides, UDP-GlcNAc-derived nucleosides, UDP-GlcNAc-derived glycolipids, UDP-GlcNAc-derived glycosides, UDP-GlcNAc-derived glycoproteins, UDP-GlcNAc-derived glycosylphosphates, UDP-GlcNAc-derived glycosylsulphates, saccharides derived from UDP-GlcNAc-derived nucleosides, glycolipids derived from UDP-GlcNAc-derived nucleosides, glycosides derived from UDP-GlcNac-derived nucleosides, glycoproteins derived from UDP-GlcNAc-derived nucleosides, glycosylphosphates derived from UDP-GlcNAc-derived nucleosides, glycosylsulphates derived from UDP-GlcNAc-derived nucleosides, comprising:

a) obtaining a suitable microorganism,
b) decreasing the synthesis or activity of at least one essential enzyme involved in the peptidoglycan biosynthesis, the pseudopeptidoglycan biosynthesis, the UDP-N-acetylmuramoyl-pentapeptide biosynthesis, the lipid IVA biosynthesis, or the chitin biosynthesis without reducing cell growth of the microorganism,
c) cultivating the microorganism wherein endogenous UDP-GlcNac is the building block of (or fuels) both the production of specialty carbohydrates and biomass formation, and,
d) extracting and purifying the specialty product.

More specifically, the present disclosure relates to a method as indicated above wherein "decreasing the endogenous conversion of UDP-GlcNAc to at least one cell envelope precursor or component" is undertaken by genetically modifying the organism or by adding an inhibitor of the enzymes of the peptidoglycan biosynthesis, pseudopeptidoglycan biosynthesis, UDP-N-acetylmuramoyl-pentapeptide biosynthesis, lipid IVA biosynthesis, or chitin biosynthesis.

The term "amino sugar" relates to a sugar molecule in which a hydroxyl group has been replaced with an amine group such as, but not limited to, GlcNac, ManNAc, GalNAc and Neu5Ac. Derivatives of amine-containing sugars, such as, but not limited to, GlcNac, ManNAc, GalNAc and Neu5Ac, whose nitrogens are part of more complex functional groups rather than formally being amines, are also considered amino sugars.

The term "saccharide" relates to monosaccharides such as, but not limited to, aldoses, ketoses, pentoses, methylpentoses, hexoses, polyols with or without either carbonyl, carboxyl, amino groups or in which a hydroxyl group is replaced by, but not limited to a hydrogen, amino, thiol, phosphate and/or similar group or a derivative of these groups. The term "saccharide" also relates to di-, oligo-, and polysaccharide that are made up of one or more monosaccharides as described above, linked to each other by a glycosidic bond.

The term "nucleoside" relates to each monosaccharide that is substituted with a nucleotide, which is, for instance, but not limited to, UDP, GDP, ADP, TDP, CMP, or dTDP.

The term "glycoside" relates to a saccharide that forms a glycosidic bond with other chemical compounds, such as, but not limited to sterols, phenols, fatty acids, phosphatidylinositols, vitamine C, cartenoides and artimisinine.

The term "glycolipid" relates to a saccharide that forms a glycosidic bond with a fatty acid or lipid.

The term "glycoprotein" relates to a saccharide that forms a glycosidic bond with a protein.

The term "glycosylphosphate" relates to a phosphorylated saccharide.

The term "glycosylsulphate" relates to a sulfated saccharide.

More specifically, the present disclosure relates to amino sugar-containing products consisting at least of a homo or hetero-oligosaccharide having one of the following degrees of polymerization: one, two, three, four, five, six, seven, eight, nine or ten.

The term "cell envelope" refers to a complex multilayered structure that serves to protect these organisms from their environment.

The term "cell envelope precursors and molecules" refers to all cell envelope components (i.e., proteins, phosphatidylserine, phosphatidylethanolamine, cardiolipin, phosphatidylglycerol, putrescine, spermidine, wall teichoic acid, lipoteichoic acid, (pseudo) peptidoglycan, glycogen, lipopolysaccharide, and/or chitin) and their precursors, i.e., intermediates of the cell wall biosynthesis comprising the peptidoglycan biosynthesis and maturation, peptidoglycan cross-bridge biosynthesis, teichoic acids biosynthesis, UDP-N-acetylmuamoyl-pentapeptide biosynthesis, lipid IVA biosynthesis, pseudopeptidoglycan biosynthesis and chitin biosynthesis pathway.

More specifically, this disclosure relates to a metabolically engineered organism as indicated above wherein "genetically modifying" meant essential genes rendered less-functional or non-functional.

The terms "essential genes" refer to genes of an organism that are critical for its survival, i.e., required to thrive in a given environment. Rendering these genes less-functional or non-functional will result in, e.g., less growth or no growth, respectively.

The terms "genes that are rendered less-functional or non-functional" refer to well-known technologies for a skilled person (such as siRNA, RNAi, miRNA, asRNA, mutating genes, knocking-out genes, transposon mutagenesis, CRISPR, CRIPRi, promoter engineering, RBS engineering, enzyme engineering, etc.) that are used to change the genes or cognate RNA in such a way that they are less-able (i.e., statistically significantly less-able compared to a functional wild-type enzyme) or completely unable (such as knocked-out gene or inactive enzyme) to produce functional final products, i.e., enzyme (Larson et al., 2013; Perez-Pinera, Kocak, and Vockley 2013; Copeland, Politz, and Pfleger 2014; Maeder et al., 2013; Politz, Copeland, and Pfleger 2013; Farzadfard, Perli, and Lu 2013; Cong et al., 2013; Cheng et al., 2013; Didovyk and Tsimring 2016; Qi et al., 2013; Qi and Arkin 2014; Geert Peters et al., 2015; Tsuda 1998; Cherepanov and Wackernagel 1995; Nevoigt et al., 2006; Palmeros et al., 2000; Bryant et al., 2014; Mutalik et al., 2013; Hoang et al., 1998; Schweizer 2003; Brophy et al., 2016; Kristensen et al., 1995; Hebert, Valdes, and Bentley 2008; Rasmussen, Sperling-Petersen, and Mortensen 2007; Sauer 1987; Agrawal et al., 2003; Datsenko and Wanner 2000; Avihoo et al., 2007; Williams, Luke, and Hodgson 2009; Balbás et al., 1996; Balbás and Gosset 2001; Van Hove et al., 2016; Pitzer et al., 2016; Van Hove et al., 2017; Alper et al., 2005; Alper and Stephanopoulos 2007; Cox, Surette, and Elowitz 2007; Salis 2011; Pirie et al., 2013; Coussement et al., 2014, 2017).

The terms "gene(s) that is/are rendered less-functional or non-functional" refers to a reduction of the activity of the corresponding gene product(s) with 0.1%, 1%, 10%, 20%, 30%, 40%, 50%, 60%, 70%, 80%, 90% to 100%. A gene may be rendered non-functional, i.e., reduced activity of the corresponding gene products with 100%, if there are multiple copies of the gene or isoenzymes present all catalyzing the same chemical reaction.

The term "(gene) knockout" thus refers to a gene that is rendered non-functional.

The term "without limiting cell fitness" refers to cells displaying equal or higher cell fitness compared to a cell in which the synthesis or activity of at least one enzyme involved in the endogenous conversion of UDP-GlcNAc to at least one cell envelope precursor or component is not decreased. In other words, wherein the cell fitness is not statistically lower compared to a cell in which the synthesis or activity of at least one enzyme involved in the endogenous conversion of UDP-GlcNAc to at least one cell envelope precursor or component is not decreased. Only when the p-value is <0.01, <0.02, <0.03, <0.04 to <0.05 the hypothesis is rejected that the cell fitness is not lower compared to a cell in which the synthesis or activity of at least one enzyme involved in the endogenous conversion of UDP-GlcNAc to at least one cell envelope precursor or component is not decreased.

The term "cell fitness" refers to the ability of a cell to thrive in a given environment, an ability determined by a number of parameters, such as cellular growth, product profile and genetic stability.

The term "cellular growth" refers to the accumulation of mass by a cell and is typically described by the maximal growth rate, maximal biomass yield and lag phase (Birch 1999).

The term "genetic stability" refers to a zero or low frequency of mutations within the genome or plasmids of a cellular lineage. These mutations may include changes in nucleic acid sequences, chromosomal/plasmid rearrangements or aneuploidy.

The term "product profile" refers to the pattern and amounts of product synthesized by the cell.

Even more specifically, the inhibitors of the enzymes of the (pseudo) peptidoglycan biosynthesis or UDP-N-acetylmuramoyl-pentapeptide biosynthesis, lipid IVA biosynthesis, or chitin biosynthesis are selected from but not limited to the group consisting of fosfomycin, bacitracin, cycloserine, vancomycin, teicoplanin, ramoplanin, an avenaciolide, a peptide inhibitor pyrazolopyrimidine, tulipaline B, cnicin, benzothioxalone, nitrovinylfuran, β-lactams, penicillins, penems, carbapenems, cephems, cephalosporins, cephamycins, monobactams, β-lactamase inhibitors, cefsulodin, ampicillin, carbenicillin, tyrothricin, teixobactin.

Additionally, the enzymes involved in the (pseudo) peptidoglycan biosynthesis, UDP-N-acetylmuramoyl-pentapeptide biosynthesis, lipid IVA biosynthesis, or chitin biosynthesis are selected from but not limited to the group consisting of a UDP-N-acetylglucosamine 1-carboxyvinyltransferase, a UDP-N-acetylenolpyruvoylglucosamine reductase, a UDP-N-acetylmuramate-L-alanine ligase, glutamate racemase, UDP-N-acetylmuramoyl-L-alanine-D-glutamate ligase, UDP-N-acetylmuramoyl-L-alanyl-D-glutamate-2,6-diaminopimelate ligase, phospho-N-acetylmuramoyl-pentapeptide-transferase, N-acetylglucosaminyl transferase, UDP-3-O-acyl-N-acetylglucosamine deacetylase, UDP-N-acetylglucosamine acyltransferase, tetraacyldisaccharide 4'-kinase, lipid A disaccharide synthase, UDP-2,3-diacylglucosamine diphosphatase, UDP-3-O-(3-hydroxymyristoyl) glucosamine N-acyltransferase, or (polymer) chitin synthase.

Additionally, the enzymes involved in the (pseudo) peptidoglycan biosynthesis, UDP-N-acetylmuramoyl-pentapeptide biosynthesis, lipid IVA biosynthesis, or chitin biosynthesis is encoded by a gene selected from but not limited to the group consisting of murAA, murAB, ine1, murZ, murA, murA1, murA2, murA_1, murA_2, murA-1, murA-2, murA3, murA5, murA22, murA.1, murA.2, murA2-1, murAA_1, murAA_2, Cgl0352, Cgl2558, sle_17140, sle_43250, nurZ, murB, murB1, murB2, murB-1, murB-2, murB_1, murB_2, Cgl0353, murB_[H], XOO2101, sle_29960, murC, murC1, murC2, murC-1, murC-2, murC_1, murC_2, XOO3603, murC_[H], sle_16170, murC_dd1A, murC-dd1A, murC_dd1, mp1, mudD, murE_1, murD, murD1, murD2, murD_1, murD_2, murD_[H], murE, murE1, murE2, murE3, murE-1, murE-2, murE.1, murE.2, murE_1, murE_2, murE_[H], mure, XOO3608, ylbD, sle_50520, murT, mur, murF_1, murC, murC2, murD2, murF, murF1, murF2, murF_1, murF_2, murf, mraY, XOO3607, STY0144, Cgl2162, sle_50530, alr, murff, murfEF murf_[H], murE, murE_1, murC_ddlA, murC-ddlA, murC, murC_ddl, mudD, murB, murF/mraY, rfe, XOO3606, murX, MRAY, murX_mraY, murY, mraY1, mraY2, mraY-1, mraY-2, mraY_1, mraY_2, sle_50540, Rfe, / murG, murG1, murG2, murG3, murG_1, murG_2, murG_3, murG_[H], sle_50570, murM, murM.1, murM.2, murM1, murM2, femB, fibA, murM_fibA, femX, murN, murN1, femA, femB fibB, femX, fmhB, femA, femA_1, femA_2, femB, femB-2, murI, murI1, murI2, murI3, murI5, murI_1, murI_2, racE, racE1, racE2, yrpC, glr, sle_60800, lpxA, lpxK, ycaH, lpxB, pgsB, lpxH, ybbF, lpxD, omsA, firA, hlpA, ssc, lpxC, asmB, envA, chs2, kkv, Chs1, Chs2, CS-2, CHS, CHS1, CHS2 CHS3, CHS8, CHS2.2, CHS5, CHS6, or CHS7.

Additionally, the expression of the genes is altered so that the mid-exponential average calibrated normalized relative quantity (CNRQ) varies from $-3.50 \times 10^{-1}$ to $2.00 \times 10^{-1}$ log (CNRQ). This corresponds with a variance in relative expression from 35% to 95% of the endogenous expression of the genes. The latter variation in expression is obtained by, but not limited to, the use of a constitutive promoter to control transcription and a 5'-UTR to control translation selected from but not limited to the group consisting of:

```
                                                (SEQ ID NO: 1)
5'- ATTTATAAATTTCTTGACACAGCATCGGAACTACCCTATAATGT

GTACATAAACACAAGCTCAACATATACTAGACAAAGTCAGGC, (SEQ ID NO: 2)
5'- ATTTATAAATTTCTTGACAACTAACACTACAGAGATTATAATGT

GTACATAAACACAAGCTCAACATATACTAGACAAAGTCAGGC, (SEQ ID NO: 3)
5'- ATTTATAAATTTCTTGACATTTTGGAATAGATGTGATATAATGT

GTACATAAACACAAGCTCAACCTATACTAGAGAAGTCAGGC, (SEQ ID NO: 4)
5'- ATTTATAAATTTCTTGACATATAGTAGATATCACCATATAATGT

GTACATAAACACAAGCTCATCCTATACTAGAGGAAGTCAGGC,
and (SEQ ID NO: 5)
5'- ATTTATAAATTTCTTGACAGGACGTCGCCAGCGCGCTATAATGT

GTACATAAACACAAGCTCATCCTATACTAGAGGAAGTCAGGC.
```

The present disclosure further relates to an organism as indicated above wherein the organism is further genetically modified so that at least one other gene than any of the altered genes of the organism is introduced and wherein the other gene encodes for a carbohydrate synthase, glycosyl transferase and/or epimerase, so that the organism is capable to convert UDP-GLcNAc to a saccharide, nucleoside, glycoside, glycolipid, glycoprotein, glycosylphosphate and/or glycosylsulphate.

More specifically, the present disclosure relates to a metabolically engineered organism as indicated above, wherein the UDP-GLcNAc derived nucleoside are selected from but not limited to the group consisting of UDP-GalNAc, UDP-ManNAc, and CMP-N-acetylneuraminic acid (CMP-Neu5Ac).

More specifically, the present disclosure relates to a metabolically engineered organism as indicated above wherein the "carbohydrate synthase, glycosyltransferase and/or epimerase" is selected from but not limited to the group consisting of UDP-N-acetylglucosamine 2-epimerase, UDP-N-acetylglucosamine 2-epimerase/N-acetylmannosamine kinase, UDP-N-acetylglucosamine 2-epimerase, UDP-N-acetyl-D-glucosamine 6-dehydrogenase, UDP-N-acetylglucosamine 4-epimerase, β-polysaccharide synthases, chitin synthase, N-acetylglucosaminyltransferase, β-1,4-N-acetylglucosaminyltransferase, Nodulation protein C (NodC), NodC-like enzyme, chitooligosaccharide synthase, N-acyltransferase nodulation protein, hyaluronan synthase, glycosyl transferase family 2, N-acylmannosamine kinase, sialic acid synthase, N-acylneuraminate-9-phosphatase, N-acetylneuraminate synthase, N-acylneuraminate/3-deoxy-D-glycero-D-galacto-nononate cytidylyltransferase, hyaluronic acid synthase, β-1,3-galactosyl-N-acetylhexosamine phosphorylase, β-1,3-N-acetylglucosaminyltransferase, sialyltransferase, 2,3-sialyltransferase, 2,6-sialyltransferase, 2,8-sialyltransferase, N-acetylmannosamine transferase, N-acetylmannosaminyltransferase N-acetylgalactosamine transferase, N-acetylgalactosaminyltransferase and β-1,3-galactosyltransferase.

Additionally, the enzymes with carbohydrate synthase, glycosyltransferase and/or epimerase activity is encoded by a gene selected from the group gne, siaA, wecB, rffE, wbpA, udg, tuaD, wecC, vipA1, capL, wblA, wbpP, vipB, tviC, wbgU, strE, galE, wbtF, ispL, CHS, NodC, chs, nodBC, nodCB, nanE, nanK, nanEK, nanS, nanP, neuA, neuB, neuC, manA, GNE, gnal, sir1975, hasA, lnpA, lgtA and wbgO.

More specifically, the present disclosure relates to a metabolically engineered organism as indicated above wherein the "carbohydrate synthase, glycosyltransferase and/or epimerase" is selected from but not limited to the group consisting of UDP-N-acetylglucosamine 2-epimerase, UDP-N-acetylglucosamine 2-epimerase/N-acetylmannosamine kinase, UDP-N-acetylglucosamine 2-epimerase, UDP-N-acetyl-D-glucosamine 6-dehydrogenase, UDP-N-acetylglucosamine 4-epimerase, β-polysaccharide synthases, chitin synthase, N-acetylglucosaminyltransferase, β-1,4-N-acetylglucosaminyltransferase, Nodulation protein C (NodC), NodC-like enzyme, chitooligosaccharide synthase, N-acyltransferase nodulation protein, glycosyl transferase family 2, N-acylmannosamine kinase, sialic acid synthase, N-acylneuraminate-9-phosphatase, N-acetylneuraminate synthase, N-acylneuraminate/3-deoxy-D-glycero-D-galacto-nononate cytidylyltransferase, β-1,3-galactosyl-N-acetylhexosamine phosphorylase, β-1,3-N-acetylglucosaminyltransferase, sialyltransferase, 2,3-sialyltransferase, 2,6-sialyltransferase, 2,8-sialyltransferase, N-acetylmannosamine transferase, N-acetylmannosaminyltransferase N-acetylgalactosamine transferase, N-acetylgalactosaminyltransferase and β-1,3-galactosyltransferase.

Additionally, the enzymes with carbohydrate synthase, glycosyltransferase and/or epimerase activity is encoded by a gene selected from the group gne, siaA, wecB, rffE, wbpA, udg, tuaD, wecC, vipA1, capL, wblA, wbpP, vipB, tviC, wbgU, strE, galE, wbtF, ispL, CHS, NodC, chs, nodBC, nodCB, nanE, nanK, nanEK, nanS, nanP, neuA, neuB, neuC, manA, GNE, gnal, sir1975, lnpA, lgtA and wbgO.

More specifically, the present disclosure relates to a metabolically engineered organism as indicated above wherein the enzymes with carbohydrate synthase, glycosyltransferase and/or epimerase activity are highly selective towards a single donor sugar or sugar-nucleotide to generate the product (De Bruyn, Maertens, et al., 2015). Additionally, the enzyme has a sugar donor specificity or sugar-nucleotide donor specificity of 70%, 75%, 80%, 85%, 90%, 95% to 100%.

An example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a N-acetylglucosamine transferase possibly (but not solely) originating from *Pseudomonas* sp., *Frankia symbiont*, *Ensifer* sp., *Streptomyces* sp., or *rhizobia* such as *Rhizobium* sp., *Azorhizobium* sp., *Mesorhizobium* sp., *Sinorhizobium* sp., *Bradyrhizobium* sp., *Neorhizobium* sp., *Rhizobiales* sp., *Paraburkholderia* sp., *Methylobacterium* sp., and *Cupriavidus* sp. is expressed having an amino acid sequence given by (but not solely) SEQ ID NOS: 6-8, or, a fragment thereof having a chitooligosaccharide synthase activity, or, a variant thereof having a sequence identity of at least 75% and having a chitooligosaccharide synthase activity to produce chitooligosaccharides (COS).

Another example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a UDP-N-acetylglucosamine 2-epimerase and N-acetylneuraminic acid synthase, respectively, possibly (but not solely) originating from *Campylobacter jejuni* and having an amino acid sequence given by (but not solely) SEQ ID NOS: 9 and 10, respectively, or, a fragment thereof having a UDP-N-acetylglucosamine 2-epimerase or N-acetylneuraminic acid synthase activity, respectively, or, a variant thereof having a sequence identity of at least 75% and having a UDP-N-acetylglucosamine 2-epimerase or N-acetylneuraminic acid synthase activity, respectively, to produce N-acetylneuraminic acid (Neu5Ac).

The present disclosure further relates to an organism as indicated above wherein the organism is further genetically modified so that at least one other gene than any of the altered genes of the organism is rendered less-functional or non-functional and wherein the other gene encodes for an enzyme with hydrolase or lyase activity.

More specifically, the present disclosure relates to a metabolically engineered organism as indicated above wherein the "hydrolase or lyase" is selected from but not limited to the group consisting of β-D-galactoside galactohydrolase, β-D-galactosidase, lactase, N-acetyl-β-neuraminate lyase, N-acetylneuraminate lyase, N-acetylneuraminic acid aldolase, acetylneuraminate lyase, sialic aldolase, sialic acid aldolase, sialate lyase, N-acetylneuraminic aldolase, neuraminic aldolase, N-acetylneuraminate aldolase, neuraminic acid aldolase, N-acetylneuraminic acid aldolase, neuraminate aldolase, N-acetylneuraminic lyase, N-acetylneuraminic acid lyase, NPL, NALase, NANA lyase, acetylneuraminate pyruvate-lyase, N-acetylneuraminate pyruvate-lyase, chitinase, endochitinase, exo-chitinase, chitinase A, (1→4)-2-acetamido-2-deoxy-beta-D-glucan diacetylchitobiohydrolase, β-N-acetylgalactosaminidase, N-acetyl-β-galactosaminidase; N-acetyl-β-D-galactosaminidase; β-acetylgalactosaminidase; β-D-N-acetylgalactosaminidase; N-acetylgalactosaminidase, β-N-acetyl-D-galactosaminide N-acetylgalactosaminohydrolase, β-N-acetylhexosaminidase, hexosaminidase; β-acetylaminodeoxyhexosidase; N-acetyl-β-D-hexosaminidase; N-acetyl-β-hexosaminidase; β-hexosaminidase; β-acetylhexosaminidinase; β-D-N-acetylhexosaminidase; β-N-acetyl-D-hexosaminidase; β-N-acetylglucosaminidase; hexosaminidase A; N-acetylhexosaminidase; β-D-hexosaminidase, N-acetyl mannosidase, and mannosidase.

Additionally, the enzymes with activity is encoded by a gene selected from but not limited to the group consisting of lacZ, lacZ1, lacZ1, lacZ2, lacZ3, lacZ-1, lacZ-2, lacZ_1, lacZ 2, lacZ_3, lacZ_4, lacZ_5, lacZ_6, lacZ_7, lacZ_8, lacZ_9, lacZ_10, lacZ_11, lacZ_12, lacZ 13, lacZ_14, lacZ_15, lacZ_16, lacZ_17, lacZ_18, lacZ_19, lacZ_20, lacZ_25, lacZ_26, lacZ_28, lacA, LacA2, lacL, lacH, lacM, lacS, LAC4, bga, bgaA, bga2A, bga35A, bgaB, bgaC, bgaE, bgaH, bgaL, bgaM, bgaS, bgaT, bga_1, bga_2, bga1, bga2, bga3, bga4, bga5, bga6, bga7, bga8, bga10, bga11, bga12, bga13, bga14, bga15, bga16, bga17, bga18, bga19, bga20, bgal-1, BGAL17, BGAL2, bbgII, GLB1, GLB1L, Glb1, glb1, glb1l, glb1l.L, glb1.L, glb2, Ect3, ebgA, ebgA_3, ebgA_6, Gal, ganA, ganA1, ganA2, ganB, gh2-3, galO, bglY, MgLAC2, MgLAC4, pbg, yesZ, gh2C, nanA, nanA1, nanA2, nanA3, nanA_1, nanA_2, dapA, dapA1, dapA_3, NPL, Npl, npl, npl.L, npl.S, nanH, chiA, chiB, CHIC, NgaP, HEXA, HEXB, HEXDC, and CELF6.

An example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a N-acetylglucosamine transferase possibly (but not solely) originating from *Pseudomonas* sp., *Frankia symbiont*, *Ensifer* sp., *Streptomyces* sp., or *rhizobia* such as *Rhizobium* sp., *Azorhizobium* sp., *Mesorhizobium* sp., *Sinorhizobium* sp., *Bradyrhizobium* sp., *Neorhizobium* sp., *Rhizobiales* sp., *Paraburkholderia* sp., *Methylobacterium* sp., and *Cupriavidus* sp. is expressed having an amino acid sequence given by (but not solely) SEQ ID NOS: 6-8 or a fragment thereof having a chitooligosaccharide synthase activity, or, a variant thereof having a sequence identity of at least 75% and having a chitooligosaccharide synthase activity to produce chitooligosaccharides (COS). Additionally, in the organism, a gene encoding for a chitinase activity given by (but not solely) SEQ ID NOS: 11 and 12 is deleted.

Another example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a UDP-N-acetylglucosamine 2-epimerase and N-acetylneuraminic acid synthase, respectively, possibly (but not solely) originating from *Campylobacter jejuni* and having an amino acid sequence given by (but not solely) SEQ ID NOS: 9 and 10, respectively, or, a fragment thereof having a UDP-N-acetylglucosamine 2-epimerase and N-acetylneuraminic acid synthase activity, respectively, or, a variant thereof having a sequence identity of at least 75% and having a UDP-N-acetylglucosamine 2-epimerase or N-acetylneuraminic acid synthase activity, respectively, to produce N-acetylneuraminic acid (Neu5Ac). Additionally, in the organism, a gene encoding for a β-D-galactoside galactohydrolase activity given by (but not solely) SEQ ID NO:13, and/or a gene encoding for a N-acetylneuraminate lyase activity given by (but not solely) SEQ ID NO:14 is deleted.

The disclosure further relates to an organism as indicated above wherein the organism is further genetically modified so that at least one other gene than any of the altered genes of the organism is introduced and wherein the other gene encodes for enzymes involved in the UDP-GlcNAc synthesis.

More specifically, the disclosure relates to a metabolically engineered organism as indicated above wherein the "enzymes involved in the UDP-GlcNAc synthesis" is selected from but not limited to the group consisting of glutamine-fructose-6-phosphate aminotransferase, phosphoglucosamine, glucosamine-1-phosphate acetyltransferase/N-acetylglucosamine-1-phosphate uridyltransferase, N-acetylglucosamine-6-phosphate deacetylase, bifunctional UDP-N-acetylglucosamine pyrophosphorylase/Glucosamine-1-phosphate N-acetyltransferase, UDP-N-acetylglucosamine pyrophosphorylase, a glucosamine-phosphate N-acetyltransferase, a phosphoacetylglucosamine mutase, and a UDP-N-acetylglucosamine diphosphorylase, UDP-N-acetylglucosamine/UDP-N-acetylgalactosamine diphosphorylase.

Additionally, the enzymes with activity is encoded by a gene selected from but not limited to the group consisting of glmS, glmS1, glmS2, glmS3, glmS4, glmS-1, glmS-2, glmS_1, glmS_2, glmS_3, glmS_4, GLMS, GLMS1, glmS_[H], ybcM, Cgl2271, sle_25030, sle_29260, sle_44510, glmD, glmS/GFPT, frlB, agaS, nagB, nagBII, nagB-II, nagB1, nagB2, nodM, gfpt1, gfpt2, GFPT1, GFPT2, Gfpt1, Gfpt2, gfpt2.L, gfpt1.S, Gfat1, Gfat2, gfat-1, gfat-2, GFAT, gfa1, GFA1, GfaA, GFA_1, GFA_2, ATF1, Dsim_GD18034, Dsim_GD19703, Dsim_GD28973, Lj1g3v2838100.1, Lj1g3v2838100.2, Lj1g3v2838100.3, PORTDRAFT_249106, OS12g0131100, NCAS0A05750, NDAI0K02700, TPHAOG03180, TBLA0H01620, TBLA0I00790, TDEL0A02530, KAFR0D03180, NEUTE1DRAFT_149837, AO090003001475, AO090003000003, An03g05940, An18g06820, AGABI1DRAFT_115602, AGABI2DRAFT_194113, 248.t00008, PC000162.03.0, 21.m02906, Tb07.10C21.470, XOO0678, XOO3696, S3959, TVG0861800, glmM, glmM1, glmM2, glmM_1, glmM_2, glmM_3, glmM-1, glmM-2, glmM_[H], glmM(femD), glmM #femD, femD, msrA, mrsA, mrsa, mrsA1, mrsA_2, MrsA, MRSA, XOO3077, ECS4055, sle_29290, PH1210, ureC, cpsG, cpsG2, cpsG_1, ybbT, manB, manB1, manB2, manB3, pmm1, pmm_1, pmmB, pmmC, pgm-1, pgm-2, glmU, glmU1, glmU2, glmU3, glmU_1, glmU_2, glmU_3, glmU-2, glmu1, glmu3, glmU_[H], GlmU, gluM, gcaD, rfbA, rfbA-4, gcd1, hddC_4, graD2, graD3, graD4, graD6, graD-2, rffH1, rffH2, PH1925, aglF, uap, UAP1, UAP1L1, Uap1, Uap1l1, uap1, uap1l1, uap1.L, uap1.S, uap1l1.L, QRI1, mmy, Dsim_GD22574, C36A4.4, GlcNAc1pUT1, GlcNAc1pUT2, Lj4g3v0243980.1, POPTRDRAFT_712364, OJ1119_C05.25, Os08g0206900, pco144375b, NCAS0B05930, NDAI0B03240, TPHA0C03700, TBLA0B07300, TDEL0G02780, KAFR0K02470, NEUTE1DRAFT_70531, AO090038000595, An12g00480, PAAG_06885, AGABI1DRAFT_110647, AGABI2DRAFT_189451, 30.t00023, 138.t00017, PC000356.03.0, 19.m02866, symbB.v1.2.001128.t1, symbB.v1.2.002197.t1, symbB.v1.2.006730.t1, galU, CPj0856, GNA1, gna-1, gna-1, Cbr-gna-1, GNPNAT1, gnpnat1, gnpnat1.L, Gnpnat1, GNAT3, NAT2, Dsim_GD21459, Lj1g3v4717300.1, Lj1g3v4753330.1, Lj1g3v4753340.1, POPTRDRAFT_669373, sJ_08156, Os02g0717700, Os09g0488000, NCASOC03940, NDAI0G03270, TPHA0D00540, TBLA0D02580, TDEL0C00840, KAFR0C03360, NEUTE1DRAFT_92433, AO090120000132, An12g07840, AGABI1DRAFT_61620, AGABI2DRAFT_229877, 405.t00007, 34.t00022, symbB.v1.2.034394.t1, PGM3, Pgm3, pgm3.L, pgm3, nst, Dsim_GD12708, F21D5.1, DRT101, Lj2g3v1986460.1, AGM1, PCM1, PAGM1, Os07g0195400, NCAS0F00200, NDAI0K02890, TPHA0M00210, TBLA0G00980, TDEL0G04600, KAFR0L00340, NEUTE1DRAFT_118413, AO090001000429, An18g05170, SNOG_08065, AGABI1DRAFT_117388, AGABI2DRAFT_214180, PC301892.00.0, symbB.v1.2.021638.t1, and Tb08.25L8.80.

An example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a N-acetylglucosamine transferase possibly (but not solely) originating from *Pseudomonas* sp., *Frankia symbiont, Ensifer* sp., *Streptomyces* sp., or rhizobia such as *Rhizobium* sp., *Azorhizobium* sp., *Mesorhizobium* sp., *Sinorhizobium* sp., *Bradyrhizobium* sp., *Neorhizobium* sp., *Rhizobiales* sp., *Paraburkholderia* sp., *Methylobacterium* sp., and *Cupriavidus* sp. is expressed having an amino acid sequence given by (but not solely) SEQ ID NOS: 6-8 or, a fragment thereof having a chitooligosaccharide synthase activity, or, a variant thereof having a sequence identity of at least 75% and having a chitooligosaccharide synthase activity to produce chitooligosaccharides (COS). Furthermore, in the organism, a gene encoding for phosphoglucosamine mutase and bifunctional UDP-N-acetylglucosamine pyrophosphorylase/Glucosamine-1-phosphate N-acetyltransferase, respectively, possibly (but not solely) originating from *Escherichia coli* and *Corynebacterium glutamicum* is expressed having an amino acid sequence given by (but not solely) SEQ ID NOS: 15 and 16 and SEQ ID NOS: 17-19, respectively, or, a fragment thereof having phosphoglucosamine mutase and bifunctional UDP-N-acetylglucosamine pyrophosphorylase/Glucosamine-1-phosphate N-acetyltransferase activity, respectively, or, a variant thereof having a sequence identity of at least 75% and having a phosphoglucosamine mutase and bifunctional UDP-N-acetylglucosamine pyrophosphorylase/Glucosamine-1-phosphate N-acetyltransferase activity, respectively.

Another example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a N-acetylglucosamine transferase possibly (but not solely) originating from *Pseudomonas* sp., *Frankia symbiont, Ensifer* sp., *Streptomyces* sp., or rhizobia such as *Rhizobium* sp., *Azorhizobium* sp., *Mesorhizobium* sp., *Sinorhizobium* sp., *Bradyrhizobium* sp., *Neorhizobium* sp., *Rhizobiales* sp., *Paraburkholderia* sp., *Methylobacterium* sp., and *Cupriavi-*

*dus* sp. is expressed having an amino acid sequence given by (but not solely) SEQ ID NOS: 6-8 or a fragment thereof having a chitooligosaccharide synthase activity, or, a variant thereof having a sequence identity of at least 75% and having a chitooligosaccharide synthase activity to produce chitooligosaccharides (COS). Furthermore, in the organism, a gene encoding for phosphoglucosamine mutase and bifunctional UDP-N-acetylglucosamine pyrophosphorylase/Glucosamine-1-phosphate N-acetyltransferase, respectively, possibly (but not solely) originating from *Escherichia coli* and *Corynebacterium glutamicum* is expressed having an amino acid sequence given by (but not solely) SEQ ID NOS: 16 and 16 and SEQ ID NOS: 17-19, respectively, or, a fragment thereof having phosphoglucosamine mutase and bifunctional UDP-N-acetylglucosamine pyrophosphorylase/Glucosamine-1-phosphate N-acetyltransferase activity, respectively, or, a variant thereof having a sequence identity of at least 75% and having a phosphoglucosamine mutase and bifunctional UDP-N-acetylglucosamine pyrophosphorylase/Glucosamine-1-phosphate N-acetyltransferase activity, respectively. Additionally, in the organism, a gene encoding for a chitinase activity given by (but not solely) SEQ ID NOS: 11 and 12 is deleted.

Another example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a UDP-N-acetylglucosamine 2-epimerase and N-acetylneuraminic acid synthase, respectively, possibly (but not solely) originating from *Campylobacter jejuni* and having an amino acid sequence given by (but not solely) SEQ ID NOS: 9 and 10, respectively, or, a fragment thereof having a UDP-N-acetylglucosamine 2-epimerase and N-acetylneuraminic acid synthase activity, respectively, or, a variant thereof having a sequence identity of at least 75% and having a UDP-N-acetylglucosamine 2-epimerase or N-acetylneuraminic acid synthase activity, respectively, to produce N-acetylneuraminic acid (Neu5Ac). Furthermore, in the organism, a gene encoding for phosphoglucosamine mutase and bifunctional UDP-N-acetylglucosamine pyrophosphorylase/Glucosamine-1-phosphate N-acetyltransferase, respectively, possibly (but not solely) originating from *Escherichia coli* and *Corynebacterium glutamicum* is expressed having an amino acid sequence given by (but not solely) SEQ ID NOS: 15 and 16 and SEQ ID NOS: 17-19, respectively, or, a fragment thereof having phosphoglucosamine mutase and bifunctional UDP-N-acetylglucosamine pyrophosphorylase/Glucosamine-1-phosphate N-acetyltransferase activity, respectively, or, a variant thereof having a sequence identity of at least 75% and having a phosphoglucosamine mutase and bifunctional UDP-N-acetylglucosamine pyrophosphorylase/Glucosamine-1-phosphate N-acetyltransferase activity, respectively.

Another example of the latter metabolically engineered organism is an organism wherein the endogenous UDP-N-acetylglucosamine 1-carboxyvinyltransferase expression is decreased with 5% to 65% by altering the endogenous promoter and 5'-UTR sequence with (but not solely) SEQ ID NOS: 1-5, and wherein a gene encoding for a UDP-N-acetylglucosamine 2-epimerase and N-acetylneuraminic acid synthase, respectively, possibly (but not solely) originating from *Campylobacter jejuni* and having an amino acid sequence given by (but not solely) SEQ ID NOS: 9 and 10, respectively, or, a fragment thereof having a UDP-N-acetylglucosamine 2-epimerase and N-acetylneuraminic acid synthase activity, respectively, or, a variant thereof having a sequence identity of at least 75% and having a UDP-N-acetylglucosamine 2-epimerase or N-acetylneuraminic acid synthase activity, respectively, to produce N-acetylneuraminic acid (Neu5Ac). Furthermore, in the organism, a gene encoding for phosphoglucosamine mutase and bifunctional UDP-N-acetylglucosamine pyrophosphorylase/Glucosamine-1-phosphate N-acetyltransferase, respectively, possibly (but not solely) originating from *Escherichia coli* and *Corynebacterium glutamicum* is expressed having an amino acid sequence given by (but not solely) SEQ ID NOS: 15 and 16 and SEQ ID NOS: 17-19, respectively, or, a fragment thereof having phosphoglucosamine mutase and bifunctional UDP-N-acetylglucosamine pyrophosphorylase/Glucosamine-1-phosphate N-acetyltransferase activity, respectively, or, a variant thereof having a sequence identity of at least 75% and having a phosphoglucosamine mutase and bifunctional UDP-N-acetylglucosamine pyrophosphorylase/Glucosamine-1-phosphate N-acetyltransferase activity, respectively. Additionally, in the organism, a gene encoding for a β-D-galactoside galactohydrolase activity given by (but not solely) SEQ ID NO: 13, and/or a gene encoding for a N-acetylneuraminate lyase activity given by (but not solely) SEQ ID NO: 14 is deleted.

The term "organism" as indicated above refers to a microorganism chosen from the list consisting of a bacterium, a yeast, fungus cell or archaea, or, refers to a plant or animal cell. The latter bacterium preferably belongs to the species *Escherichia coli*, *Lactobacillus* sp., *Corynebacterium* sp. or *Bacillus* sp. The latter yeast preferably belongs to the species *Saccharomyces cerevisiae* or *Pichia* sp. The latter archaea preferably belong to the species *Sulfolobus* sp. or *Methanobacter* sp.

The latter engineered organisms may be used to produce, for example, but not limited to, UDP-N-acetylglucosamine, chitin, chitosan, chitooligosaccharide, glycosylated chitooligosaccharide, acylated chitooligosaccharide, sulfated chitooligosaccharide, neomycin, butirosin, an —O-GlcNAcylated molecule, N-acetylglucosamine, heparin, heparin sulfate, heparosan, chondroitin, lacto-N-biose, lacto-N-triose, lacto-N-tetraose, lacto-N-neotetraose, N-acetylmannosamine, N-acetylneuramic acid, a -Neu5Acylated molecule, UDP-N-acetylmannosamine, a -ManAcylated molecule, UDP-N-acetylgalactosamine, a -GalNAcylated molecule, CMP-N-acetylneuraminic acid, 3'-sialyllactose, 6'-sialyllactose, sialyl Lewis X, Sialyl Lewis A, polysialic acid, ganglioside, hyaluronic acid, disialyllacto-n-tetraose, 3'-sialyl-3-fucosyllactose, sialyllacto-N-tetraoses 6'-sialyllactosamine, 3'-sialyllactose, 2',3-difucosyllactose, 3'-sialyllactose, 6'-sialyllactose, 3'-sialyl-3-fucosyllactose, sialylated lacto-N-triose, sialylated lacto-N-tetraose, sialylated lacto-N-neotetraose, lacto-N-fucopentaose I, lacto-N-fucopentaose II, lacto-N-fucopentaose III, lacto-N-fucopentaose V, sialyl-lacto-N-tetraose a, sialyl-lacto-N-tetraose b, sialyl-lacto-N-tetraose c, fucosyl-sialyllacto-N-neotetraose a, fucosyl-sialyllacto-N-neotetraose b, fucosyl-sialyllacto-N-neotetraose c, lacto-N-difucohexaose I, lacto-N-difucohexaose II, lacto-N-difucohexaose III, disialyllacto-N-tetraose, fucosyl-disialyllacto-N-tetraose I, disialyl-fucosyllacto-N-tetraose II, monofucosyllactose, monosialyllactose, sialyl-lacto-N-pentaose I, sialyl-lacto-N-pentaose II, sialyl-lacto-N-fucopentaose I, sialyl-lacto-N-fucopentaose II, difucosyllacto-N-hexaose, trifucosyllacto-N-hexaose, difucosyl-p-lacto-N-neohexaose, difucosyl-p-lacto-N-hexaose, difucosyllacto-N-hexaose, monofucosyllacto-N-hexaose II, lacto-N-hexaose, lacto-N-neohexaose, fucosyl-sialyllacto-N-neohexaose, sialylated molecules as amino sugar-containing product.

It is clear that any methodology known in the art to cultivate micro-organisms, and, to extract and purify specialty products from the cultivation may be employed in the present disclosure.

The following specific sequences, as indicated above, are part of the present disclosure:

| SEQ ID NO: | Sequence |
|---|---|
| 1 | Promoter-5'-UTR 1 sequence<br>5'- atttataaatttcttgacacagcatcggaactaccctataatgtgtacataaacacaagctcaacatatactagacaaagtcaggc |
| 2 | Promoter-5'-UTR 2 sequence<br>5'- atttataaatttcttgacaactaacactacagagattataatgtgtacataaacacaagctcaacatatactagacaaagtcaggc |
| 3 | Promoter-5'-UTR 3 sequence<br>5'- atttataaatttcttgacattttggaatagatgtgatataatgtgtacataaacacaagctcaacctatactagagaagtcaggc |
| 4 | Promoter-5'-UTR 4 sequence<br>5'- atttataaatttcttgacatatagtagatatcaccatataatgtgtacataaacacaagctcatcctatactagaggaagtcaggc |
| 5 | Promoter-5'-UTR 5 sequence<br>5'- atttataaatttcttgacaggacgtcgccagcgcgctataatgtgtacataaacacaagctcatcctatactagaggaagtcaggc |
| 6 | The amino acid sequence of N-acetylglucosaminyltransferase from *Rhizobium* sp. GRH2:<br>mdllntigigavscyallstahksmqtlyaqpkdqssasedfaflpsvdiivpcynenphtfseclasianqdya<br>gklrvyvvddgsanreklervhhtyagdprfdfillrenvgkrkaqiaairgssgdlvlnvdsdstlasdvvtklal<br>kmqnpeigaamgqltasnrndtwltrlidmeywlacneeraaqarfgavmcccgpcamyrrsallslldqye<br>sqffrgkpsdfgedrhltilmlkagfrtdyvpdaiaatvvpdrmgpylrqqlrwarstfrdtllalrllpgldhyitl<br>dvigqnlgplllalavltgvlqvaltatvplwtvmmiasmtmircavaavrarqlrflvfslhtpinlffllpmkay<br>alctlsnsdwlsrsspanktsaggehptteasaggtsgnatplrrlnlardsstvtpagvysdd |
| 7 | The amino acid sequence of N-acetylglucosaminyltransferase from *Sinorhizobium meliloti*:<br>mylldttstaaisiyallltayrsmqvlyarpidgpavaaepvetrplpavdvivpsfnedpgilsaclasiadqdy<br>pgelrvyvvddgsrnreaivrvrafysrdprfsfillpenvgkrkaqiaaigqssgdlvlnvdsdstiafdvvskla<br>skmrdpevgavmgqltasnsgdtwltklidmeywlacneeraaqsrfgavmcccgpcamyrrsalaslldq<br>yetqlfrgkpsdfgedrhltilmlkagfrteyvpdaivatvvpdtlkpylrqqlrwarstfrdtflalpllrglspflaf<br>davgqniggqllalsvvtglahlimtatvpwwtiliiacmtiircsvvalharqlrflgfvlhtpinlflilplkayalc<br>tlsnsdwlsrysapevpvsggkqtpiqtsgrvtpdctcsgelrrqwshpqfek |
| 8 | The amino acid sequence of N-acetylglucosaminyltransferase from *Sinorhizobium fredii* USDA 191:<br>mdllgttgavaislyaalstaykgmqaiyalptnttaastpvtgsgappsvdvivpcynedpralsaclasiakqd<br>yagelrvyvvddgsgnrnaiipvhdhyacdprfrfilmpknvgkrkaqivairessgdlvlnvdsdttiapdvv<br>tklalkmyspavgaamgqltasnrsdtwltrlidmeywlacneeraaqarfgavmcccgpcamyrrsallll<br>dkyetqlfrgrpsdfgedrhltilmlnagfrteyvpdaiaatvvpnsmgaylrqqlrwarstfrdtllalrllpgldr<br>yltldvigqnlgplllalsvltglaqlaltatvpwstilmiasmtmvrcgvaafrarelrflgfslhtllnvalllplkay<br>alctlsnsdwlsrgspaaapngvkdspephc |
| 9 | The amino acid sequence of N-acetylneuraminic acid synthase from *Campylobacter jejuni*:<br>mkeikiqniiiseekaplvvpeiginhngslelakimvdaafsagakiikhqthivedemskaakkvipgnak<br>isiyeimqkcaldykdelalkeyteklglvylstpfsraganrledmgvsafkigsgecnnyplikhiaafkkp<br>mivstgmnsiesikptvkilldneipfvlmhttnlyptphnlvrlnamlelkkefscmvglsdhttdnlaclgav<br>vlgacvlerhftdsmhrsgpdivcsmdtkalkeliiqseqmaiirgnneskkaakqeqvtidfafasvvsikdik<br>kgevlsmdniwvkrpglggisaaefenilgkkalrdiendaqlsyedfa |
| 10 | The amino acid sequence of UDP-N-acetylglucosamine 2-epimerase from *Campylobacter jejuni*:<br>mvkkilfitgsradyskikslmyrvqnssefelyifatgmhlsknfgytvkelykngfkniyefinydkyyqtd<br>kalattidgfsryanelkpdlivvhgdrieplaaaivgalnnilvahieggeisgtiddslrhaisklahihlvndefa<br>krrlmqlgedeksifiigspdlellndnkislseakkyydinyenyallmfhpvtteitsiknqadnlvkaliqsn<br>knyiviypnndlgfelilqsyeefknnprfklfpslrfeyfitllknadfiignsscilkealylktagilvgsrqngrl<br>gnentlkvnansdeilkaintihkkqdlfsakleildsskllffeylqsgdffklstqkvfkdik |

| SEQ ID NO: | Sequence |
|---|---|
| 11 | The amino acid sequence of endochitinase from *Escherichia coli*:<br>mklniftksmigmglvcsalpalameawnnqqggnkyqvifdgkiyenawwvssstncpgkakandatnp<br>wrlkrtataaeisqfgntlsceksgssssnsntpasntpanggsatpaqgtvpsnssvvawnkqqgggtwyv<br>vfngavyknawwvassncpgdaksndasnpwryvraatateisetsnpqsctsapqpspdvkpapdvkpa<br>pdvqpapadksndnyavvawkgqegsstwyviynggiyknawwvgaancpgdakendasnpwryvra<br>atateisqygnpgscsvkpdnnggavtpvdptpetpvtptpdnsepstpadsvndyslqawsgqegseiyhvi<br>fngnvyknawwvgskdcprgtsaensnnpwrlertataaelsqygnpttceidnggvivadgfqaskaysad<br>sivdyndahyktsvdqdawgfvpggdnpwkkyepakawsastvyvkgdrvvvdgqayealfwtqsdnp<br>alvanqnatgsnsrpwkplgkaqsysneelnnapqfnpetlyasdtlirfngvnyisqskvqkvspsdsnpwr<br>vfvdwtgtkervgtpkkawpkhvyapyvdftlntipdlaalaknhnvnhftlafvvskdantclptwgtayg<br>mqnyaqyskikalreaggdvmlsiggannaplaascknvddlmqhyydivdnlnlkvldfdiegtwvadq<br>asierrnlavkkvqdkwksegkdiaiwytlpilptgltpegmnvlsdakakgvelagvnvmtmdygnaicq<br>santeggqnihgkcatsaianlhsqlkglhpnksdaeidammgttpmvgvndvqgevfylsdarlvmqdaqk<br>rnlgmvgiwsiardlpggtnlspefhgltkeqapkyafseifapftkq |
| 12 | The amino acid sequence of endochitinase from *Serratia marcescens*:<br>mstrkavigyyfiptnqinnytetdtsvvpfpvsnitpakakqlthinfsfldinsnlecawdpatndakardvv<br>nrltalkahnpslrimfsiggwyysndlgvshanyvnavktpaartkfaqscvrimkdygfdgvdidweypq<br>aaevdgfiaalqeirtllnqqtiadgrqalpyqltiagaggafflsryysklaqivapldyinlmtydlagpwekit<br>nhqaalfgdaagptfynalreanlgwsweeltrafpspfsltvdaavqqhlmmegvpsakivmgvpfygraf<br>kgvsggnggqysshstpgedpypnadywlvgcdecvrdkdpriasyrqleqmlqgnygyqrlwndktktp<br>ylyhaqnglfvtyddaesfkykakyikqqqlggvmfwhlgqdnrngdllaaldryfnaadyddsqldmgtgl<br>rytgvgpgnlpimtapayvpgttyaqgalvsyqgyvwqtkwgyitsapgsdsawlkvgrla |
| 13 | The amino acid sequence of β-galactosidase from *Escherichia coli*:<br>mtmitdslavvlqrrdwenpgvtqlnrlaahppfaswrnseeartdrpsqqlrslngewrfawfpapeavpes<br>wlecdlpeadtvvvpsnwqmhgydapiytnytypitvnppfvptenptgcysltfnvdeswlqegqtriifdg<br>vnsafhlwcngrwvgygqdsrlpsefdlsaflragenrlavmvlrwsdgsyledqdmwrmsgifrdvsllhk<br>pttqisdfhvatrfnddfsravleaevqmcgelrdylrvtvslwqgetqvasgtapfggeiiderggyadrvtlrln<br>venpklwsaeipnlyravvelhtadgtlieaeacdvgfrevriengllllngkpllirgvnrhehhplhgqvmde<br>qtmvqdillmkqnnfnavrcshypnhplwytlcdryglyvvdeaniethgmvpmnrltddprwlpamser<br>vtrmvqrdrnhpsviiwslgnesghganhdalyrwiksvdpsrpvqyegggadttatdiicpmyarvdedq<br>pfpavpkwsikkwlslpgetrplilceyahamgnslggfakywqafrqyprlqggfvwdwvdqslikyden<br>gnpwsayggdfgdtpndrqfcmnglvfadrtphpalteakhqqqffqfrlsgqtievtseylfrhsdnellhw<br>mvaldgkplasgevpldvapqgkqlielpelpqpesagqlwltvrvvqpnatawseaghisawqqwrlaenl<br>svtlpaashaiphlttsemdfcielgnkrwqfnrqsgflsqmwigdkkqlltplrdqftrapldndigvseatrid<br>pnawverwkaaghyqaeaallqctadtladavlittahawqhqgktlfisrktyridgsgqmaitvdvevasdt<br>phpariglncqlaqvaervnwlglgpqenypdrltaacfdrwdlplsdmytpyvfpsenglrcgtrelnygph<br>qwrgdfqfnisrysqqqlmetshrhllhaeegtwlnidgfhmgiggddswspsvsaefqlsagryhyqlvwc<br>qk |
| 14 | The amino acid sequence of N-acetylneuraminate lyase from *Escherichia coli*:<br>matnlrgvmaalltpfdqqqaldkaslrrlvqfniqqgidglyvggstgeafvqslsereqvleivaeeakgkikl<br>iahvgcvstaesqqlaasakrygfdavsavtpfyypfsfeehcdhyraiidsadglpmvvynipalsgvkltld<br>qintlvtlpgvgalkqtsgdlyqmeqirrehpdlvlyngydeifasgllagadggigstynimgwryqgivkal<br>kegdiqtaqklqtecnkvidlliktgvfrglktvlhymdvvsvplcrkpfgpvdekylpelkalaqqlmqerg |
| 15 | The amino acid sequence of a bifunctional UDP-N-acetylglucosamine pyrophosphorylase/Glucosamine-1-phosphate N-acetyltransferase from *Escherichia coli*:<br>mlnnamsvvilaagkgtrmysdlpkvlhtlagkamvqhvidaanelgaahvhlvyghggdllkqalkddnl<br>nwvlqaeqlgtghamqqaapffaddedilmlygdvplisvetlqrlrdakpgqigglltvklddptgygritren<br>gkvtgivehkdatdeqrqiqeeintgiliangadmkrwlakltnnnaqgeyyitdiialayqegreivavhpqrls<br>evegvnnrlqlsrlervyqseqaeklllagvmlrdparfdlrgtlthgrdveidtnviiegnvtlghrvkigtgcvi<br>knsvigddceispytvvedanlaaactigpfarlrpgaellegahvgnfvemkkarlgkgskaghltylgdaei<br>gdnvnigagtitcnydgankfktiigddvfvgsdtqlvapvtvgkgatiaagttvtrnvgenalaisrvpqtqke<br>gwrrpvkkk |
| 16 | The amino acid sequence of bifunctional UDP-N-acetylglucosamine pyrophosphorylase/Glucosamine-1-phosphate N-acetyltransferase from *Corynebacterium glutamicum*:<br>msasdfssavvvlaagagtrmksdlqktlhsiggrslishslhaaaglnpehivavighrrdqvgpaysqvaeel<br>drevliaiqeeqngtghavqcamdqlegfegtiivtngdvplltddtlsalldahvevptavtvltmrlddptgyg<br>rivrneegevtaiveqkdasaeipidevnsgvfafdaailrsalaelksdnaggelyltdvlgiargeghpvraht<br>aadarelagyndrvqlaeagaelnrrtviaamrggativdpattwidvevsigrdviihpgtqlkgetvigdrve<br>vgpdttltnmtigdgasvvrthgfdstigenatvgpftyirpgttlgpegklggfvetkkatigrgskvphltyvgd<br>atigeesnigassvfvnydgenkhhttigshvrtgsdtmfiapvtvgdgaysgagtvikddvppgalavsggrq<br>rniegwvqkkrpgtaaaqaaeaaqnvhnqeg |
| 17 | The amino acid sequence of L-glutamine-D-fructose-6-phosphate aminotransferase from *Escherichia coli*:<br>mcgivgaiaqrdvaeilleglrrleyrgydsaglavvdaeghmtrlrrlgkvqmlaqaaeehplhggtgiahtr<br>wathgepsevnahphvsehivvvhngiienheplreelkargytfvsetdteviahlvnwelkqggtlreavlr<br>aipqlrgaygtvimdsrhpdtllaarsgsplviglgmgenfiasdqlallpvtrrfifleegdiaeitrrsvnifdktg<br>aevkrqdiesnlqydagdkgiyrhymqkeiyeqpnaiknltlgrishgqvdlselgpnadellskvehiqilac<br>gtsynsgmvsrywfeslagipcdveiasefryrksavrrnslmitlsqsgetadtlaglrlskelgylgslaicnvp |

| SEQ ID NO: | Sequence |
|---|---|
| | gsslvresdlalmtnagteigvastkafttqltvllmlvaklsrlkgldasiehdivhglqalpsrieqmlsqdkrie<br>alaedfsdkhhalflgrgdqypialegalklkeisyihaeayaagelkhgplalidadmpvivvapnnelleklk<br>snieevrarggqlyvfadqdagfvssdnmhiiemphveeviapifytvplqllayhvalikgtdvdqprnlaks<br>vtve |
| 18 | The amino acid sequence of L-glutamine-D-fructose-6-phosphate<br>aminotransferase from *Escherichia coli* with mutations A38T, R249C and G471S:<br>mcgivgaiaqrdvaeilleglrrleyrgydsaglavvdteghmtrlrrlgkvqmlaqaaeehplhggtgiahtrw<br>athgepsevnahphvsehivvvhngiienheplreelkargytfvsetdteviahlvnwelkqggtlreavlrai<br>pqlrgaygtvimdsrhpdtllaarsgsplviglgmgenfiasdqlallpvtrrfifleegdiaeitrrsvnifdktgae<br>vkrqdiesnlqydagdkgiychymqkeiyeqpnaikntltgrishgqvdlselgpnadellskvehiqilacgts<br>ynsgmvsrywfeslagipcdveiasefryrksavrrnslmitlsqsgetadtlaglrlskelgylgslaicnvpgss<br>lvresdlalmtnagteigvastkafttqltvllmlvaklsrlkgldasiehdivhglqalpsrieqmlsqdkriealae<br>dfsdkhhalflsrgdqypialegalklkeisyihaeayaagelkhgplalidadmpvivvapnnelleklksnie<br>evrarggqlyvfadqdagfvssdnmhiiemphveeviapifytvplqllayhvalikgtdvdqprnlaksvtve |
| 19 | The amino acid sequence of L-glutamine-D-fructose-6-phosphate<br>aminotransferase from *Corynebacterium glutamicum*:<br>mcgivgyigqagdsrdyfaldvvveglrrleyrgydsagiaihangeisyrkkagkvaaldaeiakaplpdsil<br>gightrwathggptdvnahphvvsngklavvhngiienfaelrselsakgynfvsdtdtevaasllaeiyntqan<br>gdltlamqltgqrlegaftllaihadhddrivaarrnsplvigvgegenflgsdvsgfidytrkavelandqvvtita<br>ddyaitnfdgseavgkpfdvewdaaaaekggfgsfmekeihdqpaavrdtlmgrldedgklvldelrideail<br>rsvdkivivacgtaayagqvaryaiehwcriptevelahefryrdpilnektlvvalsqsgetmdtlmavrhare<br>qgakvvaicntvgstlpreadaslytyagpeiavastkaflaqitasyllglylaqlrgnkfadevssildslrempe<br>kiqqvidaeeqikklgqdmadaksvlflgrhvgfpvalegalklkeiaylhaegfaagelkhgpialveegqpi<br>fvivpsprgrdslhskvvsniqeirargavtiviaeegdeavndyanfiiripqaptlmqpllstvplqifacavat<br>akgynvdqprnlaksvtve |
| 20 | The codon optimized nucleotide sequence encoding SEQ ID NO: 6 for expression<br>in *E. coli*:<br>atggacctgctgaacacgattggtattggtgctgtctcctgctacgctctgctgtcaacggctcataagtcgatgcaa<br>accctgtatgcccagccgaaagatcaaagctctgcatcagaagactttgctttcctgccgtcggtggatattatcgttc<br>cgtgttataacgaaaatccgcataccttagcgaatgcctggcgtctattgccaaccaggattatgcgggcaaactg<br>cgtgtgtacgtggttgatgacggtagtgccaatcgtgaaaagctggaacgcgttcatcacacctacgcaggcgatc<br>cgcgttttgacttcatcctgctgcgtgaaaacgtgggtaagcgtaaggcacagattgcagcaatccgtggcagttcc<br>ggtgatctggtgctgaatgttgatagcgactctacctggcatcagacgtcgtgacgaaactggctctgaagatgca<br>gaaccgggaaattggcgcagctatgggtcaactgaccgcgtctaaccgtaatgataccctggctgacgcgcctgatc<br>gacatggaatattggctggcctgtaatgaagaacgtgcagcacaggcacgttttggtgcagtgatgtgctgttgcgg<br>tccgtgcgcaatgtatcgtcgctcagctctgctgtcgctgctggatcagtacgaaagccaatttttccgtggcaaacc<br>gtctgatttggtgaagaccgccatctgaccattctgatgctgaaggcgggcttccgtacgattatgttccggacgc<br>catcgcagctaccgttgtcccggatcgtatgggtccgtacctcgcgcagcaactgcgttgggcacgcagcaccttc<br>cgtgatacgctgctggctctgcgtctgctgccgggtctggatcactatattacgctggacgttatcggtcagaacctg<br>ggtccgctgctgctggcactggctgtcctgaccggtgtcctgcaagtggcactgaccgctacggtcccgctgtgga<br>ccgtgatgatgattgcatcaatgacgatgatccgttgtgcagttgcagcagtccgtcacgtcagctgcgctttctgg<br>trnctcgctgcataccccgattaacctgrnttcctgctgccgatgaaagcgtacgcccgtgtgcacgctgagtaactcc<br>gattggctgagtcgctcatcgccggcgaataaaacctccgccggcggtgaacacccgaccacggaagcaagtgc<br>tggcggtacctccggcaacgcgacgccgctgcgtcgcctgaacctggctcgtgactcctctaccgttaccccggct<br>ggtgtctactccatgattga |
| 21 | The codon optimized nucleotide sequence encoding SEQ ID NO: 7 for expression<br>in *E. coli*:<br>atgtacctgatgacacaaccagcaccgccgctatctcaatctacgcgctgctcttgaccgcctacaggagcatgca<br>agtcctatatgctcggccgatagacggtccagcagtggcggcagaagtcgagacccgccctctgccagccg<br>tggatgttatcgtccccagatcaatgagaacccaggcatcctcggcgtgcctcgcgtccattgcagaccaggat<br>tatcctggagaattgcgagtctatgtcgttgatgatggttctcggaaccgcgaggccattgtgcgtgtacgcgccttct<br>attcgcgcgatccgaggttcagcttcattctgctcccagagaacgtcggaaagcggaaagcgcagattgcgcga<br>taggccaatcctctgggattggtgctgaatgtcgactcggacagcagcgatcgctttcgatgtggtctccaagcttg<br>cctcgaagatgcgagatccagaggtcggtgcggttatgggtcaactcacggctagcaattcgggtgacacttggct<br>gactaaattgatcgacatggagtattggctgcctgtaacgaagaacgcgcggcacagtcgcttcggtgctgttat<br>gtgttgctgcggcccttgtgctatgtaccgtcggtcggcgctcgcttcgctgcttgaccagtacgaaacgcaactgtt<br>tcgcggtaagccaagcgacttcggtgaggaccgccatctgacgattctcatgttgaaggcaggctttcgaactgag<br>tacgttccagacgccatagtggcaaccgtcgtcccggataacatatctgcgccaacaactgcgttggg<br>cacgcagcacgttccgtgacacgtttctagcgctccctctgttgcgcggcctcagccctttttctcgcatttgacgcgg<br>tcggacagaatatcgggcaactgttgctcgcccttcggtggtgacgggtcttgcgcatctcataatgaccgccaca<br>gtgccatggtggacaattttgattattgcgtgcatgaccattatacgctgcagcgtcgtagcattgcatgctcgccaac<br>ttagatttcttggcttcgttctgcacacacccatcaacctctttctcatacttccgctgaaagcttatgcgttgtgta<br>cattgtccaatagcgactggctgtcacgctactccgcgccagaagtaccagtcagcggggggaaagcaga<br>ccccaattcaaacctccggtcgagtgacacctgacttgcagcggcgagctccgtc<br>gacaatggtcacatcctcaatttgaaaaatag |
| 22 | The native nucleotide sequence encoding SEQ ID NO: 8:<br>atggatctgcttggcacgaccggccgctagccatctccttgtatgcagcactctcgacggcttacaaaggcatgc<br>aagctatatacgctttgccaacaaacaccacagctgcgtcaacgcccgtgaccggctccggtgcaccgccgagc<br>gtggatgttatcgtccctgctacaatgaggatccgcgcgcgctctcggcgtgcctagcttccattgcaaagcaaga<br>ctacgctggagagttgcgggtctacgtggttgacgacggttctggcaatcgcaacgccatcatacctgtacacgatc<br>attatgcgtgcgacccgaggttccgctttatcctgatgccaaagaacgtcggaaagcgcaaggcgcagattgtcgc<br>aatacggaatcatcgggagatttggtgctcaacgttgactcggacacgaccattgcgccggacgtagtcacgaa |

| SEQ ID NO: | Sequence |
|---|---|
| | acttgccctgaagatgtacagtcccgcggtcggcgcggcgatgggtcagttgacggccagcaaccgcagcgaca<br>catggctgacgcggttgatcgacatggagtactggctcgcctgcaacgaggaacgagcagcacaggctcgctttg<br>gagccgttatgtgttgctgcggcccgtgtgccatgtaccggcggtccgcactcctattgctgctcgataaatacgag<br>acgcaactgtttcgaggcaggccaagcgacttcggggaagaccgccacctcacaatcctcatgctgaatgcaggc<br>tttcgaaccgagtacgttccggacgccatcgcggcgacggtcgttccaaactcgatgggggcctatctgcgccaa<br>caactgcgctgggcacgcagcacgtttcgcgacacattgctcgcgctccgcctactgccgggccttgatcgctatc<br>ttacgctggacgtgatcggacagaatcttggtccgctgctcctggtccctctcggtcctgacggggctagcacagctc<br>gctctgacggccacagtgccttggtcgacgatcctgatgattgcatctatgcacaatggtccgctgcggcgtgcgg<br>cgtttcgagcgcgagagctgcgattccttgggttttcgctgcacaccctcctcaacgtcgctctcctgctccccctca<br>aagcatatgcgttgtgcacgttgagcaacagcgactggctgtcgcgtggttccccggctgccgcacccaacggcg<br>taaaggattctcctgaaccccattgctaa |
| 23 | The codon optimized nucleotide sequence encoding SEQ ID NO: 9 for expression in *E. coli*:<br>atgaaagagattaagatccagaatattatcatcagcgaagagaaagcgccgctggtggtgccggaaattggcatta<br>accacaacggcagcctggaactggcatagattatggtggatgcaagatgagatgagcaaggcggcgaagaagg<br>tgattcctggcaacgccaagattagcatctatgagatcatgcagaaatgcgcgcttgattataaagatgaactggcg<br>ctgaaagaatataccgagaagttaggtctggtctatctgtcgacgccattctcgcgcgcaggtgccaaccgtctgga<br>agatatgggcgtgtctgccttcaagattggttccggtgaatgtaataattatccactgatcaagcatattgccgcattca<br>agaagccgatgattgtcagcaccggcatgaacagcattgaaatctcgcaaaccgaccgttaagattctgctggataat<br>gagattccgttcgttctgatgcacaccaccaatctgtatccgacgccgcataacctggttcgcctgaacgcgatgct<br>ggagctgaagaaggagtctcctgtatggttggcctgagcgatcataccaccgataacctcgcctgtcttggcgcg<br>gtggttctcggcgcatgcgtgcttgaacgtcacttcaccgacagcatgcatcgcagcggtccggatatcgtctgctc<br>gatggataccaaggcactgaaggaactgattattcgcagcgagcaagatcgcgattattcgcggcgcaataacgatcc<br>aagaaggccgccaagcaggaacaggtgaccatcgactcgcgttcgcttcggtggtcagtattaaggacatcaag<br>aaaggcgaagtgctgtcaatggacaacatctgggtgaagcgtccaggcttaggcggcatcagtgcggcagaattc<br>gagaacattctcggtaagaaggctctgcgcgatattgagaatgatgcgcagctgagctatgaagacttcgcctgata<br>a |
| 24 | The codon optimized nucleotide sequence encoding SEQ ID NO: 10 for expression in *E. coli*:<br>atggtgaagaagatcctgttcattaccggctcccgcgccgactacagcaaaattaaatcgctgatgtatcgcgtgca<br>gaatagcagcgagtttgagctctatatcttcgccaccgggatgcacctgtcgaaaaacttcggctacacgtgaag<br>gagctgtataaaatggctttaaaaacatctacgagttcattaactacgatataattatcagaccgacaaagcgctg<br>gcgaccaccattgatggcttctcgcgctatgccaacgaactgaaaccggatctgatcgtggtgcacggcgatcgca<br>ttgaaccgctggcagcggcgattgtcggcgcgctgaataatatcctggttggcgcacatcgaaggcggcgagttt<br>ccggcaccatcgacgatagcctccgccacgccatcagcaagctcgcgcatattcatctggttaacgatgaatttgcc<br>aaacgccgcctgatgcagctgggcgaagatgagaaaagcatttttattattggctcgccgaccctggaactgctga<br>acgacaataaaatctccctgagcgaagcgaagaaatactacgacatcaattacgaaaactacgccctgttgatgttc<br>catccggtgacgaccgaaatcaccagcatcaagaatcaggcggataacctggtcaaagccctgattcagtcgaac<br>aaaaactatattgtgatttatccgaacaatgatctcggttttgaattgattctgcaaagctatgaagaattcaaaaataac<br>ccgcgcctttaagctgttcccgagcctgcgcttcgagtatttcatcacgctgctcaagaacgccgatttatcatcggca<br>acagctcctgcattctgaaagaggcgctgacctgaaaaccgcgggcattctggtgggcagccgccagaacggc<br>cgcctcggcaatgaaaatacccctgaaggtgaacgcgaactccgacgaaattctcaaagcaatcaacaccatccat<br>aaaaaacaggatttgttcagcgcgaaactggatcctcgacagcagtaaactatattgaatatctgcagagcgg<br>cgacttcttcaaactgtccacccagaaagtgttcaaggacatcaagtga |
| 25 | The native nucleotide sequence encoding SEQ ID NO: 11:<br>atgaaaattaaatatatttactaaatctatgattggtatggggctggtgttccgctctgccagcattggcaatggaagc<br>atggaataaccaacaaggtggtaataaatatcaggttattttcgatggcaaaatttatgaaaatgcctggtgggtttctt<br>ctacaaaattgcccgggaaaagcgaaagcaaatgatgcaactaacccgtggcgtttaaagcgtaccgcaacagctg<br>ctgaaattagtcagtttggcaatacactttcctgcgaaaagagcggcagctcatcttatcaaattcaaatacgcctgc<br>atccaatacgccggctaatggcggttcggctacaccagcacagggcactgttccgtctaattcttcgtagttgcctg<br>gaataaacagcagggcggtcagacctggtatgtcgtattaatggtgcggtatataaaaatgcctggtgggtagcct<br>cttctaactgtccgggtgatgcgaaaagcaatgatgccagcaacccatggcgttatgttcgtgccgctacggcaac<br>ggaaatctcagaaaccagtaatccacagtcctgtacttcagcaccacagccttcaccggatgtgaaaccggcaccg<br>gacgttaaaccggctcctgatgttcagccagcccagctgataagtcaaacgacaactatgctgtagtagcctgga<br>aaggtcaggaaggttcttctacatggtacgttatctataacggcggcatttataagaacgcctggtgggtaggcgcg<br>gcaaattgcccaggcgatgcgaaagaaaacgatgccagtaacccatggcgttatgttcgcgcggcaacggcaac<br>agaaatcagccagtatggtaaccctggctcctgttccgttaagccggataataatggcggtgctgtgactccggttg<br>atccaactcggaaacaccggtgaccccaactccggataacagcgagccatcaacaccagcggatagcgttaac<br>gattactcattgcaagcgtggagcggccaggaaggtagcgaaatttaccatgttattttcaatggtaatgtttacaaga<br>acgcctggtgggttgggtctaaagattgcccacggggtaccagcgctgaaaactccaataacccatggcgtctcg<br>agcgtacagctaccgctgcggaattgagtcagtacggtaacccgactacctgtgaaattgataacggcggcgtcat<br>tgttgcggatggtttccaggccagcaaagcgtacagcgcggacagcatcgtagattataacgatgcacattataaa<br>acttctgtcgatcaagacgcatggggcttttgtcccggggcggcgataacccgtggaagaaatacgaaccggcgaa<br>gcatggtccgcatccactgtgtacgtgaaaggtgatcgcgttgttgttgatgcggcaggcttatgaagcgctgttctgg<br>acgcaaagtgacaaccctgctctggtggcgaaccaaaacgccaccggtagcaatagccgcccgtggaagccgtt<br>aggtaaggctcagagctatagcaacgaagagctgaataatgcgccgcagtttaatccagaaacgctttatgccagc<br>gatacgctgattcgctttaacggtgtgaactacatttctcagagtaaagtgcagaaagtttctccttctgacagcaacc<br>cgtggcgtgttttgttgactggaccggaaccaaagagcgcgtaggtacgccgaagaaagcgtggccgaaacac<br>gtttatgcaccgtatgtcgacttttacgctgaatacgatcccggatctggctcgcgctggctaagaatcataacgtcaac<br>cacttcacgctggcgtttgtggtgagtaaagatgcgaacacctgtctgccgacatggggtaccgcttacgtatgca<br>gaattacgctcagtacagcaaaatcaaagctctgcgtgaggctggcggcgatgtgatgctgtctatcggtggtgcta<br>acaacgctccgctggctgcttcctgtaagaacgtagacgatctgatgcagcattattatgacatcgttgataacctga<br>acctcaaagtcctggacttcgatatcgaaggcacctgggttgcggatcaggcatctattgaacgtcgtaaccttgctg<br>tgaagaaagtgcaggataaaatggaagtcagaaggcaaagatattgctatctggtacacccttgccaattctgccgact |

| SEQ ID NO: | Sequence |
|---|---|
| | ggcctgacgccggaagggatgaatgtcctgagcgatgccaaagcgaaaggtgttgagctggcgggtgtgaacgt<br>gatgacaatggactacggtaacgcgatttgtcagtctgcaaataccgaaggccagaacattcacggtaagtgtgca<br>acgtctgcgattgccaacctgcattcacaattgaaaggcctccatcccaataagagcgatgcagaaattgacgctat<br>gatgggtaccacgccgatggttggcgtgaacgacgttcagggcgaggtgttctatctctctgatgctcgtcggtcat<br>gcaggatgcgcagaagcgtaatctcggtatggttggtatctggtcaatcgcgcgcgacctgccgggcggcactaa<br>cctgtctccggaattccacggcctgactaaagaacaggcaccgaagtacgcatttagcgaaatcttcgcgccgttta<br>ctaagcaataa |
| 26 | The native nucleotide sequence encoding SEQ ID NO: 12:<br>gtacaggcggcagtgtaatgaaaattcattgttatggtgatttatttcgacttttattctcgaggaaaataaacattaatg<br>gcgacggggaatattcccccattgtaaaaacatccactctggagaaataccatgtccacacgcaaagccgttattgg<br>gtattattttattccgaccaaccaaatcaataattacaccgagaccgatacgtctgtcgtgccattcccggtttccaaca<br>ttacgccggccaaagccaaacagctgacgcacattaacttctcgttcctggatatcaacagcaatctggaatgcgcc<br>tgggatccggccaccaacgacgccaaggcgcgcgatgtggtcaaccgtctgaccgcgctcaaagcgcacaacc<br>ccagcctgcgcatcatgttctccatcggcggctggtactactccaacgatctgggcgtgtcgcacgccaactatgtc<br>aacgcggtgaaaaccccggcgtcgcgcaccaagttcgcccaatcctgcgtgcgcatcatgaaggattacggcttc<br>gacggcgtggacatcgactgggagtacccgcaggcggcggaagtggacggtttcatcgccgcgctgcaggaga<br>tccgcaccttgctgaaccagcaaaccatcgcggacggccgccaggcgttgccgtatcagctgaccatcgccggc<br>gccggcggcgctttcttcctgtcgcgctattacagcaagctggcgcagatcgtcgcgccactcgattacatcaacct<br>gatgacctacgatctggccggccctgggagaagatcaccaaccaccaggcggcgctgttcggcgacgcggcc<br>gggccgaccttctacaacgcgctgcgcgaagccaatctgggcctggagctgggaagagctgacccgcgccttccc<br>cagcccgttcagcctgacggtcgacgccgccgtgcagcaacacctgatgatggaaggcgtgccgagcgccaaa<br>atcgtcatgggcgtgcccttctacggccgcgccttcaagggcgtcagcggcggcaacggcggccagtacagca<br>gccacagcacgccgggcgaagatccgtatccgaacgccgattactggctggtggggctgcgacgagtgcgtgga<br>cgacaaggatccgcgcatcgcctcctatcgccagctggagcagatgctgcagggcaactacgcgtatcagcggtt<br>gtggaacgataagaccaaaaccccgtatctgtatcatgcgcagaacgggctgtttgtcacctatgacgatgccgag<br>agatcaaatacaaagcgaagtacatcaagcagcagcagctgggcggcgtaatgttctggcatttgggcaagac<br>aaccgcaacggcgatctgctggccgcgctggatcgctatttcaacgccgcagactacgacgacgacagctgga<br>tatgggcaccggcctgcgataccggcgtcggccccggcaacctgcctatcatgaccgcgccggcttatgtgcc<br>gggcaccacttacgcgcagggcgcgctggtgtcctaccaaggctacgtctggcagaccaagtgggggttacatca<br>cctcggcgcccggctcagacagcgcctggctgaaggtgggccgcctggcgtaagccgtaaaaaaaccccgtag<br>ccgaatgctgcggggttttcattgagttaaccgtttgattttcgcgtcccttcgtctcaattccttcagttgtggcaccat<br>ggatagccgccatcccgcaccacttcgcggcccatcaggctgtagacatcgcatta |
| 27 | The native nucleotide sequence encoding SEQ ID NO: 13:<br>atgaccatgattacggattcactggccgtcgttttacaacgtcgtgactgggaaaaccctggcgttacccaacttaat<br>cgccttgcagcacatccccctttcgccagctggcgtaataggcgaagaggcccgcaccgatcgcccttcccaacag<br>ttgcgcagcctgaatggcgaatggcgctttgcctggtttccggcaccagaagcggtgccggaaagctggctggag<br>tgcgatcttcctgaggccgatactgtcgtcgtcccctcaaactggcagatgcacggttacgatgcgcccatctacac<br>caacgtgacctatcccattacggtcaatccgccgtttgttcccacggagaatccgacgggttgttactgcgctcacattt<br>aatgttgatgaaagctggctacaggaaggccagacgcgaattatttttgatggcgttaactcggcgtttcatctgtggt<br>gcaacgggcgctggtcggttacggccaggacagtcgtttgccgtctgaatttgacctgagcgcattttacgcgcc<br>ggagaaaaccgcctcgcggtgatggtgctgcgctggagtgacggcagttatctgaagatcaggatatgtggcg<br>gatgagcggcattttccgtgacgtctcgttgctgcataaaccgactacacaaatcagcgatttccatgttgccactcg<br>ctttaatgatgatttcagccgcgctgtactggaggctgaagttcagatgtgcggcgagttgcgtgactacctacgggt<br>aacagtttctttatggcagggtgaaacgcaggtcgccagcggccaccgcgcctttcggcggtgaaattatcgatgag<br>cgtggtggttatgccgatcgcgtcacactacgtctgaacgtcgaaaaacccgaaactgtggagcgccgaaatcccg<br>aatctctatcgtgcggtggttgaactgcacaccgccgacggcacgctgattgaagcagaagcctgcgatgtcggtt<br>tccgcgaggtcggattgaaaatggtctgctgctgctgaacggcaaccgcgttgctgattcgaggcgttaaccgtca<br>cgagcatcatcctctgcatggtcaggtcatggatgagcagacgatggtgcaggatatcctgctgatgaagcagaac<br>aactttaacgccgtgcgctgttcgcattatccgaaccatccgctgtggtacacgctgtgcgaccgctacggcctgtat<br>gtggtggatgaagccaatattgaaaccccacgcatggtgccaatgaatcgtctgaccgatgatccgcgctggctac<br>cggcgatgagcgaacgcgtaacgcgaatggtgcagcgcgatcgtaatcacccgagtgtgatcatctggtcgctgg<br>ggaatgaatcaggccacggcgctaatcacgacgcgctgtatcgctggatcaaatctgtcgatccttcccgcccggt<br>gcagtatgaaggcggcggagccgacaccacggccaccgatattatttgcccgatgtacgcgcgcgtggatgaag<br>accagccctccccggctgtgccgaaatggtccatcaaaaaatggctttcgctacctggagagacgcgcccgctgat<br>cctttgcgaatacgcccacgcgatgggtaacagtcttggcggtttcgctaaatactggcaggcgtttcgtcagtatcc<br>ccgtttacagggcgcttcgtctgggactgggtggatcagtcgctcgattaaatatgatgaaaacggcaaccgtggt<br>cggcttacggcggtgattttggcgatacgccgaacgatcgccagttctgtatgaacggtctggtctttgccgaccgc<br>acgccgcatccagcgctgacggaagcaaaacaccagcagcagttttttccagttccgtttatccgggcaaaccatcg<br>aagtgaccagcgaatacctgttccgtcatagcgataacgagctcctgcactggatggtggcgctggatggtaagcc<br>gctggcaagcggtgaagtgcctctggatgtcgctccacaaggtaaacagttgattgaactgcctgaactaccgcag<br>ccggagagcgccgggcaactctggctcacagtacgcgtagtgcaaccgaacgcgaccgcatggtcagaagccg<br>ggcacatcagcgcctggcagcagtggcgtctggcggaaaacctcagtgtgacgctccccgccgcgtcccacgc<br>catcccgcatctgaccaccagcgaaatggattttttgcatcgagctgggtaataagcgttggcaatttaaccgccagt<br>caggcttctttcacagatgtggattggcgataaaaaacaactgctgacgccgctgcgcgatcagttcacccgtgca<br>ccgctggataacgacattggcgtaagtgaagcgaccgcattgagcctgggtcgaacgcctggaaggc<br>ggcggcgccattaccaggccgaagcagcgttgttgcagtgcacggcagatacacttgctgatgcggtgctgattac<br>gaccgctcacgcgtggcagcatcaggggaaaaccttatttatcagccggaaaacctaccggattgatggtagtggt<br>caaatggcgattaccgttgatgttgaagtggcgagcgatacaccgcatccggcgcggattggcctgaactgccag<br>ctggcgcaggtagcagagcgggtaaactggctcggattagggccgcaagaaaactatcccgaccgccttactgc<br>cgcctgttttgaccgctgggatctgccattgtcagacatgtataccccgtacgtcttcccgagcgaaaacgtctgcg<br>ctgcgggacgcgcgaattgaattatgcccacaccagtggcgcggcgacttccagttcaacatcagccgctacag<br>tcaacagcaactgatgaaaccagccatcgccatctgctgcacgcggaagaaggcacatggctgaatatcgacg<br>gtttccatatggggattggtggcgacgactcctggagcccgtcagtatcggcggaattccagctgagcgccggtcg<br>ctaccattaccagttggtctggtgtcaaaaataa |

| SEQ ID NO: | Sequence |
|---|---|
| 28 | The native nucleotide sequence encoding SEQ ID NO: 14:<br>atggcaacgaatttacgtggcgtaatggctgcactcctgactccttttgaccaacaacaagcactggataaagcgag<br>tctgcgtcgcctggttcagttcaatattcagcagggcatcgacggtttatacgtgggtggttcgaccggcgaggcctt<br>tgtacaaagcctttccgagcgtgaacaggtactggaaatcgtcgccgaagaggcgaaaggtaagattaaactcatc<br>gcccacgtcggttgcgtcagcaccgccgaaagccaacaacttgcggcatcggctaaacgttatggcttcgatgcc<br>gtctccgccgtcacgccgttctactatccttcagctttgaagaacactgcgatcactatcgggcaattattgattcggc<br>ggatggtttgccgatggtggtgtacaacattccagccctgagtggggtaaaactgaccctggatcagatcaacaca<br>cttgttacattgcctggcgtaggtgcgctgaaacagaccctctggcgatctctatcagatggagcagatccgtcgtga<br>acatcctgatcttgtgctctataacggttacgacgaaatcttcgcctctggtctgctggcgggcgctgatggtggtatc<br>ggcagtacctacaacatcatgggctggcgctatcaggggatcgttaaggcgctgaaagaaggcgatatccagacc<br>gcgcagaaactgcaaactgaatgcaataaagtcattgatttactgatcaaaacgggcgtattccgcggcctgaaaa<br>ctgtcctccattatatggatgtcgtttctgtgccgctgtgccgcaaaccgtttggaccggtagatgaaaaatatctgcc<br>agaactgaaggcgctggcccagcagttgatgcaagagcgcgggtga |
| 29 | The native nucleotide sequence encoding SEQ ID NO: 15:<br>atgttgaataatgctatgagcgtagtgatccttgccgcaggcaaaggcacgcgcatgtattccgatcttccgaaagt<br>gctgcatacccttgccgggaaagcgatggttcagcatgtcattgatgctgcgaatgaattaggcgcagcgcacgtt<br>cacctggtgtacggtcacggcggcgatctgctaaaacaggcgctgaaagacgacaaccttaactgggtgcttcag<br>gcagagcagctgggtacgggtcatgcaatgcagcaggccgccacctttctttgccgatgatgaagacattttaatgct<br>ctacggcgacgtgccgctgatctctgtcgaaacactccagcgtgctgcgtgatgctaaaccgcagggtggcattggt<br>ctgctgacggtgaaactggatgatccgaccggttatggacgtatcacccgtgaaaacggcaaagttaccggcattg<br>ttgagcacaaagatgccaccgacgagcagctcagattcaggagatcaacaccggcattctgattgccaacggcg<br>cagatatgaaacgctggctggcgaagctgaccaacaataatgctcagggcgaatactacatcaccgacattattgc<br>gctggcgtatcaggaagggcgtgaaatcgtcgccgttcatccgcaacgtttaagcgaagtagaaggcgtgaataa<br>ccgcctgcaactctcccgtctggagcgtgtttatcagtccgaacaggctgaaaaactgctgttagcaggcgttatgct<br>gcgcgatccagcgcgttttgatctgcgtggtacgctaactcacgggcgcgatgttgaaattgatactaacgttatcat<br>cgagggcaacgtgactctcggtcatcgcgtgaaaattggcaccggttgcgtgattaaaaacagcgtgattggcgat<br>gattgcgaaatcagtccgtataccgttgtggaagatgcgaatctggcagcggcctgtaccattggcccgtttgcccg<br>tttgcgtcctggtgctgagttgctggaaggtgctcacgtcggtaacttcgttgagatgaaaaaagcgcgtctgggtaa<br>aggctcgaaagctggtcatctgacttacctgggcgatgcggaaattggcgataacgttaacatcggcgcggaac<br>cattacctgcaactacgatggtgcgaataaatttaagaccattatcggcgacgatgtgtttgttggtccgacactcag<br>ctggtggccccggtaacagtaggcaaaggcgcgaccattgctgcgggtacaactgtgacgcgtaatgtcggcga<br>aaatgcattagctatcagccgtgtgccgcagactcagaaagaaggctggcgtcgtccggtaaagaaaaagtg a |
| 30 | The native nucleotide sequence encoding SEQ ID NO: 16:<br>ttgagcgcaagcgatttctcgagcgcagttgtcgttttggcagctggtgccggaacccgaatgaaatcagacttaca<br>aaaaacgttgcatagcatcggtggacgcagtctcatttcacatagcttgcatgcagctgccgggcttaatcccgagc<br>acattgttgcagtaattggacatggacgcgaccaggtgggtccagccgttgcccaggttgcagaagaactggacc<br>gggaagtcctcatcgctatccaagaggaacaaaatggcacgggacacgctgtgcagtgcgccatggatcagctc<br>gagggattgaaggcacgatcattgtcaccaacggcgatgttcccctgctcaccgaccacactctgtctgcactgct<br>ggatgcacacgtggaagttccaaccgctgtcaccgtgttgaccatgcgtctggatgaccccaccggctacggccg<br>catcgtgcgcaacgaagaaggcgaagtcaccgccatcgttgagcaaaaagatgcttcagcagaagtccaagcca<br>tcgatgaggtcaactccggtgtctttgctttcgacgccgccatcttgcgttccgcactggctgaactgaagtccgaca<br>acgctcagggcgagctgtacctgaccgacgtatgggcattgctcgtggcgagggccacccagtgcgcgcccac<br>accgccgccgatgctcgtgaactcgccggtgtcaacgatcgtgtgcagctcgcagaagccggcgtgaactaaa<br>ccgtcgcaccgtcatcgccgctatgcgtggtggcgcaaccatcgttgatccagcaaccacctggatcgatgtgga<br>ggtttctatcggccgcgacgtgatcatccaccctggcaccagctcaagggcgaaactgtcatcggagaccgcgtt<br>gaagttggtccagacaccaccttgaccaacatgaccatcggcgacggcgcatccgtaatccgcacccacggtttc<br>gactccaccatcggtgaaaacgccaccgttggcccctttcacctacatccgcaggaaccacactgggaccaga<br>aggcaagctcggtggcttcgtagaaaccaagaaggccacaatcggccgtggctccaaggttccacacctcaccta<br>tgtcggcgacgccaccatcggcgaggaatccaacatcggagcctcctctgtcttcgtgaactacgacggtgaaaa<br>caagcaccacaccaccatcggcagccacgttcgcactggttctgacaccatgtttatcgctccagtgaccgtgggt<br>gacggagcgtattccggagccggtacagtaattaaagacgatgttccgccaggagcccttgccgtgtccggcgga<br>cgcaacgaaacatcgaaggctgggtgcaaaagaagcgccctggaaccgctgcagcacaagccgcagaagcc<br>gcccaaaacgtccacaaccaggaaggctaa |
| 31 | The codon optimized nucleotide sequence encoding SEQ ID NO: 16 for expression in Escherichia coli:<br>atgaaaagcgatctgcagaaaacgctgcactctatcggtggccgcagcctgatttctcacagcctgcacgccgctg<br>cgggtctgaacccggaacacatcgttgcggttattggtcacggtcgtgatcaggtgggtccggctgttgcgcaggtt<br>gcagaagaactggaccgtgaagtgctgatcgctatccaagaagaacagaacggcaccggccacgctgtccagtg<br>cgcaatggatcagctggaaggtttcgaaggcactatcatcgttactaacggtgacgtgccactgctgactgatcata<br>ccctgtctgctctgctggacgctcacgttgaagtcccgaccgctgttactgttctgaccatgcgtctggacgatccga<br>ctggctacgccgcatcgtacgtaatgaagagggcgaagtcactgcaattgttgagcagaaagatgcgtctgccg<br>aagttcaggcgatcgatgaagtaaactccggcgttttcgcgttcgatgccgcgattctgcgcagcgctctggcaga<br>gctgaaatccgataacgcgcagggtgaactgtacctgaccgacgttctgggcatcgcccgtggcgaaggtcaccc<br>ggttcgcgcacacactgctgcagacgctcgtgaactggccggtgttaacgacgtgttcagctggccgaagctggt<br>gcagagctgaaccgtcgtacggttatcgcggctatgcgtggcggtgctacgatcgtggacccagctactacttgga<br>tcgatgtggaagtttctattggtcgtgacgtaatcatccaccgggtacccaactgaaaggtgaaacggtaatcggt<br>gatcgtgttgaggttggtccggacaccaccctgactaatatgaccatcggcgacggcgcagcgttatccgcactc<br>acgggctttgattctactatcggcgaaaacgccaccgttggtccattcacctatattcgtccaggcactactctgggtcc<br>ggaaggcaaactggcggtttcgttgaaactaagaaagctactatcggtcgtggtagcaaagtgccgcatctgacg<br>tacgttggcgatgctaccatcggcgaggaatccaacatcggtcaagcagcgtctttgtgaattatgacggtgaaaa<br>caaacaccacaccacgatcggttcccatgttcgtaccggctctgataccatgttcatcgcaccggtcaccgtgggtg<br>atggcgcatactccggcgcgggtaccgtgatcaaggacgacgtgccaccgggtgcactgctgtgtttccggtggc<br>cgccagcgtaacatcgaaggttgggttcagaaaaaacgtccaggtaccgcggcggcccaggccgctgaagctg<br>ctcaaaacgttcacaaccaggaaggttga |

| SEQ ID NO: | Sequence |
|---|---|
| 32 | The native nucleotide sequence encoding SEQ ID NO: 17:
atgtgtggaattgttggcgcgatcgcgcaacgtgatgtagcagaaatccttcttgaaggtttacgtcgtctggaatac
cgcggatatgactctgccggtctggccgttgttgatgcagaaggtcatatgacccgcctgcgtcgcctcggtaaagt
ccagatgctggcacaggcagcggaagaacatcctctgcatggcggcactggtattgctcacactcgctgggcgac
ccacggtgaaccttcagaagtgaatgcgcatccgcatgtttctgaacacattgtggtggtgcataacggcatcatcg
aaaaccatgaaccgctgcgtgaagagctaaaagcgcgtggctatacccttcgtttctgaaaccgacaccgaagtgat
tgcccatctggtgaactgggagctgaaacaaggcgggactctgcgtgaggccgttctgcgtgctatcccgcagct
gcgtggtgcgtacggtacagtgatcatggactcccgtcaccgggataccctgctggcggcacgttctggtagtccg
ctggtgattggcctggggatgggcgaaaactttatcgcttctgaccagctggcgctgttgccggtgaccgtcgcttt
atcttccttgaagagggcgatattgcggaaatcactcgccgttcggtaaacatcttcgataaaactggcgcggaagt
aaaacgtcaggatatcgaatccaatctgcaatatgacgcgggcgataaaagcattaccgtcactacatgcagaaa
gagatctacgaacagccgaacgcgatcaaaaacacccttaccggacgcatcagccacggtcaggttgatttaagc
gagctgggaccgaacgccgacgaactgctgtcgaaggttgagcatattcagatcctcgcctgtggtacttcttataa
ctccggtatggtttcccgctactggtttgaatcgctagcaggtattccgtgcgacgtcgaaatcgcctctgaattccgc
tatcgcaaatctgccgtgcgtcgtaacagcctgatgatcaccttgtcacagtctggcgaaccgccggataccctggc
tggcctgcgtctgtcgaaagagctgggttaccttggttcactggcaatctgtaacgttccgggttccttctctggtgcgc
gaatccgatctggcgctaatgaccaacgcgggtacagaaatcggcgtggcatccactaaagcattcaccactcagt
taactgtgctgttgatgctggtggcgaagctgtctcgcctgaaaggtctggatgcctccattgaacatgacatcgtgc
atggtctgcaggcgctgccgagccgtattgagcagatgctgtctcaggacaaacgcattgaagcgctggcagaag
atttctctgacaaacatcacgcgctgttcctgggccgtggcgatcagtacccaatcgcgctggaaggcgcattgaa
gttgaaagagatctcttacattcacgctgaagcctacgctgctggcgaactgaaacacggtccgctggcgctaattg
atgccgatatgccggttattgttgttgcaccgaacaacgaattgctggaaaaactgaaatccaacattgaagaagttc
gcgcgcgtggcggtcagttgtatgtcttcgccgatcaggatgcgggttttgtaagtagcgataacatgcacatcatc
gagatgccgcatgtggaagaggtgattgcaccgatcttctacaccgttccgctgcagctgctggcttaccatgtcgc
gctgatcaaaggcaccgacgttgaccagccgcgtaacctggcaaaatcggttacggttgagtaa |
| 33 | The codon optimized nucleotide sequence encoding SEQ ID NO: 18 for expression in Escherichia coli:
atgtgcggtatcgttggtgccatcgcgcagcgtgacgtggctgaaatcctgctggagggtctgcgtcgtctggaata
ccgtggctacgacagcgcgggcctggcagttgtcgatactgagggtcatatgacccgtctgcgtcgtctgggtaaa
gtacagatgctggcgcaggcagcggaagaacatccgctgcacggcggcaccggtattgcacacacgcgctggg
cgacccatggcgaaccgagcgaagtcaacgcacaccccgcatgtttctgagcatattgttgtggttcacaacggcat
catcgaaaaccacgagccgctgcgtgaagaactgaaagcccgcggttacacctttgtatctgaaacggatactga
ggttatcgctcacctggtaaactgggagctgaagcaaggcggcaccctgcgcgaagcggtactgcgtgctattcc
acagctgcgtggcgcctatggtaccgttattatggatagccgtcatcctgataccgctggcagcccgttctggttct
ccgctggtaattggcctgggcatgggcgagaactttatcgccagcgaccaactggctctgctgccggttactcgtc
gcttcatttttctggaagaaggcgacatcgcagaaatcactcgtcgctccgtgaatattttgataaaaccggcgctga
gtcaaacgtcaggacatcgagtctaacctgcagtacgatgcaggtgacaaaggcatttattgccattatatgcaga
aagaaatctacgaacagccgaacgctatcaagaataccctgactggtcgtatctcccacggtcaggttgatctgtcc
gaactgggtccgaacgctgacgaactgctgtctaaagtggacaacatccagattctggcgtgcgcggtactagctaca
actccggtatggtttctcgttactggttcgaatctctggctggtatcccgtgcgacgttgaaatcgcgtctgaatttcgtt
accgcaaaagcgctgttcgtcgtaacagcctgatgatcaccctgtcccagtctggtgaaaccgctgacaccctggc
aggcctgcgcctgagcaaagaactgggttacctgggttctctggcgatctgcaacgtgccgggctcttctctggtgc
gcgagtctgacctggcactgatgaccaacgctggcaccgaaatcggcgttgcatcctaccaaggcctcttcaccactca
gctgactgtgctgctgatgctggtggctaaactgtctcgtctgaaaggtctggacgcgagcatcgaacacgatatcg
ttcacggcctgcaggcgctgccttctcgtatcgaacagatgctgagccaggacaagcgcatcgaagcgctggcg
gaagatttctccgacaaacatcatgcgctgttcctgtcccgtggtgaccagtatccgattgctctggaaggcgctctg
aaactgaaagaaattagctacatccacgctgaggcatatgctgcagctggtgaactgaaacacggcccgctggctctg
atcgatgcggacatgccagttatcgttgtagccccgaacaacgagctgctggaaaaactgaaatccaacattgaag
aagtgcgcgctcgtggcggccaactgtacgtttcgctgaccaggacgctggttttgttagcagcgataacatgcac
attattgaaatgccgcacgttgaagaagttatcgctccgatcttctacaccgttccgctgcagctgctggcataccac
gttgctctgatcaaaggtactgacgtggatcagccacgtaatctggctaaaagcgtgactgttgaataa |
| 34 | The native nucleotide sequence encoding SEQ ID NO:19:
atgtgtggaattgttggatatattggccaagcgggcgactcccgtgattactttgctctagatgtagttgttgaaggact
acgtcgcctggaataccgcggatatgactcccgcaggtattgctattcacgccaatggtgagattagctaccgaaag
aaggccggaaaggttgctgcactagatgcagaaatcgctaaagcacctatccagattctattttgggaattggaca
cacccgttgggcaactcatggtggcccaaccgatgtcaacgctcaccccacgttgtttccaatggcaagcttgcc
gtagtacacaacggcatcatcgaaaactttgcggaactgcgctctgagctttccgctaagggctacaactttgtatcc
gataccgataccgaagttgctgcttctttgcttgctgaaatttacaatactcaggcaaacggtgacctcacccttgctat
gcagctgaccggtcagcgccttgagggtgcttcaccctgctagctattcatgctgatcacgatgaccgcatcgttg
cagctcgtcgtcactccttcttggttatcggcgtcggcgagggcgagaacttcctcggatctgacgtttctggctttatt
gattacacccgcaaggctgtagagctggctcaatgaccaggttgttaccatcaccgctgatgattacgccatcaccaa
ctttgatggatcagaagcagttggcaagccttcgacgtggagtgggacgctgcagctgctgaaaagggtggcttc
ggttccttcatggagaaggaaatccacgatcagccagcagctgttcgcgatacctgatgggccgtcttgatgaag
atggcaagctcgtcttgatgagctgcgcatcgatgaagctattctgctagtgtcgacaagatcgtcattgttgcttgt
ggtactgcagcttatgcaggccaggttgctcgttacgccattgagcactggtgccgcatcccaaccgaggtggagc
tggctcacgagttccgttaccgcgacccaatcctcaacgagaagacccttgttgtggcattgtcccagtccggcga
gaccatggataccccatggctgttcgccacgcacgtgagcagggtgccaaggttgttgctatttgtaacactgttgg
atccactcttccacgtgaagcagatgcgtccctgtacacctacgctggccctgagatcgctgtggcgtccaccaag
gcgttcttggctcagatcactgcttcttctacttggcttggcctcagctgcgcggcaacaagttcgctgatg
aggtttcttccattctggacagcctgcgtgagatgcctgagaagattcagcaggtcatcgatgcagaagagcagatc
aagaagcttggccaagatatggcagatgctaagtctgtgctgttcctgggccgccacgttggtttcccagttgcgctt
gagggtgcgttgaagctcaaggagatcgcatacctgcacgctgaaggtttcgctgcaggcgagctcaagcacgg
cccaattgctttggttgaggaaggccagccgatcttcgttatcgtgccttcacctcgtggtcgcgattcctgcactcc
aaggttgtctccaacattcaggagatccgtgcacgtggcgctgtcaccatcgtgattgcagaggaaggcgatgag |

| SEQ ID NO: | Sequence |
|---|---|
| | gctgtcaacgattacgccaacttcatcatccgcattcctcaggccccaaccctgatgcagcctctgctgtccaccgtg<br>cctctgcagatctttgcgtgcgctgtggcaaccgcaaagggctacaacgtggatcagcctcgtaacctggcaaagt<br>ctgtcaccgtcgaataa |

EXAMPLES

Material and Methods
1. Chemicals, Oligonucleotides and Molecular Biology

All reagents were purchased from Sigma-Aldrich (Bornem, Belgium), unless otherwise stated. Agarose and ethidium bromide were purchased from Thermo Fisher Scientific (Erembodegem, Belgium). Standard molecular biology procedures were conducted as described by Sambrook et al. (Sambrook and Russell 2001). Qiagen kits (Hilden, Germany) were used for all DNA preparations. Oligonucleotides were purchased from Integrated DNA Technologies (Leuven, Belgium), genes were purchased from Geneart (Thermo Fisher Scientific, Erembodegem, Belgium). Sequencing services were conducted by Macrogen (Amsterdam, The Netherlands).

The sequence of the *E. coli* murA operon was obtained from *E. coli* K-12 MG1655 complete genome (Genbank access code: NC_000913; MurA, Genbank accession code: NP 417656.1, Table 1). The sequence of the *Corynebacterium glutamicum* murA operons was obtained from *C. glutamicum* ATCC 13032 complete genome (Genbank access code: NC_003450).

The sequence of L-glutamine: D-fructose-6-phosphate aminotransferase was obtained from *E. coli* (EcGlmS, Genbank accession code: NP418185, Table 1). A mutant GlmS was used, GlmS*54, which contains 3 non-silent mutations, i.e., A38T, R249C and G471S (Deng et al., 2006). The sequence of a fused N-acetylglucosamine-1-phosphate uridyltransferase and glucosamine-1-phosphate acetyltransferase was obtained from *Corynebacterium glutamicum* (GlmU, Genbank accession code: WP038583267, Table 1).

The sequence of the oligomer chitin synthase (oCHS) was obtained from *Rhizobium* sp. GRH2 (NodC, Genbank access code: AJW76243, Table 1).

The sequence of the UDP-N-acetylglucosamine 2-epimerase, N-acetylneuraminic acid synthase and the CMP-Neu5Ac synthetase were obtained from *Campylobacter jejuni* strain ATCC 43438 (NeuC, NeuB1, and NeuA, respectively, Genbank access code: AF400048, Table 1) (Fierfort and Samain 2008). The sequence for the α-2,3-sialyltransferase was obtained from *Neisseria meningitidis* (NST, Genbank access code: U60660, Table 1).

The sequence of the β-1,3-N-acetylglucosaminyltransferase was obtained from *Neisseria meningitidis* (LgtA, Genbank accession code: U25839, Table 1) and β-1,3-galactosyltransferase was obtained from *Escherichia coli* O55: H7 (WgbO, Genbank accession code: AF461121, Table 1).

TABLE 1

Sequences of used enzymes

| SEQ ID NO: | Enzyme | Protein sequence (Genbank accession code) |
|---|---|---|
| 35 | MurA | NP_417656.1<br>mdkfrvqgpt klqgevtisg aknaalpilf aallaeepve iqnvpklkdv dtsmkllsql<br>gakverngsv hidardynvf capydlvktm rasiwalgpl varfgqgqvs lpggctigar<br>pvdlhisgle qlgatiklee gyvkasvdgr lkgahivmdk vsvgatvtim caatlaegtt<br>iienaarepe ivdtanflit lgakisgqgt driviegver lgggyyrylp drietgtflv<br>aaaisrgkii crnaqpdtld avlaklrdag adievgedwi sldmhgkrpk avnvrtaphp<br>afptdmqaqf tllnlvaegt gfitetvfen rfmhvpelsr mgahaeiesn tvichgvekl<br>sgaqvmatdl rasaslvlag ciaegttvvd riyhidrgye riedklralg aniervkge |
| 36 | MurA1 | NCgl0345<br>myaeinggfipegtvrvsgaknsatrllaaalltdevvhlgnfptklvdvehkirfieelggkvhvd<br>hdeqilvvdakdlaaremttdelnipirttyllaaaqigrgeiarvpfpggcaigggpaggrgydlhl<br>mvweqlgckilekddhievtapqgfiggvidfpistvggtenallcasiasgdtkianayitpeitdl<br>iellrrmgaeitvygtsrihvkgragllqgaymdvmpdriealtwivygiisggritvegvpfssm<br>evpfihlekagvdlfrnsssvyitpeclpsgsvqpfelacgthpgvisdmqalfvllglkgagtsrvy<br>dyryperiafveeltnlvsgdklsaeagkitiqgdatfrpgyanstdlrgsmavvlaalcadgkstin<br>nvhmalrgyneldkklrllgadltiregevpsp |
| 37 | MurA2 | NCgl2470<br>vkdkflvtggaqlqgavkvygaknsvlklmaaallaegtttltncpeildvplmrdvlvglgcdvti<br>dgstvtittpaelssnadfpavtqfrasvcvlgpltarcgravvslpggdaigsrpldmhqsgleklg<br>attrishgavvaeaeklvganitldfpsvgateniltasvmaegrtvldnaarepeivdlcrmlrsmg<br>aniegegsptitiegvekltptqhevigdrivagtwayaaamtrgditvggiaprylhlpleklkiag<br>akvetyengfrvqmdkqpeatdyqtlpfpgfptdlqpmaiginavsngtsvitenvfesrfrfvde<br>mlrlgadanvdghhvvirgieqlsstsvwssdiragaglvlaalcadgvtevhdvfhidrgypnfv<br>enlqklgatiervss |
| 6 | NodC | AJW76243<br>mdllntigigavscyallstahksmqtlyaqpkdqssasedfaflpsvdiivpcynenphtfsecla<br>sianqdyagklrvyvvddgsanreklervhhtyagdprfdfillrenvgkrkaqiaairgssgdlvl<br>nvdsdstlasdvvtklalkmqnpeigaamgqltasnrndtwltrlidmeywlacneeraaqarfg |

TABLE 1-continued

Sequences of used enzymes

| SEQ ID NO: | Enzyme | Protein sequence (Genbank accession code) |
|---|---|---|
| | | avmcccgpcamyrrsallslldqyesqffrgkpsdfgedrhltilmlkagfrtdyvpdaiaatvvp<br>drmgpylrqqlrwarstfrdtlllalrllpgldhyitldvigqnlgplllalavltgvlqvaltatvplwtv<br>mmiasmtmircavaavrarqlrflvfslhtpinlffllpmkayalctlsnsdwlsrsspanktsagg<br>ehptteasaggtsgnatplrrlnlardsstvtpagvysdd |
| 38 | LgtA | U25839<br>mqplvsvlicaynvekyfaqslaavvnqtwcnldilivddgstdgtlaiakdfqkrdsrikilaqaq<br>nsglipslnigldelaksggeyiartdaddiaapdwiekivgemekdrsiiamgawlevlseekd<br>gnrlarhhrhgkiwkkptrhediadffpfgnpihnntmimrrsvidgglrynterdwaedyqfw<br>ydvsklgrlayypealvkyrlhanqvsskysvrqheiaqgiqktarndflqsmgfktrfdsleyrqi<br>kavayellekhlpeedferarrflyqcfkrtdtlpagawldfaadgrmrrlftlrqyfgilhrllknr |
| 39 | WbgO | AF461121<br>miideaesaesthpvvsvilpvnkknpfldeainsilsqtfssfeiiivancctddfynelkhkvndk<br>iklirtniaylpyslnkaidlsngefiarmdsddishpdrftkqvdflknnpyvdvvgtnaifiddkg<br>reinktklpeenldivknlpykccivhpsvmfrkkviasiggymfsnysedyelwnrlslakikfq<br>nlpeylfyyrlheggstakknlymvmvndlvikmkcffltgninylfggirtiasfiyckyik |
| 40 | NeuA | AF400048<br>mslaiiparggskgiknknlvllnnkpliyytikaalnaksiskvvvssdsdeilnyaksqnvdilkr<br>pislaqddttsdkvllhalkfykdyedvvflqptsplrtnihineafnlyknsnanalisvsecdnkil<br>kafvcndcgdlagicndeypfmprqklpktymsngaiyilkikeflnnpsflqsktkhflmdess<br>sldidcledlkkveqiwkk |
| 41 | NST | U60660<br>mglkkacltvlclivfcfgifytfdrvnqgernavsllkeklfneegepvnlifcytilqmkvaerim<br>aqhpgerfyvvlmsenrnekydyyfnqikdkaerayffhlpyglnksfnfiptmaelkvksmll<br>pkvkriylaslekvsiaaflstypdaeiktfddgtgnliqsssylgdefsvngtikrnfarmmigdw<br>siaktrnasdehytifkglknimddgrrkmtylplfdaselktgdetggtvrillgspdkemkeise<br>kaaknfkiqyvaphprqtyglsgvttlnspyviedyilreikknphtryeiytffsgaaltmkdfpn<br>vhvyalkpaslpedywlkpvyalftqsgipiltfddkn |
| 9 | NeuB1 | AF400048<br>mkeikiqniiiseekaplvvpeiginhngslelakimvdaafsagakiikhqthivedemskaak<br>kvipgnakisiyeimqkcaldykdelalkeyteklglvylstpfsraganrledmgvsafkigsge<br>cnnyplikhiaafkkpmivstgmnsiesikptvkilldneipfvlmhttnlyptphnlvflnamlel<br>kkefscmvglsdhttdnlaclgavvlgacvlerhftdsmhrsgpdivcsmdtkalkeliiqseqm<br>aiirgnneskkaakqeqvtidfafasvvsikdikkgevlsmdniwvkrpglggisaaefenilgkk<br>alrdiendaqlsyedfa |
| 10 | NeuC | AF400048<br>mvkkilfitgsradyskikslmyrvqnssefelyifatgmhlsknfgytvkelykngfkniyefiny<br>dkyyqtdkalattidgfsryanelkpdlivvhgdrieplaaaivgalnnilvahieggeisgtiddslr<br>haisklahihlvndefakrrlmqlgedeksifiigspdlellndnkislseakkyydinyenyallmf<br>hpvtteitsiknqadnlvkaliqsnknyiviypnndlgfelilqsyeefknnprfklfpslrfeyfitllk<br>nadfiignsscilkealylktagilvgsrqngrlgnentlkvnansdeilkaintihkkqdlfsakleil<br>dssklffeylqsgdffklstqkvfkdik |
| 17 | GlmS | NP418185<br>mcgivgaiaqrdvaeilleglrrleyrgydsaglavvdaeghmtrlrrlgkvqmlaqaaeehplhg<br>gtgiahtrwathgepsevnahphvsehivvvhngiienheplreelkargytfvsetdteviahlvn<br>welkqggtlreavlraipqlrgaygtvimdsrhpdtlllaarsgsplviglgmgenfiasdqlallpvtr<br>rfifleegdiaeitrrsvnifdktgaevkrqdiesnlqydagdkgiyrhymqkeiyeqpnaikntltg<br>rishgqvdlselgpnadellskvehiqilacgtsynsgmvsrywfeslagipcdveiasefryrksa<br>vrrnslmitlsqsgetadtlaglrlskelgylgslaicnvpgsslvresdlalmtnagteigvastkaftt<br>qltvllmlvaklsrlkgldasiehdivhglqalpsriemlsqdkriealaedfsdkhhalflgrgdq<br>ypialegalklkeisyihaeayaagelkhgplalidadmpvivvapnnellekklksnieevrarggq<br>lyvfadqdagfvssdnmhiiemphveeviapifytvplqllayhvalikgtdvdqprnlaksvtve |
| 16 | GlmU | WP038583267<br>msasdfssavvvlaagagtrmksdlqktlhsiggrslishslhaaaglnpehivavighrrdqvgp<br>avsqvaeeldrevliaiqeeqngtghavqcamdqlegfegtiivtngdvplltddtlsalldahvev<br>ptavtvltmrlddptgygrivrneegevtaiveqkdasaeiqaidevnsgvfafdaailrsalaelks<br>dnaqgelyltdvlgiargeghpvrahtaadarelagvndrvqlaeagaelnrrtviaamrggativd<br>pattwidvevsigrdviihpgtqlkgetvigdrvevgpdttltnmtigdgasvvrthgfdstigenat<br>vgpftyirpgttlgpegklggfvetkkatigrgskvphltyvgdatigeesnigassvfvnydgenk<br>hhttigshvrtgsdtmfiapvtvgdgaysgagtvikddvppgalavsggrqrniegwvqkkrpgt<br>aaaqaaeaaqnvhnqeg |

2. Strains

*Escherichia coli* TOP10 cells (Invitrogen) were used for the construction of all plasmids. *Escherichia coli* K12 MG1655 (code: *E. coli* sWT) was used as the parent for all strain engineering experiments and was obtained from ATCC. *Escherichia coli* K12 MG1655 ΔrecA ΔendA DE3 (code: *E. coli* sDE3) was used in experiments with pT7 and was carried from Ajikumar et al. (Ajikumar et al., 2010).

Site-directed chromosomal alterations in *E. coli* was accomplished by homologous recombination mediated by λ-Red recombinase (induced from pKD46) as described by Datsenko and Wanner (Datsenko and Wanner 2000). Linear DNA for homologous recombination was generated by amplifying the FRT flanked antibiotic resistance cassette from the appropriate template (pKD3 or pKD4 for gene deletion, p_P22RBS-cITCmurA for knocking in the translational coupled cassette cITCmurA and p_P22-layY for knocking in lacY under control of P22). Knocking in the translational coupled library was performed identically, with the exception that the linear fragment was amplified directly from the single stranded assembly (SSA) mix. Positive transformants were cured from the antibiotic resistance cassette using FLP recombinase (induced from pCP20). Successful chromosomal integration/deletion was confirmed by colony PCR and subsequent sequencing. All oligonucleotides used are listed in Table 2.

Chromosomal alteration in *C. glutamicum* was established using the CRISPR/Cpf1 system as described by (Jiang et al., 2017). This system, based on the CRISPR mechanism of *Francisella novicida*, uses two plasmids (pjYS1 and pJYS2) to perform genomic alterations.

A list of all used strains is given in Table 3. Genomic sequences of promoter and 5'-UTR regions of the P22RBS-cITCmurA knock-in (sP22) and seven selected mutants from the library (sRND1-sRND7) is given in Table 4.

TABLE 2

List of used oligonucleotides

| SEQ ID NO: | | Oligonucleotides (5'-3') |
|---|---|---|
| | Construction pIndicator | |
| 42 | Fw_pR_pIndicator | GGTTATTGTCTCATGAGCGGTAGAGTAACACCGTGCGTGTTG |
| 43 | Fw_pR_pIndicator | CTCCTTATGTATTCTCTGGGCAACCATTATCACC |
| 44 | Fw_mKate2_pIndicator | CCCAGAGAATACATAAGGAGGTACGACATGGTTAGC |
| 45 | Rv_mKate2_pIndicator | CTAGGACTCTTGATCCGGATATAGTTCCTCCTTTC |
| 46 | Fw_Backbone_pIndicator | CTATATCCGGATCAAGAGTCCTAGGATGCTAGC |
| 47 | Rv_Backbone_pIndicator | CACGGTGTTACTCTACCGCTCATGAGACAATAACC |
| | p_P22-cITCmurA | |
| 48 | Fw_cI_LVA_pcITCmurA | TCGGAGGAAACAAAGATGAGCACAAAAAAGAAACC |
| 49 | Rv_cI_LVA_pcITCmurA | ACCATCCTAATGATGGTGGTGATGATGGAGCTACTAAAGCGTAGTTTTCG |
| 50 | Fw_murA_pcITCmurA | ACCACCATCATTAGGATGGTGGTGATGATAATGGATAAATTTCGTGTTCAGG |
| 51 | Rv_murA_pcITCmurA | TTAAGCGGAAGTTATTCGCCTTTCACACGCTC |
| 52 | Fw_FRT_CmR_FRT_pcITCmurA | GACGCTCAGTGGAACGGAAGCTGAGTTGGCTGCTG |
| 53 | Rv_FRT_CmR_FRT_pcITCmurA | GCTTGTCTGTAAGCGCCATGGTCCATATGAATATCC |
| 54 | Fw_P22_pcITCmurA | TCATATGGACCATGGCGCTTACAGACAAGCTGTGACC |
| 55 | Rv_P22_pcITCmurA | CTTTTTTGTGCTCATCTTTGTTTCCTCCGAATTCG |
| | p_P22_LacY | |
| 56 | Fw_LacY_pP22LacY | CCGTCGACCTCGAATTCGGAGGAAACAAAGATGTACTATTTAAAAAACACAAACTTTTGG |
| 57 | Rv_LacY_pP22LacY | GCTGGCACATGTTCTTTAAGCGGAAGTTAAGCGACTTCATTCACC |
| 58 | Fw_Backbone_pP22LacY | CGTCAGGTGAATGAAGTCGCTTAACTTCCGCTTAAAGAACATGTGCCAGC |

TABLE 2-continued

List of used oligonucleotides

| SEQ ID NO: | | Oligonucleotides (5'-3') |
|---|---|---|
| 59 | Rv_Backbone_pP22LacY | CCAAAAGTTTGTGTTTTTAAATAGTACAT CTTTGTTTCCTCCGAATTCG |

Alteration
KO chb

| 60 | Fw_KO_chb | GGAATTAATCGCCGGATGCAAGGTTCACG CCGCATCTGGCAAACATCCTCACGTGTAG GCTGGAGCTGCTTC |
| 61 | Rv_KO_chb | GGCTTGCGGAGTGTCTGGCTGACAGATAA TCGTCGATGAGGGCAGTTTTCATATGAAT ATCCTCCTTAG |
| 62 | Fw_control_chb | TATTCCCATCCGCGTCTGTTC |
| 63 | Rv_control_chb | AAGCGCCCAATGTATTCCAGG |

KO nagZ

| 64 | Fw_KO_nagZ | GGCTGGCCGATGACACCTGGCGGCAGCTA TTAATAAAACAATAAGGAGAGCAGTCAGC ATTACACGTCTTGAGCG |
| 65 | Rv_KO_nagZ | CTGATTCAGACGGGTGCTGATCGCTTTCCA GCGAGCCGAGTCCATCAGTTCCTGCCATA TGAATATCCTCCTTAG |
| 66 | Fw_control_nagZ | CGGCGCAATTATGGCGTCAG |
| 67 | Rv_control_nagZ | CGGACTGTTAGAGTCAAAACC |

KO chiA

| 68 | Fw_KO_chiA | TAATTCCTGCGTAGGACTTTTGTTTTGCAG TTTTTACGTCACAAGGGCATATGAATATCC TCCTTAG |
| 69 | Rv_KO_chiA | GTAGCCCATTGACAAAAAATGCGGCGATA CTGGAAGGTATCGCCAACACGTGTAGGCT GGAGCTGGAGCTGCTTC |
| 70 | Fw_control_chiA | GAGACTCCCGTATACTTTCTTC |
| 71 | Rv_control_chiA | CGCCCTTTTTGCATTTGTTG |

KI cITCmurA

| 72 | Fw-KI-murA | AGTGGGCGCGCGATCGCAAACTGAACGGC TTTTGAGCTATGGGCGATTCGGTGGAACG GAAGCTGAGTTG |
| 73 | Rv-KI-murA | GCGCCAACGCTGACTTTATC |

Randomization promoter and 5'-UTR upstream of cITCmurA

| 74 | Fw-Backbone-randomization | AAGTCAGGCATGAGCACAAAAAAGAAAC C |
| 75 | Rv-Backbone-randomization | TGTCAAGAAATTTATAAATGAAGC |
| 76 | Fw-SSA-randomization | TGTGTACATAAACACAAGCTCARCMTATA CTAGASRAAGTCAGGCATGAGCACAAAAA AG |
| 77 | Rv-SSA-randomization | GTGTTTATGTACACATTATA NNNNNNNNTGTCAAGAAATTTATAAAT |

KO nanRATEK

| 78 | Fw_KO_nanRATEK | TAATGCGCCGCCAGTAAATCAACATGAAA TGCCGCTGGCTCCGTGTAGGCTGGAGCTG CTTC |

TABLE 2-continued

List of used oligonucleotides

| SEQ ID NO: | | Oligonucleotides (5'-3') |
|---|---|---|
| 79 | Rv_KO_nanRATEK | CAATCCTGTGATAGGATGTCACTGATGAT GTTAATCACACTGACCTTACAGACATATG AATATCCTCCTTAG |
| 80 | Fw_control_nanRATEK | GTCGCCCTGTAATTCGTAAC |
| 81 | Rv_control_nanRATEK | TTTATGGTGCGGATGTCGTG |
| qPCR murA | | |
| 82 | Fw_qPCR_murA | GCGGGCATCAATATGCACAG |
| 83 | Rv_qPCR_murA | GATCCAGAACGTCCCGAAAC |
| KO LacZ | | |
| 84 | Fw_KO_lacZ | CATAATGGATTTCCTTACGCGAAATACGG GCAGACATGGCCTGCCCGGTTATTAGTGT AGGCTGGAGCTGCTTC |
| 85 | Rv_KO_lacZ | GTATGTTGTGTGGAATTGTGAGCGGATAA CAATTTCACACAGGAAACAGCTCATATGA ATATCCTCCTTAG |
| 86 | Fw_control_lacZ | GCGGTTGGAATAATAGCG |
| 87 | Rv_control_lacZ | CAGGTTTCCCGACTGGAAAG |
| KI prom-LacY | | |
| 88 | Fw_KI_P22LacY | TCGCTGAACTTGTAGGCCTGATAAGCGCA GCGTATCAGGCAATTTTATAATTTAAGCG ACTTCATTCACCTGACG |
| 89 | Rv_KI_P22LacY | GTATGTTGTGTGGAATTGTGAGCGGATAA CAATTTCACACAGGAAACAGCGTGGAACG GAAGCTGAGTTG |
| 90 | Fw_control_KIP22LacY | ACGCTTGTTCCTGCGCTTTG |
| 91 | Rv_control_KIP22LacY | TTATGCTTCCGGCTCGTATG |

TABLE 3

List of all used strains

| code | genotype | Reference |
|---|---|---|
| E. coli sTOPO | Escherichia coli One Shot TOP 10 Electro-comp ™ | Life Technologies |
| E. coli sWT | Escherichia coli K12 MG1655 | ATCC |
| E. coli sDE3 | Escherichia coli K12 MG1655 ΔrecA ΔendA DE3 | (Ajikumar et al., 2010) |
| E. coli s3KO | Escherichia coli K12 MG1655 Δchb ΔchiA ΔnagZ | |
| E. coli sP22 | Escherichia coli MG1655 ibaG:: $TT_{TT}$-P22-cITCmurA | |
| E. coli sRND | Escherichia coli MG1655 ibaG:: $TT_{TT}$-PRND-RBSlibrary-cITCmurA | |
| E. coli sCOS | Escherichia coli sRND + pCOS | |
| E. coli sSA | Escherichia coli sRND ΔnanRATEK + pSA | |
| C. glutamicum sWT | Corynebacterium glutamicum 13032 | ATCC |

TABLE 4

Genomic sequences of promoter and 5'-UTR regions of the P22RBS-cITCmurA knock-in (sP22) and seven selected mutants from the derived library (sRND1-sRND7)

| SEQ ID NO: | Strain | Promoter and 5'-UTR sequence |
|---|---|---|
| 92 | sP22 | 5'- atttataaatttcttgacattttggaatagatgtgatataatgtgtacatatccatggcggccgctcta gaagaagcttgggatccgtcgacctcgaattcggaggaaacaaag |
| 1 | sRND1 | 5'- atttataaatttcttgacacagcatcggaactaccctataatgtgtacataaacacaagctcaacat atactagacaaagtcaggc |
| 2 | sRND2 | 5'- atttataaatttcttgacaactaacactacagagattataatgtgtacataaacacaagctcaacata tactagacaaagtcaggc |
| 3 | sRND3 | 5'- atttataaatttcttgacattttggaatagatgtgatataatgtgtacataaacacaagctcaacctat actagagaagtcaggc |
| 4 | sRND4 | 5'- atttataaatttcttgacatatagtagatatcaccataatgtgtacataaacacaagctcatcctat actagaggaagtcaggc |
| 5 | sRND5 | 5'- atttataaatttcttgacaggacgtcgccagcgcgctataatgtgtacataaacacaagctcatcct atactagaggaagtcaggc |
| 93 | sRND6 | 5'- atttataaatttcttgacaaacataggaataaattttataatgtgtacataaacacaagctcaacatat actaggcaaagtcaggc |
| 94 | sRND7 | 5'- atttataaatttcttgacaggaggtgacaattaacctataatgtgtacataaacacaagctcagcat atactagagaaagtcaggc |

3. Plasmids

All plasmids used in this study are listed in Table 5. All plasmids were constructed using Circular Polymerase Extension Cloning (CPEC) assembly (Quan and Tian 2009). DNA oligonucleotides were purchased from IDT and are listed in Table 2. All E. coli expression vectors contained a pBR322 origin of replication (Prentki and Krisch 1982) except for the pIndicator plasmid that contained a pSC101 origin of replication (Kazuo and Mitsuyo 1984) and for the pHBP plasmid that contained the p15A origin of replication (Selzer et al., 1983). The pIndicator plasmid was provided with a kanamycin resistance marker (Pridmore 1987), p_P22RBS-cITCmurA, p_PRND-cITCmurA and p_P22LacY, with a chloramphenicol resistance marker (Alton and Vapnek 1979), pHBP with a spectinomycin resistance marker (Bose, Fey, and Bayles 2013) and the production plasmids pCOS, pSA, and pLNT with an ampicillin resistance marker (Hedges and Jacob 1974).

The pCOS production plasmid was based on the pCXhP14-mKATE2 expression vector (origin, antibiotic resistance and P14 promoter and RBS (De Mey et al., 2007; Aerts et al., 2011; Shcherbo et al., 2009)). The sequence of the chitin synthase was obtained from Rhizobium sp. GRH2 (NodC, Genbank accession code: AJW7624371 (Hamer et al., 2015)). The pSA production plasmid used was constructed as described by Peters et al. (Gert Peters et al., 2018). The pLNT production plasmid was based on the pSA vector (Gert Peters et al., 2018). The CMP-Neu5 Ac synthetase was obtained from Campylobacter jejuni strain ATCC 43438 (NeuA, Genbank access code: AF400048) (Fierfort and Samain 2008). The sequence for the α-2,3-sialyltransferase was obtained from Neisseria meningitidis (NST, Genbank accession code: U60660).

The pIndicator plasmid was provided with a lambda-promoter PR (Ptashne 2004), derived from the pDAWN plasmid (Ohlendorf et al., 2012) that drove the fluorescent mKATE2 reporter (Shcherbo et al., 2009) derived from the in-house pCXhP22-mKATE2 plasmid. The p P22RBS-cITCmurA plasmid was composed of the cI repressor gene with LVA tag, derived from the pDAWN plasmid (Ohlendorf et al., 2012), translationally coupled to the first 1000 bp of the murA coding sequence derived from the E. coli genome. An FRT-site flanked chloramphenicol cassette was cloned from the pKD3 plasmid (Datsenko and Wanner 2000) and the P22 promoter and RBS (De Mey et al., 2007) were derived from the in-house pCXhP22-mKATE2 plasmid. Detailed maps of all plasmids are provided in FIGS. 3A-3E.

The introduction of degenerated DNA sequences, resulting in the p_PRND-cITCmurA plasmid, was performed using single strand assembly (SSA), as described in the 2-P CPEC protocol of Coussement et al. (Coussement et al., 2017). Oligonucleotidess used for randomization are summarized in Table 2. Sequencing confirmed the full and partial randomization of the promoter and 5'-UTR region, respectively.

The pHBP plasmid was constructed by golden gate assembly (Coussement et al., 2017) whereby codon optimized glmU from C. glutamicum is controlled by a PTrc promoter (Nielsen and Voigt 2014), with IPTG as inducer, codon optimized glmS*54 is controlled by a PTet promoter, with anhydrinetetracycline (aTc) as inducer (Nielsen and Voigt 2014) and nodC is controlled by the constitutive promoter P14 (De Mey et al., 2007).

The pCOSCg production plasmid for Corynebacterium glutamicum is based on the pEKEx3 E. coli/C. glutamicum shuttle vector (Stansen et al., 2005). The constitutive P14 promoter (De Mey et al., 2007) controlled the nodC expression. The sequence of the chitin synthase was obtained from Rhizobium sp. GRH2 (NodC, Genbank accession code: AJW7624371 (Hamer et al., 2015)). The pSACg production plasmid for Corynebacterium glutamicum is based on the pEKEx3 E. coli/C. glutamicum shuttle vector (Stansen et al., 2005). The constitutive P14 promoter (De Mey et al., 2007) controlled the NeuC and NeuB1 expression. The sequence of the UDP-N-acetylglucosamine 2-epimerase and N-acetylneuraminic acid synthase were obtained from Campylobacter jejuni strain ATCC 43438 (NeuC and NeuB1, respectively, Genbank access code: AF400048).

TABLE 5

Overview of the used, constructed and characterized plasmids

| Plasmid name | Description | Reference |
|---|---|---|
| pKD46 | Helper plasmid for genome modification (λ-Red recombinase) | (Datsenko and Wanner 2000) |
| pCP20 | Helper plasmid for genome modification (FLP recombinase) | (Datsenko and Wanner 2000) |
| pKD3 | FRT-CmR-FRT | (Datsenko and Wanner 2000) |
| pKD4 | FRT-KanR-FRT | (Datsenko and Wanner 2000) |
| pDAWN | pFixK2-cI-PR$_{lambda}$-MCS | (Ohlendorf et al., 2012) |
| pCXhP22-mKate2 | pBR322-P22-mKATE2 | (Aerts et al., 2011; Shcherbo et al., 2009) |
| pCXhP14-mKate2 | pBR322-P14-mKATE2 | (Aerts et al., 2011; Shcherbo et al., 2009) |
| pCOS | pBR322-P14-nodC | |
| pSA | pBR322-PFAB46(mut)-RBS$_{T7}$-neuC-neuB1 | (Gert Peters et al., 2018) |
| pIndicator | pSC101-PR$_{lambda}$-mKATE2 | |
| p_P22-cITCmurA | TT$_{T7}$-FRT-CmR-FRT-P22-RBS-cI'-TCC-'murA' | |
| p_PRND-cITCmurA | TT$_{T7}$-FRT-CmR-FRT-PRND-RBS$_{library}$-cI'-TCC-'murA' | |
| P_P22LacY | TT$_{T7}$-FRT-CmR-FRT-P22-lacY | |
| pHBP | p15A-PTrc-glmU-PTet-glmS*54-P14-nodC-lacIq | |
| pLNT | pBR322-PFAB46(mut)-RBS$_{T7}$-neuC-neuB1-P14-nst-neuA | |
| pCOSCg | pEKE-P14-nodC | |
| pSACg | pEKE-P14- neuC-neuB1 | |

4. Media

Lysogeni broth (LB) medium consisted of 10 g/L tryptone peptone (Difco, Belgium), 5 g/L yeast extract (Difco) and 10 g/L NaCl and was autoclaved for 21 minutes at 121° C. Luria Bertani Agar (LBA) is similarly composed to LB, be it for the addition of 10 g/L agar. Minimal medium contained 2 g/L NH+CL, 5 g/L (NH$_4$)$_2$SO$_4$, 3 g/L KH$_2$PO$_4$, 7.3 g/L K$_2$HPO$_4$, 8.4 g/L MOPS, 0.5 g/L NaCl, 0.5 g/L MgSO$_4$.7H$_2$O, and 16.5 g/L glucose.H$_2$O or 15.3 g/L glycerol as carbon source, 1 mL/L trace element solution and 100 µL/L molybdate solution. Trace element solution consisted of 3.6 g/L FeCl$_2$·4H$_2$O, 5 g/L CaCl$_2$·2H$_2$O, 1.3 g/L MnCl$_2$·2H$_2$O, 0.38 g/L CuCl$_2$·2H$_2$O, 0.5 g/L CoCl$_2$.6H$_2$O, 0.94 g/L ZnCl$_2$, 0.0311 g/L H$_3$BO$_4$, 0.4 g/L Na$_2$EDTA. 2H$_2$O, 1.01 g/L thiamine·HCl. The molybdate solution contained 0.967 g/L Na$_2$MoO$_4$·2H$_2$O. To avoid Maillard reaction and precipitation during sterilization of the shake flask medium, the glucose and magnesium sulphate were autoclaved separately from the remaining salts. Glucose and magnesium sulphate were autoclaved in a 200 mL solution, the remaining salts in an 800 mL solution. Prior to autoclaving, the latter was set to a pH of 7 with 1 M KOH. After autoclaving, these two solutions were cooled down and mixed. Subsequently, the trace element and molybdate solutions were added filter-sterilized with a bottle top filter (Corning PTFE filter, 0.22 µm). If required, the culture medium was supplemented with appropriate antibiotics. Stock concentrations for antibiotics were 100 mg/mL for spectinomycin, 100 mg/mL for ampicillin, 25 mg/mL for chloramphenicol, and 50 mg/L for kanamycin. Antibiotic stocks were diluted 1000× for cell culture experiments. If required, the culture medium was supplemented with inducers.

Brain Heart Infusion (BHI) medium is used as liquid medium for growth as well as basis for agar medium used when working with C. glutamicum strains. The liquid medium consists of 12.5 g/L brain infusion solids, 5.0 g/L beef heart infusion solids, 10.0 g/L proteose peptone, 2.0 g/L glucose, 5 g/L NaCl and 2.5 g/L disodium phosphate. The mixture is bought ready-made from Sigma-Aldrigh (USA). In case BHI agar is needed 12 g/L agar is added before autoclaving. If required, the culture medium was supplemented with appropriate antibiotics. Stock concentrations for antibiotics were 250 mg/mL for spectinomycin, 5 mg/mL for chloramphenicol, and 25 mg/L for kanamycin. Antibiotic stocks were diluted 1000× for cell culture experiments. If required, the culture medium was supplemented with inducers.

CGXII medium is used as synthetic medium for *C. glutamicum*. To make CGXII agar plates 12 g/L agar is added. CGXII medium contained 20 g/L $(NH_4)_2SO$, 1 g/L $KH_2PO_4$, 1 g/L $K_2HPO_4$, 0.25 g/L $MgSO_4 \cdot 7H_2O$, 10 mg/L $CaCl_2$), 42 g/L MOPS, 0.2 mg/L Biotin, 1 mL/L Trace elements solution, 1 mL/L 3% Protocatechuic acid solution, 100 mL/L 40% glucose solution. The trace elements solution consisted of 10 g/L $FeSO_4 \cdot 7H_2O$, 10 g/L $MnSO_4 \cdot H_2O$, 1 g/L $ZnSO_4 \cdot 7H_2O$, 0.2 g/L $CuSO_4 \cdot 5H_2O$, 20 mg/L $NiCl_2 \cdot 6H_2O$. The glucose solution is made separately and autoclaved. The trace elements solution is made and components are dissolved by adding concentrated HCl until a final pH of about 1 is reached. This solution is sterilized via filter sterilization. The protocatechuatic acid is dissolved in diluted NaOH in $H_2O$, sterilized via filtration and stored at 4° C. The CGXII medium is made by dissolving all components except the trace elements, glucose and protocatchuate in 798 mL. The solution is brought to pH 7 and sterilized by autoclaving at 121° C. for 21 minutes (1 atm overpressure). After autoclaving the three remaining components are added once the solution is lukewarm.

5. Culture Conditions, Optical Density (OD) Measurements

For strain engineering and plasmid construction strains were grown in lysogeny broth (LB) at 30° C. with shaking (200 rpm, LS-X AppliTek orbital shaker, Nazareth, Belgium).

In vivo library evaluation was performed in 96-well flat-bottomed microtiter plates (MTP, Greiner) at 30° C. with shaking (200 rpm, LS-X AppliTek orbital shaker, Nazareth, Belgium).

For growth experiments, *E. coli* and *C. glutamicum* strains were plated on LBA or BHI agar medium, respectively, with appropriate antibiotics for maintenance and selection of the various plasmids used, incubated for 16 hours at 30° C. and a single colony was used for a preculture. For flask experiments, precultures were grown in 50 ml centrifuge tubes containing 10 ml LB or BHI medium, respectively, with the necessary antibiotic for selection pressure. Pre-cultures were grown overnight (16 hours) at 30° C. and 200 rpm (LS-X AppliTek orbital shaker, Nazareth, Belgium) and subsequently, used for 1% inoculation of 100 ml glucose defined medium, i.e., minimal medium or CGXII medium respectively, in 500 ml shake flasks and grown at 30° C. and 200 rpm (LS-X AppliTek orbital shaker, Nazareth, Belgium). At regular intervals, samples for extracellular metabolites analysis were collected and optical density (OD) at 600 nm is determined. For 24-well deep well plates (DWP) experiments, precultures were grown in 50 ml centrifuge tubes containing 10 ml LB or BHI medium, respectively, with the necessary antibiotic for selection pressure. Pre-cultures were grown overnight (16 hours) at 30° C. and 200 rpm (LS-X AppliTek orbital shaker, Nazareth, Belgium) and subsequently, used for 1% inoculation of 3 ml glucose defined medium, i.e., minimal medium or CGXII, respectively, in 24-well DWP plates with sandwich covers (EnzyScreen, Heemstede, The Netherlands) and grown at 30° C. and 200 rpm (LS-X AppliTek orbital shaker, Nazareth, Belgium). In 24-well DWPs, cultures were sampled at regular intervals for extracellular metabolite analysis and OD measurement. OD was measured at 600 nm using a Jasco V-630Bio spectrophotometer (Easton, UK).

6. Cell Fitness and In Vivo Fluorescence Measurements for Library Evaluation and Strain Characterization For screening purposes 276 colonies were picked randomly with an automated colony-picker (QPix2, Genetix) and inoculated into sterile 96-well flat-bottomed microtiter plates (Greiner) enclosed by a sandwich cover (Enzyscreen, Leiden, Netherlands) containing 150 μL minimal medium per well, supplemented with appropriate antibiotics and grown overnight on a Compact Digital Microplate Shaker (Thermo Scientific) at 800 rpm and 30° C. Subsequently, these cultures were 1:200 diluted in 150 μL of fresh minimal medium containing the appropriate antibiotics and were cultured for 24 hours at 30° C. and measured every 20 minutes for fluorescence and optical density using a Tecan M200 infinite PRO (Tecan, Mechelen, Belgium). Excitation and emission wavelengths were 588 and 633 nm respectively. Optical density was measured for biomass correction and for maximal growth rate calculations at a wavelength of 600 nm. Data collection was based on single colony measurements, except for sWT and sWT+strains that were analyzed in triplicate.

For strain characterization, a similar protocol is adopted with the exception that strains are not randomly picked and 3 biological replicates were analysed (n=3). Strains were analysed using a Biotek Synergy H1 (Biotek, Vermont, USA), excitation, emission and optical density wavelengths were identical.

7. Culture Conditions for Glycan Biosynthesis

Chitopentaose biosynthesis experiments were performed in defined medium (minimal medium for *E. coli* and CGXII medium for *C. glutamicum*) supplemented with the appropriate antibiotics. Experiments were performed for 24 hours, in triplicate (n=3), in pyramide-bottom square 24-deepwell microplates (0.5 ml) (Enzyscreen, Heemstede, The Netherlands) at 30° C. with shaking (250 rpm/50 mm).

Sialic acid biosynthesis experiments were performed in defined medium (minimal medium for *E. coli* and CGXII medium for *C. glutamicum*) supplemented with the appropriate antibiotics. Experiments were performed for 48 hours, in duplicate (n=2), in 250 ml shake flasks (25 ml) at 30° C. with shaking (250 rpm/50 mm).

8 UDP-GlcNAc Pool Determination for Strain Characterization

UDP-GlcNAc was extracted from the wild type strain (sWT) and the seven library strains (sRND1-7) that were cured from their pIndicator plasmid, in 3 biological replicates (n=3) unless stated otherwise. Strains were cultivated in minimal medium until the mid-exponential phase in pytamid-bottom square 24-deepwell microplates (0.5 ml) (Enzyscreen, 150 Heemstede, The Netherlands) at 30° C. with shaking (250 rpm/50 mm).

9. Sample Preparation

For chitopentaose biosynthesis, first 0.1 mL broth was diluted 10 times in physiological water for OD600 measurements in a Jasco V-630Bio spectrophotometer (Easton, UK). Subsequently, 0.3 mL broth was centrifuged at 14000 rpm for 10 minutes. The supernatant was stored at −80° C. for the analysis of extracellular metabolites. Pellets were stored at −80° C. until further use. Pellets were resuspended in 100 μL 60% ACN, vortexed and centrifuged at 14000 rpm for 10 minutes. The supernatant was subsequently applied for COS analysis. UDP-GlcNAc samples were prepared identically, but were resuspended in 200 μL 60% ACN before analysis.

Sialic acid synthesis samples were collected by collecting 2 mL broth, measuring OD600 as described above, and centrifuged at 14000 rpm for 10 minutes. The supernatant was subsequently stored at −80° C. for SA analysis.

10. HPLC-ELSD/ESI-MS Analysis

The applied HPLC-ELSD/ESI-MS method was developed based on the methods described (Leijdekkers et al., 2011; Remoroza et al., 2012). Analyses of COS were performed using a Shimadzu HPLC system (Shimadzu, Jette, Belgium) coupled to an evaporative light scattering detector or/and an ESI-MS-detector. COS were separated by hydrophilic interaction chromatography (HILIC) using a Kinetix 2.6_HILIC 100A column (2.6_m, 4.6 mm×150 mm; Phenomenex, Utrecht, The Netherlands) in combination with an appropriate SecurityGuard ULTRA Cartridge.

Glycan molecules were analyzed on a Waters ACQUITY UPLC system (Waters, Milford, MA, USA). Chitopentaose was separated by hydrophilic interaction chromatography (HILIC) using an ACQUITY UPLC BEH Amide 1.7 μm column (2.1×100 mm, Waters) connected to a ELSD detector. Sialic acid was separated by ion exclusion chromatography using a Rezex ROA-Organic Acid H+8 μm column (7.8×300 mm, Phenomenex) connected to a UV-detector. Detailed information is summarized in Table 6. Sialyllactose was separated using an ACQUITY UPLC BEH Amide, 130 A, 1.7 μm column (2.1 mm×50 mm) connected to a ELSD detector. A mixture of 75/25 acetonitrile/water solution with 1% formic acid was used as mobile phase. The flow rate was set to 0.130 mL/minute and the column temperature to 35° C. Lacto-N-tetraose was separated using an XBridge UPLC BEH Amide 1.8 μm 2.1×100 mm Column (Waters). Chromatographic conditions involved 1 μL sample injection, gradient elution of acetonitrile/water with 0.1% formic acid at 50° C. and at a flow rate of 0.3 ml/minute.

UDP-GlcNAc analysis was performed on a Dionex ICS-3000 (Thermo Scientific) using a Carbopac PA20 column (Thermo Scientific) and a ICS-5000 electrochemical detector cell (Thermo Scientific). Flow rate was set to 0.5 ml/minute, column temperature at 30° C. 5 μL sample was injected, the elution profile was isocratical and eluent consisted of 500 mM acetic acid and 100 mM NaOH.

11. TLC Analysis

The different chitooligosaccharides (fully acetylated chitopentamers, fully acetylated chitotetramers) are analyzed using thin layer chromatography (TLC). The TLC plates used are HPTLC silica gel 60$F_{254}$ plates (Merck). The eluent comprises butanol, methanol, 25% $NH_3$ and $H_2O$ with ratio 5:4:2:1. Spots of 3 UL sample (supernatant) or standard solution are applied to the TLC plate. Next, the TLC plates are placed in the equilibrium tank and the eluent allowed to develop. The plates are then removed from the tank and quickly dried. Subsequently the TLC plate is stained with 30% [w/v] $NH_4HSO_4$ and heat up till 500° C. to visualize the components under UV-light. The standard solutions are 10 g/L glucose, 10 g/L GlcNAc, and 10 g/L COS mixture (15% fully acetylated chitotetramers (A4), 85% fully acetylated chitopentamers (A5)).

12. Quantitative PCR

Quantitative PCR was performed on the wild type strain (sWT) and the seven library strains (sRND1-7) that were cured from their pIndicator plasmid. Measuring the expression levels, RNA was isolated from 3 biological replications (n=3); mid-exponentially growing E. coli cells using RNA later in combination with a RNeasy Mini Kit (QIAGEN, Hilden, Germany). mRNA was subsequently stored at −80° C. until further use.

DNA was synthesized using a First Strand cDNA synthesis kit with random hexamers (Thermo Scientific). For the amplification of the three E. coli reference genes (cysG, hcaT and idnT) oligos were ordered as described in Zhou et al. (Zhou et al., 2011). QPCR oligos for murA are charted in Table 2.

QPCR was performed as a technical duplicate (n=2) using a CFX96 Touch™ Real-Time PCR Detection System (Bio-Rad, Hercules, CA, USA) and data was analysed using CFX manager Version 3.1.1517.0823 (Bio-Rad).

13. Sequencing

Every constructed plasmid was verified by sequencing. Genetic parts of interest were sequenced upon alteration (Knock-out, Knock-in). All sequencing was performed via sequencing services (Macrogen Inc.).

14. Data and Statistical Analysis

All data analysis was performed using pandas unless stated otherwise. Library evaluation and strain characterization consisted of maximal growth rate and fluorescent measurements. Maximal growth rates were determined by plotting the OD600 values in function of time and fitting Richards growth-model (Birch 1999). A fluorescent parameter was calculated by correcting each individual fluorescent data-point for its concurrent biomass (OD600), plotting them in function of time and scanning for a typical maximum.

TABLE 6

UPLC details and elution profile for glycan analysis

| | | Method | | |
|---|---|---|---|---|
| | Details | Time (min) | % A | % B |
| Chitopentaose | | | | |
| Column: | Acquity UPLC BEH Amide | 0 | 20 | 80 |
| Column temperature: | 45° C. | 2 | 20 | 80 |
| ELSD detector: | 40° C., Gain 400 | 7 | 50 | 50 |
| Eluens A: | 10 mM $NH_4$-formate in $H_2O$ | 7.26 | 65 | 35 |
| Eluens B: | 100% AcN | 7.75 | 65 | 35 |
| Injection volume: | 1 μL | 8.8 | 20 | 80 |
| Flow rate (mL/min) | 450 | 10 | 20 | 80 |
| Sialic acid | | | | |
| Column: | Rezex ROA-Organic Acid H+ | 0 | 100 | 0 |
| Column temperature: | ambient | 20 | 100 | 0 |
| UV-detector: | 205 nm | | | |
| Eluens A: | 5 mM $H_2SO_4$ | | | |
| Injection volume | 1 μL | | | |
| Flow rate (mL/min) | 0.200 | | | |

The cellular volumetric determination of the UDP-GlcNAc was determined based on a calibration curve and was calculated assuming an OD600 of $1.0=8\times10^8$ cells/ml, and assuming 1 fL volume per cell. Chromatogram analysis was performed using the Chromeleon 7.2 software package (Thermo Scientific).

Final glycan concentrations were determined based on a calibration curve, and were corrected for biomass by OD600 measurements in order to overcome influences that were caused by the differences in culturing methods. Chromatogram analysis was performed using the Openchrom 1.1.0 software package.

Example 1—Influence of Cell Envelope Synthesis on COS Production

Figure 4:
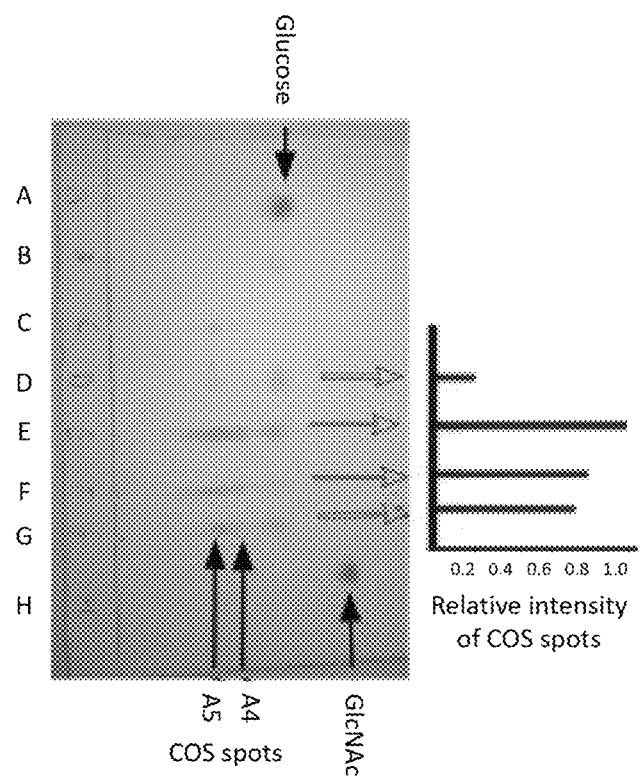
FIG. 4. TLC results of fosfomycin inhibition experiment with E. coli s3KO+pCOS. Legend: A. minimal medium (MM)+glucose; B. E. coli sWT grown on MM+glucose; C. chitooligosaccharides (COS)-mixture (15% fully acetylated chitotetramers (A4), 85% fully acetylated chitopentamers (A5)) (10 g/l); D. 0 mM fosfomycin; E. 0.1 mM fosfomycin; F. 0.25 mM fodfomycin; G. 1 mM fosfomycin; H. N-acetylglucosamine (GlcNAc). Bars are a measure for the intensity of the COS spots determined with ImageJ.
Figure 5:
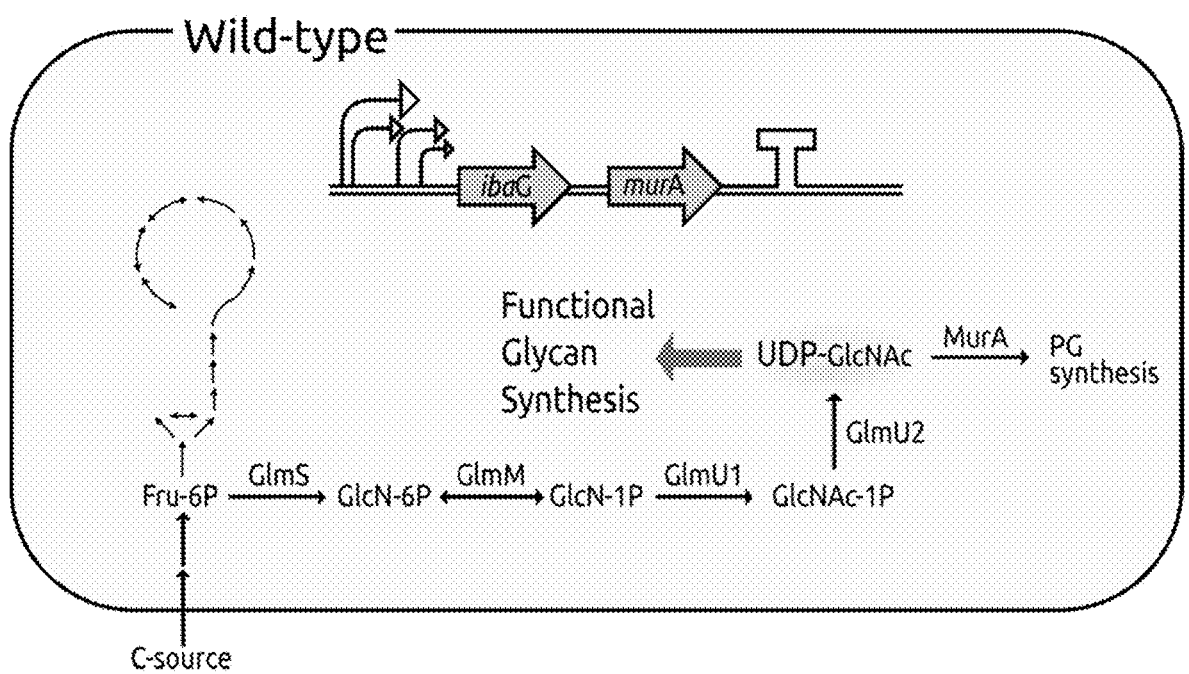
FIG. 5. The genetic situation of the wild-type Escherichia coli MG1655. Four predicted promoter (and operator) sites that drive the ibaG-murA operon (Weaver et al., 2014) and the pathway towards the UDP-GlcNAc pool are depicted. The gray arrow represents the branch point where heterologous pathways for complex carbohydrates may be installed.

To evaluate the potential of increasing UDP-GlcNAc supply for a UDP-derived product, i.e., COS titer, by decreasing the conversion of UDP-GlcNAc to at least one cell envelope precursors or component, *Escherichia coli* s3KO transformed with pCOS is grown on minimal medium with glucose until OD600 of 3 is reached. At that point, all cells are collected through centrifugation and resuspended in fresh minimal medium with glucose. This batch is divided in four sub-batches and various concentrations of fosfomycin are added, i.e., 0 mM, 0.1 mM, 0.25 mM and 1 mM, respectively. Subsequently, samples are taken for COS analysis. FIG. 4 gives the result of the TLC analysis of the corresponding cultures. Addition of fosfomycin to an *E. coli* culture has a positive effect on COS production. Hence, lowering the peptidoglycan synthesis results in an increased conversion of UDP-GlcNAc to COS.

Example 2—Engineering murA in *Escherichia coli*

Figure 6:
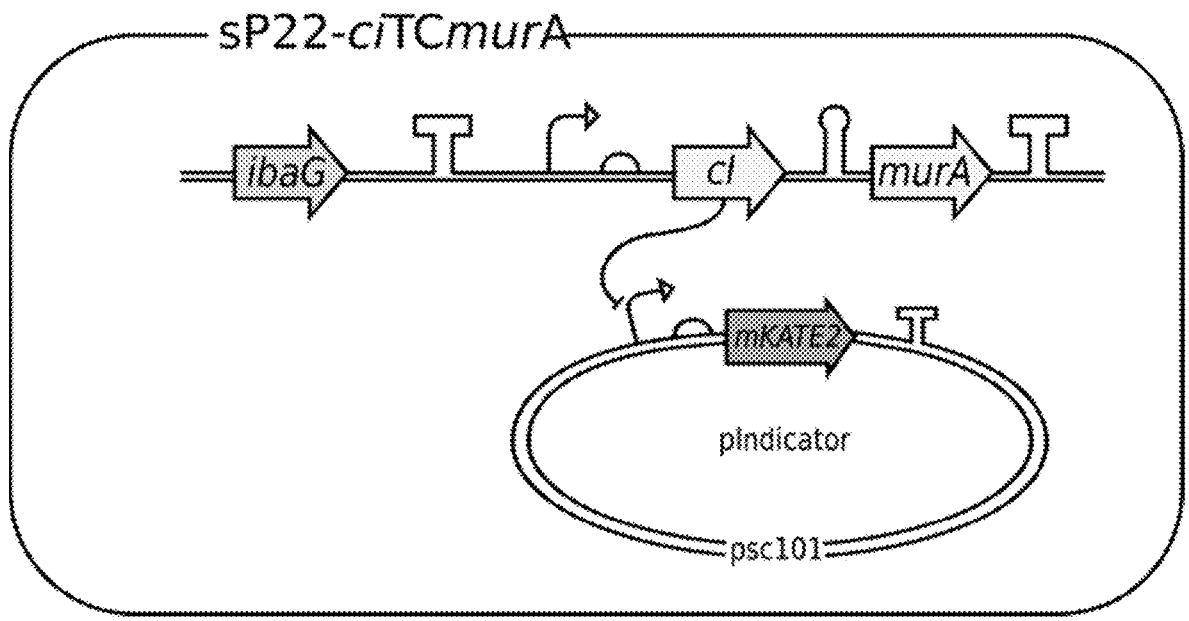
FIG. 6. The genetic situation after knocking in the targeted fragment generated from p_P22RBS-cITCmurA. The expression of cI represses the expression of mKATE2, converting the expression of murA into a measurable signal.
Figure 7:
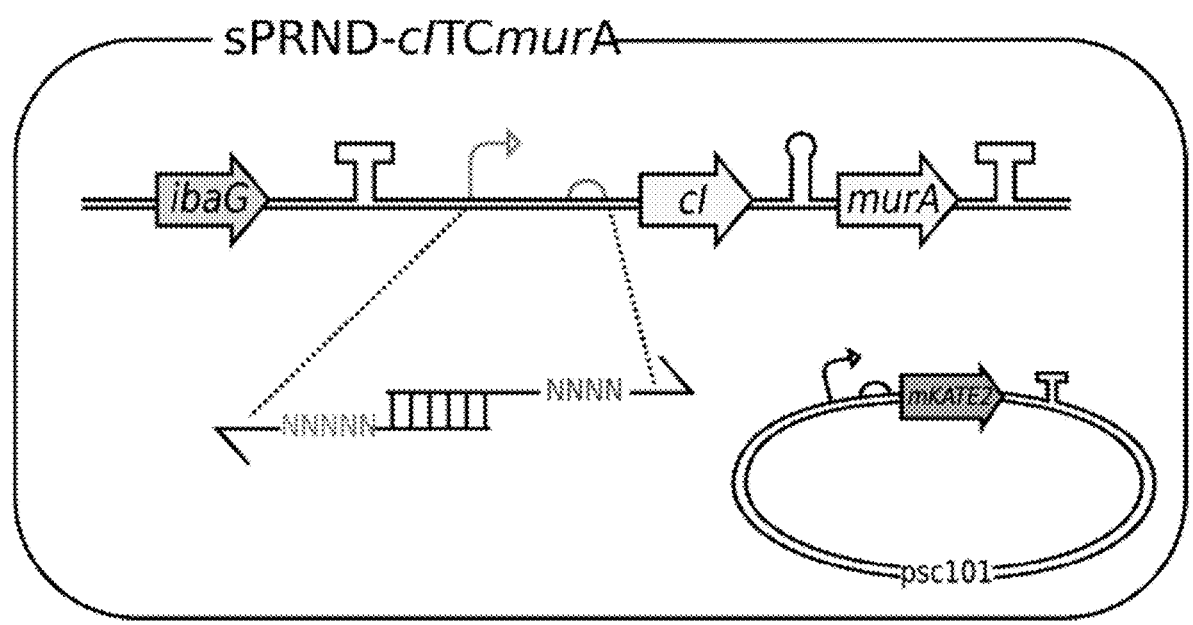
FIG. 7. The genetic situation after knocking in the targeted fragments generated from p_PRND-cITCmurA showing how expression randomization was effectuated and how it generated strain library sRND.
Figure 8:
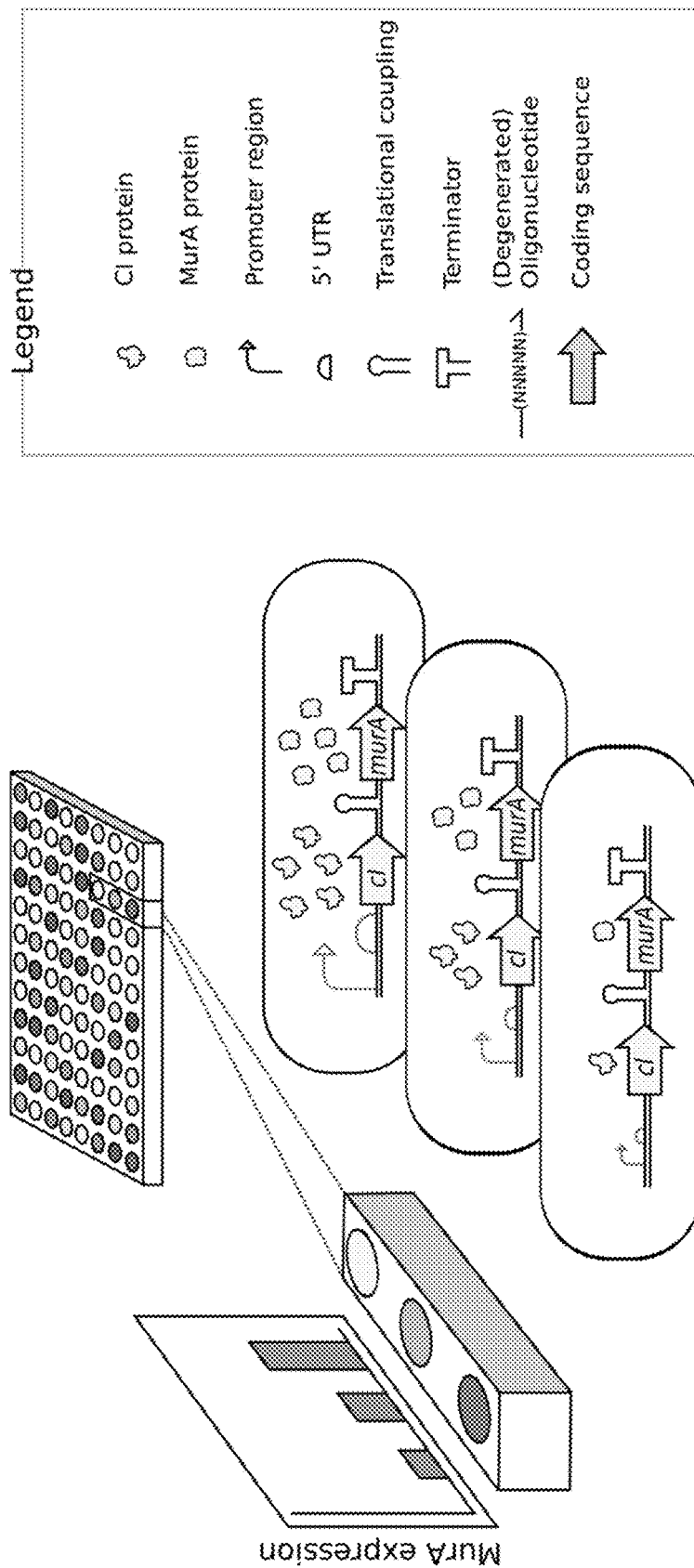
FIG. 8. The high-throughput MTP-based fluorescence screening of strain library sRND. Low expression of the cI repressor (and thus low murA expression), correlates with a high fluorescent signal, and vice versa.
Figure 9:
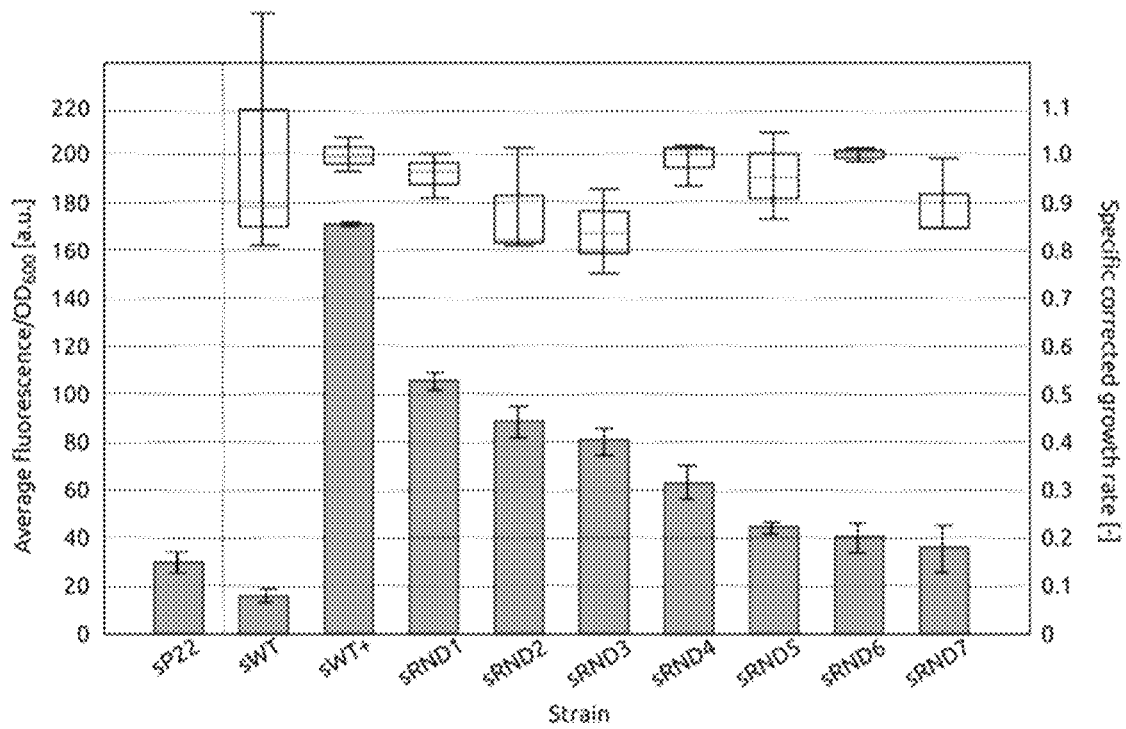
FIG. 9. Specific fluorescence and specific corrected maximal growth rate measurements for the seven selected mutant strain library (sRND). Bar plots show the average specific fluorescence per strain. Box plots indicate the distribution of the specific corrected maximal growth rate per strain. sWT, sWT+ (E. coli sWT carrying pIndicator) and sP22 are also depicted as control.
Figure 10:
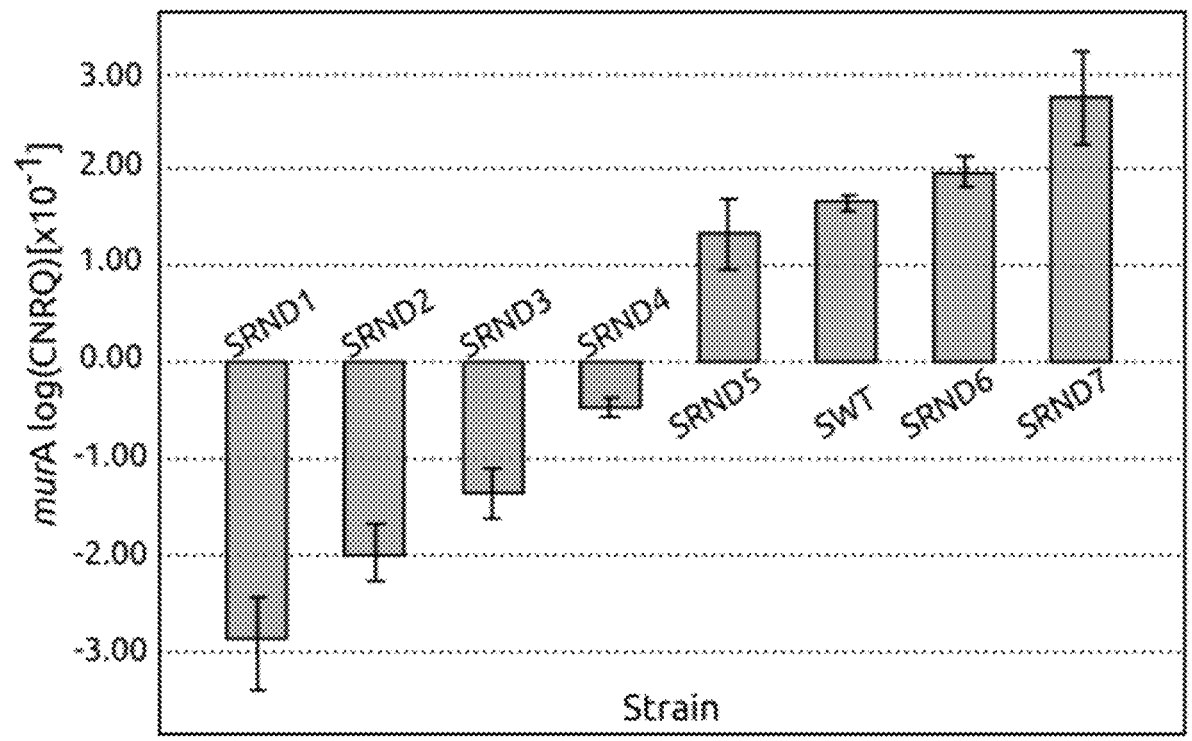
FIG. 10. qPCR data for murA of E. coli sRND1-7 and sWT. For each strain the mid-exponential average calibrated normalized relative quantity (CNRQ) of MurA mRNA and standard deviations of 3 biological and 2 technical replicates are depicted.
Figure 11:
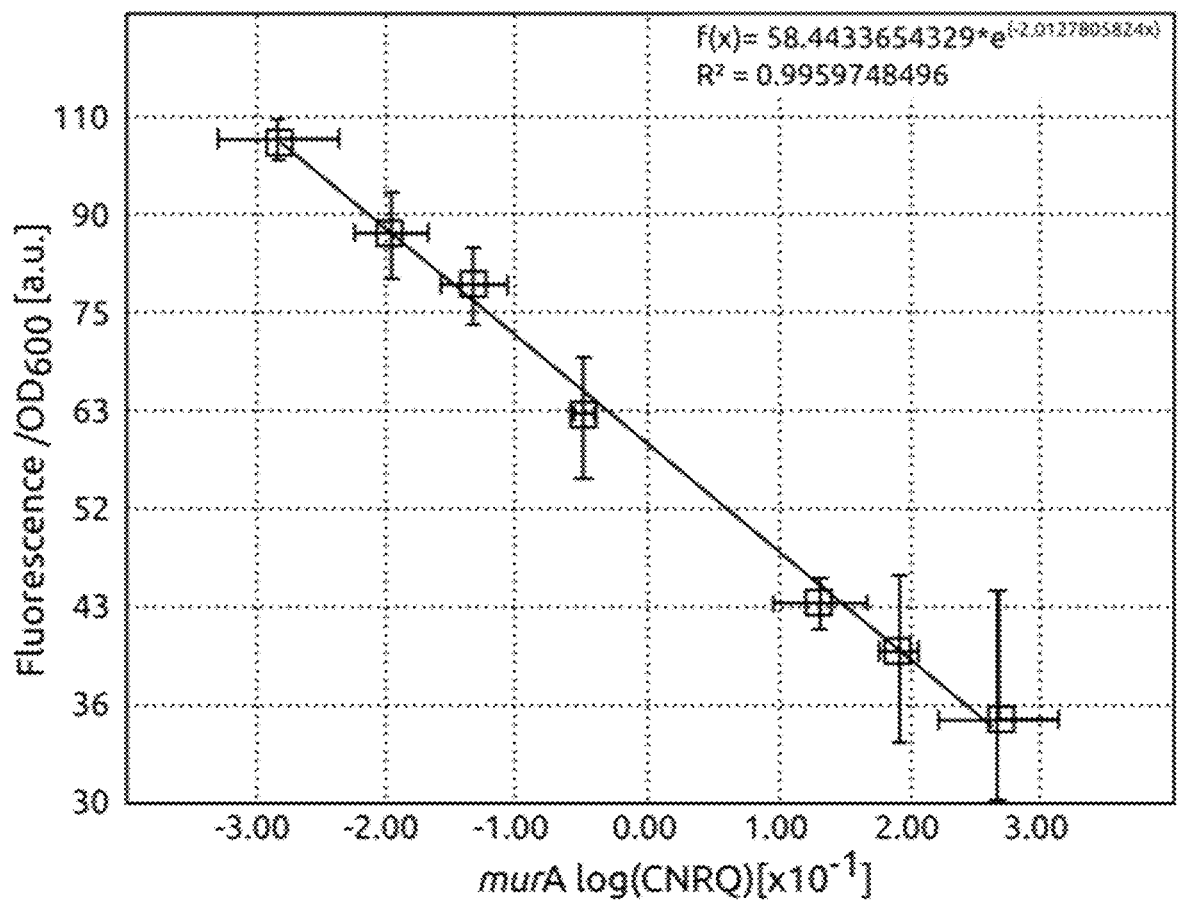
FIG. 11. Validation of the fluorescent high-throughput screening technique. mRNA levels of the E. coli sRND strains highly correlate with the specific fluorescence ($R^2$=0.9960)
Figure 12:
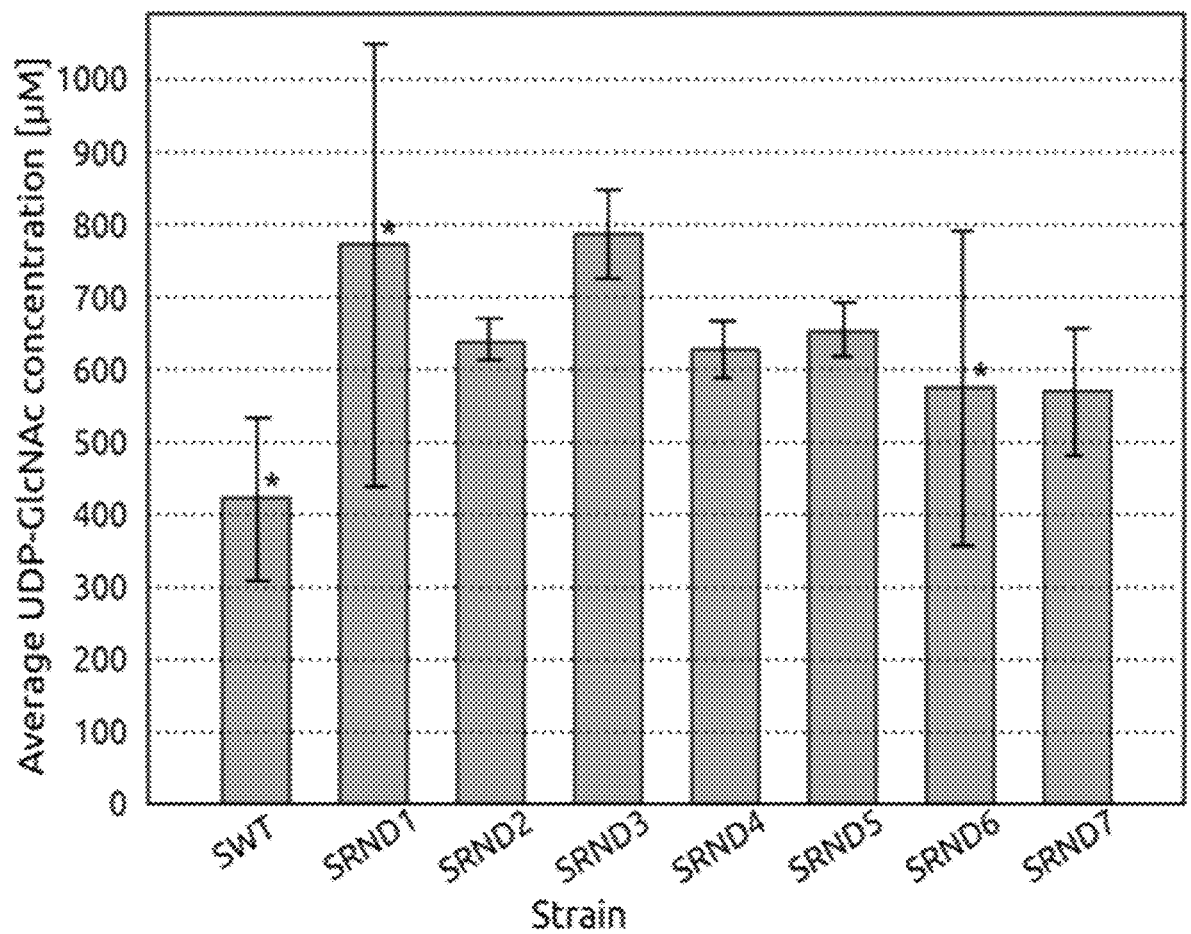
FIG. 12. The average cellular UDP-GlcNAc pools of mid-exponentially grown E. coli sRND1-7 and sWT, and standard deviations of 2 (3*) biological replicates are depicted. Cellular concentrations were assessed assuming an intracellular volume of 1 fL and 8*108 cells per OD600.

In order to explore the expression profile of MurA, which catalyzes the first committed step in the peptidoglycan synthesis pathway, its expression must be varied as widely as possible and, therefore, a high-throughput screening method is required (see FIGS. 5-8). To this end, *E. coli* sP22 is generated in which the endogenous ibaG-murA operon (FIG. 5) is replaced by cI gene translational coupled to murA under control of the P22RBS (FIG. 6). To convert the expression of MurA into a measurable signal, i.e., fluorescence, pIndicator is constructed. Next, the p_PRND_cITCmurA plasmid is constructed randomizing the promoter and 5'-UTR regions. The translationally coupled randomized conformations are installed in a pIndicator-mKATE2 containing *E. coli* sP22, yielding a phenotypically diverse strain library (*E. coli* sRND, FIG. 7) in terms of fluorescence levels (FIG. 8). From the library seven mutants are randomly selected (displaying a range of red intensity) and characterized in depth. FIG. 9 depicts the specific fluorescence and specific corrected maximal growth rate measurements. Analysis of variance indicated that the maximal growth rate of all the selected strains were comparable to one another (one-way ANOVA, p=0.5436, F=0.8906), despite the substantial variation in murA expression we anticipated. The ability of the selected strains to maintain their fitness, despite the diverse murA expression is further substantiated by qPCR (FIG. 10). Furthermore, the data clearly showed that the fluorescence is inversely correlated to the amount of MurA mRNA ($R^2=0.996$), validating the translationally coupled screening technique (FIG. 11). Two out of the seven selected strains (sRND6 and sRND7, with the lowest fluorescence) showed an increased MurA expression compared to the wild type strain (*E. coli* sWT) (FIG. 10). Investigating the peptidoglycan synthesis metabolic network and quantifying mutant UDP-GlcNAc pools, surprisingly resulted in comparable titers (FIG. 12). Analysis of variance confirmed that altering MurA expression does not affect UDP-GlcNAc levels (one-way ANOVA, p=0.4065, F=1.1384).

Example 3—Production of Fully Acetylated Chitopentaose in *Escherichia coli*

Figure 13:
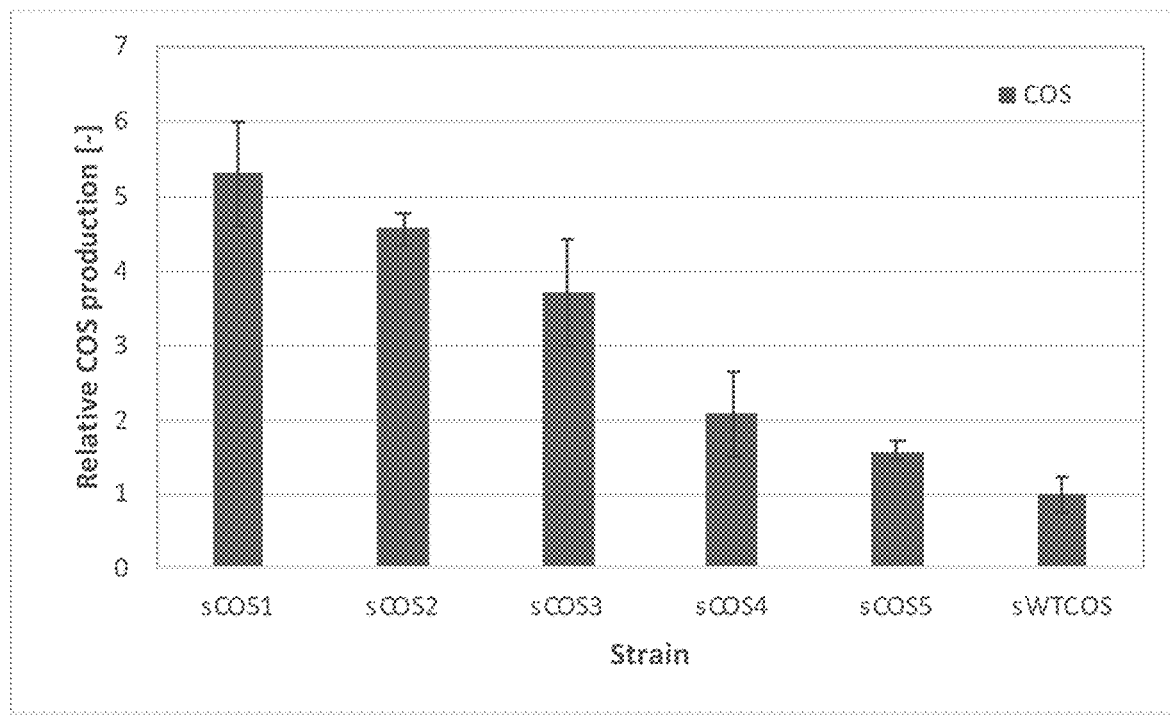
FIG. 13. Production of chitopentaose in E. coli sCOS1-5, relatively compared to the wild type production titre in sWTCOS. Error bars depict the propagated error.

For the production of fully acetylated chitopentaose *E. coli* sRND1-5 and sWT are transformed with pCOS yielding sCOS1-5 and sWTCOS, respectively. These metabolically engineered strains are grown in minimal medium with glucose. Production of chitopentaose is depicted in FIG. 13. Production titers for fully acetylated chitopentaose ranged from 1.58 up to 5.43 times that of sWTCOS.

Example 4—Production of N-Acetylneuramic Acid (Neu5Ac) in *Escherichia coli*

Figure 14:
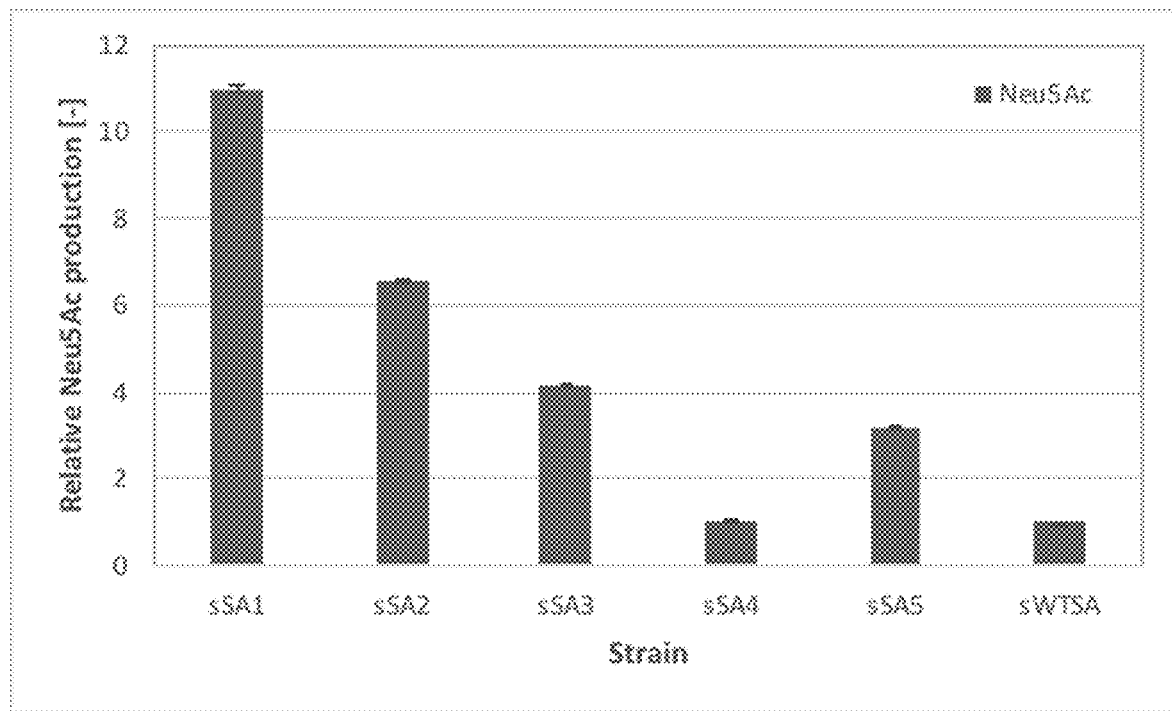
FIG. 14. Production of Neu5Ac in E. coli sSA1-5, relatively compared to the wild type production titre in sWTSA. Error bars depict the propagated error.

For the production of Neu5Ac, *E. coli* sRND1-5 and sWT were first made deficient in *E. coli*'s native catabolic sialic acid pathway, yielding sRNDΔnanRATEK1-5 and sWTΔnanRATEK, respectively. Next these metabolically engineered strains are transformed with pSA yielding sSA1-5 and sWTSA, respectively, and grown in minimal medium with glucose. Production of Neu5Ac is depicted in (FIG. 14. Specific production showed that the engineered MurA expression levels have a major impact on Neu5Ac synthesis. Upon decreasing MurA levels, *E. coli* sSA1-5 strains were able to produce up to 10.99 times that of *E. coli* sWTSA.

Example 5—Production of Lacto-N-Tetraose (LNT) in *Escherichia coli*

For the production of Lacto-N-tetraose, lacZ, coding for β-galactosidase, is knocked out to avoid lactose degradation and the expression of lacY, coding for a lactose permease, is ensured by means of a medium strong constitutive promoter in *E. coli* sRND1-5. Further, the genes lgtA and wbgO encoding β-1,3-N-acetylglucosaminyltransferase and β-1,3-galactosyltransferase, respectively, are expressed under control of the artificial promoter P14 from production plasmid pBR322 (pLNT). These metabolically engineered strains are grown in minimal medium with glucose, which is supplemented with 10 g/L lactose. Strains are cultivated in shake-flask and yielded mg amounts of LNT.

Example 6—Production of 3'-Sialyllactose

For the production of 3'-sialyllactose, lacZ, coding for β-galactosidase, is additionally knocked out to avoid lactose degradation and the expression of lacY, coding for a lactose permease, is ensured by means of a medium strong constitutive promoter in *E. coli* SRND1-5. The metabolically engineered *E. coli* strains additionally expresses UDP-N-acetylglucosamine 2-epimerase (NeuC), N-acetylneuraminic acid synthase (NeuB1), CMP-NeuAc synthetase (NeuA) obtained from *Campylobacter jejuni* and a α-2,3-sialyltransferase (NST) obtained from *Neisseria meningitidis*. These metabolically engineered strains are grown in minimal medium with glucose, which is supplemented with 10 g/L lactose. This system yielded mg amounts of 3'-sialyllactose.

Example 7—Engineering of murA in *Corynebacterium glutamicum*

For the engineering of MurA in *C. glutamicum* the gene murA2, coding for a UDP-N-acetylglucosamine 1-carboxyvinyltransferase (NCgl2470), is deleted yielding strain *C. glutamicum* sCg1. Additionally, the expression of murA1, coding for a UDP-N-acetylglucosamine 1-carboxyvinyltransferase (NCgl0345), is altered by replacing the endogeneous promoter and 5'-UTR sequence with the cognate promoter and 5'-UTR sequence of sRND2 in *C. glutamicum* sWT and sCg1 yielding *C. glutamicum* sCg2 and *C. glutamicum* sCg3, respectively.

Example 8—Production of N-Acetylneuramic Acid (Neu5Ac) in *Corynebacterium glutamicum*

For the production of N-acetylneuramic acid (Neu5Ac) in *C. glutamicum*, *C. glutamicum* sCg1-1 and sWT are first made deficient in *C. glutamicum*'s native catabolic sialic acid pathway, yielding *C. glutamicum* sCgΔnanA1-3 and sWTΔnanA, respectively. The metabolically engineered *C. glutamicum* strains additionally express UDP-N-acetylglucosamine 2-epimerase (NeuC) and N-acetylneuraminic acid synthase (NeuB1) obtained from *Campylobacter jejuni*. These metabolically engineered strains are grown in CGXII medium with glucose, which is supplemented with 10 g/L lactose. This system yielded mg amounts of Neu5Ac.

Example 9—Production of Fully Acetylated Chitopentaose in *Corynebacterium glutamicum*

For the production of fully acetylated chitopentaose *C. glutamicum* sCg1-1 and sWT additionally expresses the chitin synthase obtained from *Rhizobium* sp. GRH2 under the control of the artificial promoter P14 from plasmid pEXK3. These metabolically engineered strains are grown in CGXII medium with glucose.

Figure 15:
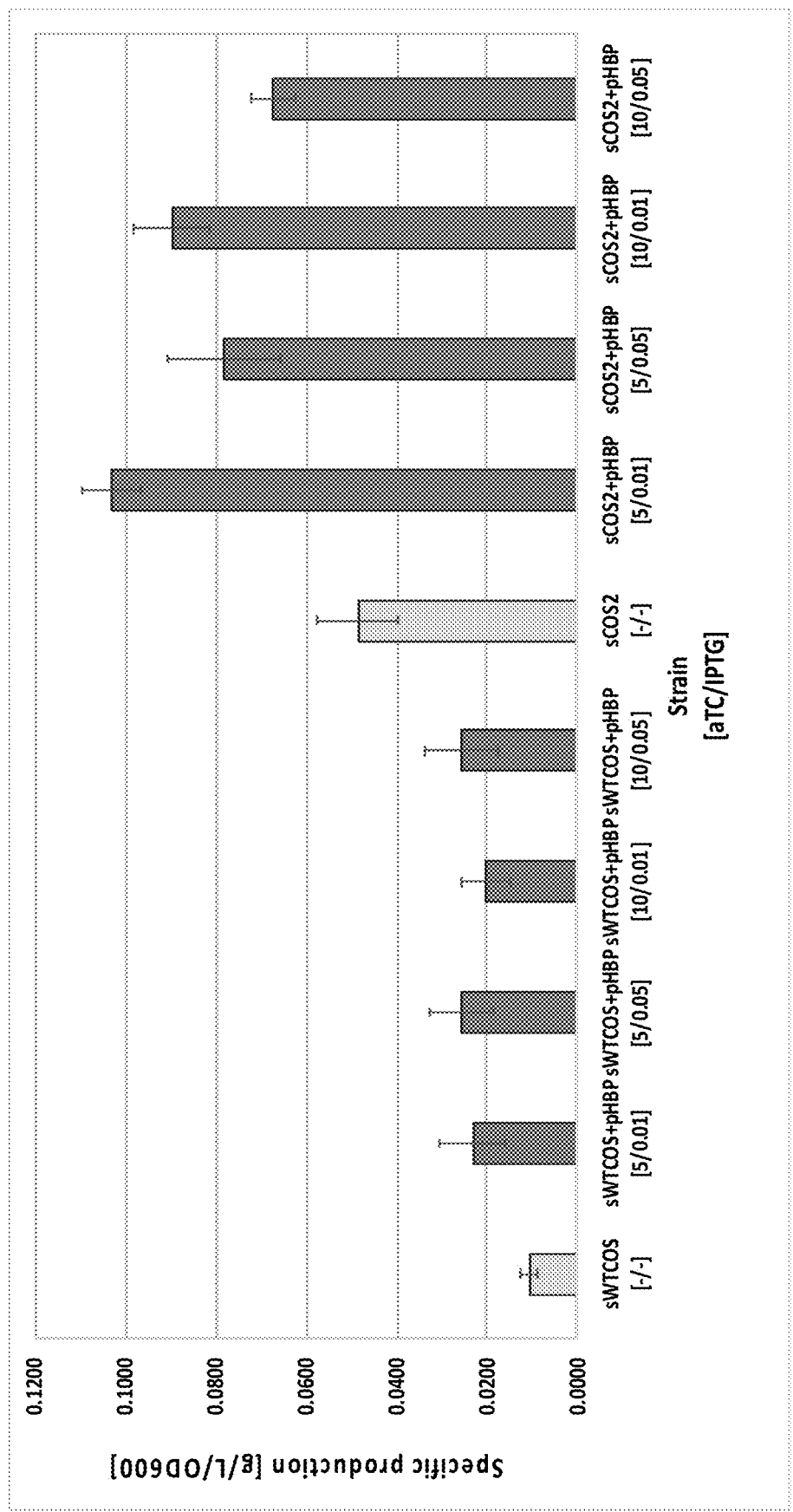
FIG. 15. Production of COS in E. coli sCOS2+pHBP, sWTCOS+pHBP, sCOS2 and sWTCOS grown in minimal medium with glucose and varies inducer concentrations: aTc/IPTG [mM/mM] of 5/0.01, 5/0.05, 10/0.01 and 10/0.05. Error bars depict the propagated error.

Example 10—Production of Fully Acetylated Chitopentaose in *Escherichia coli* with Optimized Hexosmanine Biosynthesis Pathway For COS production in *E. coli* with optimized hexosmanine biosynthesis pathway strain sWT and sRND2 additionally expresses a chitin synthase obtained from *Rhizobium* sp. GRH2 (NodC) under control of the constitutive promoter P14, a fused N-acetylglucosamine-1-phosphate uridyltransferase and glucosamine-1-phosphate acetyltransferase (GlmU) obtained from *Corynebacterium glutamicum* under control of a PTrc promoter and a L-glutamine: D-fructose-6-phosphate aminotransferase (GlmS) obtained from *E. coli* with three mutations A38T, R249C and G471S under control of a PTet promoter (pHBP) yielding sWTCOS+pHBP and sCOS2+pHBP, respectively. These metabolically engineered strains together with sCOS2 and sWTCOS are grown in minimal medium with varies inducer concentrations (aTc/IPTG [mM/mM]: 5/0.01, 5/0.05, 10/0.01 and 10/0.05]. FIG. 15 depicts the COS production. The sWTCOS+pHBP strain and sCOS2+pHBP strain were able to produce up to 2.2 and 6.8 times that of *E. coli* sWTCOS, respectively.

LIST OF ABBREVIATIONS USED IN THE TEXT

5'-UTR: 5' untranslated region
ADP: adenosine diphosphate
aTc: anhydrinetetracycline
CmR: chloramphenicol resistance
CDW: cell dry weight
CMP: cytidine-5'-monophosphate
CMP-Neu5Ac: CMP-N-acetylneuramic acid
CNRQ: calibrated normalized relative quantity
COS: chitooligosaccharide
CPEC: Circular Polymerase Extension Cloning
DWP: deep well plate
GalNAc: N-acetylgalactosamine
GDP: guanosine diphosphate
GG: Golden Gate
GH: glycoside hydrolase
Glc: glucose
GlcN: N-glucosamine
GlcNAc: N-acetylglucosamine
GlcUA: D-glucuronic acid
Gly: glycerol
GP: glycoside phosphorylase
GT: glycosyltransferase
HA: hyaleuronic acid
IPTG: isopropyl β-D-1-thiogalactopyranoside
KanR: kanamycin resistance
KO: knock-out
KI: knock-in
LB: lysogeni broth
LNT: lacto-N-tetraose
ManNAc: N-acetylmannosamine
MurNac: N-acetylmuramic acid
Neu5Ac: N-acetyl-neuramic acid
oCHS: oligomer chitin synthase
OD: optical density
P14: promoter 14 of the promoter library of De Mey et al. (De Mey et al., 2007)
P22: promoter 22 of the promoter library of De Mey et al. (De Mey et al., 2007)
Pyr: Pyruvate
pCHS: polymer chitin synthase
RBS: ribosome binding site
rpm: rotations per minute
SSA: single stranded assembly
TC: translational coupling
TCC: translational coupling cassette
TDP: thymidine diphosphate
TG: transglycosidase
UDP: uridine diphosphate
UDP-GalNAc: UDP-N-acetylgalactosamine
UDP-GlcNAc: UDP-N-acetylglucosamine
UDP-GlcUA: UDP-α-D-glucuronic acid
UDP-ManNAc: UDP-N-acetylmannosamine
UDP-MurNAc: N-acetylmuramic acid (MurNac)
WT: wild type

REFERENCES

Aerts, Dirk, Tom Verhaeghe, Marjan De Mey, Tom Desmet, and Wim Soetaert. 2011. "A Constitutive Expression System for High-Throughput Screening." *Engineering in Life Sciences* 11 (1): 10-19. doi.org/10.1002/elsc.201000065.

Agrawal, Neema, P V N Dasaradhi, Asif Mohmmed, Pawan Malhotra, Raj K Bhatnagar, and Sunil K Mukherjee. 2003. "RNA Interference: Biology, Mechanism, and Applications." *Microbiology and Molecular Biology Reviews: MMBR* 67 (4): 657-85. doi.org/10.1128/MMBR.67.4.657.

Aguilar-Uscanga, B, and J M Francois. 2003. "A Study of the Yeast Cell Wall Composition and Structure in Response to Growth Conditions and Mode of Cultivation." *Letters in Applied Microbiology* 37:268-74. doi.org/10.1046/j.1472-765X.2003.01394.x.

Ajikumar, Parayil Kumaran, Wen-hai Xiao, Keith E J Tyo, Yong Wang, Fritz Simeon, Effendi Leonard, Oliver Mucha, Too Heng Phon, Blaine Pfeifer, and Gregory Stephanopoulos. 2010. "Isoprenoid Pathway Optimization for Taxol Precursor Overproduction in *Escherichia Coli*." *Science* 330 (October): 70-74. www.sciencemag.org/content/330/6000/70.short.

Alper, Hal, Curt Fischer, Elke Nevoigt, and Gregory Stephanopoulos. 2005. "Tuning Genetic Control through Promoter Engineering." *Proceedings of the National Academy of Sciences of the United States of America* 102 (36): 12678-83. doi.org/10.1073/pnas.0504604102.

Alper, Hal, and Gregory Stephanopoulos. 2007. "Global Transcription Machinery Engineering: A New Approach for Improving Cellular Phenotype." *Metabolic Engineering* 9 (3): 258-67. doi.org/10.1016/j.ymben.2006.12.002.

Alton, N. K., and D. Vapnek. 1979. "Nucleotide Sequence Analysis of the Chloramphenicol Resistance Transposon Tn9." *Nature* 282 (5741): 864-69.

Antoine, Tatiana, Claude Bosso, Alain Heyraud, and Eric Samain. 2005. "Large Scale in Vivo Synthesis of Globotriose and Globotetraose by High Cell Density Culture of Metabolically Engineered *Escherichia Coli*." *Biochimie* 87 (2): 197-203. doi.org/10.1016/j.biochi.2004.10.010.

Avihoo, a., I. Gabdank, M. Shapira, and D. Barash. 2007. "<emphasis> In Silico</Emphasis>Design of Small RNA Switches." *IEEE Transactions on NanoBioscience* 6 (1): 4-11. doi.org/10.1109/TNB.2007.891894.

Balbás, Paulina, Mikhail Alexeyev, Inna Shokolenko, Francisco Bolivar, and Fernando Valle. 1996. "A PBRINT Family of Plasmids for Integration of Cloned DNA into the *Escherichia Coli* Chromosome." *Gene* 172 (1): 65-69. doi.org/10.1016/0378-1119 (96) 00028-5.

Balbás, Paulina, and Guillermo Gosset. 2001. "Chromosomal Editing in *Escherichia Coli*: Vectors for DNA Integration and Excision." *Molecular Biotechnology* 19 (1): 001-012. doi.org/10.1385/MB: 19:1:001.

Bernardi, Anna, and Pavel Cheshev. 2008. "Interfering with the Sugar Code: Design and Synthesis of Oligosaccharide Mimics." *Chemistry—A European Journal* 14 (25): 7434-41. doi.org/10.1002/chem.200800597.

Bertozzi, Carolyn R. 1995. "Cracking the Carbohydrate Code for Selectin Recognition." *Chemistry and Biology* 2 (11): 703-8. doi.org/10.1016/1074-5521 (95) 90096-9.

Bhan, Namita, Peng Xu, and Mattheos Ag Koffas. 2013. "Pathway and Protein Engineering Approaches to Produce Novel and Commodity Small Molecules." *Current Opinion in Biotechnology* 24 (6): 1137-43. doi.org/10.1016/j.copbio.2013.02.019.

Biggs, Bradley Walters, Chin Giaw Lim, Kristen Sagliani, Smriti Shankar, Gregory Stephanopoulos, Marjan De Mey, and Parayil Kumaran Ajikumar. 2016. "Overcoming Heterologous Protein Interdependency to Optimize P450-Mediated Taxol Precursor Synthesis in *Escherichia Coli*." *Proceedings of the National Academy of Sciences of the United States of America* 113 (12): 3209-14. doi.org/10.1073/pnas. 1515826113.

Biggs, Bradley Walters, Brecht De Paepe, Christine Nicole S Santos, Marjan De Mey, and Parayil Kumaran Ajikumar. 2014. "Multivariate Modular Metabolic Engineering for Pathway and Strain Optimization." *Current Opinion in Biotechnology* 29 (1): 156-62. doi.org/10.1016/j.copbio.2014.05.005.

Birch, Colin P. D. 1999. "A New Generalized Logistic Sigmoid Equation Compared with the Richards Growth Equation." *Annals of Botany* 83:713-23. doi.org/10.1006/anbo.1999.0877.

Boddy, Christopher, N., Ian C. Schoenhofen, Susan M. Logan, Dennis M. Whitfield, and Benjamin R. Lundgren. 2011. Cell-based production of nonulosonates. WO/2011/130836, PCT/CA2011/000449, issued 2011.

Boltje, T. J., T Buskas, and G. J. Boone. 2009. "Opportunities and Challenges in Synthetic Oligosaccharide and Glycoconjugate Research." *Nature Chemistry* 1 (8): 611-22.

Bose, Jeffrey L., Paul D. Fey, and Kenneth W. Bayles. 2013. "Genetic Tools to Enhance the Study of Gene Function and Regulation in *Staphylococcus Aureus*." *Applied and Environmental Microbiology* 79 (7): 2218-24. doi.org/10.1128/AEM.00136-13.

Brophy, J. A., C. A. Voigt, G. André, S. Even, H. Putzer, P. Burguière, C. Croux, et al. 2016. "Antisense Transcription as a Tool to Tune Gene Expression." *Molecular Systems Biology* 12 (1): 854-854. doi.org/10.15252/msb.20156540.

Bruyn, Frederik De, Maarten Van Brempt, Jo Maertens, Wouter Van Bellegem, Dries Duchi, and Marjan De Mey. 2015. "Metabolic Engineering of *Escherichia Coli* into a Versatile Glycosylation Platform: Production of Bio-Active Quercetin Glycosides." *Microbial Cell Factories* 14 (1): 138. doi.org/10.1186/s12934-015-0326-1.

Bruyn, Frederik De, Jo Maertens, Joeri Beauprez, Wim Soetaert, and Marjan De Mey. 2015. "Biotechnological Advances in UDP-Sugar-Based Glycosylation of Small Molecules." *Biotechnology Advances* 33 (2): 288-302. doi.org/10.1016/j.biotechadv.2015.02.005.

Bruyn, Frederik De, Brecht De Paepe, Jo Maertens, Joeri Beauprez, Pieter De Cocker, Stein Mincke, Christian Stevens, and Marjan De Mey. 2015. "Development of an in Vivo Glucosylation Platform by Coupling Production to Growth: Production of Phenolic Glucosides by a Glycosyltransferase of *Vitis Vinifera*." *Biotechnology and Bioengineering* 112 (8): 1594-1603. doi.org/10.1002/bit.25570.

Bryant, Jack a, Laura E Sellars, Stephen J W Busby, and David J Lee. 2014. "Chromosome Position Effects on Gene Expression in *Escherichia Coli* K-12." *Nucleic Acids Research* 42 (18): 11383-92. doi.org/10.1093/nar/gku828.

Byun, Seong Goo, Myoung Dong Kim, Won Heong Lee, Kun Jae Lee, Nam Soo Han, and Jin Ho Seo. 2007. "Production of GDP-L-Fucose, L-Fucose Donor for Fucosyloligosaccharide Synthesis, in Recombinant *Escherichia Coli*." *Applied Microbiology and Biotechnology* 74 (4): 768-75. doi.org/10.1007/s00253-006-0730-x.

Chang, Ching-Ming, Jeffy Chern, Ming-Yi Chen, Kai-Fa Huang, Chein-Hung Chen, Yu-Liang Yang, and Shih-Hsiung Wu. 2015. "Avenaciolides: Potential MurA-Targeted Inhibitors Against Peptidoglycan Biosynthesis in Methicillin-Resistant *Staphylococcus Aureus* (MRSA)." *Journal of the American Chemical Society* 137:267-75. doi.org/10.1021/ja510375f.

Cheng, Albert W, Haoyi Wang, Hui Yang, Linyu Shi, Yarden Katz, Thorold W Theunissen, Sudharshan Rangarajan, Chikdu S Shivalila, Daniel B Dadon, and Rudolf Jaenisch. 2013. "Multiplexed Activation of Endogenous Genes by CRISPR-on, an RNA-Guided Transcriptional Activator System." *Cell Research* 23 (10): 1163-71. doi.org/10.1038/cr.2013.122.

Cherepanov, Peter P., and Wilfried Wackernagel. 1995. "Gene Disruption in *Escherichia Coli*: TcR and KmR Cassettes with the Option of Flp-Catalyzed Excision of the Antibiotic-Resistance Determinant." *Gene* 158 (1): 9-14. doi.org/10.1016/0378-1119 (95) 00193-A.

Cocinero, Emilio J., and Pierre Carcabal. 2013. "Carbohydrates." *Topics in Current Chemistry* 364:299-334. doi.org/10.1007/128.

Cong, Le, F Ann Ran, David Cox, Shuailiang Lin, Robert Barretto, Naomi Habib, Patrick D Hsu, et al. 2013. "Multiplex Genome Engineering Using CRISPR/Cas Systems." *Science* 339 (6121): 819-23. doi.org/10.1126/science.1231143.

Copeland, Matthew F, Mark C Politz, and Brian F Pfleger. 2014. "Application of TALEs, CRISPR/Cas and SRNAs as Trans-Acting Regulators in Prokaryotes." *Current Opinion in Biotechnology* 29C (March): 46-54. doi.org/10.1016/j.copbio.2014.02.010.

Coussement, Pieter, David Bauwens, Jo Maertens, Wim Soetaert, and Marjan De Mey. 2017. "Direct Combinatorial Pathway Optimization." *ACS Synthetic Biology* 6 (2): 224-32. doi.org/10.1021/acssynbio.6b00122.

Coussement, Pieter, Jo Maertens, Joeri Beauprez, Wouter Van Bellegem, and Marjan De Mey. 2014. "One Step DNA Assembly for Combinatorial Metabolic Engineering." *Metabolic Engineering* 23 (March): 70-77. doi.org/10.1016/j.ymben.2014.02.012.

Cox, Robert Sidney, Michael G Surette, and Michael B Elowitz. 2007. "Programming Gene Expression with Combinatorial Promoters." *Molecular Systems Biology* 3 (January): 145. doi.org/10.1038/msb4100187.

Datsenko, K A, and B L Wanner. 2000. "One-Step Inactivation of Chromosomal Genes in *Escherichia Coli* K-12 Using PCR Products." *Proceedings of the National Academy of Sciences* 97 (12): 6640-45. doi.org/10.1073/pnas.120163297.

Demchick, P, and A L Koch. 1996. "The Permeability of the Wall Fabric of *Escherichia Coli* and *Bacillus Subtilis*" 178 (3): 768-73.

Deng, Ming-De, Alan D. Grund, Sarah L. Wassink, Susan S. Peng, Kathleen L. Nielsen, Brian D. Huckins, Bonnie L. Walsh, and Richard P. Burlingame. 2006. "Directed Evolution and Characterization of *Escherichia Coli* Glucosamine Synthase." *Biochimie* 88 (5): 419-29. doi.org/10.1016/j.biochi.2005.10.002.

Didovyk, A., and L. Tsimring. 2016. "Orthogonal Modular Gene Repression in *Escherichia Coli* Using Engineered CRISPR/Cas9." *ACS Synthetic Biology* 5:81-88.

Farmer, W R, and J C Liao. 2000. "Improving Lycopene Production in *Escherichia Coli* by Engineering Metabolic Control." *Nature Biotechnology* 18:533-37. www.nature.com/nbt/journal/v18/n5/abs/nbt0500_533.html.

Farzadfard, Fahim, Samuel D Perli, and Timothy K Lu. 2013. "Tunable and Multifunctional Eukaryotic Transcription Factors Based on CRISPR/Cas." *ACS Synthetic Biology* 2 (10): 604-13. doi.org/10.1021/sb400081r.

Fierfort, Nicolas, and Eric Samain. 2008. "Genetic Engineering of *Escherichia Coli* for the Economical Production of Sialylated Oligosaccharides." *Journal of Biotechnology* 134:261-65. doi.org/10.1016/j.jbiotec.2008.02.010.

Gabius, Hans Joachim. 2000. "Biological Information Transfer beyond the Genetic Code: The Sugar Code." *Naturwissenshaften* 87 (3): 108-21.

Gabius, Hans Joachim, Sabine Andre, Jesus Jimenez-Barbero, Antonio Romero, and Dolores Solís. 2011. "From Lectin Structure to Functional Glycomics: Principles of the Sugar Code." *Trends in Biochemical Sciences* 36 (6): 298-313. doi.org/10.1016/j.tibs.2011.01.005.

Gabius, Hans Joachim, and Jorgen Roth. 2017. "An Introduction to the Sugar Code." *Histochemistry and Cell Biology* 147 (2): 111-17. doi.org/10.1007/s00418-016-1521-9.

Gaj, Thomas, Shannon J Sirk, and Carlos F Barbas. 2014. "Expanding the Scope of Site-Specific Recombinases for Genetic and Metabolic Engineering." *Biotechnology and Bioengineering* 111 (1): 1-15. doi.org/10.1002/bit.25096.

Goedl, Christiane, Alexandra Schwarz, Alphonse Minani, and Bernd Nidetzky. 2007. "Recombinant Sucrose Phosphorylase from *Leuconostoc Mesenteroides*: Characterization, Kinetic Studies of Transglucosylation, and Application of Immobilised Enzyme for Production of Alfa-d-Glucose 1-Phosphate." *Journal of Biotechnology* 129 (1): 77-86. doi.org/10.1016/j.jbiotec.2006.11.019.

Goh, Shan, Jaroslaw M. Boberek, Nobutaka Nakashima, Jem Stach, and Liam Good. 2009. "Concurrent Growth Rate and Transcript Analyses Reveal Essential Gene Stringency in *Escherichia Coli*." *PLOS ONE* 4 (6). doi.org/10.1371/journal.pone.0006061.

Graslund, S., P. Nordlund, J. Weigelt, B. M. Hallberg, J. Bray, O. Gileadi, S. Knapp, et al. 2008. "Protein Production and Purification." *Nature Methods* 5 (2): 135-46. doi.org/10.1038/nmeth.f.202.Protein.

Hamer, Stefanie Nicole, Stefan Cord-Landwehr, Xevi Biarnés, Antoni Planas, Hendrik Waegeman, Bruno Maria Moerschbacher, and Stephan Kolkenbrock. 2015. "Enzymatic Production of Defined Chitosan Oligomers with a Specific Pattern of Acetylation Using a Combination of Chitin Oligosaccharide Deacetylases." *Scientific Reports* 5:8716. doi.org/10.1038/srep08716.

Hebert, Colin G., James J. Valdes, and William E. Bentley. 2008. "Beyond Silencing-Engineering Applications of RNA Interference and Antisense Technology for Altering Cellular Phenotype." *Current Opinion in Biotechnology* 19 (5): 500-505. doi.org/10.1016/j.copbio.2008.08.006.

Hedges, R., and A. Jacob. 1974. "Transposition of Ampicillin Resistance from RP4 to Other Replicon." *Molecular and General Genetics MGG* 132:31-40.

Hendlin, D., E. O. Stapley, M. Jackson, H. Wallick, A. K. Miller, F. J. Wolf, T. W. Miller, et al. 1967. "Phosphonomycin, a New Antibiotic Produced by Strains of *Streptomyces*." *Science* 166 (3901): 20122-123-22.

Hoang, Tung T., Roxann R. Karkhoff-Schweizer, Alecksandr J. Kutchma, and Herbert P. Schweizer. 1998. "A Broad-Host-Range Flp-FRT Recombination System for Site-Specific Excision of Chromosomally-Located DNA Sequences: Application for Isolation of Unmarked *Pseudomonas Aeruginosa* Mutants." *Gene* 212 (1): 77-86. doi.org/10.1016/S0378-1119 (98) 00130-9.

Hove, Bob Van, Chiara Guidi, Jo De Wannemaeker, Lien Maertens, and Marjan De Mey. 2017. "Recursive DNA Assembly Using Protected Oligonucleotide Duplex Assisted Cloning (PODAC)." *ACS Synthetic Biology* 6 (6): 943-49. doi.org/10.1021/acssynbio.7b00017.

Hove, Bob Van, Aaron M Love, Parayil Kumaran Ajikumar, and Marjan De Mey. 2016. "Programming Biology: Expanding the Toolset for the Engineering of Transcription." In *Synthetic Biology*, edited by Anton Glieder, Christian P Kubicek, Diethard Mattanovich, Birgit Wiltschi, and Michael Sauer, 1-64. Springer Cham Heidelberg New York Dordrecht London: Springer International Publishing.

Hrast, Martina, Izidor Sosic, Roman Šink, and Stanislav Gobec. 2014. "Inhibitors of the Peptidoglycan Biosynthesis Enzymes MurA-F." Bioorganic Chemistry 55:2-15. doi.org/10.1016/j.bioorg.2014.03.008.

Jennewein, Stefan. 2014. Total fermentation of oligosaccharides. EP2927316A1, issued 2014.

Jiang, Yu, Fenghui Qian, Junjie Yang, Yingmiao Liu, Feng Dong, Chongmao Xu, Bingbing Sun, et al. 2017. "CRISPR-Cpf1 Assisted Genome Editing of Corynebacterium Glutamicum." Nature Communications 8:15179. doi.org/10.1038/ncomms15179.

Kahan, Frederick M, Jean S Kahan, Patrick J Cassidy, and Helmut Kropp. 1974. "The Mechanism of Action of Fosfomycin (Phosphonomycin)." Annals of the New York Academy of Sciences 235:364-86.

Kazuo, Yamaguchi, and Yamaguchi Mitsuyo. 1984. "The Replication Origin of PSC101: The Nucleotide Sequence and Replication Functions of the Ori Region." Gene 29 (1-2): 211-19. doi.org/10.1016/0378-1119 (84) 90181-1.

Keseler, Ingrid M., Amanda Mackie, Martin Peralta-Gil, Alberto Santos-Zavaleta, Socorro Gama-Castro, César Bonavides-Martínez, Carol Fulcher, et al. 2013. "EcoCyc: Fusing Model Organism Databases with Systems Biology." Nucleic Acids Research 41 (November 2012): 605-12. doi.org/10.1093/nar/gks1027.

Kogure, Takahisa, Naoki Wakisaka, Hiroaki Takaku, and Masamichi Takagi. 2007. "Efficient Production of 2-De-oxy-Scyllo-Inosose from d-Glucose by Metabolically Engineered Recombinant Escherichia Coli." Journal of Biotechnology 129 (3): 502-9. doi.org/10.1016/j.jbiotec.2007.01.016.

Kristensen, C. S., L. Eberl, J. M. Sanchez-Romero, M. Givskov, S. Molin, and V. De Lorenzo. 1995. "Site-Specific Deletions of Chromosomally Located DNA Segments with the Multimer Resolution System of Broad-Host-Range Plasmid RP4." Journal of Bacteriology 177 (1): 52-58.

Larson, Matthew H, Luke a Gilbert, Xiaowo Wang, Wendell a Lim, Jonathan S Weissman, and Lei S Qi. 2013. "CRISPR Interference (CRISPRi) for Sequence-Specific Control of Gene Expression." Nature Protocols 8 (11): 2180-96. doi.org/10.1038/nprot.2013.132.

Lipke, Peter N, and Rafael Ovalle. 1998. "Cell Wall Architecture in Yeast: New Structure and New Challenges †" 180 (15): 3735-40.

Maeder, Morgan L, Samantha J Linder, Deepak Reyon, James F Angstman, Yanfang Fu, Jeffry D Sander, and J Keith Joung. 2013. "Robust, Synergistic Regulation of Human Gene Expression Using TALE Activators." Nature Methods 10 (3): 243-45. doi.org/10.1038/nmeth.2366.

Maertens, Jo, Joeri Beauprez, and Marjan De Mey. 2010. Metabolically engineered organisms for the production of added value bio-products. EP 10169304.2 (Dec. 7, 2010)/ WO2012/007481, issued 2010.

Merzendorfer, Hans. 2011. "European Journal of Cell Biology The Cellular Basis of Chitin Synthesis in Fungi and Insects: Common Principles and Differences." European Journal of Cell Biology 90 (9): 759-69. doi.org/10.1016/j.ejcb.2011.04.014.

Mey, Marjan De, Jo Maertens, Gaspard J Lequeux, Wim K Soetaert, and Erick J Vandamme. 2007. "Construction and Model-Based Analysis of a Promoter Library for E. Coli: An Indispensable Tool for Metabolic Engineering." BMC Biotechnology 7 (January): 34. doi.org/10.1186/1472-6750-7-34.

Molina-Lopez, Jose, Francois Sanschagrin, and Roger C Levesque. 2006. "A Peptide Inhibitor of MurA UDP—N-Acetylglucosamine Enolpyruvyl Transferase: The First Committed Step in Peptidoglycan Biosynthesis." Peptides 27 (3000): 3115-21. doi.org/10.1016/j.peptides.2006.08.023.

Moon, Tae Seok, Chunbo Lou, Alvin Tamsir, Brynne C Stanton, and Christopher a Voigt. 2012. "Genetic Programs Constructed from Layered Logic Gates in Single Cells." Nature 491 (7423): 249-53. doi.org/10.1038/nature11516.

Mutalik, Vivek K, Joao C Guimaraes, Guillaume Cambray, Colin Lam, Marc Juul Christoffersen, Quynh-Anh Mai, Andrew B Tran, et al. 2013. "Precise and Reliable Gene Expression via Standard Transcription and Translation Initiation Elements." Nature Methods 10 (4): 354-60. doi.org/10.1038/nmeth.2404.

Neidhardt, Frederick C, and Roy Curtiss. 1996. Escherichia Coli and Salmonella: Cellular and Molecular Biology. 2nd ed. Washington, DC: ASM Press.

Nevoigt, Elke, Jessica Kohnke, Curt R Fischer, Hal Alper, Ulf Stahl, and Gregory Stephanopoulos. 2006. "Engineering of Promoter Replacement Cassettes for Fine-Tuning of Gene Expression in Saccharomyces Cerevisiae." Applied and Environmental Microbiology 72 (8): 5266-73. doi.org/10.1128/AEM.00530-06.

Nielsen, Alec A K, and Christopher A Voigt. 2014. "Multi-Input CRISPR/Cas Genetic Circuits That Interface Host Regulatory Networks." Molecular Systems Biology 10 (January): 763. www.ncbi.nlm.nih.gov/pubmed/25422271.

Ohlendorf, Robert, Roee R Vidavski, Avigdor Eldar, Keith Moffat, and Andreas Möglich. 2012. "From Dusk till Dawn: One-Plasmid Systems for Light-Regulated Gene Expression." Journal of Molecular Biology 416 (4): 534-42. doi.org/10.1016/j.jmb.2012.01.001.

Palmeros, Beatriz, Jadwiga Wild, Waclaw Szybalski, Sylvie Le Borgne, Georgina Hernández-Chávez, Guillermo Gosset, Fernando Valle, and Francisco Bolivar. 2000. "A Family of Removable Cassettes Designed to Obtain Antibiotic-Resistance-Free Genomic Modifications of Escherichia Coli and Other Bacteria." Gene 247 (1-2): 255-64. doi.org/10.1016/S0378-1119 (00) 00075-5.

Patil, Kiran Raosaheb, Mats Åkesson, and Jens Nielsen. 2004. "Use of Genome-Scale Microbial Models for Metabolic Engineering." Current Opinion in Biotechnology 15:64-69. doi.org/10.1016/j.copbio.2003.11.003.

Perez-Pinera, P, D D Kocak, and C M Vockley. 2013. "RNA-Guided Gene Activation by CRISPR-Cas9-Based Transcription Factors." Nature Methods 10 (10): 973-76. doi.org/10.1038/nmeth.2600.RNA-guided.

Peters, Geert, Pieter Coussement, Jo Maertens, Jeroen Lammertyn, and Marjan De Mey. 2015. "Putting RNA to Work: Translating RNA Fundamentals into Biotechnological Engineering Practice." Biotechnology Advances 33 (8): 1829-44.

Peters, Gert, Brecht De Paepe, Lien De Wannemaeker, Dries Duchi, Jo Maertens, Jeroen Lammertyn, and Marjan De Mey. 2018. "Development of N-Acetylneuraminic Acid Responsive Biosensors Based on the Transcriptional Regulator NanR." Biotechnology and Bioengineering 115:1855-65. doi.org/10.1002/bit.26586.

Pirie, Christopher M, Marjan De Mey, Kristala L Prather, and Parayil K Ajikumar. 2013. "Integrating the Protein and Metabolic Engineering Toolkits for Next-Generation *ACS Chemical Biology* 8 (4): 662-72. doi.org/10.1021/cb300634b. Chemical Biosynthesis."

Pitzer, Julia, Bob Van Hove, Aaron M Love, Parayil Kumaran Ajikumar, Marjan De Mey, and Anton Glieder. 2016. "Novel DNA and RNA Elements." In *Synthetic Biology*, edited by Anton Glieder, Christian P Kubicek, Diethard Mattanovich, Birgit Wiltschi, and Michael Sauer, 65-100. Springer Cham Heidelberg New York Dordrecht London: Springer International Publishing.

Politz, Mark C, Matthew F Copeland, and Brian F Pfleger. 2013. "Artificial Repressors for Controlling Gene Expression in Bacteria." *Chemical Communications* 49 (39): 4325-27. doi.org/10.1039/c2cc37107c.

Prentki, Pierre, and Henry M Krisch. 1982. "A Modified PBR322 Vector with Improved Properties for the Cloning, Recovery, and Sequencing of Blunt-Ended DNA Fragments." *Gene* 17:189-96.

Pridmore, Raymond David. 1987. "New and Versatile Cloning Vectors with Kanamycin-Resistance Marker." *Gene* 56:309-12.

Priem, B, M Gilbert, W. W. Wakarchuk, A Heyraud, and Eric Samain. 2002. "A New Fermentation Process Allows Large-Scale Production of Human Milk Oligosaccharides by Metabolically Engineered Bacteria." *Glycobiology* 12 (4): 235-40.

Ptashne, M. 2004. *A Genetic Switch: Phage Lambda Revisited*. 3rd ed. CHS Laboratory Press.

Qi, Lei S, and Adam P Arkin. 2014. "A Versatile Framework for Microbial Engineering Using Synthetic Non-Coding RNAs." *Nature Reviews. Microbiology* 12 (5): 341-54. doi.org/10.1038/nrmicro3244.

Qi, Lei S, Matthew H Larson, Luke a Gilbert, Jennifer a Doudna, Jonathan S Weissman, Adam P Arkin, and Wendell a Lim. 2013. "Repurposing CRISPR as an RNA-Guided Platform for Sequence-Specific Control of Gene Expression." *Cell* 152 (5): 1173-83. doi.org/10.1016/j.cell.2013.02.022.

Quan, Jiayuan, and Jingdong Tian. 2009. "Circular Polymerase Extension Cloning of Complex Gene Libraries and Pathways." *Plos One* 4 (7): e6441. doi.org/10.1007/978-1-62703-764-8_8.

Rasmussen, Louise, Hans Sperling-Petersen, and Kim Mortensen. 2007. "Hitting Bacteria at the Heart of the Central Dogma: Sequence-Specific Inhibition." *Microbial Cell Factories* 6 (1): 24. doi.org/10.1186/1475-2859-6-24.

Rodríguez-Diaz, Jesus, Antonio Rubio-del-Campo, and Maria J. Yebra. 2012. "Metabolic Engineering of *Lactobacillus Casei* for Production of UDP—N-Acetylglucosamine." *Biotechnology and Bioengineering* 109 (7): 1704-12. doi.org/10.1002/bit.24475.

Rozman, Kaja, Samo Lešnik, Boris Brus, Martina Hrast, Matej Sova, Delphine Patin, Helene Barreteau, Janez Konc, Dusanka Janezic, and Stanislav Gobec. 2017. "Discovery of New MurA Inhibitors Using Induced-Fit Simulation and Docking." *Bioorganic & Medicinal Chemistry Letters* 27:944-49. doi.org/10.1016/j.bmcl.2016.12.082.

Ruffing, Anne, and Rachel Ruizhen Chen. 2006. "Metabolic Engineering of Microbes for Oligosaccharide and Polysaccharide Synthesis." *Microbial Cell Factories* 5:25. doi.org/10.1186/1475-2859-5-25.

Salis, Howard M. 2011. "The Ribosome Binding Site Calculator." *Methods in Enzymology* 498:19-42. doi.org/10.1016/B978-0-12-385120-8.00002-4.

Samain, Eric, Sophie Drouillard, Alain Heyraud, Hugues Driguez, and Roberto a Geremia. 1997. "Gram-Scale Synthesis of Recombiant Chitooligosaccharides in *Escherichia Coli*." *Carbohydrate Research* 302:35-42.

Sambrook, J. F., and D. W. Russell. 2001. *Molecular Cloning: A Laboratory Manual*. 3rd ed. Cold Spring Harbor Laboratory Press.

Sauer, B. 1987. "Functional Expression of the Cre-Lox Site-Specific Recombination System in the Yeast *Saccharomyces Cerevisiae*." *Molecular and Cellular Biology* 7 (6): 2087-96. doi.org/10.1128/MCB.7.6.2087.

Schweizer, Herbert P. 2003. "Applications of the *Saccharomyces Cerevisiae* Flp-FRT System in Bacterial Genetics." *Journal of Molecular Microbiology and Biotechnology* 5 (2): 67-77. doi.org/10.1159/000069976.

Selzer, G, T Som, T Itoh, and J Tomizawa. 1983. "The Origin of Replication of Plasmid P15A and Comparative Studies on the Nucleotide Sequences around the Origin of Related Plasmids." *Cell* 32 (1): 119-29.

Shcherbo, Dmitry, Christopher S Murphy, Galina V Ermakova, Elena A Solovieva, Tatiana V Chepurnykh, Aleksandr S Shcheglov, V Vladislav, et al. 2009. "Far-Red Fluorescent Tags for Protein Imaging in Living Tissues." *Biochemical Journal* 418 (3): 567-74. doi.org/10.1042/BJ20081949.Far-red.

Silhavy, Thomas, Daniel Kahne, and Suzanne Walker. 2010. "The Bacterial Cell Envelope." *Cold Spring Harbor Perspectives in Biology* 2 (5): 1-16. doi.org/10.1101/cshperspect.a000414.

Stansen, Corinna, Davin Uy, Stephane Delaunay, Lothar Eggeling, Jean Louis Goergen, and Volker F. Wendisch. 2005. "Characterization of a *Corynebacterium Glutamicum* Lactate Utilization Operon Induced during Temperature-Triggered Glutamate Production." *Applied and Environmental Microbiology* 71 (10): 5920-28. doi.org/10.1128/AEM.71.10.5920-5928.2005.

Stephanopoulos, Gregory. 2012. "Synthetic Biology and Metabolic Engineering." *ACS Synthetic Biology* 1 (11): 514-25. doi.org/10.1021/sb300094q.

Trantas, Emmanouil A., Mattheos A. G. Koffas, Peng Xu, and Filippos Ververidis. 2015. "When Plants Produce Not Enough or at All: Metabolic Engineering of Flavonoids in Microbial Hosts." *Frontiers in Plant Science* 6 (7): 1-16. doi.org/10.3389/fpls.2015.00007 When.

Tsuda, Masataka. 1998. "Use of a Transposon-Encoded Site-Specific Resolution System for Construction of Large and Defined Deletion Mutations in Bacterial Chromosome." *Gene* 207 (1): 33-41. doi.org/10.1016/S0378-1119 (97) 00601-X.

Tweeddale, Helen, Lucinda Notley-m C Robb, and Thomas Ferenci. 2006. "Effect of Slow Growth on Metabolism of *Escherichia Coli*, as Revealed by Global Metabolite Pool ('Metabolome') Analysis" 180 (19): 5109-16.

Tyo, Keith E, Hal S Alper, and Gregory N Stephanopoulos. 2007. "Expanding the Metabolic Engineering Toolbox: More Options to Engineer Cells." *Trends in Biotechnology* 25 (3): 132-37. doi.org/10.1016/j.tibtech.2007.01.003.

Varki, Ajit. 1993. "Biological Roles of Oligosaccharides: All of the Theories Are Correct." *Glycobiology* 3 (2): 97-130.

Verpoorte, R., R. Van Der Hejden, H. J G Ten Hoopen, and J. Memelink. 1999. "Metabolic Engineering of Plant Secondary Metabolite Pathways for the Production of Fine Chemicals." *Biotechnology Letters* 21 (6): 467-79. doi.org/10.1023/A: 1005502632053.

Weaver, Daniel S, Ingrid M Keseler, Amanda Mackie, Ian T Paulsen, and Peter D Karp. 2014. "A Genome-Scale Metabolic Flux Model of *Escherichia Coli* K-12 Derived from the EcoCyc Database." *BMC Systems Biology* 8:79. doi.org/10.1186/1752-0509-8-79.

Westbrook, Adam W, Xiang Ren, Jaewon Oh, Murray Moo-young, and C Perry Chou. 2018. "Metabolic Engineering to Enhance Heterologous Production of Hyaluronic Acid in *Bacillus Subtilis.*" *Metabolic Engineering* 47 (November 2017): 401-13. doi.org/10.1016/j.ymben.2018.04.016.

Williams, James A., Jeremy Luke, and Clague Hodgson. 2009. "Strain Engineering by Genome Mass Transfer: Efficient Chromosomal Trait Transfer Method Utilizing Donor Genomic DNA and Recipient Recombineering Hosts." *Molecular Biotechnology* 43 (1): 41-51. doi.org/10.1007/s12033-009-9177-5.

Xie, Xianfa, and Peter N. Lipke. 2011. "On the Evolution of Fungal and Yeast Cell Walls Xianfa." *Yeast* 27 (8): 479-88. doi.org/10.1002/yea.1787.On.

Yadav, Vikramaditya G., Marjan De Mey, Chin Giaw Lim, Parayil K Ajikumar, and Gregory Stephanopoulos. 2013. "The Future of Metabolic Engineering and Synthetic Biology: Towards a Systematic Practice" 14 (3): 233-41. doi.org/10.1016/j.ymben.2012.02.001. The.

Zhang, Dawei, Peng George Wang, and Qingsheng Qi. 2007. "A Two-Step Fermentation Process for Efficient Production of Penta-N-Acetyl-Chitopentaose in Recombinant *Escherichia Coli.*" *Biotechnology Letters* 29 (11): 1729-33. doi.org/10.1007/s10529-007-9462-y.

Zhang, J., P. Kowal, X. Chen, and P. G. Wang. 2003. "Large-Scale Synthesis of Globotriose Derivatives through Recombinant *E. Coli.*" *Organic & Biomolecular Chemistry* 1 (17): 3048-53.

Zhou, Kang, Lihan Zhou, Qing 'En Lim, Ruiyang Zou, Gregory Stephanopoulos, and Heng-Phon Too. 2011. "Novel Reference Genes for Quantifying Transcriptional Responses of *Escherichia Coli* to Protein Overexpression by Quantitative PCR." *BMC Molecular Biology* 12:18. doi.org/10.1186/1471-2199-12-18.

---

The invention claimed is:

1. A method of producing a UDP-N-acetylglucosamine (UDP-GlcNAc)-derived saccharide in a gram-negative bacterium, wherein the method comprises:
   a) decreasing but not inactivating expression of a murA gene in a gram-negative bacterium, wherein the expression of the murA gene is decreased by modifying a promoter or 5'-UTR region(s) of the murA gene of the gram-negative bacterium,
   b) cultivating the gram-negative bacterium with decreased murA gene expression to produce a UDP-GlcNAc-derived saccharide, and
   c) extracting and purifying UDP-GlcNAc-derived saccharide therefrom.

2. The method according to claim 1, wherein the bacterium is of the genus *Escherichia*.

* * * * *

SEQUENCE LISTING

```
<160> NUMBER OF SEQ ID NOS: 94

<210> SEQ ID NO 1
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 1
atttataaat ttcttgacac agcatcggaa ctaccctata atgtgtacat aaacacaagc    60
tcaacatata ctagacaaag tcaggc                                        86

<210> SEQ ID NO 2
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 2
atttataaat ttcttgacaa ctaacactac agagattata atgtgtacat aaacacaagc    60
tcaacatata ctagacaaag tcaggc                                        86

<210> SEQ ID NO 3
<211> LENGTH: 85
<212> TYPE: DNA
<213> ORGANISM: Artificial sequence
<220> FEATURE:
<223> OTHER INFORMATION: artificial promotor+5'UTR

<400> SEQUENCE: 3
atttataaat ttcttgacat tttggaatag atgtgatata atgtgtacat aaacacaagc    60
tcaacctata ctagagaagt caggc                                         85

<210> SEQ ID NO 4
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 4
atttataaat ttcttgacat atagtagata tcaccatata atgtgtacat aaacacaagc    60
```
tcatcctata ctagaggaag tcaggc                                              86

<210> SEQ ID NO 5
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 5
atttataaat ttcttgacag gacgtcgcca gcgcgctata atgtgtacat aaacacaagc        60
tcatcctata ctagaggaag tcaggc                                              86

<210> SEQ ID NO 6
<211> LENGTH: 443
<212> TYPE: PRT
<213> ORGANISM: Rhizobium sp. GRH2

<400> SEQUENCE: 6

Met Asp Leu Leu Asn Thr Ile Gly Ile Gly Ala Val Ser Cys Tyr Ala
1               5                   10                  15

Leu Leu Ser Thr Ala His Lys Ser Met Gln Thr Leu Tyr Ala Gln Pro
            20                  25                  30

Lys Asp Gln Ser Ser Ala Ser Glu Asp Phe Ala Phe Leu Pro Ser Val
        35                  40                  45

Asp Ile Ile Val Pro Cys Tyr Asn Glu Asn Pro His Thr Phe Ser Glu
    50                  55                  60

Cys Leu Ala Ser Ile Ala Asn Gln Asp Tyr Ala Gly Lys Leu Arg Val
65                  70                  75                  80

Tyr Val Val Asp Asp Gly Ser Ala Asn Arg Glu Lys Leu Glu Arg Val
                85                  90                  95

His His Thr Tyr Ala Gly Asp Pro Arg Phe Asp Phe Ile Leu Leu Arg
            100                 105                 110

Glu Asn Val Gly Lys Arg Lys Ala Gln Ile Ala Ala Ile Arg Gly Ser
        115                 120                 125

Ser Gly Asp Leu Val Leu Asn Val Asp Ser Asp Ser Thr Leu Ala Ser
    130                 135                 140

Asp Val Val Thr Lys Leu Ala Leu Lys Met Gln Asn Pro Glu Ile Gly
145                 150                 155                 160

Ala Ala Met Gly Gln Leu Thr Ala Ser Asn Arg Asn Asp Thr Trp Leu
                165                 170                 175

Thr Arg Leu Ile Asp Met Glu Tyr Trp Leu Ala Cys Asn Glu Glu Arg
            180                 185                 190

Ala Ala Gln Ala Arg Phe Gly Ala Val Met Cys Cys Cys Gly Pro Cys
        195                 200                 205

Ala Met Tyr Arg Arg Ser Ala Leu Leu Ser Leu Leu Asp Gln Tyr Glu
    210                 215                 220

Ser Gln Phe Phe Arg Gly Lys Pro Ser Asp Phe Gly Glu Asp Arg His
225                 230                 235                 240

Leu Thr Ile Leu Met Leu Lys Ala Gly Phe Arg Thr Asp Tyr Val Pro
                245                 250                 255

Asp Ala Ile Ala Ala Thr Val Val Pro Asp Arg Met Gly Pro Tyr Leu
            260                 265                 270

Arg Gln Gln Leu Arg Trp Ala Arg Ser Thr Phe Arg Asp Thr Leu Leu
        275                 280                 285

Ala Leu Arg Leu Leu Pro Gly Leu Asp His Tyr Ile Thr Leu Asp Val

```
              290                 295                 300
Ile Gly Gln Asn Leu Gly Pro Leu Leu Leu Ala Leu Ala Val Leu Thr
305                 310                 315                 320

Gly Val Leu Gln Val Ala Leu Thr Ala Thr Val Pro Leu Trp Thr Val
                325                 330                 335

Met Met Ile Ala Ser Met Thr Met Ile Arg Cys Ala Val Ala Ala Val
                340                 345                 350

Arg Ala Arg Gln Leu Arg Phe Leu Val Phe Ser Leu His Thr Pro Ile
            355                 360                 365

Asn Leu Phe Phe Leu Leu Pro Met Lys Ala Tyr Ala Leu Cys Thr Leu
        370                 375                 380

Ser Asn Ser Asp Trp Leu Ser Arg Ser Ser Pro Ala Asn Lys Thr Ser
385                 390                 395                 400

Ala Gly Gly Glu His Pro Thr Thr Glu Ala Ser Ala Gly Gly Thr Ser
                405                 410                 415

Gly Asn Ala Thr Pro Leu Arg Arg Leu Asn Leu Ala Arg Asp Ser Ser
                420                 425                 430

Thr Val Thr Pro Ala Gly Val Tyr Ser Asp Asp
            435                 440

<210> SEQ ID NO 7
<211> LENGTH: 438
<212> TYPE: PRT
<213> ORGANISM: Sinorhizobium meliloti

<400> SEQUENCE: 7

Met Tyr Leu Leu Asp Thr Thr Ser Thr Ala Ala Ile Ser Ile Tyr Ala
1               5                   10                  15

Leu Leu Leu Thr Ala Tyr Arg Ser Met Gln Val Leu Tyr Ala Arg Pro
                20                  25                  30

Ile Asp Gly Pro Ala Val Ala Ala Glu Pro Val Glu Thr Arg Pro Leu
            35                  40                  45

Pro Ala Val Asp Val Ile Val Pro Ser Phe Asn Glu Asp Pro Gly Ile
        50                  55                  60

Leu Ser Ala Cys Leu Ala Ser Ile Ala Asp Gln Asp Tyr Pro Gly Glu
65                  70                  75                  80

Leu Arg Val Tyr Val Val Asp Asp Gly Ser Arg Asn Arg Glu Ala Ile
                85                  90                  95

Val Arg Val Arg Ala Phe Tyr Ser Arg Asp Pro Arg Phe Ser Phe Ile
            100                 105                 110

Leu Leu Pro Glu Asn Val Gly Lys Arg Lys Ala Gln Ile Ala Ala Ile
        115                 120                 125

Gly Gln Ser Ser Gly Asp Leu Val Leu Asn Val Asp Ser Asp Ser Thr
130                 135                 140

Ile Ala Phe Asp Val Val Ser Lys Leu Ala Ser Lys Met Arg Asp Pro
145                 150                 155                 160

Glu Val Gly Ala Val Met Gly Gln Leu Thr Ala Ser Asn Ser Gly Asp
                165                 170                 175

Thr Trp Leu Thr Lys Leu Ile Asp Met Glu Tyr Trp Leu Ala Cys Asn
            180                 185                 190

Glu Glu Arg Ala Ala Gln Ser Arg Phe Gly Ala Val Met Cys Cys Cys
        195                 200                 205

Gly Pro Cys Ala Met Tyr Arg Arg Ser Ala Leu Ala Ser Leu Leu Asp
210                 215                 220
```

Gln Tyr Glu Thr Gln Leu Phe Arg Gly Lys Pro Ser Asp Phe Gly Glu
225                 230                 235                 240

Asp Arg His Leu Thr Ile Leu Met Leu Lys Ala Gly Phe Arg Thr Glu
            245                 250                 255

Tyr Val Pro Asp Ala Ile Val Ala Thr Val Pro Asp Thr Leu Lys
        260                 265                 270

Pro Tyr Leu Arg Gln Gln Leu Arg Trp Ala Arg Ser Thr Phe Arg Asp
            275                 280                 285

Thr Phe Leu Ala Leu Pro Leu Leu Arg Gly Leu Ser Pro Phe Leu Ala
    290                 295                 300

Phe Asp Ala Val Gly Gln Asn Ile Gly Gln Leu Leu Ala Leu Ser
305                 310                 315                 320

Val Val Thr Gly Leu Ala His Leu Ile Met Thr Ala Thr Val Pro Trp
            325                 330                 335

Trp Thr Ile Leu Ile Ile Ala Cys Met Thr Ile Ile Arg Cys Ser Val
            340                 345                 350

Val Ala Leu His Ala Arg Gln Leu Arg Phe Leu Gly Phe Val Leu His
            355                 360                 365

Thr Pro Ile Asn Leu Phe Leu Ile Leu Pro Leu Lys Ala Tyr Ala Leu
    370                 375                 380

Cys Thr Leu Ser Asn Ser Asp Trp Leu Ser Arg Tyr Ser Ala Pro Glu
385                 390                 395                 400

Val Pro Val Ser Gly Lys Gln Thr Pro Ile Gln Thr Ser Gly Arg
            405                 410                 415

Val Thr Pro Asp Cys Thr Cys Ser Gly Glu Leu Arg Arg Gln Trp Ser
            420                 425                 430

His Pro Gln Phe Glu Lys
        435

<210> SEQ ID NO 8
<211> LENGTH: 413
<212> TYPE: PRT
<213> ORGANISM: Sinorhizobium fredii USDA 191

<400> SEQUENCE: 8

Met Asp Leu Leu Gly Thr Thr Gly Ala Val Ala Ile Ser Leu Tyr Ala
1               5                   10                  15

Ala Leu Ser Thr Ala Tyr Lys Gly Met Gln Ala Ile Tyr Ala Leu Pro
            20                  25                  30

Thr Asn Thr Thr Ala Ala Ser Thr Pro Val Thr Gly Ser Gly Ala Pro
        35                  40                  45

Pro Ser Val Asp Val Ile Val Pro Cys Tyr Asn Glu Asp Pro Arg Ala
    50                  55                  60

Leu Ser Ala Cys Leu Ala Ser Ile Ala Lys Gln Asp Tyr Ala Gly Glu
65                  70                  75                  80

Leu Arg Val Tyr Val Val Asp Asp Gly Ser Gly Asn Arg Asn Ala Ile
            85                  90                  95

Ile Pro Val His Asp His Tyr Ala Cys Asp Pro Arg Phe Arg Phe Ile
            100                 105                 110

Leu Met Pro Lys Asn Val Gly Lys Arg Lys Ala Gln Ile Val Ala Ile
        115                 120                 125

Arg Glu Ser Ser Gly Asp Leu Val Leu Asn Val Asp Ser Asp Thr Thr
    130                 135                 140

Ile Ala Pro Asp Val Val Thr Lys Leu Ala Leu Lys Met Tyr Ser Pro
145                 150                 155                 160

```
Ala Val Gly Ala Ala Met Gly Gln Leu Thr Ala Ser Asn Arg Ser Asp
            165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
            195                 200                 205

Gly Pro Cys Ala Met Tyr Arg Arg Ser Ala Leu Leu Leu Leu Leu Asp
            210                 215                 220

Lys Tyr Glu Thr Gln Leu Phe Arg Gly Arg Pro Ser Asp Phe Gly Glu
225                 230                 235                 240

Asp Arg His Leu Thr Ile Leu Met Leu Asn Ala Gly Phe Arg Thr Glu
            245                 250                 255

Tyr Val Pro Asp Ala Ile Ala Ala Thr Val Val Pro Asn Ser Met Gly
            260                 265                 270

Ala Tyr Leu Arg Gln Gln Leu Arg Trp Ala Arg Ser Thr Phe Arg Asp
            275                 280                 285

Thr Leu Leu Ala Leu Arg Leu Leu Pro Gly Leu Asp Arg Tyr Leu Thr
            290                 295                 300

Leu Asp Val Ile Gly Gln Asn Leu Gly Pro Leu Leu Leu Ala Leu Ser
305                 310                 315                 320

Val Leu Thr Gly Leu Ala Gln Leu Ala Leu Thr Ala Thr Val Pro Trp
            325                 330                 335

Ser Thr Ile Leu Met Ile Ala Ser Met Thr Met Val Arg Cys Gly Val
            340                 345                 350

Ala Ala Phe Arg Ala Arg Glu Leu Arg Phe Leu Gly Phe Ser Leu His
            355                 360                 365

Thr Leu Leu Asn Val Ala Leu Leu Leu Pro Leu Lys Ala Tyr Ala Leu
            370                 375                 380

Cys Thr Leu Ser Asn Ser Asp Trp Leu Ser Arg Gly Ser Pro Ala Ala
385                 390                 395                 400

Ala Pro Asn Gly Val Lys Asp Ser Pro Glu Pro His Cys
            405                 410

<210> SEQ ID NO 9
<211> LENGTH: 346
<212> TYPE: PRT
<213> ORGANISM: Campylobacter jejuni

<400> SEQUENCE: 9

Met Lys Glu Ile Lys Ile Gln Asn Ile Ile Ser Glu Glu Lys Ala
1               5                   10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Ala Gly Ala Lys Ile
            35                  40                  45

Ile Lys His Gln Thr His Ile Val Glu Asp Glu Met Ser Lys Ala Ala
            50                  55                  60

Lys Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
            85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
```

```
              115                 120                 125
Ser Gly Glu Cys Asn Asn Tyr Pro Leu Ile Lys His Ile Ala Ala Phe
    130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Val Leu
    210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Ile Arg Gly Asn Asn Glu Ser
            260                 265                 270

Lys Lys Ala Ala Lys Gln Glu Gln Val Thr Ile Asp Phe Ala Phe Ala
        275                 280                 285

Ser Val Ser Ile Lys Asp Ile Lys Lys Gly Glu Val Leu Ser Met
    290                 295                 300

Asp Asn Ile Trp Val Lys Arg Pro Gly Leu Gly Ile Ser Ala Ala
305                 310                 315                 320

Glu Phe Glu Asn Ile Leu Gly Lys Lys Ala Leu Arg Asp Ile Glu Asn
                325                 330                 335

Asp Ala Gln Leu Ser Tyr Glu Asp Phe Ala
            340                 345

<210> SEQ ID NO 10
<211> LENGTH: 373
<212> TYPE: PRT
<213> ORGANISM: Campylobacter jejuni

<400> SEQUENCE: 10

Met Val Lys Lys Ile Leu Phe Ile Thr Gly Ser Arg Ala Asp Tyr Ser
1               5                   10                  15

Lys Ile Lys Ser Leu Met Tyr Arg Val Gln Asn Ser Ser Glu Phe Glu
            20                  25                  30

Leu Tyr Ile Phe Ala Thr Gly Met His Leu Ser Lys Asn Phe Gly Tyr
        35                  40                  45

Thr Val Lys Glu Leu Tyr Lys Asn Gly Phe Lys Asn Ile Tyr Glu Phe
    50                  55                  60

Ile Asn Tyr Asp Lys Tyr Gln Thr Asp Lys Ala Leu Ala Thr Thr
65                  70                  75                  80

Ile Asp Gly Phe Ser Arg Tyr Ala Asn Glu Leu Lys Pro Asp Leu Ile
                85                  90                  95

Val Val His Gly Asp Arg Ile Glu Pro Leu Ala Ala Ala Ile Val Gly
            100                 105                 110

Ala Leu Asn Asn Ile Leu Val Ala His Ile Glu Gly Gly Glu Ile Ser
        115                 120                 125

Gly Thr Ile Asp Asp Ser Leu Arg His Ala Ile Ser Lys Leu Ala His
    130                 135                 140
```

Ile His Leu Val Asn Asp Glu Phe Ala Lys Arg Arg Leu Met Gln Leu
145                 150                 155                 160

Gly Glu Asp Glu Lys Ser Ile Phe Ile Ile Gly Ser Pro Asp Leu Glu
            165                 170                 175

Leu Leu Asn Asp Asn Lys Ile Ser Leu Ser Glu Ala Lys Lys Tyr Tyr
            180                 185                 190

Asp Ile Asn Tyr Glu Asn Tyr Ala Leu Leu Met Phe His Pro Val Thr
            195                 200                 205

Thr Glu Ile Thr Ser Ile Lys Asn Gln Ala Asp Asn Leu Val Lys Ala
            210                 215                 220

Leu Ile Gln Ser Asn Lys Asn Tyr Ile Val Ile Tyr Pro Asn Asn Asp
225                 230                 235                 240

Leu Gly Phe Glu Leu Ile Leu Gln Ser Tyr Glu Glu Phe Lys Asn Asn
            245                 250                 255

Pro Arg Phe Lys Leu Phe Pro Ser Leu Arg Phe Glu Tyr Phe Ile Thr
            260                 265                 270

Leu Leu Lys Asn Ala Asp Phe Ile Ile Gly Asn Ser Ser Cys Ile Leu
            275                 280                 285

Lys Glu Ala Leu Tyr Leu Lys Thr Ala Gly Ile Leu Val Gly Ser Arg
290                 295                 300

Gln Asn Gly Arg Leu Gly Asn Glu Asn Thr Leu Lys Val Asn Ala Asn
305                 310                 315                 320

Ser Asp Glu Ile Leu Lys Ala Ile Asn Thr Ile His Lys Lys Gln Asp
            325                 330                 335

Leu Phe Ser Ala Lys Leu Glu Ile Leu Asp Ser Ser Lys Leu Phe Phe
            340                 345                 350

Glu Tyr Leu Gln Ser Gly Asp Phe Phe Lys Leu Ser Thr Gln Lys Val
            355                 360                 365

Phe Lys Asp Ile Lys
370

<210> SEQ ID NO 11
<211> LENGTH: 897
<212> TYPE: PRT
<213> ORGANISM: Escherichia coli

<400> SEQUENCE: 11

Met Lys Leu Asn Ile Phe Thr Lys Ser Met Ile Gly Met Gly Leu Val
1               5                   10                  15

Cys Ser Ala Leu Pro Ala Leu Ala Met Glu Ala Trp Asn Asn Gln Gln
            20                  25                  30

Gly Gly Asn Lys Tyr Gln Val Ile Phe Asp Gly Lys Ile Tyr Glu Asn
            35                  40                  45

Ala Trp Trp Val Ser Ser Thr Asn Cys Pro Gly Lys Ala Lys Ala Asn
50                  55                  60

Asp Ala Thr Asn Pro Trp Arg Leu Lys Arg Thr Ala Thr Ala Ala Glu
65                  70                  75                  80

Ile Ser Gln Phe Gly Asn Thr Leu Ser Cys Glu Lys Ser Gly Ser Ser
            85                  90                  95

Ser Ser Ser Asn Ser Asn Thr Pro Ala Ser Asn Thr Pro Ala Asn Gly
            100                 105                 110

Gly Ser Ala Thr Pro Ala Gln Gly Thr Val Pro Ser Asn Ser Ser Val
            115                 120                 125

Val Ala Trp Asn Lys Gln Gln Gly Gly Gln Thr Trp Tyr Val Val Phe
130                 135                 140

```
Asn Gly Ala Val Tyr Lys Asn Ala Trp Trp Val Ala Ser Ser Asn Cys
145                 150                 155                 160

Pro Gly Asp Ala Lys Ser Asn Asp Ala Ser Asn Pro Trp Arg Tyr Val
                165                 170                 175

Arg Ala Ala Thr Ala Thr Glu Ile Ser Glu Thr Ser Asn Pro Gln Ser
            180                 185                 190

Cys Thr Ser Ala Pro Gln Pro Ser Pro Asp Val Lys Pro Ala Pro Asp
        195                 200                 205

Val Lys Pro Ala Pro Asp Val Gln Pro Ala Pro Ala Asp Lys Ser Asn
210                 215                 220

Asp Asn Tyr Ala Val Val Ala Trp Lys Gly Gln Glu Gly Ser Ser Thr
225                 230                 235                 240

Trp Tyr Val Ile Tyr Asn Gly Gly Ile Tyr Lys Asn Ala Trp Trp Val
                245                 250                 255

Gly Ala Ala Asn Cys Pro Gly Asp Ala Lys Glu Asn Asp Ala Ser Asn
                260                 265                 270

Pro Trp Arg Tyr Val Arg Ala Ala Thr Ala Thr Glu Ile Ser Gln Tyr
                275                 280                 285

Gly Asn Pro Gly Ser Cys Ser Val Lys Pro Asp Asn Gly Gly Ala
                290                 295                 300

Val Thr Pro Val Asp Pro Thr Pro Glu Thr Pro Val Thr Pro Thr Pro
305                 310                 315                 320

Asp Asn Ser Glu Pro Ser Thr Pro Ala Asp Ser Val Asn Asp Tyr Ser
                325                 330                 335

Leu Gln Ala Trp Ser Gly Gln Glu Gly Ser Glu Ile Tyr His Val Ile
                340                 345                 350

Phe Asn Gly Asn Val Tyr Lys Asn Ala Trp Trp Val Gly Ser Lys Asp
                355                 360                 365

Cys Pro Arg Gly Thr Ser Ala Glu Asn Ser Asn Asn Pro Trp Arg Leu
                370                 375                 380

Glu Arg Thr Ala Thr Ala Ala Glu Leu Ser Gln Tyr Gly Asn Pro Thr
385                 390                 395                 400

Thr Cys Glu Ile Asp Asn Gly Gly Val Ile Val Ala Asp Gly Phe Gln
                405                 410                 415

Ala Ser Lys Ala Tyr Ser Ala Asp Ser Ile Val Asp Tyr Asn Asp Ala
                420                 425                 430

His Tyr Lys Thr Ser Val Asp Gln Asp Ala Trp Gly Phe Val Pro Gly
                435                 440                 445

Gly Asp Asn Pro Trp Lys Lys Tyr Glu Pro Ala Lys Ala Trp Ser Ala
                450                 455                 460

Ser Thr Val Tyr Val Lys Gly Asp Arg Val Val Asp Gly Gln Ala
465                 470                 475                 480

Tyr Glu Ala Leu Phe Trp Thr Gln Ser Asp Asn Pro Ala Leu Val Ala
                485                 490                 495

Asn Gln Asn Ala Thr Gly Ser Asn Ser Arg Pro Trp Lys Pro Leu Gly
                500                 505                 510

Lys Ala Gln Ser Tyr Ser Asn Glu Glu Leu Asn Asn Ala Pro Gln Phe
                515                 520                 525

Asn Pro Glu Thr Leu Tyr Ala Ser Asp Thr Leu Ile Arg Phe Asn Gly
                530                 535                 540

Val Asn Tyr Ile Ser Gln Ser Lys Val Gln Lys Val Ser Pro Ser Asp
545                 550                 555                 560
```

Ser Asn Pro Trp Arg Val Phe Val Asp Trp Thr Gly Thr Lys Glu Arg
              565                 570                 575

Val Gly Thr Pro Lys Lys Ala Trp Pro Lys His Val Tyr Ala Pro Tyr
          580                 585                 590

Val Asp Phe Thr Leu Asn Thr Ile Pro Asp Leu Ala Ala Leu Ala Lys
          595                 600                 605

Asn His Asn Val Asn His Phe Thr Leu Ala Phe Val Val Ser Lys Asp
          610                 615                 620

Ala Asn Thr Cys Leu Pro Thr Trp Gly Thr Ala Tyr Gly Met Gln Asn
625                 630                 635                 640

Tyr Ala Gln Tyr Ser Lys Ile Lys Ala Leu Arg Glu Ala Gly Gly Asp
              645                 650                 655

Val Met Leu Ser Ile Gly Gly Ala Asn Asn Ala Pro Leu Ala Ala Ser
              660                 665                 670

Cys Lys Asn Val Asp Asp Leu Met Gln His Tyr Tyr Asp Ile Val Asp
              675                 680                 685

Asn Leu Asn Leu Lys Val Leu Asp Phe Asp Ile Glu Gly Thr Trp Val
          690                 695                 700

Ala Asp Gln Ala Ser Ile Glu Arg Arg Asn Leu Ala Val Lys Lys Val
705                 710                 715                 720

Gln Asp Lys Trp Lys Ser Gly Lys Asp Ile Ala Ile Trp Tyr Thr
              725                 730                 735

Leu Pro Ile Leu Pro Thr Gly Leu Thr Pro Glu Gly Met Asn Val Leu
              740                 745                 750

Ser Asp Ala Lys Ala Lys Gly Val Glu Leu Ala Gly Val Asn Val Met
              755                 760                 765

Thr Met Asp Tyr Gly Asn Ala Ile Cys Gln Ser Ala Asn Thr Glu Gly
          770                 775                 780

Gln Asn Ile His Gly Lys Cys Ala Thr Ser Ala Ile Ala Asn Leu His
785                 790                 795                 800

Ser Gln Leu Lys Gly Leu His Pro Asn Lys Ser Asp Ala Glu Ile Asp
              805                 810                 815

Ala Met Met Gly Thr Thr Pro Met Val Gly Val Asn Asp Val Gln Gly
              820                 825                 830

Glu Val Phe Tyr Leu Ser Asp Ala Arg Leu Val Met Gln Asp Ala Gln
          835                 840                 845

Lys Arg Asn Leu Gly Met Val Gly Ile Trp Ser Ile Ala Arg Asp Leu
850                 855                 860

Pro Gly Gly Thr Asn Leu Ser Pro Glu Phe His Gly Leu Thr Lys Glu
865                 870                 875                 880

Gln Ala Pro Lys Tyr Ala Phe Ser Glu Ile Phe Ala Pro Phe Thr Lys
              885                 890                 895

Gln

<210> SEQ ID NO 12
<211> LENGTH: 499
<212> TYPE: PRT
<213> ORGANISM: Serratia marcescens

<400> SEQUENCE: 12

Met Ser Thr Arg Lys Ala Val Ile Gly Tyr Tyr Phe Ile Pro Thr Asn
1               5                   10                  15

Gln Ile Asn Asn Tyr Thr Glu Thr Asp Thr Ser Val Val Pro Phe Pro
            20                  25                  30

-continued

Val Ser Asn Ile Thr Pro Ala Lys Ala Lys Gln Leu Thr His Ile Asn
         35                  40                  45

Phe Ser Phe Leu Asp Ile Asn Ser Asn Leu Glu Cys Ala Trp Asp Pro
 50                  55                  60

Ala Thr Asn Asp Ala Lys Ala Arg Asp Val Val Asn Arg Leu Thr Ala
 65                  70                  75                  80

Leu Lys Ala His Asn Pro Ser Leu Arg Ile Met Phe Ser Ile Gly Gly
                 85                  90                  95

Trp Tyr Tyr Ser Asn Asp Leu Gly Val Ser His Ala Asn Tyr Val Asn
            100                 105                 110

Ala Val Lys Thr Pro Ala Ala Arg Thr Lys Phe Ala Gln Ser Cys Val
            115                 120                 125

Arg Ile Met Lys Asp Tyr Gly Phe Asp Gly Val Asp Ile Asp Trp Glu
            130                 135                 140

Tyr Pro Gln Ala Ala Glu Val Asp Gly Phe Ile Ala Ala Leu Gln Glu
145                 150                 155                 160

Ile Arg Thr Leu Leu Asn Gln Gln Thr Ile Ala Asp Gly Arg Gln Ala
                165                 170                 175

Leu Pro Tyr Gln Leu Thr Ile Ala Gly Ala Gly Gly Ala Phe Phe Leu
            180                 185                 190

Ser Arg Tyr Tyr Ser Lys Leu Ala Gln Ile Val Ala Pro Leu Asp Tyr
            195                 200                 205

Ile Asn Leu Met Thr Tyr Asp Leu Ala Gly Pro Trp Glu Lys Ile Thr
            210                 215                 220

Asn His Gln Ala Ala Leu Phe Gly Asp Ala Ala Gly Pro Thr Phe Tyr
225                 230                 235                 240

Asn Ala Leu Arg Glu Ala Asn Leu Gly Trp Ser Trp Glu Glu Leu Thr
                245                 250                 255

Arg Ala Phe Pro Ser Pro Phe Ser Leu Thr Val Asp Ala Ala Val Gln
            260                 265                 270

Gln His Leu Met Met Glu Gly Val Pro Ser Ala Lys Ile Val Met Gly
            275                 280                 285

Val Pro Phe Tyr Gly Arg Ala Phe Lys Gly Val Ser Gly Gly Asn Gly
            290                 295                 300

Gly Gln Tyr Ser Ser His Ser Thr Pro Gly Glu Asp Pro Tyr Pro Asn
305                 310                 315                 320

Ala Asp Tyr Trp Leu Val Gly Cys Asp Glu Cys Val Arg Asp Lys Asp
                325                 330                 335

Pro Arg Ile Ala Ser Tyr Arg Gln Leu Glu Gln Met Leu Gln Gly Asn
            340                 345                 350

Tyr Gly Tyr Gln Arg Leu Trp Asn Asp Lys Thr Lys Thr Pro Tyr Leu
            355                 360                 365

Tyr His Ala Gln Asn Gly Leu Phe Val Thr Tyr Asp Asp Ala Glu Ser
            370                 375                 380

Phe Lys Tyr Lys Ala Lys Tyr Ile Lys Gln Gln Leu Gly Gly Val
385                 390                 395                 400

Met Phe Trp His Leu Gly Gln Asp Asn Arg Asn Gly Asp Leu Leu Ala
                405                 410                 415

Ala Leu Asp Arg Tyr Phe Asn Ala Asp Tyr Asp Ser Gln Leu
            420                 425                 430

Asp Met Gly Thr Gly Leu Arg Tyr Thr Gly Val Gly Pro Gly Asn Leu
            435                 440                 445

Pro Ile Met Thr Ala Pro Ala Tyr Val Pro Gly Thr Thr Tyr Ala Gln

```
            450                 455                 460
Gly Ala Leu Val Ser Tyr Gln Gly Tyr Val Trp Gln Thr Lys Trp Gly
465                 470                 475                 480

Tyr Ile Thr Ser Ala Pro Gly Ser Asp Ser Ala Trp Leu Lys Val Gly
                    485                 490                 495

Arg Leu Ala

<210> SEQ ID NO 13
<211> LENGTH: 1024
<212> TYPE: PRT
<213> ORGANISM: Escherichia coli

<400> SEQUENCE: 13

Met Thr Met Ile Thr Asp Ser Leu Ala Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Glu Ala Arg Thr Asp Arg Pro
        35                  40                  45

Ser Gln Gln Leu Arg Ser Leu Asn Gly Glu Trp Arg Phe Ala Trp Phe
50                  55                  60

Pro Ala Pro Glu Ala Val Pro Glu Ser Trp Leu Glu Cys Asp Leu Pro
65                  70                  75                  80

Glu Ala Asp Thr Val Val Pro Ser Asn Trp Gln Met His Gly Tyr
                85                  90                  95

Asp Ala Pro Ile Tyr Thr Asn Val Thr Tyr Pro Ile Thr Val Asn Pro
                100                 105                 110

Pro Phe Val Pro Thr Glu Asn Pro Thr Gly Cys Tyr Ser Leu Thr Phe
            115                 120                 125

Asn Val Asp Glu Ser Trp Leu Gln Glu Gly Gln Thr Arg Ile Ile Phe
        130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
210                 215                 220

Asp Phe His Val Ala Thr Arg Phe Asn Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
```

-continued

```
            325                 330                 335
Arg Ile Glu Asn Gly Leu Leu Leu Asn Gly Lys Pro Leu Leu Ile
            340                 345                 350
Arg Gly Val Asn Arg His Glu His His Pro Leu His Gly Gln Val Met
            355                 360                 365
Asp Glu Gln Thr Met Val Gln Asp Ile Leu Leu Met Lys Gln Asn Asn
            370                 375                 380
Phe Asn Ala Val Arg Cys Ser His Tyr Pro Asn His Pro Leu Trp Tyr
385                 390                 395                 400
Thr Leu Cys Asp Arg Tyr Gly Leu Tyr Val Val Asp Glu Ala Asn Ile
                405                 410                 415
Glu Thr His Gly Met Val Pro Met Asn Arg Leu Thr Asp Asp Pro Arg
                420                 425                 430
Trp Leu Pro Ala Met Ser Glu Arg Val Thr Arg Met Val Gln Arg Asp
                435                 440                 445
Arg Asn His Pro Ser Val Ile Ile Trp Ser Leu Gly Asn Glu Ser Gly
                450                 455                 460
His Gly Ala Asn His Asp Ala Leu Tyr Arg Trp Ile Lys Ser Val Asp
465                 470                 475                 480
Pro Ser Arg Pro Val Gln Tyr Glu Gly Gly Ala Asp Thr Thr Ala
                485                 490                 495
Thr Asp Ile Ile Cys Pro Met Tyr Ala Arg Val Asp Glu Asp Gln Pro
                500                 505                 510
Phe Pro Ala Val Pro Lys Trp Ser Ile Lys Lys Trp Leu Ser Leu Pro
                515                 520                 525
Gly Glu Thr Arg Pro Leu Ile Leu Cys Glu Tyr Ala His Ala Met Gly
                530                 535                 540
Asn Ser Leu Gly Gly Phe Ala Lys Tyr Trp Gln Ala Phe Arg Gln Tyr
545                 550                 555                 560
Pro Arg Leu Gln Gly Gly Phe Val Trp Asp Trp Val Asp Gln Ser Leu
                565                 570                 575
Ile Lys Tyr Asp Glu Asn Gly Asn Pro Trp Ser Ala Tyr Gly Gly Asp
                580                 585                 590
Phe Gly Asp Thr Pro Asn Asp Arg Gln Phe Cys Met Asn Gly Leu Val
                595                 600                 605
Phe Ala Asp Arg Thr Pro His Pro Ala Leu Thr Glu Ala Lys His Gln
                610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
                660                 665                 670
Val Ala Pro Gln Gly Lys Gln Leu Ile Glu Leu Pro Glu Leu Pro Gln
                675                 680                 685
Pro Glu Ser Ala Gly Gln Leu Trp Leu Thr Val Arg Val Val Gln Pro
                690                 695                 700
Asn Ala Thr Ala Trp Ser Glu Ala Gly His Ile Ser Ala Trp Gln Gln
705                 710                 715                 720
Trp Arg Leu Ala Glu Asn Leu Ser Val Thr Leu Pro Ala Ala Ser His
                725                 730                 735
Ala Ile Pro His Leu Thr Thr Ser Glu Met Asp Phe Cys Ile Glu Leu
                740                 745                 750
```

```
Gly Asn Lys Arg Trp Gln Phe Asn Arg Gln Ser Gly Phe Leu Ser Gln
            755                 760                 765

Met Trp Ile Gly Asp Lys Lys Gln Leu Leu Thr Pro Leu Arg Asp Gln
        770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
                820                 825                 830

Asp Ala Val Leu Ile Thr Thr Ala His Ala Trp Gln His Gln Gly Lys
                835                 840                 845

Thr Leu Phe Ile Ser Arg Lys Thr Tyr Arg Ile Asp Gly Ser Gly Gln
            850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
            915                 920                 925

Pro Tyr Val Phe Pro Ser Glu Asn Gly Leu Arg Cys Gly Thr Arg Glu
        930                 935                 940

Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp Ser Pro Ser Val Ser Ala Glu Phe
        995                 1000                1005

Gln Leu Ser Ala Gly Arg Tyr His Tyr Gln Leu Val Trp Cys Gln
    1010                1015                1020

Lys

<210> SEQ ID NO 14
<211> LENGTH: 297
<212> TYPE: PRT
<213> ORGANISM: Escherichia coli

<400> SEQUENCE: 14

Met Ala Thr Asn Leu Arg Gly Val Met Ala Ala Leu Leu Thr Pro Phe
1               5                   10                  15

Asp Gln Gln Gln Ala Leu Asp Lys Ala Ser Leu Arg Arg Leu Val Gln
                20                  25                  30

Phe Asn Ile Gln Gln Gly Ile Asp Gly Leu Tyr Val Gly Gly Ser Thr
            35                  40                  45

Gly Glu Ala Phe Val Gln Ser Leu Ser Glu Arg Glu Gln Val Leu Glu
        50                  55                  60

Ile Val Ala Glu Glu Ala Lys Gly Lys Ile Lys Leu Ile Ala His Val
65                  70                  75                  80

Gly Cys Val Ser Thr Ala Glu Ser Gln Gln Leu Ala Ala Ser Ala Lys
                85                  90                  95
```

```
Arg Tyr Gly Phe Asp Ala Val Ser Ala Val Thr Pro Phe Tyr Pro
                100                 105                 110

Phe Ser Phe Glu Glu His Cys Asp His Tyr Arg Ala Ile Ile Asp Ser
            115                 120                 125

Ala Asp Gly Leu Pro Met Val Val Tyr Asn Ile Pro Ala Leu Ser Gly
        130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
    210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
    290                 295

<210> SEQ ID NO 15
<211> LENGTH: 456
<212> TYPE: PRT
<213> ORGANISM: Escherichia coli

<400> SEQUENCE: 15

Met Leu Asn Asn Ala Met Ser Val Val Ile Leu Ala Ala Gly Lys Gly
1               5                   10                  15

Thr Arg Met Tyr Ser Asp Leu Pro Lys Val Leu His Thr Leu Ala Gly
            20                  25                  30

Lys Ala Met Val Gln His Val Ile Asp Ala Ala Asn Glu Leu Gly Ala
        35                  40                  45

Ala His Val His Leu Val Tyr Gly His Gly Gly Asp Leu Leu Lys Gln
    50                  55                  60

Ala Leu Lys Asp Asp Asn Leu Asn Trp Val Leu Gln Ala Glu Gln Leu
65                  70                  75                  80

Gly Thr Gly His Ala Met Gln Gln Ala Ala Pro Phe Phe Ala Asp Asp
                85                  90                  95

Glu Asp Ile Leu Met Leu Tyr Gly Asp Val Pro Leu Ile Ser Val Glu
            100                 105                 110

Thr Leu Gln Arg Leu Arg Asp Ala Lys Pro Gln Gly Gly Ile Gly Leu
        115                 120                 125

Leu Thr Val Lys Leu Asp Asp Pro Thr Gly Tyr Gly Arg Ile Thr Arg
    130                 135                 140

Glu Asn Gly Lys Val Thr Gly Ile Val Glu His Lys Asp Ala Thr Asp
145                 150                 155                 160

Glu Gln Arg Gln Ile Gln Glu Ile Asn Thr Gly Ile Leu Ile Ala Asn
```

165                 170                 175
Gly Ala Asp Met Lys Arg Trp Leu Ala Lys Leu Thr Asn Asn Asn Ala
            180                 185                 190

Gln Gly Glu Tyr Tyr Ile Thr Asp Ile Ile Ala Leu Ala Tyr Gln Glu
        195                 200                 205

Gly Arg Glu Ile Val Ala Val His Pro Gln Arg Leu Ser Glu Val Glu
    210                 215                 220

Gly Val Asn Asn Arg Leu Gln Leu Ser Arg Leu Glu Arg Val Tyr Gln
225                 230                 235                 240

Ser Glu Gln Ala Glu Lys Leu Leu Leu Ala Gly Val Met Leu Arg Asp
                245                 250                 255

Pro Ala Arg Phe Asp Leu Arg Gly Thr Leu Thr His Gly Arg Asp Val
            260                 265                 270

Glu Ile Asp Thr Asn Val Ile Ile Glu Gly Asn Val Thr Leu Gly His
        275                 280                 285

Arg Val Lys Ile Gly Thr Gly Cys Val Ile Lys Asn Ser Val Ile Gly
    290                 295                 300

Asp Asp Cys Glu Ile Ser Pro Tyr Thr Val Val Glu Asp Ala Asn Leu
305                 310                 315                 320

Ala Ala Ala Cys Thr Ile Gly Pro Phe Ala Arg Leu Arg Pro Gly Ala
                325                 330                 335

Glu Leu Leu Glu Gly Ala His Val Gly Asn Phe Val Glu Met Lys Lys
            340                 345                 350

Ala Arg Leu Gly Lys Gly Ser Lys Ala Gly His Leu Thr Tyr Leu Gly
        355                 360                 365

Asp Ala Glu Ile Gly Asp Asn Val Asn Ile Gly Ala Gly Thr Ile Thr
    370                 375                 380

Cys Asn Tyr Asp Gly Ala Asn Lys Phe Lys Thr Ile Ile Gly Asp Asp
385                 390                 395                 400

Val Phe Val Gly Ser Asp Thr Gln Leu Val Ala Pro Val Thr Val Gly
                405                 410                 415

Lys Gly Ala Thr Ile Ala Ala Gly Thr Thr Val Thr Arg Asn Val Gly
            420                 425                 430

Glu Asn Ala Leu Ala Ile Ser Arg Val Pro Gln Thr Gln Lys Glu Gly
        435                 440                 445

Trp Arg Arg Pro Val Lys Lys Lys
    450                 455

<210> SEQ ID NO 16
<211> LENGTH: 485
<212> TYPE: PRT
<213> ORGANISM: Corynebacterium glutamicum

<400> SEQUENCE: 16

Met Ser Ala Ser Asp Phe Ser Ser Ala Val Val Leu Ala Ala Gly
1               5                   10                  15

Ala Gly Thr Arg Met Lys Ser Asp Leu Gln Lys Thr Leu His Ser Ile
            20                  25                  30

Gly Gly Arg Ser Leu Ile Ser His Ser Leu His Ala Ala Ala Gly Leu
        35                  40                  45

Asn Pro Glu His Ile Val Ala Val Ile Gly His Arg Arg Asp Gln Val
    50                  55                  60

Gly Pro Ala Val Ser Gln Val Ala Glu Glu Leu Asp Arg Glu Val Leu
65                  70                  75                  80

-continued

```
Ile Ala Ile Gln Glu Glu Gln Asn Gly Thr Gly His Ala Val Gln Cys
                85                  90                  95
Ala Met Asp Gln Leu Glu Gly Phe Glu Gly Thr Ile Ile Val Thr Asn
            100                 105                 110
Gly Asp Val Pro Leu Leu Thr Asp Asp Thr Leu Ser Ala Leu Leu Asp
            115                 120                 125
Ala His Val Glu Val Pro Thr Ala Val Thr Val Leu Thr Met Arg Leu
        130                 135                 140
Asp Asp Pro Thr Gly Tyr Gly Arg Ile Val Arg Asn Glu Glu Gly Glu
145                 150                 155                 160
Val Thr Ala Ile Val Glu Gln Lys Asp Ala Ser Ala Glu Ile Gln Ala
                165                 170                 175
Ile Asp Glu Val Asn Ser Gly Val Phe Ala Phe Asp Ala Ala Ile Leu
            180                 185                 190
Arg Ser Ala Leu Ala Glu Leu Lys Ser Asp Asn Ala Gln Gly Glu Leu
        195                 200                 205
Tyr Leu Thr Asp Val Leu Gly Ile Ala Arg Gly Glu Gly His Pro Val
    210                 215                 220
Arg Ala His Thr Ala Ala Asp Ala Arg Glu Leu Ala Gly Val Asn Asp
225                 230                 235                 240
Arg Val Gln Leu Ala Glu Ala Gly Ala Glu Leu Asn Arg Arg Thr Val
                245                 250                 255
Ile Ala Ala Met Arg Gly Gly Ala Thr Ile Val Asp Pro Ala Thr Thr
            260                 265                 270
Trp Ile Asp Val Glu Val Ser Ile Gly Arg Asp Val Ile Ile His Pro
        275                 280                 285
Gly Thr Gln Leu Lys Gly Glu Thr Val Ile Gly Asp Arg Val Glu Val
    290                 295                 300
Gly Pro Asp Thr Thr Leu Thr Asn Met Thr Ile Gly Asp Gly Ala Ser
305                 310                 315                 320
Val Val Arg Thr His Gly Phe Asp Ser Thr Ile Gly Glu Asn Ala Thr
                325                 330                 335
Val Gly Pro Phe Thr Tyr Ile Arg Pro Gly Thr Thr Leu Gly Pro Glu
            340                 345                 350
Gly Lys Leu Gly Gly Phe Val Glu Thr Lys Lys Ala Thr Ile Gly Arg
        355                 360                 365
Gly Ser Lys Val Pro His Leu Thr Tyr Val Gly Asp Ala Thr Ile Gly
    370                 375                 380
Glu Glu Ser Asn Ile Gly Ala Ser Ser Val Phe Val Asn Tyr Asp Gly
385                 390                 395                 400
Glu Asn Lys His His Thr Thr Ile Gly Ser His Val Arg Thr Gly Ser
                405                 410                 415
Asp Thr Met Phe Ile Ala Pro Val Thr Val Gly Asp Gly Ala Tyr Ser
            420                 425                 430
Gly Ala Gly Thr Val Ile Lys Asp Asp Val Pro Pro Gly Ala Leu Ala
        435                 440                 445
Val Ser Gly Gly Arg Gln Arg Asn Ile Glu Gly Trp Val Gln Lys Lys
    450                 455                 460
Arg Pro Gly Thr Ala Ala Gln Ala Ala Glu Ala Ala Gln Asn Val
465                 470                 475                 480

His Asn Gln Glu Gly
            485
```

<210> SEQ ID NO 17
<211> LENGTH: 609
<212> TYPE: PRT
<213> ORGANISM: Escherichia coli

<400> SEQUENCE: 17

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
    370                 375                 380

```
Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 18
<211> LENGTH: 609
<212> TYPE: PRT
<213> ORGANISM: Artificial sequence
<220> FEATURE:
<223> OTHER INFORMATION: mutated amino acid sequence

<400> SEQUENCE: 18

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Thr Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
```

```
            130                 135                 140
Ala Val Leu Arg Ala Ile Pro Gln Leu Arg Gly Ala Tyr Gly Thr Val
145                 150                 155                 160

Ile Met Asp Ser Arg His Pro Asp Thr Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
                195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Cys His Tyr Met Gln Lys Glu
                245                 250                 255

Ile Tyr Glu Gln Pro Asn Ala Ile Lys Asn Thr Leu Thr Gly Arg Ile
                260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
                420                 425                 430

Asp Ile Val His Gly Leu Gln Ala Leu Pro Ser Arg Ile Glu Gln Met
            435                 440                 445

Leu Ser Gln Asp Lys Arg Ile Glu Ala Leu Ala Glu Asp Phe Ser Asp
450                 455                 460

Lys His His Ala Leu Phe Leu Ser Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
            515                 520                 525

Lys Leu Lys Ser Asn Ile Glu Glu Val Arg Ala Arg Gly Gly Gln Leu
530                 535                 540

Tyr Val Phe Ala Asp Gln Asp Ala Gly Phe Val Ser Ser Asp Asn Met
545                 550                 555                 560
```

```
His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
                580                 585                 590

Gly Thr Asp Val Asp Gln Pro Arg Asn Leu Ala Lys Ser Val Thr Val
                595                 600                 605

Glu

<210> SEQ ID NO 19
<211> LENGTH: 623
<212> TYPE: PRT
<213> ORGANISM: Corynebacterium glutamicum

<400> SEQUENCE: 19

Met Cys Gly Ile Val Gly Tyr Ile Gly Gln Ala Gly Asp Ser Arg Asp
1               5                   10                  15

Tyr Phe Ala Leu Asp Val Val Glu Gly Leu Arg Arg Leu Glu Tyr
                20                  25                  30

Arg Gly Tyr Asp Ser Ala Gly Ile Ala Ile His Ala Asn Gly Glu Ile
            35                  40                  45

Ser Tyr Arg Lys Lys Ala Gly Lys Val Ala Ala Leu Asp Ala Glu Ile
    50                  55                  60

Ala Lys Ala Pro Leu Pro Asp Ser Ile Leu Gly Ile Gly His Thr Arg
65                  70                  75                  80

Trp Ala Thr His Gly Gly Pro Thr Asp Val Asn Ala His Pro His Val
                85                  90                  95

Val Ser Asn Gly Lys Leu Ala Val Val His Asn Gly Ile Ile Glu Asn
                100                 105                 110

Phe Ala Glu Leu Arg Ser Glu Leu Ser Ala Lys Gly Tyr Asn Phe Val
                115                 120                 125

Ser Asp Thr Asp Thr Glu Val Ala Ala Ser Leu Leu Ala Glu Ile Tyr
            130                 135                 140

Asn Thr Gln Ala Asn Gly Asp Leu Thr Leu Ala Met Gln Leu Thr Gly
145                 150                 155                 160

Gln Arg Leu Glu Gly Ala Phe Thr Leu Leu Ala Ile His Ala Asp His
                165                 170                 175

Asp Asp Arg Ile Val Ala Ala Arg Arg Asn Ser Pro Leu Val Ile Gly
            180                 185                 190

Val Gly Glu Gly Glu Asn Phe Leu Gly Ser Asp Val Ser Gly Phe Ile
        195                 200                 205

Asp Tyr Thr Arg Lys Ala Val Glu Leu Ala Asn Asp Gln Val Val Thr
    210                 215                 220

Ile Thr Ala Asp Asp Tyr Ala Ile Thr Asn Phe Asp Gly Ser Glu Ala
225                 230                 235                 240

Val Gly Lys Pro Phe Asp Val Glu Trp Asp Ala Ala Ala Glu Lys
                245                 250                 255

Gly Gly Phe Gly Ser Phe Met Glu Lys Glu Ile His Asp Gln Pro Ala
            260                 265                 270

Ala Val Arg Asp Thr Leu Met Gly Arg Leu Asp Glu Asp Gly Lys Leu
        275                 280                 285

Val Leu Asp Glu Leu Arg Ile Asp Glu Ala Ile Leu Arg Ser Val Asp
    290                 295                 300

Lys Ile Val Ile Val Ala Cys Gly Thr Ala Ala Tyr Ala Gly Gln Val
305                 310                 315                 320
```

-continued

Ala Arg Tyr Ala Ile Glu His Trp Cys Arg Ile Pro Thr Glu Val Glu
            325                 330                 335

Leu Ala His Glu Phe Arg Tyr Arg Asp Pro Ile Leu Asn Glu Lys Thr
        340                 345                 350

Leu Val Val Ala Leu Ser Gln Ser Gly Glu Thr Met Asp Thr Leu Met
            355                 360                 365

Ala Val Arg His Ala Arg Glu Gln Gly Ala Lys Val Val Ala Ile Cys
        370                 375                 380

Asn Thr Val Gly Ser Thr Leu Pro Arg Glu Ala Asp Ala Ser Leu Tyr
385                 390                 395                 400

Thr Tyr Ala Gly Pro Glu Ile Ala Val Ala Ser Thr Lys Ala Phe Leu
                405                 410                 415

Ala Gln Ile Thr Ala Ser Tyr Leu Leu Gly Leu Tyr Leu Ala Gln Leu
            420                 425                 430

Arg Gly Asn Lys Phe Ala Asp Glu Val Ser Ser Ile Leu Asp Ser Leu
        435                 440                 445

Arg Glu Met Pro Glu Lys Ile Gln Gln Val Ile Asp Ala Glu Glu Gln
        450                 455                 460

Ile Lys Lys Leu Gly Gln Asp Met Ala Asp Ala Lys Ser Val Leu Phe
465                 470                 475                 480

Leu Gly Arg His Val Gly Phe Pro Val Ala Leu Glu Gly Ala Leu Lys
                485                 490                 495

Leu Lys Glu Ile Ala Tyr Leu His Ala Glu Gly Phe Ala Ala Gly Glu
            500                 505                 510

Leu Lys His Gly Pro Ile Ala Leu Val Glu Glu Gly Gln Pro Ile Phe
        515                 520                 525

Val Ile Val Pro Ser Pro Arg Gly Arg Asp Ser Leu His Ser Lys Val
        530                 535                 540

Val Ser Asn Ile Gln Glu Ile Arg Ala Arg Gly Ala Val Thr Ile Val
545                 550                 555                 560

Ile Ala Glu Glu Gly Asp Gly Ala Val Asn Asp Tyr Ala Asn Phe Ile
                565                 570                 575

Ile Arg Ile Pro Gln Ala Pro Thr Leu Met Gln Pro Leu Leu Ser Thr
            580                 585                 590

Val Pro Leu Gln Ile Phe Ala Cys Ala Val Ala Thr Ala Lys Gly Tyr
        595                 600                 605

Asn Val Asp Gln Pro Arg Asn Leu Ala Lys Ser Val Thr Val Glu
610                 615                 620

<210> SEQ ID NO 20
<211> LENGTH: 1331
<212> TYPE: DNA
<213> ORGANISM: Artificial sequence
<220> FEATURE:
<223> OTHER INFORMATION: codon-optimized nucleotide sequence

<400> SEQUENCE: 20
atggacctgc tgaacacgat tggtattggt gctgtctcct gctacgctct gctgtcaacg      60
gctcataagt cgatgcaaac cctgtatgcc cagccgaaag atcaaagctc tgcatcagaa     120
gactttgctt tcctgccgtc ggtggatatt atcgttccgt gttataacga aaatccgcat     180
acctttagcg aatgcctggc gtctattgcc aaccaggatt atgcgggcaa actgcgtgtg     240
tacgtggttg atgacggtag tgccaatcgt gaaaagctgg aacgcgttca tcacacctac     300
gcaggcgatc cgcgttttga cttcatcctg ctgcgtgaaa acgtgggtaa gcgtaaggca     360

| | | | | |
|---|---|---|---|---|
| cagattgcag | caatccgtgg | cagttccggt | gatctggtgc | tgaatgttga tagcgactct | 420 |
| accctggcat | cagacgtcgt | gacgaaactg | gctctgaaga | tgcagaaccc ggaaattggc | 480 |
| gcagctatgg | gtcaactgac | cgcgtctaac | cgtaatgata | cctggctgac gcgcctgatc | 540 |
| gacatggaat | attggctggc | ctgtaatgaa | gaacgtgcag | cacaggcacg ttttggtgca | 600 |
| gtgatgtgct | gttgcggtcc | gtgcgcaatg | tatcgtcgct | cagctctgct gtcgctgctg | 660 |
| gatcagtacg | aaagccaatt | tttccgtggc | aaaccgtctg | attttggtga agaccgccat | 720 |
| ctgaccattc | tgatgctgaa | ggcgggcttc | cgtacggatt | atgttccgga cgccatcgca | 780 |
| gctaccgttg | tcccggatcg | tatgggtccg | tacctgcgcc | agcaactgcg ttgggcacgc | 840 |
| agcaccttcc | gtgatacgct | gctggctctg | cgtctgctgc | cgggtctgga tcactatatt | 900 |
| acgctggacg | ttatcggtca | gaacctgggt | ccgctgctgc | tggcactggc tgtcctgacc | 960 |
| ggtgtcctgc | aagtggcact | gaccgctacg | gtcccgctgt | ggaccgtgat gatgattgca | 1020 |
| tcaatgacga | tgatccgttg | tgcagttgca | gcagtccgtg | cacgtcagct gcgctttctg | 1080 |
| gttttctcgc | tgcatacccc | gattaacctg | tttttcctgc | tgccgatgaa agcgtacgcc | 1140 |
| ctgtgcacgc | tgagtaactc | cgattggctg | agtcgctcat | cgccggcgaa taaaacctcc | 1200 |
| gccggcggtg | aacacccgac | cacggaagca | agtgctggcg | gtacctccgg caacgcgacg | 1260 |
| ccgctgcgtc | gcctgaacct | ggctcgtgac | tcctctaccg | ttaccccggc tggtgtctac | 1320 |
| tccatgattg | a | | | | 1331 |

<210> SEQ ID NO 21
<211> LENGTH: 1317
<212> TYPE: DNA
<213> ORGANISM: Artificial sequence
<220> FEATURE:
<223> OTHER INFORMATION: codon-optimized nucleotide sequence

<400> SEQUENCE: 21

| | | | | | |
|---|---|---|---|---|---|
| atgtacctgc | ttgacacaac | cagcaccgcc | gctatctcaa | tctacgcgct gctcttgacc | 60 |
| gcctacagga | gcatgcaagt | cctatatgct | cggccgatag | acggtccagc agtggcggca | 120 |
| gaaccggtcg | agacccgccc | tctgccagcc | gtggatgtta | tcgtccccag cttcaatgag | 180 |
| gacccaggca | tcctctcggc | gtgcctcgcg | tccattgcag | accaggatta tcctggagaa | 240 |
| ttgcgagtct | atgtcgttga | tgatggttct | cggaaccgcg | aggccattgt gcgtgtacgc | 300 |
| gccttctatt | cgcgcgatcc | gaggttcagc | ttcattctgc | tcccagagaa cgtcggaaag | 360 |
| cggaaagcgc | agattgccgc | gataggccaa | tcctctgggg | atttggtgct gaatgtcgac | 420 |
| tcggacagca | cgatcgcttt | cgatgtggtc | tccaagcttg | cctcgaagat gcgagatcca | 480 |
| gaggtcggtc | cggttatggg | tcaactcacg | gctagcaatt | cgggtgacac ttggctgact | 540 |
| aaattgatcg | acatggagta | ttggcttgcc | tgtaacgaag | aacgcgcggc acagtctcgc | 600 |
| ttcggtgctg | ttatgtgttg | ctgcggccct | tgtgctatgt | accgtcggtc ggcgctcgct | 660 |
| tcgctgcttg | accagtacga | aacgcaactg | tttcgcggta | agccaagcga cttcggtgag | 720 |
| gaccgccatc | tgacgattct | catgttgaag | gcaggctttc | gaactgagta cgttccagac | 780 |
| gccatagtgg | caaccgtcgt | cccggatacg | ctgaaaccat | atctgcgcca acaactgcgt | 840 |
| tgggcacgca | gcacgttccg | tgacacgttt | ctagcgctcc | ctctgttgcg cggcctcagc | 900 |
| ccttttctcg | catttgacgc | ggtcggacag | aatatcgggc | aactgttgct cgcccttcg | 960 |
| gtggtgacgg | gtcttgcgca | tctcataatg | accgccacag | tgccatggtg gacaattttg | 1020 |

| | | |
|---|---|---|
| attattgcgt gcatgaccat tatacgctgc agcgtcgtag cattgcatgc tcgccaactt | | 1080 |
| agatttcttg gcttcgttct gcacacaccc atcaacctct ttctcatact tccgctgaaa | | 1140 |
| gcttatgcgt tgtgtacatt gtccaatagc gactggctgt cacgctactc cgcgccagaa | | 1200 |
| gtaccagtca gcgggggaaa gcagacccca attcaaacct ccggtcgagt gacacctgac | | 1260 |
| tgcacttgca gcggcgagct ccgtcgacaa tggtcacatc ctcaatttga aaaatag | | 1317 |

<210> SEQ ID NO 22
<211> LENGTH: 1242
<212> TYPE: DNA
<213> ORGANISM: Sinorhizobium fredii USDA 191

<400> SEQUENCE: 22

| | | |
|---|---|---|
| atggatctgc ttggcacgac cggcgccgta gccatctcct tgtatgcagc actctcgacg | | 60 |
| gcttacaaag gcatgcaagc tatatacgct ttgccaacaa acaccacagc tgcgtcaacg | | 120 |
| cccgtgaccg gctccggtgc accgccgagc gtggatgtta cgtcccctg ctacaatgag | | 180 |
| gatccgcgcg cgctctcggc gtgcctagct tccattgcaa agcaagacta cgctggagag | | 240 |
| ttgcgggtct acgtggttga cgacggttct ggcaatcgca acgccatcat acctgtacac | | 300 |
| gatcattatg cgtgcgaccc gaggttccgc tttatcctga tgccaaagaa cgtcggaaag | | 360 |
| cgcaaggcgc agattgtcgc aatacgggaa tcatcgggag atttggtgct caacgttgac | | 420 |
| tcggacacga ccattgcgcc ggacgtagtc acgaaacttg ccctgaagat gtacagtccc | | 480 |
| gcggtcggcg cggcgatggg tcagttgacg gccagcaacc gcagcgacac atggctgacg | | 540 |
| cggttgatcg acatggagta ctggctcgcc tgcaacgagg aacgagcagc acaggctcgc | | 600 |
| tttggagccg ttatgtgttg ctgcggcccg tgtgccatgt accggcggtc cgcactccta | | 660 |
| ttgctgctcg ataaatacga gacgcaactg tttcgaggca ggccaagcga cttcggggaa | | 720 |
| gaccgccacc tcacaatcct catgctgaat gcaggctttc gaaccgagta cgttccggac | | 780 |
| gccatcgcgg cgacggtcgt tccaaactcg atggggcct atctgcgcca acaactgcgc | | 840 |
| tgggcacgca gcacgtttcg cgacacattg ctcgcgctcc gcctactgcc gggccttgat | | 900 |
| cgctatctta cgctggacgt gatcggacag aatcttggtc cgctgctcct agccctctcg | | 960 |
| gtcctgacgg ggctagcaca gctcgctctg acggccacag tgccttggtc gacgatcctg | | 1020 |
| atgattgcat ctatgacaat ggtccgctgc ggcgtggcgg cgtttcgagc gcgagagctg | | 1080 |
| cgattccttg ggttttcgct gcacaccctc ctcaacgtcg ctctcctgct ccccctcaaa | | 1140 |
| gcatatgcgt tgtgcacgtt gagcaacagc gactggctgt cgcgtggttc cccggctgcc | | 1200 |
| gcacccaacg gcgtaaagga ttctcctgaa ccccattgct aa | | 1242 |

<210> SEQ ID NO 23
<211> LENGTH: 994
<212> TYPE: DNA
<213> ORGANISM: Artificial sequence
<220> FEATURE:
<223> OTHER INFORMATION: codon-optimized nucleotide sequence

<400> SEQUENCE: 23

| | | |
|---|---|---|
| atgaaagaga ttaagatcca gaatattatc atcagcgaag agaaagcgcc gctggtggtg | | 60 |
| ccggaaattg gcattaacca caacggcagc ctggaactgg ctaagattat ggtggatgca | | 120 |
| agatgagatg agcaaggcgg cgaagaaggt gattcctggc aacgccaaga ttagcatcta | | 180 |
| tgagatcatg cagaaatgcg cgcttgatta taaagatgaa ctggcgctga agaatatac | | 240 |
| cgagaagtta ggtctggtct atctgtcgac gccattctcg cgcgcaggtg ccaaccgtct | | 300 |

```
ggaagatatg ggcgtgtctg ccttcaagat tggttccggt gaatgtaata attatccact    360
gatcaagcat attgccgcat tcaagaagcc gatgattgtc agcaccggca tgaacagcat    420
tgaatctatc aaaccgaccg ttaagattct gctggataat gagattccgt tcgttctgat    480
gcacaccacc aatctgtatc cgacgccgca taacctggtt cgcctgaacg cgatgctgga    540
gctgaagaag gagttctcct gtatggttgg cctgagcgat cataccaccg ataacctcgc    600
ctgtcttggc gcggtggttc tcggcgcatg cgtgcttgaa cgtcacttca ccgacagcat    660
gcatcgcagc ggtccggata tcgtctgctc gatggatacc aaggcactga aggaactgat    720
tattcagagc gagcagatgg cgattattcg cggcaataac gaatccaaga aggccgccaa    780
gcaggaacag gtgaccatcg acttcgcgtt cgcttcggtg gtcagtatta aggacatcaa    840
gaaaggcgaa gtgctgtcaa tggacaacat ctgggtgaag cgtccaggct taggcggcat    900
cagtgcggca gaattcgaga acattctcgg taagaaggct ctgcgcgata ttgagaatga    960
tgcgcagctg agctatgaag acttcgcctg ataa                                994
```

<210> SEQ ID NO 24
<211> LENGTH: 1122
<212> TYPE: DNA
<213> ORGANISM: Artificial sequence
<220> FEATURE:
<223> OTHER INFORMATION: codon-optimized nucleotide sequence

<400> SEQUENCE: 24

```
atggtgaaga gatcctgtt cattaccggc tcccgcgccg actacagcaa aattaaatcg     60
ctgatgtatc gcgtgcagaa tagcagcgag tttgagctct atatcttcgc caccgggatg    120
cacctgtcga aaaacttcgg ctacaccgtg aaggagctgt ataaaaatgg ctttaaaaac    180
atctacgagt tcattaacta cgataaatat tatcagaccg acaaagcgct ggcgaccacc    240
attgatggct ctcgcgcta tgccaacgaa ctgaaaccgg atctgatcgt ggtgcacggc    300
gatcgcattg aaccgctggc agcggcgatt gtcggcgcgc tgaataatat cctggtggcg    360
cacatcgaag cggcgagat tccggcacc atcgacgata gcctccgcca cgccatcagc     420
aagctcgcgc atattcatct ggttaacgat gaatttgcca acgccgcct gatgcagctg     480 ggcgaagatg agaaaagcat ttttattatt ggctcgccgg acctggaact gctgaacgac    540
aataaaatct ccctgagcga agcgaagaaa tactacgaca tcaattacga aaactacgcc    600
ctgttgatgt ccatccggt gacgaccgaa atcaccagca tcaagaatca ggcggataac    660
ctggtcaaag ccctgattca gtcgaacaaa actatattg tgatttatcc gaacaatgat    720
ctcggttttg aattgattct gcaaagctat gaagaattca aaaataaccc gcgctttaag    780
ctgttcccga gcctgcgctt cgagtatttc atcacgctgc tcaagaacgc cgatttatc    840 atcggcaaca gctcctgcat tctgaaagag gcgctgtacc tgaaaaccgc gggcattctg    900
gtgggcagcc gccagaacgg ccgcctcggc aatgaaaata ccctgaaggt gaacgcgaac    960
tccgacgaaa ttctcaaagc aatcaacacc atccataaaa acaggatttt gttcagcgcg    1020
aaactggaga tcctcgacag cagtaaaactc ttctttgaat atctgcagag cggcgacttc    1080
ttcaaactgt ccacccagaa agtgttcaag gacatcaagt ga                      1122
```

<210> SEQ ID NO 25
<211> LENGTH: 2694
<212> TYPE: DNA
<213> ORGANISM: Escherichia coli

<400> SEQUENCE: 25

```
atgaaattaa atatatttac taaatctatg attggtatgg ggctggtgtg ttccgctctg      60
ccagcattgg caatggaagc atggaataac caacaaggtg gtaataaata tcaggttatt     120
ttcgatggca aaatttatga aaatgcctgg tgggtttctt ctacaaattg cccgggaaaa     180
gcgaaagcaa atgatgcaac taacccgtgg cgtttaaagc gtaccgcaac agctgctgaa     240
attagtcagt ttggcaatac actttcctgc gaaaagagcg gcagctcatc ttcttcaaat     300
tcaaatacgc ctgcatccaa tacgccggct aatggcggtt cggctacacc agcacagggc     360
actgttccgt ctaattcttc tgtagttgcc tggaataaac agcagggcgg tcagacctgg     420
tatgtcgtct ttaatggtgc ggtatataaa atgcctggt gggtagcctc ttctaactgt     480
ccgggtgatg cgaaaagcaa tgatgccagc aacccatggc gttatgttcg tgccgctacg     540
gcaacggaaa tctcagaaac cagtaatcca cagtcctgta cttcagcacc acagccttca     600
ccggatgtga accggcaccg gacgttaaac cggctcctg atgttcagcc agccccagct     660
gataagtcaa acgacaacta tgctgtagta gcctggaaag tcaggaagg ttcttctaca     720
tggtacgtta tctataacgg cggcatttat aagaacgcct ggtgggtagg cgcggcaaat     780
tgcccaggcg atgcgaaaga aaacgatgcc agtaacccat ggcgttatgt tcgcgcggca     840
acggcaacag aaatcagcca gtatggtaac cctggctcct gttccgttaa gccggataat     900
aatggcggtg ctgtgactcc ggttgatcca actccgaaaa caccggtgac cccaactccg     960
gataacagcg agccatcaac accagcggat agcgttaacg attactcatt gcaagcgtgg    1020
agcggccagg aagtagcga aatttaccat gttattttca atggtaatgt ttacaagaac    1080
gcctggtggg ttgggtctaa agattgccca cggggtacca gcgctgaaaa ctccaataac    1140
ccatggcgtc tcgagcgtac agctaccgct gcggaattga gtcagtacgg taacccgact    1200
acctgtgaaa ttgataacgg cggcgtcatt gttgcggatg gtttccaggc cagcaaagcg    1260
tacagcgcgc acagcatcgt agattataac gatgcacatt ataaaacttc tgtcgatcaa    1320
gacgcatggg gctttgtccc gggcggcgat aacccgtgga gaaatacga accggcgaaa    1380
gcatggtccg catccactgt gtacgtgaaa ggtgatcgcg ttgttgttga tgggcaggct    1440
tatgaagcgc tgttctggac gcaaagtgac aaccctgctc tggtggcgaa ccaaaacgcc    1500
accggtagca atagccgccc gtggaagccg ttaggtaagg ctcagagcta tagcaacgaa    1560
gagctgaata tgcgccgca gtttaatcca gaaacgcttt atgccagcga tacgctgatt    1620
cgctttaacg gtgtgaacta catttctcag agtaaagtgc agaaagtttc tccttctgac    1680
agcaacccgt ggcgtgtttt tgttgactgg accggaacca agagcgcgt aggtacgccg    1740
aagaaagcgt ggccgaaaca cgtttatgca ccgtatgtcg actttacgct gaatacgatc    1800
ccggatctgg ctgcgctggc taagaatcat aacgtcaacc acttcacgct ggcgtttgtg    1860
gtgagtaaag atgcgaacac ctgtctgccg acatggggta ccgcttacgg tatgcagaat    1920
tacgctcagt acagcaaaat caaagctctg cgtgaggctg cgggcgatgt gatgctgtct    1980
atcggtggtg ctaacaacgc tccgctggct gcttcctgta agaacgtaga cgatctgatg    2040
cagcattatt atgacatcgt tgataacctg aacctcaaag tcctggactt cgatatcgaa    2100
ggcacctggg ttgcggatca ggcatctatt gaacgtcgta accttgctgt gaagaaagtg    2160
caggataaat ggaagtcaga aggcaaagat attgctatct ggtacaccct gccaattctg    2220
ccgactggcc tgacgccgga agggatgaat gtcctgagcg atgccaaagc gaaaggtgtt    2280
gagctggcgg gtgtgaacgt gatgacaatg gactacggta acgcgatttg tcagtctgca    2340
```

```
aataccgaag gccagaacat tcacggtaag tgtgcaacgt ctgcgattgc caacctgcat    2400
tcacaattga aaggcctcca tcccaataag agcgatgcag aaattgacgc tatgatgggt    2460
accacgccga tggttggcgt gaacgacgtt cagggcgagg tgttctatct ctctgatgct    2520
cgtctggtca tgcaggatgc gcagaagcgt aatctcggta tggttggtat ctggtcaatc    2580
gcgcgcgacc tgccgggcgg cactaacctg tctccggaat ccacggcct gactaaagaa    2640 caggcaccga agtacgcatt tagcgaaatc ttcgcgccgt ttactaagca ataa          2694

<210> SEQ ID NO 26
<211> LENGTH: 1789
<212> TYPE: DNA
<213> ORGANISM: Serratia marcescens

<400> SEQUENCE: 26
gtacaggcgg cagtgtaatg aaaattcatt gttatggtga tttatttcga cttttattct      60
cgaggaaaat aaacattaat ggcgacgggg aatattcccc cattgtaaaa acatccactc     120
tggagaaata ccatgtccac acgcaaagcc gttattgggt attattttat tccgaccaac     180
caaatcaata attacaccga gaccgatacg tctgtcgtgc cattcccggt ttccaacatt     240
acgccggcca agccaaaaca gctgacgcac attaacttct cgttcctgga tatcaacagc     300
aatctggaat gcgcctggga tccggccacc aacgacgcca aggcgcgcga tgtggtcaac     360
cgtctgaccg cgctcaaagc gcacaacccc agcctgcgca tcatgttctc catcggcggc     420
tggtactact ccaacgatct gggcgtgtcg cacgccaact atgtcaacgc ggtgaaaacc     480
ccggcgtcgc gcaccaagtt cgcccaatcc tgcgtgcgca tcatgaagga ttacggcttc     540
gacggcgtgg acatcgactg ggagtacccg caggcggcgg aagtggacgg tttcatcgcc     600
gcgctgcagg agatccgcac cttgctgaac cagcaaacca tcgcggacgg ccgccaggcg     660
ttgccgtatc agctgaccat cgccggcgcc ggcggcgctt tcttcctgtc gcgctattac     720
agcaagctgg cgcagatcgt cgcgccactc gattacatca acctgatgac ctacgatctg     780
gccggcccct gggagaagat caccaaccac caggcggcgc tgttcggcga cgcggccggg     840
ccgaccttct acaacgcgct gcgcgaagcc aatctgggct ggagctggga agagctgacc     900
cgcgccttcc ccagcccgtt cagcctgacg gtcgacgccg ccgtgcagca cacctgatg     960 atggaaggcg tgccgagcgc caaaatcgtc atgggcgtgc ccttctacgg ccgcgccttc    1020
aagggcgtca gcggcggcaa cggcggccag tacagcagcc acagcacgcc gggcgaagat    1080
ccgtatccga acgccgatta ctggctggtg ggctgcgacg agtgcgtgcg cgacaaggat    1140
ccgcgcatcg cctcctatcg ccagctggag cagatgctgc agggcaacta cggctatcag    1200
cggttgtgga acgataagac caaaaccccg tatctgtatc atgcgcagaa cgggctgttt    1260
gtcacctatg acgatgccga gagcttcaaa tacaaagcga agtacatcaa gcagcagcag    1320
ctgggcggca taatgttctg gcatttgggg caagacaacc gcaacggcga tctgctggcc    1380
gcgctggatc gctatttcaa cgccgcagac tacgacgaca gccagctgga tatgggcacc    1440
ggcctgcgat acaccggcgt cggccccggc aacctgccta tcatgaccgc gccggcttat    1500
gtgccgggca ccacttacgc gcagggcgcg ctggtgtcct accaaggcta cgtctggcag    1560
accaagtggg gttacatcac ctcgggcgcc ggctcagaca gcgcctggct gaaggtgggc    1620
cgcctggcgt aagccgtaaa aaacccgcgt agccgaatgc tgcggggttt tcattgagtt    1680
aaccgtttga ttttcgcgtc ccttcgtctc aattccttca gttgtggcac catggatagc    1740
```

-continued

```
cgccatcccg caccacttcg cggcccatca ggctgtagac atcgcatta          1789
```

<210> SEQ ID NO 27
<211> LENGTH: 3075
<212> TYPE: DNA
<213> ORGANISM: Escherichia coli

<400> SEQUENCE: 27

```
atgaccatga ttacggattc actggccgtc gttttacaac gtcgtgactg ggaaaaccct    60
ggcgttaccc aacttaatcg ccttgcagca catcccccct tcgccagctg gcgtaatagc   120
gaagaggccc gcaccgatcg cccttcccaa cagttgcgca gcctgaatgg cgaatggcgc   180
tttgcctggt ttccggcacc agaagcggtg ccggaaagct ggctggagtg cgatcttcct   240
gaggccgata ctgtcgtcgt cccctcaaac tggcagatgc acggttacga tgcgcccatc   300
tacaccaacg tgacctatcc cattacggtc aatccgccgt ttgttccac ggagaatccg    360
acgggttgtt actcgctcac atttaatgtt gatgaaagct ggctacagga aggccagacg   420
cgaattattt ttgatggcgt taactcggcg tttcatctgt ggtgcaacgg cgctgggtc    480
ggttacggcc aggacagtcg tttgccgtct gaatttgacc tgagcgcatt tttacgcgcc   540
ggagaaaacc gcctcgcggt gatggtgctg cgctggagtg acggcagtta ctggaagat   600
caggatatgt ggcggatgag cggcattttc cgtgacgtct cgttgctgca taaaccgact   660
acacaaatca gcgatttcca tgttgccact cgctttaatg atgatttcag ccgcgctgta   720
ctggaggctg aagttcagat gtgcggcgag ttgcgtgact acctacgggt aacagtttct   780
ttatggcagg gtgaaacgca ggtcgccagc ggcaccgcgc ctttcggcgg tgaaattatc   840
gatgagcgtg gtggttatgc cgatcgcgtc acactacgtc tgaacgtcga aaacccgaaa   900
ctgtggagcg ccgaaatccc gaatctctat cgtgcggtgg ttgaactgca caccgccgac   960
ggcacgctga ttgaagcaga agcctgcgat gtcggtttcc gcgaggtgcg gattgaaaat  1020
ggtctgctgc tgctgaacgg caagccgttg ctgattcgag gcgttaaccg tcacgagcat  1080
catcctctgc atggtcaggt catggatgag cagacgatgg tgcaggatat cctgctgatg  1140
aagcagaaca acttaacgc cgtgcgctgt tcgcattatc cgaaccatcc gctgtggtac   1200
acgctgtgcg accgctacgg cctgtatgtg gtggatgaag ccaatattga aacccacggc  1260
atggtgccaa tgaatcgtct gaccgatgat ccgcgctggc taccggcgat gagcgaacgc  1320
gtaacgcgaa tggtgcagcg cgatcgtaat cacccgagtg tgatcatctg gtcgctgggg  1380
aatgaatcag ccacggcgc taatcacgac gcgctgtatc gctggatcaa atctgtcgat  1440
ccttcccgcc cggtgcagta tgaaggcggc ggagccgaca ccacgccac cgatattatt  1500
tgcccgatgt acgcgcgcgt ggatgaagac cagcccttcc cggctgtgcc gaaatggtcc  1560
atcaaaaaat ggctttcgct acctggagag acgcgcccgc tgatcctttg cgaatacgcc  1620
cacgcgatgg gtaacagtct tggcggtttc gctaaatact ggcaggcgtt tcgtcagtat  1680
ccccgtttac agggcggctt cgtctgggac tgggtggatc agtcgctgat taaatatgat  1740
gaaaacggca accgtggtc ggcttacggc ggtgattttg gcgatacgcc gaacgatcgc  1800
cagttctgta tgaacggtct ggtctttgcc gaccgcacgc cgcatccagc gctgacggaa  1860
gcaaaacacc agcagcagtt tttccagttc cgtttatccg gcaaaccat cgaagtgacc  1920
agcgaatacc tgttccgtca tagcgataac gagctcctgc actggatggt ggcgctggat  1980
ggtaagccgc tggcaagcgg tgaagtgcct ctggatgtcg ctccacaagg taaacagttg  2040
attgaactgc ctgaactacc gcagccggag agcgccgggc aactctggct cacagtacgc  2100
```

```
gtagtgcaac cgaacgcgac cgcatggtca gaagccgggc acatcagcgc ctggcagcag   2160
tggcgtctgg cggaaaacct cagtgtgacg ctccccgccg cgtcccacgc catcccgcat   2220
ctgaccacca gcgaaatgga tttttgcatc gagctgggta ataagcgttg gcaatttaac   2280
cgccagtcag gctttctttc acagatgtgg attggcgata aaaacaact gctgacgccg    2340 ctgcgcgatc agttcacccg tgcaccgctg gataacgaca ttggcgtaag tgaagcgacc   2400
cgcattgacc ctaacgcctg ggtcgaacgc tggaaggcgg cgggccatta ccaggccgaa   2460
gcagcgttgt tgcagtgcac ggcagataca cttgctgatg cggtgctgat tacgaccgct   2520
cacgcgtggc agcatcaggg gaaaacctta tttatcagcc ggaaaaccta ccggattgat   2580
ggtagtggtc aaatggcgat taccgttgat gttgaagtgg cgagcgatac accgcatccg   2640
gcgcggattg gcctgaactg ccagctggcg caggtagcag agcgggtaaa ctggctcgga   2700
ttagggccgc aagaaaacta tcccgaccgc cttactgccg cctgttttga ccgctgggat   2760
ctgccattgt cagacatgta taccccgtac gtcttcccga gcgaaaacgg tctgcgctgc   2820
gggacgcgcg aattgaatta tggcccacac cagtggcgcg cgacttcca gttcaacatc     2880 agccgctaca gtcaacagca actgatgaaa accagccatc gccatctgct gcacgcggaa   2940
gaaggcacat ggctgaatat cgacggtttc catatgggga ttggtggcga cgactcctgg   3000
agcccgtcag tatcggcgga attccagctg agcgccggtc gctaccatta ccagttggtc   3060
tggtgtcaaa aataa                                                   3075

<210> SEQ ID NO 28
<211> LENGTH: 894
<212> TYPE: DNA
<213> ORGANISM: Escherichia coli

<400> SEQUENCE: 28
atggcaacga atttacgtgg cgtaatggct gcactcctga ctccttttga ccaacaacaa     60
gcactggata aagcgagtct gcgtcgcctg gttcagttca atattcagca gggcatcgac   120
ggtttatacg tgggtggttc gaccggcgag gcctttgtac aaagcctttc cgagcgtgaa   180
caggtactgg aaatcgtcgc cgaagaggcg aaaggtaaga ttaaactcat cgcccacgtc   240
ggttgcgtca gcaccgccga aagccaacaa cttgcggcat cggctaaacg ttatggcttc   300
gatgccgtct ccgccgtcac gccgttctac tatcctttca gctttgaaga acactgcgat   360
cactatcggg caattattga ttcggcggat ggtttgccga tggtggtgta caacattcca   420
gccctgagtg gggtaaaact gaccctggat cagatcaaca cacttgttac attgcctggc   480
gtaggtgcgc tgaaacagac ctctggcgat ctctatcaga tggagcagat ccgtcgtgaa   540
catcctgatc ttgtgctcta taacggttac gacgaaatct cgcctctggg tctgctggcg   600
ggcgctgatg gtggtatcgg cagtacctac aacatcatgg ctggcgcta tcagggatc     660 gttaaggcgc tgaaagaagg cgatatccag accgcgcaga aactgcaaac tgaatgcaat   720
aaagtcattg atttactgat caaaacgggc gtattccgcg gcctgaaaac tgtcctccat   780
tatatggatg tcgtttctgt gccgctgtgc cgcaaaccgt ttggaccggt agatgaaaaa   840
tatctgccag aactgaaggc gctggcccag cagttgatgc aagagcgcgg gtga          894

<210> SEQ ID NO 29
<211> LENGTH: 1371
<212> TYPE: DNA
<213> ORGANISM: Escherichia coli
```

<400> SEQUENCE: 29

```
atgttgaata atgctatgag cgtagtgatc cttgccgcag gcaaaggcac gcgcatgtat      60
tccgatcttc cgaaagtgct gcatacccct gccgggaaag cgatggttca gcatgtcatt     120
gatgctgcga atgaattagg cgcagcgcac gttcacctgg tgtacggtca cggcggcgat     180
ctgctaaaac aggcgctgaa agacgacaac cttaactggg tgcttcaggc agagcagctg     240
ggtacgggtc atgcaatgca gcaggccgca ccttctcttg ccgatgatga agacattta      300
atgctctacg gcgacgtgcc gctgatctct gtcgaaacac tccagcgtct gcgtgatgct     360
aaaccgcagg gtggcattgg tctgctgacg gtgaaactgg atgatccgac cggttatgga     420
cgtatcaccc gtgaaaacgg caaagttacc ggcattgttg agcacaaaga tgccaccgac     480
gagcagcgtc agattcagga gatcaacacc ggcattctga ttgccaacgg cgcagatatg     540
aaacgctggc tggcgaagct gaccaacaat aatgctcagg gcgaatacta catcaccgac     600
attattgcgc tggcgtatca ggaagggcgt gaaatcgtcg ccgttcatcc gcaacgttta     660
agcgaagtag aaggcgtgaa taaccgcctg caactctccc gtctggagcg tgtttatcag     720
tccgaacagg ctgaaaaact gctgttagca ggcgttatgc tgcgcgatcc agcgcgtttt     780
gatctgcgtg gtacgctaac tcacgggcgc gatgttgaaa ttgatactaa cgttatcatc     840
gagggcaacg tgactctcgg tcatcgcgtg aaaattggca ccggttgcgt gattaaaaac     900
agcgtgattg gcgatgattg cgaaatcagt ccgtataccg ttgtggaaga tgcgaatctg     960
gcagcggcct gtaccattgg cccgtttgcc cgtttgcgtc ctggtgctga gttgctggaa    1020
ggtgctcacg tcggtaactt cgttgagatg aaaaaagcgc gtctgggtaa aggctcgaaa    1080
gctggtcatc tgacttacct gggcgatgcg gaaattggcg ataacgttaa catcggcgcg    1140
ggaaccatta cctgcaacta cgatggtgcg aataaattta agaccattat cggcgacgat    1200
gtgtttgttg gttccgacac tcagctggtg gccccggtaa cagtaggcaa aggcgcgacc    1260
attgctgcgg gtacaactgt gacgcgtaat gtcggcgaaa atgcattagc tatcagccgt    1320
gtgccgcaga ctcagaaaga aggctggcgt cgtccggtaa agaaaaagtg a             1371
```

<210> SEQ ID NO 30
<211> LENGTH: 1458
<212> TYPE: DNA
<213> ORGANISM: Corynebacterium glutamicu

<400> SEQUENCE: 30

```
ttgagcgcaa gcgatttctc gagcgcagtt gtcgttttgg cagctggtgc cggaacccga      60
atgaaatcag acttacaaaa aacgttgcat agcatcggtg gacgcagtct catttcacat     120
agcttgcatg cagctgccgg gcttaatccc gagcacattg ttgcagtaat ggacatggaa     180
cgcgaccagg tgggtccagc cgttgcccag gttgcagaag aactggaccg ggaagtcctc     240
atcgctatcc aagaggaaca aaatggcacg gacacgctg tgcagtgcgc catggatcag      300
ctcgagggct ttgaaggcac gatcattgtc accaacggcg atgttcccct gctcaccgac     360
cacactctgt ctgcactgct ggatgcacac gtggaagttc aaccgctgt caccgtgttg      420
accatgcgtc tggatgaccc caccggctac ggccgcatcg tgcgcaacga agaaggcgaa     480
gtcaccgcca tcgttgagca aaaagatgct tcagcagaag tccaagccat cgatgaggtc     540
aactccggtg tctttgcttt cgacgccgcc atcttgcgtt ccgcactggc tgaactgaag     600
tccgacaacg ctcagggcga gctgtacctg accgacgtat gggcattgc tcgtggcgag     660
ggccacccag tgcgcgccca caccgccgcc gatgctcgtg aactcgccgg tgtcaacgat     720
```

```
cgtgtgcagc tcgcagaagc cggcgccgaa ctaaaccgtc gcaccgtcat cgccgctatg      780
cgtggtggcg caaccatcgt tgatccagca accacctgga tcgatgtgga ggtttctatc      840
ggccgcgacg tgatcatcca ccctggcacc cagctcaagg gcgaaactgt catcggagac      900
cgcgttgaag ttggtccaga caccaccttg accaacatga ccatcggcga cggcgcatcc      960
gtaatccgca cccacggttt cgactccacc atcggtgaaa cgccaccgt tggcccttc      1020 acctacatcc gcccaggaac cacactggga ccagaaggca agctcggtgg cttcgtagaa     1080
accaagaagg ccacaatcgg ccgtggctcc aaggttccac acctcaccta tgtcggcgac     1140
gccaccatcg gcgaggaatc caacatcgga gcctcctctg tcttcgtgaa ctacgacggt     1200
gaaaacaagc accacaccac catcggcagc cacgttcgca ctggttctga caccatgttt     1260
atcgctccag tgaccgtggg tgacggagcg tattccggag ccggtacagt aattaaagac     1320
gatgttccgc caggagccct tgccgtgtcc ggcggacgcc aacgaaacat cgaaggctgg     1380
gtgcaaaaga gcgccctgg aaccgctgca gcacaagccg cagaagccgc ccaaaacgtc      1440
cacaaccagg aaggctaa                                                   1458

<210> SEQ ID NO 31
<211> LENGTH: 1397
<212> TYPE: DNA
<213> ORGANISM: Artificial sequence
<220> FEATURE:
<223> OTHER INFORMATION: codon-optimized nucleotide sequence

<400> SEQUENCE: 31
atgaaaagcg atctgcagaa aacgctgcac tctatcggtg ccgcagcct gatttctcac       60 agcctgcacg ccgctgcggg tctgaacccg aacacatcg ttgcggttat tggtcacggt      120
cgtgatcagg tgggtccggc tgttgcgcag gttgcagaag aactggaccg tgaagtgctg      180
atcgctatcc aagaagaaca gaacggcacc ggccacgctg tccagtgcgc aatggatcag      240
ctggaaggtt tcgaaggcac tatcatcgtt actaacggtg acgtgccact gctgactgat      300 catacccctgt ctgctctgct ggacgctcac gttgaagtcc cgaccgctgt tactgttctg      360
accatgcgtc tggacgatcc gactggctac ggccgcatcg tacgtaatga agagggcgaa      420
gtcactgcaa ttgttgagca gaaagatgcg tctgccgaag ttcaggcgat cgatgaagta      480
aactccggcg ttttcgcgtt cgatgccgcg attctgcgca cgctctggc agagctgaaa      540 tccgataacg cgcagggtga actgtacctg accgacgttc tgggcatcgc ccgtggcgaa      600
ggtcacccgg ttcgcgcaca cactgctgca gacgctcgtg aactggcggg tgttaacgac      660
gtgttcagct ggccgaagct ggtgcagagc tgaaccgtcg tacggttatc gcggctatgc      720
gtggcggtgc tacgatcgtg gacccagcta ctacttggat cgatgtggaa gtttctattg      780
gtcgtgacgt aatcatccac ccgggtaccc aactgaaagg tgaaacggta atcggtgatc      840
gtgttgaggt tggtccggac accaccctga ctaatatgac catcggcgac ggcgcgagcg      900
ttatccgcac tcacggcttt gattctacta tcggcgaaaa cgccaccgtt ggtccattca      960
cctatattcg tccaggcact actctgggtc cggaaggcaa actgggcggt ttcgttgaaa     1020
ctaagaaagc tactatcggt cgtggtagca agtgccgca tctgacgtac gttggcgatg     1080
ctaccatcgg cgaggaatcc aacatcggtg caagcagcgt ctttgtgaat tatgacggtg     1140
aaaacaaaca ccacaccacg atcggttccc atgttcgtac cggctctgat accatgttca     1200
tcgcaccggt caccgtgggt gatggcgcat actccggcgc gggtaccgtg atcaaggacg     1260
```

| | |
|---|---|
| acgtgccacc gggtgcactg cgtgtttccg gtggccgcca gcgtaacatc gaaggttggg | 1320 |
| ttcagaaaaa acgtccaggt accgcggcgg cccaggccgc tgaagctgct caaaacgttc | 1380 |
| acaaccagga aggttga | 1397 |

```
<210> SEQ ID NO 32
<211> LENGTH: 1830
<212> TYPE: DNA
<213> ORGANISM: Escherichia coli

<400> SEQUENCE: 32
```

| | |
|---|---|
| atgtgtggaa ttgttggcgc gatcgcgcaa cgtgatgtag cagaaatcct tcttgaaggt | 60 |
| ttacgtcgtc tggaataccg cggatatgac tctgccggtc tggccgttgt tgatgcagaa | 120 |
| ggtcatatga cccgcctgcg tcgcctcggt aaagtccaga tgctggcaca ggcagcggaa | 180 |
| gaacatcctc tgcatggcgg cactggtatt gctcacactc gctgggcgac ccacggtgaa | 240 |
| ccttcagaag tgaatgcgca tccgcatgtt tctgaacaca ttgtggtggt gcataacggc | 300 |
| atcatcgaaa accatgaacc gctgcgtgaa gagctaaaag cgcgtggcta taccttcgtt | 360 |
| tctgaaaccg acaccgaagt gattgcccat ctggtgaact gggagctgaa acaaggcggg | 420 |
| actctgcgtg aggccgttct gcgtgctatc ccgcagctgc gtggtgcgta cggtacagtg | 480 |
| atcatggact cccgtcaccc ggataccctg ctggcggcac gttctggtag tccgctggtg | 540 |
| attggcctgg ggatgggcga aactttatc gcttctgacc agctggcgct gttgccggtg | 600 |
| acccgtcgct ttatcttcct tgaagagggc gatattgcgg aaatcactcg ccgttcggta | 660 |
| aacatcttcg ataaaactgg cgcggaagta aacgtcagg atatcgaatc caatctgcaa | 720 |
| tatgacgcgg gcgataaagg catttaccgt cactacatgc agaaagagat ctacgaacag | 780 |
| ccgaacgcga tcaaaaacac ccttaccgga cgcatcagcc acgtcaggt tgatttaagc | 840 |
| gagctgggac cgaacgccga cgaactgctg tcgaaggttg agcatattca gatcctcgcc | 900 |
| tgtggtactt cttataactc cggtatggtt tcccgctact ggtttgaatc gctagcaggt | 960 |
| attccgtgcg acgtcgaaat cgcctctgaa ttccgctatc gcaaatctgc cgtgcgtcgt | 1020 |
| aacagcctga tgatcacctt gtcacagtct ggcgaaaccg cggatacct ggctggcctg | 1080 |
| cgtctgtcga agagctgggg ttaccttggt tcactggcaa tctgtaacgt tccgggttct | 1140 |
| tctctggtgc gcgaatccga tctggcgcta atgaccaacg cgggtacaga atcggcgtg | 1200 |
| gcatccacta aagcattcac cactcagtta actgtgctgt tgatgctggt ggcgaagctg | 1260 |
| tctcgcctga aggtctgga tgcctccatt gaacatgaca tcgtgcatgg tctgcaggcg | 1320 |
| ctgccgagcc gtattgagca gatgctgtct caggacaaac gcattgaagc gctggcagaa | 1380 |
| gatttctctg acaaacatca cgcgctgttc ctgggccgtg gcgatcagta cccaatcgcg | 1440 |
| ctggaaggcg cattgaagtt gaaagagatc tcttacattc acgctgaagc ctacgctgct | 1500 |
| ggcgaactga acacggtcc gctggcgcta attgatgccg atatgccggt tattgttgtt | 1560 |
| gcaccgaaca cgaattgct ggaaaaactg aaatccaaca ttgaagaagt tcgcgcgcgt | 1620 |
| ggcggtcagt tgtatgtctt cgccgatcag gatgcgggtt ttgtaagtag cgataacatg | 1680 |
| cacatcatcg agatgccgca tgtggaagag gtgattgcac cgatcttcta caccgttccg | 1740 |
| ctgcagctgc tggcttacca tgtcgcgctg atcaaaggca ccgacgttga ccagccgcgt | 1800 |
| aacctggcaa atcggttac ggttgagtaa | 1830 |

```
<210> SEQ ID NO 33
<211> LENGTH: 1830
```

```
<212> TYPE: DNA
<213> ORGANISM: Artificial sequence
<220> FEATURE:
<223> OTHER INFORMATION: codon-optimized nucleotide sequence

<400> SEQUENCE: 33
atgtgcggta tcgttggtgc catcgcgcag cgtgacgtgg ctgaaatcct gctggagggt      60
ctgcgtcgtc tggaataccg tggctacgac agcgcgggcc tggcagttgt cgatactgag     120
ggtcatatga cccgtctgcg tcgtctgggt aaagtacaga tgctggcgca ggcagcggaa     180
gaacatccgc tgcacggcgg caccggtatt gcacacacgc gctgggcgac ccatggcgaa     240
ccgagcgaag tcaacgcaca cccgcatgtt tctgagcata ttgttgtggt tcacaacggc     300
atcatcgaaa accacgagcc gctgcgtgaa gaactgaaag cccgcggtta ccctttgta      360
tctgaaacgg atactgaggt tatcgctcac ctggtaaact gggagctgaa gcaaggcggc     420
accctgcgcg aagcggtact gcgtgctatt ccacagctgc gtggcgccta tggtaccgtt     480
attatggata gccgtcatcc tgatacccctg ctggcagccc gttctggttc ccgctggta    540
attggcctgg gcatgggcga aactttatc gccagcgacc aactggctct gctgccggtt     600
actcgtcgct tcattttttct ggaagaaggc gacatcgcag aaatcactcg tcgctccgtg    660
aatattttg ataaaaccgg cgctgaagtc aaacgtcagg acatcgagtc taacctgcag     720
tacgatgcag gtgacaaagg catttattgc cattatatgc agaaagaaat ctacgaacag     780
ccgaacgcta tcaagaatac cctgactggt cgtatctccc acggtcaggt tgatctgtcc     840
gaactgggtc cgaacgctga cgaactgctg tctaaagtgg aacacatcca gattctggcg    900
tgcggtacta gctacaactc cggtatggtt ctcgttact ggttcgaatc tctggctggt     960
atcccgtgcg acgttgaaat cgcgtctgaa tttcgttacc gcaaaagcgc tgttcgtcgt    1020
aacagcctga tgatcaccct gtcccagtct ggtgaaaccg ctgacacccct ggcaggcctg   1080
cgcctgagca agaactgggt tacctgggt tctctggcga tctgcaacgt gccgggctct    1140
tctctggtgc gcgagtctga cctggcactg atgaccaacg ctggcaccga atcggcgtt    1200
gcatctacca aggccttcac cactcagctg actgtgctgc tgatgctggt ggctaaactg   1260
tctcgtctga aggtctgga cgcgagcatc gaacacgata tcgttcacgg cctgcaggcg   1320
ctgccttctc gtatcgaaca gatgctgagc caggacaagc gcatcgaagc gctggcggaa   1380
gatttctccg acaaacatca tgcgctgttc ctgtcccgtg tgaccagta tccgattgct    1440
ctggaaggcg ctctgaaact gaaagaaatt agctacatcc acgctgaggc atatgctgca   1500
ggtgaactga acacggccc gctggctctg atcgatgcgg acatgccagt atcgttgta    1560
gccccgaaca acgagctgct ggaaaaactg aaatccaaca ttgaagaagt gcgcgctcgt   1620
ggcggccaac tgtacgtttt cgctgaccag gacgctggtt ttgttagcag cgataacatg   1680
cacattattg aaatgccgca cgttgaagaa gttatcgctc cgatcttcta caccgttccg   1740
ctgcagctgc tggcatacca cgttgctctg atcaaaggta ctgacgtgga tcagccacgt   1800
aatctggcta aaagcgtgac tgttgaataa                                      1830

<210> SEQ ID NO 34
<211> LENGTH: 1872
<212> TYPE: DNA
<213> ORGANISM: Corynebacterium glutamicum

<400> SEQUENCE: 34
atgtgtggaa ttgttggata tattggccaa gcgggcgact cccgtgatta ctttgctcta      60
```

```
gatgtagttg ttgaaggact acgtcgcctg aataccgcg gatatgactc cgcaggtatt      120
gctattcacg ccaatggtga gattagctac cgaaagaagg ccggaaaggt tgctgcacta    180
gatgcagaaa tcgctaaagc acctcttcca gattctattt tgggaattgg acacacccgt   240
tgggcaactc atggtggccc aaccgatgtc aacgctcacc cccacgttgt tccaatggc    300
aagcttgccg tagtacacaa cggcatcatc gaaaactttg cggaactgcg ctctgagctt   360
tccgctaagg gctacaactt tgtatccgat accgataccg aagttgctgc ttctttgctt   420
gctgaaattt acaatactca ggcaaacggt gacctcaccc ttgctatgca gctgaccggt   480
cagcgccttg agggtgcttt cacccctgcta gctattcatg ctgatcacga tgaccgcatc  540
gttgcagctc gtcgtaactc tcctttggtt atcggcgtcg gcgagggcga aacttcctc    600
ggatctgacg tttctggctt tattgattac acccgcaagg ctgtagagct ggctaatgac   660
caggttgtta ccatcaccgc tgatgattac gccatcacca actttgatgg atcagaagca   720
gttggcaagc ctttcgacgt ggagtgggac gctgcagctg ctgaaaaggg tggcttcggt   780
tccttcatgg agaaggaaat ccacgatcag ccagcagctg ttcgcgatac cctgatgggc   840
cgtcttgatg aagatggcaa gctcgttctt gatgagctgc gcatcgatga agctattctg   900
cgtagtgtcg acaagatcgt cattgttgct tgtggtactg cagcttatgc aggccaggtt   960
gctcgttacg ccattgagca ctggtgccgc atcccaaccg aggtggagct ggctcacgag  1020
ttccgttacc gcgacccaat cctcaacgag aagacccttg ttgtggcatt gtcccagtcc  1080
ggcgagacca tggatacccct catggctgtt cgccacgcac gtgagcaggg tgccaaggtt 1140
gttgctattt gtaacactgt tggatccact cttccacgtg aagcagatgc gtccctgtac  1200
acctacgctg gccctgagat cgctgtggcg tccaccaagg cgttcttggc tcagatcact  1260
gcttcttact tgcttggcct gtacttggct cagctgcgcg caacaagtt cgctgatgag   1320
gtttcttcca ttctggacag cctgcgtgag atgcctgaga agattcagca ggtcatcgat  1380
gcagaagagc agatcaagaa gcttggccaa gatatggcag atgctaagtc tgtgctgttc  1440
ctgggccgcc acgttggttt cccagttgcg cttgagggtg cgttgaagct caaggagatc  1500
gcatacctgc acgctgaagg tttcgctgca ggcgagctca gcacggccc aattgctttg   1560
gttgaggaag gccagccgat cttcgttatc gtgccttcac ctcgtggtcg cgattccctg  1620
cactccaagg ttgtctccaa cattcaggag atccgtgcac gtggcgctgt caccatcgtg  1680
attgcagagg aaggcgatga ggctgtcaac gattacgcca acttcatcat ccgcattcct  1740
caggccccaa ccctgatgca gcctctgctg tccaccgtgc ctctgcagat ctttgcgtgc  1800
gctgtggcaa ccgcaaaggg ctacaacgtg gatcagcctc gtaacctggc aaagtctgtc  1860
accgtcgaat aa                                                        1872
```

<210> SEQ ID NO 35
<211> LENGTH: 419
<212> TYPE: PRT
<213> ORGANISM: Escherichia coli

<400> SEQUENCE: 35

```
Met Asp Lys Phe Arg Val Gln Gly Pro Thr Lys Leu Gln Gly Glu Val
1               5                   10                  15

Thr Ile Ser Gly Ala Lys Asn Ala Ala Leu Pro Ile Leu Phe Ala Ala
            20                  25                  30

Leu Leu Ala Glu Glu Pro Val Glu Ile Gln Asn Val Pro Lys Leu Lys
        35                  40                  45
```

```
Asp Val Asp Thr Ser Met Lys Leu Leu Ser Gln Leu Gly Ala Lys Val
 50                  55                  60

Glu Arg Asn Gly Ser Val His Ile Asp Ala Arg Asp Val Asn Val Phe
 65                  70                  75                  80

Cys Ala Pro Tyr Asp Leu Val Lys Thr Met Arg Ala Ser Ile Trp Ala
                 85                  90                  95

Leu Gly Pro Leu Val Ala Arg Phe Gly Gln Gly Gln Val Ser Leu Pro
            100                 105                 110

Gly Gly Cys Thr Ile Gly Ala Arg Pro Val Asp Leu His Ile Ser Gly
        115                 120                 125

Leu Glu Gln Leu Gly Ala Thr Ile Lys Leu Glu Glu Gly Tyr Val Lys
130                 135                 140

Ala Ser Val Asp Gly Arg Leu Lys Gly Ala His Ile Val Met Asp Lys
145                 150                 155                 160

Val Ser Val Gly Ala Thr Val Thr Ile Met Cys Ala Ala Thr Leu Ala
                165                 170                 175

Glu Gly Thr Thr Ile Ile Glu Asn Ala Ala Arg Glu Pro Glu Ile Val
            180                 185                 190

Asp Thr Ala Asn Phe Leu Ile Thr Leu Gly Ala Lys Ile Ser Gly Gln
        195                 200                 205

Gly Thr Asp Arg Ile Val Ile Glu Gly Val Glu Arg Leu Gly Gly Gly
210                 215                 220

Val Tyr Arg Val Leu Pro Asp Arg Ile Glu Thr Gly Thr Phe Leu Val
225                 230                 235                 240

Ala Ala Ala Ile Ser Arg Gly Lys Ile Ile Cys Arg Asn Ala Gln Pro
                245                 250                 255

Asp Thr Leu Asp Ala Val Leu Ala Lys Leu Arg Asp Ala Gly Ala Asp
            260                 265                 270

Ile Glu Val Gly Glu Asp Trp Ile Ser Leu Asp Met His Gly Lys Arg
275                 280                 285

Pro Lys Ala Val Asn Val Arg Thr Ala Pro His Pro Ala Phe Pro Thr
290                 295                 300

Asp Met Gln Ala Gln Phe Thr Leu Leu Asn Leu Val Ala Glu Gly Thr
305                 310                 315                 320

Gly Phe Ile Thr Glu Thr Val Phe Glu Asn Arg Phe Met His Val Pro
                325                 330                 335

Glu Leu Ser Arg Met Gly Ala His Ala Glu Ile Glu Ser Asn Thr Val
            340                 345                 350

Ile Cys His Gly Val Glu Lys Leu Ser Gly Ala Gln Val Met Ala Thr
        355                 360                 365

Asp Leu Arg Ala Ser Ala Ser Leu Val Leu Ala Gly Cys Ile Ala Glu
370                 375                 380

Gly Thr Thr Val Val Asp Arg Ile Tyr His Ile Asp Arg Gly Tyr Glu
385                 390                 395                 400

Arg Ile Glu Asp Lys Leu Arg Ala Leu Gly Ala Asn Ile Glu Arg Val
                405                 410                 415

Lys Gly Glu

<210> SEQ ID NO 36
<211> LENGTH: 438
<212> TYPE: PRT
<213> ORGANISM: Corynebacterium glutamicum

<400> SEQUENCE: 36
```

-continued

```
Met Tyr Ala Glu Ile Asn Gly Gly Phe Ile Pro Glu Gly Thr Val Arg
1               5                   10                  15

Val Ser Gly Ala Lys Asn Ser Ala Thr Arg Leu Leu Ala Ala Ala Leu
            20                  25                  30

Leu Thr Asp Glu Val Val His Leu Gly Asn Phe Pro Thr Lys Leu Val
        35                  40                  45

Asp Val Glu His Lys Ile Arg Phe Ile Glu Glu Leu Gly Gly Lys Val
    50                  55                  60

His Val Asp His Asp Glu Gln Ile Leu Val Val Asp Ala Lys Asp Leu
65                  70                  75                  80

Ala Ala Arg Glu Met Thr Thr Asp Glu Leu Asn Ile Pro Ile Arg Thr
                85                  90                  95

Thr Tyr Leu Leu Ala Ala Ala Gln Ile Gly Arg Gly Glu Ile Ala Arg
            100                 105                 110

Val Pro Phe Pro Gly Gly Cys Ala Ile Gly Gly Pro Ala Gly Gly
        115                 120                 125

Arg Gly Tyr Asp Leu His Leu Met Val Trp Glu Gln Leu Gly Cys Lys
    130                 135                 140

Ile Leu Glu Lys Asp Asp His Ile Glu Val Thr Ala Pro Gln Gly Phe
145                 150                 155                 160

Ile Gly Gly Val Ile Asp Phe Pro Ile Ser Thr Val Gly Gly Thr Glu
                165                 170                 175

Asn Ala Leu Leu Cys Ala Ser Ile Ala Ser Gly Asp Thr Lys Ile Ala
            180                 185                 190

Asn Ala Tyr Ile Thr Pro Glu Ile Thr Asp Leu Ile Glu Leu Leu Arg
            195                 200                 205

Arg Met Gly Ala Glu Ile Thr Val Tyr Gly Thr Ser Arg Ile His Val
    210                 215                 220

Lys Gly Arg Ala Gly Leu Leu Gln Gly Ala Tyr Met Asp Val Met Pro
225                 230                 235                 240

Asp Arg Ile Glu Ala Leu Thr Trp Ile Val Tyr Gly Ile Ile Ser Gly
                245                 250                 255

Gly Arg Ile Thr Val Glu Gly Val Pro Phe Ser Ser Met Glu Val Pro
            260                 265                 270

Phe Ile His Leu Glu Lys Ala Gly Val Asp Leu Phe Arg Asn Ser Ser
            275                 280                 285

Ser Val Tyr Ile Thr Pro Glu Cys Leu Pro Ser Gly Ser Val Gln Pro
    290                 295                 300

Phe Glu Leu Ala Cys Gly Thr His Pro Gly Val Ile Ser Asp Met Gln
305                 310                 315                 320

Ala Leu Phe Val Leu Leu Gly Leu Lys Gly Ala Gly Thr Ser Arg Val
                325                 330                 335

Tyr Asp Tyr Arg Tyr Pro Glu Arg Ile Ala Phe Val Glu Glu Leu Thr
            340                 345                 350

Asn Leu Val Ser Gly Asp Lys Leu Ser Ala Glu Ala Gly Lys Ile Thr
            355                 360                 365

Ile Gln Gly Asp Ala Thr Phe Arg Pro Gly Tyr Ala Asn Ser Thr Asp
    370                 375                 380

Leu Arg Gly Ser Met Ala Val Val Leu Ala Ala Leu Cys Ala Asp Gly
385                 390                 395                 400

Lys Ser Thr Ile Asn Asn Val His Met Ala Leu Arg Gly Tyr Asn Glu
                405                 410                 415

Leu Asp Lys Lys Leu Arg Leu Leu Gly Ala Asp Leu Thr Ile Arg Glu
```

```
                420              425              430
Gly Glu Val Pro Ser Pro
            435

<210> SEQ ID NO 37
<211> LENGTH: 418
<212> TYPE: PRT
<213> ORGANISM: Corynebacterium glutamicum

<400> SEQUENCE: 37

Val Lys Asp Lys Phe Leu Val Thr Gly Gly Ala Gln Leu Gln Gly Ala
1               5                   10                  15

Val Lys Val Tyr Gly Ala Lys Asn Ser Val Leu Lys Leu Met Ala Ala
            20                  25                  30

Ala Leu Leu Ala Glu Gly Thr Thr Thr Leu Thr Asn Cys Pro Glu Ile
        35                  40                  45

Leu Asp Val Pro Leu Met Arg Asp Val Leu Val Gly Leu Gly Cys Asp
    50                  55                  60

Val Thr Ile Asp Gly Ser Thr Val Thr Ile Thr Pro Ala Glu Leu
65                  70                  75                  80

Ser Ser Asn Ala Asp Phe Pro Ala Val Thr Gln Phe Arg Ala Ser Val
                85                  90                  95

Cys Val Leu Gly Pro Leu Thr Ala Arg Cys Gly Arg Ala Val Val Ser
            100                 105                 110

Leu Pro Gly Gly Asp Ala Ile Gly Ser Arg Pro Leu Asp Met His Gln
        115                 120                 125

Ser Gly Leu Glu Lys Leu Gly Ala Thr Thr Arg Ile Ser His Gly Ala
    130                 135                 140

Val Val Ala Glu Ala Glu Lys Leu Val Gly Ala Asn Ile Thr Leu Asp
145                 150                 155                 160

Phe Pro Ser Val Gly Ala Thr Glu Asn Ile Leu Thr Ala Ser Val Met
                165                 170                 175

Ala Glu Gly Arg Thr Val Leu Asp Asn Ala Ala Arg Glu Pro Glu Ile
            180                 185                 190

Val Asp Leu Cys Arg Met Leu Arg Ser Met Gly Ala Asn Ile Glu Gly
        195                 200                 205

Glu Gly Ser Pro Thr Ile Thr Ile Glu Gly Val Glu Lys Leu Thr Pro
    210                 215                 220

Thr Gln His Glu Val Ile Gly Asp Arg Ile Val Ala Gly Thr Trp Ala
225                 230                 235                 240

Tyr Ala Ala Ala Met Thr Arg Gly Asp Ile Thr Val Gly Gly Ile Ala
                245                 250                 255

Pro Arg Tyr Leu His Leu Pro Leu Glu Lys Leu Lys Ile Ala Gly Ala
            260                 265                 270

Lys Val Glu Thr Tyr Glu Asn Gly Phe Arg Val Gln Met Asp Lys Gln
        275                 280                 285

Pro Glu Ala Thr Asp Tyr Gln Thr Leu Pro Phe Pro Gly Phe Pro Thr
    290                 295                 300

Asp Leu Gln Pro Met Ala Ile Gly Ile Asn Ala Val Ser Asn Gly Thr
305                 310                 315                 320

Ser Val Ile Thr Glu Asn Val Phe Glu Ser Arg Phe Arg Phe Val Asp
                325                 330                 335

Glu Met Leu Arg Leu Gly Ala Asp Ala Asn Val Asp Gly His His Val
            340                 345                 350
```

Val Ile Arg Gly Ile Glu Gln Leu Ser Ser Thr Ser Val Trp Ser Ser
            355                 360                 365

Asp Ile Arg Ala Gly Ala Gly Leu Val Leu Ala Ala Leu Cys Ala Asp
    370                 375                 380

Gly Val Thr Glu Val His Asp Val Phe His Ile Asp Arg Gly Tyr Pro
385                 390                 395                 400

Asn Phe Val Glu Asn Leu Gln Lys Leu Gly Ala Thr Ile Glu Arg Val
                405                 410                 415

Ser Ser

<210> SEQ ID NO 38
<211> LENGTH: 331
<212> TYPE: PRT
<213> ORGANISM: Neisseria meningitidis

<400> SEQUENCE: 38

Met Gln Pro Leu Val Ser Val Leu Ile Cys Ala Tyr Asn Val Glu Lys
1               5                   10                  15

Tyr Phe Ala Gln Ser Leu Ala Ala Val Val Asn Gln Thr Trp Cys Asn
                20                  25                  30

Leu Asp Ile Leu Val Asp Asp Gly Ser Thr Asp Gly Thr Leu Ala
            35                  40                  45

Ile Ala Lys Asp Phe Gln Lys Arg Asp Ser Arg Ile Lys Ile Leu Ala
    50                  55                  60

Gln Ala Gln Asn Ser Gly Leu Ile Pro Ser Leu Asn Ile Gly Leu Asp
65                  70                  75                  80

Glu Leu Ala Lys Ser Gly Gly Glu Tyr Ile Ala Arg Thr Asp Ala Asp
                85                  90                  95

Asp Ile Ala Ala Pro Asp Trp Ile Glu Lys Ile Val Gly Glu Met Glu
            100                 105                 110

Lys Asp Arg Ser Ile Ile Ala Met Gly Ala Trp Leu Glu Val Leu Ser
    115                 120                 125

Glu Glu Lys Asp Gly Asn Arg Leu Ala Arg His His Arg His Gly Lys
130                 135                 140

Ile Trp Lys Lys Pro Thr Arg His Glu Asp Ile Ala Asp Phe Phe Pro
145                 150                 155                 160

Phe Gly Asn Pro Ile His Asn Asn Thr Met Ile Met Arg Arg Ser Val
                165                 170                 175

Ile Asp Gly Gly Leu Arg Tyr Asn Thr Glu Arg Asp Trp Ala Glu Asp
            180                 185                 190

Tyr Gln Phe Trp Tyr Asp Val Ser Lys Leu Gly Arg Leu Ala Tyr Tyr
    195                 200                 205

Pro Glu Ala Leu Val Lys Tyr Arg Leu His Ala Asn Gln Val Ser Ser
210                 215                 220

Lys Tyr Ser Val Arg Gln His Glu Ile Ala Gln Gly Ile Gln Lys Thr
225                 230                 235                 240

Ala Arg Asn Asp Phe Leu Gln Ser Met Gly Phe Lys Thr Arg Phe Asp
                245                 250                 255

Ser Leu Glu Tyr Arg Gln Ile Lys Ala Val Ala Tyr Glu Leu Leu Glu
            260                 265                 270

Lys His Leu Pro Glu Glu Asp Phe Glu Arg Ala Arg Arg Phe Leu Tyr
    275                 280                 285

Gln Cys Phe Lys Arg Thr Asp Thr Leu Pro Ala Gly Ala Trp Leu Asp
290                 295                 300

```
Phe Ala Ala Asp Gly Arg Met Arg Arg Leu Phe Thr Leu Arg Gln Tyr
305                 310                 315                 320

Phe Gly Ile Leu His Arg Leu Leu Lys Asn Arg
                325                 330

<210> SEQ ID NO 39
<211> LENGTH: 265
<212> TYPE: PRT
<213> ORGANISM: Escherichia coli

<400> SEQUENCE: 39

Met Ile Ile Asp Glu Ala Glu Ser Ala Glu Ser Thr His Pro Val Val
1               5                   10                  15

Ser Val Ile Leu Pro Val Asn Lys Lys Asn Pro Phe Leu Asp Glu Ala
                20                  25                  30

Ile Asn Ser Ile Leu Ser Gln Thr Phe Ser Ser Phe Glu Ile Ile Ile
            35                  40                  45

Val Ala Asn Cys Cys Thr Asp Asp Phe Tyr Asn Glu Leu Lys His Lys
50                  55                  60

Val Asn Asp Lys Ile Lys Leu Ile Arg Thr Asn Ile Ala Tyr Leu Pro
65                  70                  75                  80

Tyr Ser Leu Asn Lys Ala Ile Asp Leu Ser Asn Gly Glu Phe Ile Ala
                85                  90                  95

Arg Met Asp Ser Asp Asp Ile Ser His Pro Asp Arg Phe Thr Lys Gln
            100                 105                 110

Val Asp Phe Leu Lys Asn Asn Pro Tyr Val Asp Val Val Gly Thr Asn
        115                 120                 125

Ala Ile Phe Ile Asp Asp Lys Gly Arg Glu Ile Asn Lys Thr Lys Leu
130                 135                 140

Pro Glu Glu Asn Leu Asp Ile Val Lys Asn Leu Pro Tyr Lys Cys Cys
145                 150                 155                 160

Ile Val His Pro Ser Val Met Phe Arg Lys Lys Val Ile Ala Ser Ile
                165                 170                 175

Gly Gly Tyr Met Phe Ser Asn Tyr Ser Glu Asp Tyr Glu Leu Trp Asn
            180                 185                 190

Arg Leu Ser Leu Ala Lys Ile Lys Phe Gln Asn Leu Pro Glu Tyr Leu
        195                 200                 205

Phe Tyr Tyr Arg Leu His Glu Gly Gln Ser Thr Ala Lys Lys Asn Leu
210                 215                 220

Tyr Met Val Met Val Asn Asp Leu Val Ile Lys Met Lys Cys Phe Phe
225                 230                 235                 240

Leu Thr Gly Asn Ile Asn Tyr Leu Phe Gly Gly Ile Arg Thr Ile Ala
                245                 250                 255

Ser Phe Ile Tyr Cys Lys Tyr Ile Lys
            260                 265

<210> SEQ ID NO 40
<211> LENGTH: 221
<212> TYPE: PRT
<213> ORGANISM: Campylobacter jejuni

<400> SEQUENCE: 40

Met Ser Leu Ala Ile Ile Pro Ala Arg Gly Gly Ser Lys Gly Ile Lys
1               5                   10                  15

Asn Lys Asn Leu Val Leu Leu Asn Lys Pro Leu Ile Tyr Tyr Thr
                20                  25                  30
```

Ile Lys Ala Ala Leu Asn Ala Lys Ser Ile Ser Lys Val Val Ser
    35                  40                  45

Ser Asp Ser Asp Glu Ile Leu Asn Tyr Ala Lys Ser Gln Asn Val Asp
 50                  55                  60

Ile Leu Lys Arg Pro Ile Ser Leu Ala Gln Asp Asp Thr Thr Ser Asp
65                  70                  75                  80

Lys Val Leu Leu His Ala Leu Lys Phe Tyr Lys Asp Tyr Glu Asp Val
                85                  90                  95

Val Phe Leu Gln Pro Thr Ser Pro Leu Arg Thr Asn Ile His Ile Asn
            100                 105                 110

Glu Ala Phe Asn Leu Tyr Lys Asn Ser Asn Ala Asn Ala Leu Ile Ser
            115                 120                 125

Val Ser Glu Cys Asp Asn Lys Ile Leu Lys Ala Phe Val Cys Asn Asp
130                 135                 140

Cys Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
                165                 170                 175

Leu Lys Ile Lys Glu Phe Leu Asn Asn Pro Ser Phe Leu Gln Ser Lys
            180                 185                 190

Thr Lys His Phe Leu Met Asp Glu Ser Ser Ser Leu Asp Ile Asp Cys
            195                 200                 205

Leu Glu Asp Leu Lys Lys Val Glu Gln Ile Trp Lys Lys
            210                 215                 220

<210> SEQ ID NO 41
<211> LENGTH: 371
<212> TYPE: PRT
<213> ORGANISM: Neisseria meningitidis

<400> SEQUENCE: 41

Met Gly Leu Lys Lys Ala Cys Leu Thr Val Leu Cys Leu Ile Val Phe
1               5                   10                  15

Cys Phe Gly Ile Phe Tyr Thr Phe Asp Arg Val Asn Gln Gly Glu Arg
                20                  25                  30

Asn Ala Val Ser Leu Leu Lys Glu Lys Leu Phe Asn Glu Glu Gly Glu
            35                  40                  45

Pro Val Asn Leu Ile Phe Cys Tyr Thr Ile Leu Gln Met Lys Val Ala
        50                  55                  60

Glu Arg Ile Met Ala Gln His Pro Gly Glu Arg Phe Tyr Val Val Leu
65                  70                  75                  80

Met Ser Glu Asn Arg Asn Glu Lys Tyr Asp Tyr Tyr Phe Asn Gln Ile
                85                  90                  95

Lys Asp Lys Ala Glu Arg Ala Tyr Phe His Leu Pro Tyr Gly Leu
            100                 105                 110

Asn Lys Ser Phe Asn Phe Ile Pro Thr Met Ala Glu Leu Lys Val Lys
            115                 120                 125

Ser Met Leu Leu Pro Lys Val Lys Arg Ile Tyr Leu Ala Ser Leu Glu
130                 135                 140

Lys Val Ser Ile Ala Ala Phe Leu Ser Thr Tyr Pro Asp Ala Glu Ile
145                 150                 155                 160

Lys Thr Phe Asp Asp Gly Thr Gly Asn Leu Ile Gln Ser Ser Ser Tyr
                165                 170                 175

Leu Gly Asp Glu Phe Ser Val Asn Gly Thr Ile Lys Arg Asn Phe Ala
            180                 185                 190

```
Arg Met Met Ile Gly Asp Trp Ser Ile Ala Lys Thr Arg Asn Ala Ser
            195                 200                 205
Asp Glu His Tyr Thr Ile Phe Lys Gly Leu Lys Asn Ile Met Asp Asp
        210                 215                 220
Gly Arg Arg Lys Met Thr Tyr Leu Pro Leu Phe Asp Ala Ser Glu Leu
225                 230                 235                 240
Lys Thr Gly Asp Glu Thr Gly Gly Thr Val Arg Ile Leu Leu Gly Ser
                245                 250                 255
Pro Asp Lys Glu Met Lys Glu Ile Ser Glu Lys Ala Ala Lys Asn Phe
            260                 265                 270
Lys Ile Gln Tyr Val Ala Pro His Pro Arg Gln Thr Tyr Gly Leu Ser
        275                 280                 285
Gly Val Thr Thr Leu Asn Ser Pro Tyr Val Ile Glu Asp Tyr Ile Leu
    290                 295                 300
Arg Glu Ile Lys Lys Asn Pro His Thr Arg Tyr Glu Ile Tyr Thr Phe
305                 310                 315                 320
Phe Ser Gly Ala Ala Leu Thr Met Lys Asp Phe Pro Asn Val His Val
                325                 330                 335
Tyr Ala Leu Lys Pro Ala Ser Leu Pro Glu Asp Tyr Trp Leu Lys Pro
            340                 345                 350
Val Tyr Ala Leu Phe Thr Gln Ser Gly Ile Pro Ile Leu Thr Phe Asp
        355                 360                 365
Asp Lys Asn
    370

<210> SEQ ID NO 42
<211> LENGTH: 42
<212> TYPE: DNA
<213> ORGANISM: Artificial sequence
<220> FEATURE:
<223> OTHER INFORMATION: Primer

<400> SEQUENCE: 42
ggttattgtc tcatgagcgg tagagtaaca ccgtgcgtgt tg                    42

<210> SEQ ID NO 43
<211> LENGTH: 34
<212> TYPE: DNA
<213> ORGANISM: Artificial sequence
<220> FEATURE:
<223> OTHER INFORMATION: Primer

<400> SEQUENCE: 43
ctccttatgt attctctggg caaccattat cacc                            34

<210> SEQ ID NO 44
<211> LENGTH: 36
<212> TYPE: DNA
<213> ORGANISM: Artificial sequence
<220> FEATURE:
<223> OTHER INFORMATION: Primer

<400> SEQUENCE: 44
cccagagaat acataaggag gtacgacatg gttagc                          36

<210> SEQ ID NO 45
<211> LENGTH: 35
<212> TYPE: DNA
<213> ORGANISM: Artificial sequence
<220> FEATURE:
```

<223> OTHER INFORMATION: Primer

<400> SEQUENCE: 45
ctaggactct tgatccggat atagttcctc ctttc                           35

<210> SEQ ID NO 46
<211> LENGTH: 33
<212> TYPE: DNA
<213> ORGANISM: Artificial sequence
<220> FEATURE:
<223> OTHER INFORMATION: Primer

<400> SEQUENCE: 46
ctatatccgg atcaagagtc ctaggatgct agc                             33

<210> SEQ ID NO 47
<211> LENGTH: 35
<212> TYPE: DNA
<213> ORGANISM: Artificial sequence
<220> FEATURE:
<223> OTHER INFORMATION: Primer

<400> SEQUENCE: 47
cacggtgtta ctctaccgct catgagacaa taacc                           35

<210> SEQ ID NO 48
<211> LENGTH: 35
<212> TYPE: DNA
<213> ORGANISM: Artificial sequence
<220> FEATURE:
<223> OTHER INFORMATION: Primer

<400> SEQUENCE: 48
tcggaggaaa caaagatgag cacaaaaaag aaacc                           35

<210> SEQ ID NO 49
<211> LENGTH: 50
<212> TYPE: DNA
<213> ORGANISM: Artificial sequence
<220> FEATURE:
<223> OTHER INFORMATION: Primer

<400> SEQUENCE: 49
accatcctaa tgatggtggt gatgatggag ctactaaagc gtagttttcg           50

<210> SEQ ID NO 50
<211> LENGTH: 52
<212> TYPE: DNA
<213> ORGANISM: Artificial sequence
<220> FEATURE:
<223> OTHER INFORMATION: Primer

<400> SEQUENCE: 50
accaccatca ttaggatggt ggtgatgata atggataaat ttcgtgttca gg        52

<210> SEQ ID NO 51
<211> LENGTH: 32
<212> TYPE: DNA
<213> ORGANISM: Artificial sequence
<220> FEATURE:
<223> OTHER INFORMATION: Primer

<400> SEQUENCE: 51
ttaagcggaa gttattcgcc tttcacacgc tc                              32

```
<210> SEQ ID NO 52
<211> LENGTH: 35
<212> TYPE: DNA
<213> ORGANISM: Artificial sequence
<220> FEATURE:
<223> OTHER INFORMATION: Primer

<400> SEQUENCE: 52
gacgctcagt ggaacggaag ctgagttggc tgctg                           35

<210> SEQ ID NO 53
<211> LENGTH: 36
<212> TYPE: DNA
<213> ORGANISM: Artificial sequence
<220> FEATURE:
<223> OTHER INFORMATION: Primer

<400> SEQUENCE: 53
gcttgtctgt aagcgccatg gtccatatga atatcc                          36

<210> SEQ ID NO 54
<211> LENGTH: 37
<212> TYPE: DNA
<213> ORGANISM: Artificial sequence
<220> FEATURE:
<223> OTHER INFORMATION: Primer

<400> SEQUENCE: 54
tcatatggac catggcgctt acagacaagc tgtgacc                         37

<210> SEQ ID NO 55
<211> LENGTH: 35
<212> TYPE: DNA
<213> ORGANISM: Artificial sequence
<220> FEATURE:
<223> OTHER INFORMATION: Primer

<400> SEQUENCE: 55
cttttttgtg ctcatctttg tttcctccga attcg                           35

<210> SEQ ID NO 56
<211> LENGTH: 60
<212> TYPE: DNA
<213> ORGANISM: Artificial sequence
<220> FEATURE:
<223> OTHER INFORMATION: Primer

<400> SEQUENCE: 56
ccgtcgacct cgaattcgga ggaaacaaag atgtactatt taaaaaacac aaactttttgg   60

<210> SEQ ID NO 57
<211> LENGTH: 45
<212> TYPE: DNA
<213> ORGANISM: Artificial sequence
<220> FEATURE:
<223> OTHER INFORMATION: Primer

<400> SEQUENCE: 57
gctggcacat gttctttaag cggaagttaa gcgacttcat tcacc                45

<210> SEQ ID NO 58
<211> LENGTH: 50
<212> TYPE: DNA
<213> ORGANISM: Artificial sequence
<220> FEATURE:
<223> OTHER INFORMATION: Primer
```

<400> SEQUENCE: 58
cgtcaggtga atgaagtcgc ttaacttccg cttaaagaac atgtgccagc                50

<210> SEQ ID NO 59
<211> LENGTH: 50
<212> TYPE: DNA
<213> ORGANISM: Artificial sequence
<220> FEATURE:
<223> OTHER INFORMATION: Primer

<400> SEQUENCE: 59
ccaaaagttt gtgttttta aatagtacat ctttgtttcc tccgaattcg                50

<210> SEQ ID NO 60
<211> LENGTH: 72
<212> TYPE: DNA
<213> ORGANISM: Artificial sequence
<220> FEATURE:
<223> OTHER INFORMATION: Primer

<400> SEQUENCE: 60
ggaattaatc gccggatgca aggttcacgc cgcatctggc aaacatcctc acgtgtaggc    60
tggagctgct tc                                                        72

<210> SEQ ID NO 61
<211> LENGTH: 69
<212> TYPE: DNA
<213> ORGANISM: Artificial sequence
<220> FEATURE:
<223> OTHER INFORMATION: Primer

<400> SEQUENCE: 61
ggcttgcgga gtgtctggct gacagataat cgtcgatgag ggcagttttc atatgaatat    60
cctccttag                                                            69

<210> SEQ ID NO 62
<211> LENGTH: 21
<212> TYPE: DNA
<213> ORGANISM: Artificial sequence
<220> FEATURE:
<223> OTHER INFORMATION: Primer

<400> SEQUENCE: 62
tattcccatc cgcgtctgtt c                                              21

<210> SEQ ID NO 63
<211> LENGTH: 21
<212> TYPE: DNA
<213> ORGANISM: Artificial sequence
<220> FEATURE:
<223> OTHER INFORMATION: Primer

<400> SEQUENCE: 63
aagcgcccaa tgtattccag g                                              21

<210> SEQ ID NO 64
<211> LENGTH: 75
<212> TYPE: DNA
<213> ORGANISM: Artificial sequence
<220> FEATURE:
<223> OTHER INFORMATION: Primer

<400> SEQUENCE: 64
ggctggccga tgcacctggc ggcagctat taataaaaca ataaggagag cagtcagcat     60

```
tacacgtctt gagcg                                                      75

<210> SEQ ID NO 65
<211> LENGTH: 75
<212> TYPE: DNA
<213> ORGANISM: Artificial sequence
<220> FEATURE:
<223> OTHER INFORMATION: Primer

<400> SEQUENCE: 65
ctgattcaga cgggtgctga tcgctttcca gcgagccgag tccatcagtt cctgccatat     60
gaatatcctc cttag                                                      75

<210> SEQ ID NO 66
<211> LENGTH: 20
<212> TYPE: DNA
<213> ORGANISM: Artificial sequence
<220> FEATURE:
<223> OTHER INFORMATION: Primer

<400> SEQUENCE: 66
cggcgcaatt atggcgtcag                                                 20

<210> SEQ ID NO 67
<211> LENGTH: 21
<212> TYPE: DNA
<213> ORGANISM: Artificial sequence
<220> FEATURE:
<223> OTHER INFORMATION: Primer

<400> SEQUENCE: 67
cggactgtta gagtcaaaac c                                               21

<210> SEQ ID NO 68
<211> LENGTH: 67
<212> TYPE: DNA
<213> ORGANISM: Artificial sequence
<220> FEATURE:
<223> OTHER INFORMATION: Primer

<400> SEQUENCE: 68
taattcctgc gtaggacttt tgttttgcag ttttacgtc acaagggcat atgaatatcc      60
tccttag                                                               67

<210> SEQ ID NO 69
<211> LENGTH: 75
<212> TYPE: DNA
<213> ORGANISM: Artificial sequence
<220> FEATURE:
<223> OTHER INFORMATION: Primer

<400> SEQUENCE: 69
gtagcccatt gacaaaaaat gcggcgatac tggaaggtat cgccaacacg tgtaggctgg     60
agctggagct gcttc                                                      75

<210> SEQ ID NO 70
<211> LENGTH: 22
<212> TYPE: DNA
<213> ORGANISM: Artificial sequence
<220> FEATURE:
<223> OTHER INFORMATION: Primer

<400> SEQUENCE: 70
```
gagactcccg tatactttct tc                                           22

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
cgcccttttt gcatttgttg                                              20

<210> SEQ ID NO 72
<211> LENGTH: 70
<212> TYPE: DNA
<213> ORGANISM: Artificial sequence
<220> FEATURE:
<223> OTHER INFORMATION: Primer

<400> SEQUENCE: 72
agtgggcgcg cgatcgcaaa ctgaacggct tttgagctat gggcgattcg gtggaacgga   60
agctgagttg                                                         70

<210> SEQ ID NO 73
<211> LENGTH: 20
<212> TYPE: DNA
<213> ORGANISM: Artificial sequence
<220> FEATURE:
<223> OTHER INFORMATION: Primer

<400> SEQUENCE: 73
gcgccaacgc tgactttatc                                              20

<210> SEQ ID NO 74
<211> LENGTH: 29
<212> TYPE: DNA
<213> ORGANISM: Artificial sequence
<220> FEATURE:
<223> OTHER INFORMATION: Primer

<400> SEQUENCE: 74
aagtcaggca tgagcacaaa aaagaaacc                                    29

<210> SEQ ID NO 75
<211> LENGTH: 24
<212> TYPE: DNA
<213> ORGANISM: Artificial sequence
<220> FEATURE:
<223> OTHER INFORMATION: Primer

<400> SEQUENCE: 75
tgtcaagaaa tttataaatg aagc                                         24

<210> SEQ ID NO 76
<211> LENGTH: 60
<212> TYPE: DNA
<213> ORGANISM: Artificial sequence
<220> FEATURE:
<223> OTHER INFORMATION: Primer

<400> SEQUENCE: 76
tgtgtacata aacacaagct carcmtatac tagasraagt caggcatgag cacaaaaaag   60

<210> SEQ ID NO 77
<211> LENGTH: 56

```
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(37)
<223> OTHER INFORMATION: n is a, c, g, or t

<400> SEQUENCE: 77
gtgtttatgt acacattata nnnnnnnnnn nnnnnnntgt caagaaattt ataaat         56

<210> SEQ ID NO 78
<211> LENGTH: 62
<212> TYPE: DNA
<213> ORGANISM: Artificial sequence
<220> FEATURE:
<223> OTHER INFORMATION: Primer

<400> SEQUENCE: 78
taatgcgccg ccagtaaatc aacatgaaat gccgctggct ccgtgtaggc tggagctgct    60
tc                                                                   62

<210> SEQ ID NO 79
<211> LENGTH: 72
<212> TYPE: DNA
<213> ORGANISM: Artificial sequence
<220> FEATURE:
<223> OTHER INFORMATION: Primer

<400> SEQUENCE: 79
caatcctgtg ataggatgtc actgatgatg ttaatcacac tgaccttaca gacatatgaa    60
tatcctcctt ag                                                        72

<210> SEQ ID NO 80
<211> LENGTH: 20
<212> TYPE: DNA
<213> ORGANISM: Artificial sequence
<220> FEATURE:
<223> OTHER INFORMATION: Primer

<400> SEQUENCE: 80
gtcgccctgt aattcgtaac                                                20

<210> SEQ ID NO 81
<211> LENGTH: 20
<212> TYPE: DNA
<213> ORGANISM: Artificial sequence
<220> FEATURE:
<223> OTHER INFORMATION: Primer

<400> SEQUENCE: 81
tttatggtgc ggatgtcgtg                                                20

<210> SEQ ID NO 82
<211> LENGTH: 20
<212> TYPE: DNA
<213> ORGANISM: Artificial sequence
<220> FEATURE:
<223> OTHER INFORMATION: Primer

<400> SEQUENCE: 82
gcgggcatca atatgcacag                                                20

<210> SEQ ID NO 83
```

```
<211> LENGTH: 20
<212> TYPE: DNA
<213> ORGANISM: Artificial sequence
<220> FEATURE:
<223> OTHER INFORMATION: Primer

<400> SEQUENCE: 83
gatccagaac gtcccgaaac                                                       20

<210> SEQ ID NO 84
<211> LENGTH: 74
<212> TYPE: DNA
<213> ORGANISM: Artificial sequence
<220> FEATURE:
<223> OTHER INFORMATION: Primer

<400> SEQUENCE: 84
cataatggat ttccttacgc gaaatacggg cagacatggc ctgcccggtt attagtgtag          60
gctggagctg cttc                                                             74

<210> SEQ ID NO 85
<211> LENGTH: 71
<212> TYPE: DNA
<213> ORGANISM: Artificial sequence
<220> FEATURE:
<223> OTHER INFORMATION: Primer

<400> SEQUENCE: 85
gtatgttgtg tggaattgtg agcggataac aatttcacac aggaaacagc tcatatgaat          60
atcctcctta g                                                                71

<210> SEQ ID NO 86
<211> LENGTH: 18
<212> TYPE: DNA
<213> ORGANISM: Artificial sequence
<220> FEATURE:
<223> OTHER INFORMATION: Primer

<400> SEQUENCE: 86
gcggttggaa taatagcg                                                         18

<210> SEQ ID NO 87
<211> LENGTH: 20
<212> TYPE: DNA
<213> ORGANISM: Artificial sequence
<220> FEATURE:
<223> OTHER INFORMATION: Primer

<400> SEQUENCE: 87
caggtttccc gactggaaag                                                       20

<210> SEQ ID NO 88
<211> LENGTH: 76
<212> TYPE: DNA
<213> ORGANISM: Artificial sequence
<220> FEATURE:
<223> OTHER INFORMATION: Primer

<400> SEQUENCE: 88
tcgctgaact tgtaggcctg ataagcgcag cgtatcaggc aatttttata atttaagcga          60
cttcattcac ctgacg                                                           76

<210> SEQ ID NO 89
<211> LENGTH: 70
```

```
<212> TYPE: DNA
<213> ORGANISM: Artificial sequence
<220> FEATURE:
<223> OTHER INFORMATION: Primer

<400> SEQUENCE: 89
gtatgttgtg tggaattgtg agcggataac aatttcacac aggaaacagc gtggaacgga      60
agctgagttg                                                              70

<210> SEQ ID NO 90
<211> LENGTH: 20
<212> TYPE: DNA
<213> ORGANISM: Artificial sequence
<220> FEATURE:
<223> OTHER INFORMATION: Primer

<400> SEQUENCE: 90
acgcttgttc ctgcgctttg                                                   20

<210> SEQ ID NO 91
<211> LENGTH: 20
<212> TYPE: DNA
<213> ORGANISM: Artificial sequence
<220> FEATURE:
<223> OTHER INFORMATION: Primer

<400> SEQUENCE: 91
ttatgcttcc ggctcgtatg                                                   20

<210> SEQ ID NO 92
<211> LENGTH: 114
<212> TYPE: DNA
<213> ORGANISM: Artificial sequence
<220> FEATURE:
<223> OTHER INFORMATION: artificial promotor+5'UTR

<400> SEQUENCE: 92
atttataaat tcttgacat tttggaatag atgtgatata atgtgtacat atccatggcg       60
gccgctctag aagaagcttg ggatccgtcg acctcgaatt cggaggaaac aaag           114

<210> SEQ ID NO 93
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 93
atttataaat tcttgacaa acataggaat aaattttata atgtgtacat aaacacaagc       60
tcaacatata ctaggcaaag tcaggc                                            86

<210> SEQ ID NO 94
<211> LENGTH: 86
<212> TYPE: DNA
<213> ORGANISM: Artificial sequence
<220> FEATURE:
<223> OTHER INFORMATION: artificial promotor+5'UTR

<400> SEQUENCE: 94
atttataaat tcttgacag gaggtgacaa ttaacctata atgtgtacat aaacacaagc       60
tcagcatata ctagagaaag tcaggc                                            86
```